United States Patent
Kojima et al.

(10) Patent No.: US 12,032,288 B2
(45) Date of Patent: Jul. 9, 2024

(54) ACTINIC RAY-SENSITIVE OR RADIATION-SENSITIVE RESIN COMPOSITION, RESIST FILM, PATTERN FORMING METHOD, AND METHOD FOR MANUFACTURING ELECTRONIC DEVICE

(71) Applicant: FUJIFILM Corporation, Tokyo (JP)

(72) Inventors: Masafumi Kojima, Shizuoka (JP); Minoru Uemura, Shizuoka (JP); Akihiro Kaneko, Shizuoka (JP); Akiyoshi Goto, Shizuoka (JP); Kei Yamamoto, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 433 days.

(21) Appl. No.: 17/307,091

(22) Filed: May 4, 2021

(65) Prior Publication Data

US 2021/0356862 A1    Nov. 18, 2021

Related U.S. Application Data

(63) Continuation of application No. PCT/JP2020/000835, filed on Jan. 14, 2020.

(30) Foreign Application Priority Data

Jan. 28, 2019  (JP) .................................. 2019-012485
Dec. 26, 2019  (JP) .................................. 2019-237307

(51) Int. Cl.
| | | |
|---|---|---|
| G03F 7/004 | (2006.01) | |
| C07C 25/18 | (2006.01) | |
| C07C 309/06 | (2006.01) | |
| C07C 309/12 | (2006.01) | |
| C07C 309/17 | (2006.01) | |
| C07C 311/48 | (2006.01) | |
| C07C 381/12 | (2006.01) | |
| C07D 327/06 | (2006.01) | |
| C07D 333/46 | (2006.01) | |

(52) U.S. Cl.
CPC ............ *G03F 7/0045* (2013.01); *C07C 25/18* (2013.01); *C07C 309/06* (2013.01); *C07C 309/12* (2013.01); *C07C 309/17* (2013.01); *C07C 311/48* (2013.01); *C07C 381/12* (2013.01); *C07D 327/06* (2013.01); *C07D 333/46* (2013.01); *C07C 2602/42* (2017.05); *C07C 2603/74* (2017.05)

(58) Field of Classification Search
CPC ... C07C 381/12; C07C 309/06; C07C 309/17; C07C 311/00; C07C 311/48
See application file for complete search history.

(56) References Cited

U.S. PATENT DOCUMENTS

| | | | | |
|---|---|---|---|---|
| 2010/0255418 A1* | 10/2010 | Yamaguchi | ........... | G03F 7/0397 562/66 |
| 2015/0331314 A1 | 11/2015 | Yamaguchi et al. | | |

FOREIGN PATENT DOCUMENTS

| | | | |
|---|---|---|---|
| JP | 2005-275153 | A | 10/2005 |
| JP | 2008-129433 | A | 6/2008 |
| JP | 2011-215385 | A | 10/2011 |
| JP | 2014-149409 | A | 8/2014 |
| JP | 2015-024989 | A | 2/2015 |
| JP | 2019008277 | A * | 1/2019 |
| JP | 2019156831 | A * | 9/2019 |
| JP | 2019156832 | A * | 9/2019 |
| TW | 201435505 | A | 9/2014 |
| WO | 2012/118168 | A1 | 9/2012 |
| WO | 2013/187520 | A1 | 12/2013 |
| WO | 2014/119698 | A1 | 8/2014 |

OTHER PUBLICATIONS

Machine translation of JP 2005-275153 (no date).*
Extended European Search Report dated Mar. 1, 2022 from the European Patent Office in EP application No. 20749362.8.
Office Action issued Apr. 24, 2023 in Korean Application No. 10-2021-7014942.
Office Action issued Mar. 13, 2023 in Taiwanese Application No. 109101205.
Office Action issued Aug. 2, 2022 in Japanese Application No. 2020-569485.
International Search Report issued Mar. 17, 2020 in International Application No. PCT/JP2020/000835.
Written Opinion of the International Searching Authority issued Mar. 17, 2020 in International Application No. PCT/JP2020/000835.
International Preliminary Report on Patentability issued Jul. 27, 2021 in International Application No. PCT/JP2020/000835.
Office Action dated Dec. 4, 2023 in Chinese Application No. 202080006371.4.

* cited by examiner

*Primary Examiner* — Amanda C. Walke
(74) *Attorney, Agent, or Firm* — Sughrue Mion, PLLC

(57) ABSTRACT

An actinic ray-sensitive or radiation-sensitive resin composition includes a compound represented by General Formula (I) and an acid-decomposable resin.

$$M_1^+A^--L-B^-M_2^+ \qquad (I)$$

7 Claims, No Drawings

ACTINIC RAY-SENSITIVE OR RADIATION-SENSITIVE RESIN COMPOSITION, RESIST FILM, PATTERN FORMING METHOD, AND METHOD FOR MANUFACTURING ELECTRONIC DEVICE

CROSS-REFERENCE TO RELATED APPLICATIONS

This application is a Continuation of PCT International Application No. PCT/JP2020/000835 filed on Jan. 14, 2020, which claims priority under 35 U.S.C § 119(a) to Japanese Patent Application No. 2019-012485 filed on Jan. 28, 2019, and Japanese Patent Application No. 2019-237307 filed on Dec. 26, 2019. Each of the above application(s) is hereby expressly incorporated by reference, in its entirety, into the present application.

BACKGROUND OF THE INVENTION

1. Field of the Invention

The present invention relates to an actinic ray-sensitive or radiation-sensitive resin composition, a resist film, a pattern forming method, and a method for manufacturing an electronic device.

2. Description of the Related Art

Since the advent of a resist for KrF excimer laser (248 nm), a pattern forming method utilizing chemical amplification has been used in order to compensate for a decrease in sensitivity due to light absorption. For example, in a positive tone chemical amplification method, first, a photoacid generator included in the exposed area decomposes upon irradiation with light to generate an acid. Then, in a post-exposure baking (PEB) step and the like, a solubility in a developer changes by, for example, changing an alkali-insoluble group contained in a resin included in an actinic ray-sensitive or radiation-sensitive resin composition to an alkali-soluble group by the catalytic action of an acid thus generated. Thereafter, development is performed using a basic aqueous solution, for example. As a result, the exposed area is removed to obtain a desired pattern.

Under these circumstances, various configurations have been proposed as actinic ray-sensitive or radiation-sensitive resin compositions for miniaturization of semiconductor elements.

For example, JP2015-024989A discloses an acid generator including a salt represented by Formula (I) as a component used in a composition.

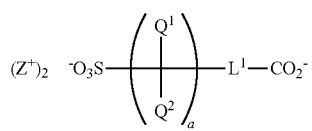

(I)

SUMMARY OF THE INVENTION

The present inventors have conducted specific studies on the techniques disclosed in JP2015-024989A, and have thus found that in a case where the composition of JP2015-024989A is applied to pattern formation after the composition is produced and then stored for a long period of time (for example, 3 months), it has room for improvement in the line width roughness (LWR) performance of a pattern thus obtained.

Therefore, an object of the present invention is to provide an actinic ray-sensitive or radiation-sensitive resin composition that is capable of obtaining a pattern having excellent LWR performance even in a case of long-term storage.

In addition, another object of the present invention is to provide a resist film, a pattern forming method, and a method for manufacturing an electronic device, each relating to the actinic ray-sensitive or radiation-sensitive resin composition.

The present inventors have conducted intensive studies to accomplish the objects, and as a result, have found that the objects can be accomplished by the following configurations.

[1] An actinic ray-sensitive or radiation-sensitive resin composition, comprising:
  a compound represented by General Formula (I) which will be described later; and
  an acid-decomposable resin.

[2] The actinic ray-sensitive or radiation-sensitive resin composition as described in [1],
  in which in the compound represented by General Formula (I) which will be described later, W represents a group represented by any of General Formulae (B-1) to (B-3) which will be described later.

[3] The actinic ray-sensitive or radiation-sensitive resin composition as described in [1] or [2],
  in which in the compound represented by General Formula (I) which will be described later, B$^-$ represents a group represented by either of General Formulae (B-1) and (B-2).

[4] The actinic ray-sensitive or radiation-sensitive resin composition as described in any one of [1] to [3],
  in which in the compound represented by General Formula (I) which will be described later, A$^-$ represents a group represented by either of General Formulae (A-1) and (A-2).

[5] A resist film formed of the actinic ray-sensitive or radiation-sensitive resin composition as described in any one of [1] to [4].

[6] A pattern forming method comprising:
  a step of forming a resist film on a support, using the actinic ray-sensitive or radiation-sensitive resin composition as described in any one of [1] to [4];
  a step of exposing the resist film; and
  a step of developing the exposed resist film using a developer.

[7] A method for manufacturing an electronic device, comprising the pattern forming method as described in [6].

According to the present invention, it is possible to provide an actinic ray-sensitive or radiation-sensitive resin composition that is capable of obtaining a pattern having excellent LWR performance even in a case of long-term storage.

In addition, the present invention can also provide a resist film, a pattern forming method, and a method for manufacturing an electronic device, each relating to the actinic ray-sensitive or radiation-sensitive resin composition.

DESCRIPTION OF THE PREFERRED EMBODIMENTS

Hereinafter, the present invention will be described in detail.

Description of configuration requirements described below may be made on the basis of representative embodiments of the present invention in some cases, but the present invention is not limited to such embodiments.

In notations for a group (atomic group) in the present specification, in a case where the group is cited without specifying whether it is substituted or unsubstituted, the group includes both a group having no substituent and a group having a substituent as long as this does not impair the spirit of the present invention. For example, an "alkyl group" includes not only an alkyl group having no substituent (unsubstituted alkyl group), but also an alkyl group having a substituent (substituted alkyl group). In addition, an "organic group" in the present specification refers to a group including at least one carbon atom.

The substituent is preferably a monovalent substituent unless otherwise specified.

"Actinic rays" or "radiation" in the present specification means, for example, a bright line spectrum of a mercury lamp, far ultraviolet rays typified by an excimer laser, extreme ultraviolet rays (EUV light), X-rays, electron beams (EB), or the like. "Light" in the present specification means actinic rays or radiation.

Unless otherwise specified, "exposure" in the present specification encompasses not only exposure by a bright line spectrum of a mercury lamp, far ultraviolet rays typified by an excimer laser, extreme ultraviolet rays (EUV light), X-rays, or the like, but also lithography by particle beams such as electron beams and ion beams.

In the present specification, a numerical range expressed using "to" is used in a meaning of a range that includes the preceding and succeeding numerical values of "to" as the lower limit value and the upper limit value, respectively.

The bonding direction of divalent groups cited in the present specification is not limited unless otherwise specified. For example, in a case where Y in a compound represented by General Formula "X—Y—Z" is —COO—, Y may be —CO—O— or —O—CO—. In addition, the compound may be "X—CO—O—Z" or "X—O—CO—Z".

In the present specification, (meth)acrylate represents acrylate and methacrylate, and (meth)acryl represents acryl and methacryl.

In the present specification, a weight-average molecular weight (Mw), a number-average molecular weight (Mn), and a dispersity (also referred to as a molecular weight distribution) (Mw/Mn) of a resin are defined as values expressed in terms of polystyrene by means of gel permeation chromatography (GPC) measurement (solvent: tetrahydrofuran, flow amount (amount of a sample injected): 10 μL, columns: TSK gel Multipore HXL-M manufactured by Tosoh Corporation, column temperature: 40° C., flow rate: 1.0 mL/min, and detector: differential refractive index detector) using a GPC apparatus (HLC-8120GPC manufactured by Tosoh Corporation).

In the present specification, an acid dissociation constant (pKa) represents a pKa in an aqueous solution, and is specifically a value determined by computation from a value based on a Hammett's substituent constant and database of publicly known literature values, using the following software package 1. Any of the pKa values described in the present specification indicates values determined by computation using the software package.

Software Package 1: Advanced Chemistry Development (ACD/Labs) Software V 8.14 for Solaris (1994-2007 ACD/Labs).

On the other hand, the pKa can also be determined by a molecular orbital computation method. Examples of a specific method therefor include a method for performing calculation by computing $H^+$ dissociation free energy in a solvent based on a thermodynamic cycle. (Further, in the present specification, water is usually used as the solvent, and in a case where a pKa is not determined with water, dimethyl sulfoxide (DMSO) is used.)

With regard to a computation method for $H^+$ dissociation free energy, the $H^+$ dissociation free energy can be calculated by, for example, density functional theory (DFT), but various other methods have been reported in literature and the like, and are not limited thereto. Further, there are a plurality of software applications capable of performing DFT, and examples thereof include Gaussian 16.

As described above, the pKa in the present specification refers to a value determined by computation from a value based on a Hammett's substituent constant and database of publicly known literature values, using the software package 1, but in a case where the pKa cannot be calculated by the method, a value obtained by Gaussian 16 based on density functional theory (DFT) shall be adopted.

In the present specification, examples of the halogen atom include a fluorine atom, a chlorine atom, a bromine atom, and an iodine atom.

[Actinic Ray-Sensitive or Radiation-Sensitive Resin Composition]

The actinic ray-sensitive or radiation-sensitive resin composition of an embodiment of the present invention (hereinafter also simply referred to as the "composition" or the "composition of the embodiment of the present invention") will be described.

The composition of the embodiment of the present invention is a so-called resist composition, and may be either a positive tone resist composition or a negative tone resist composition. In addition, the resist composition may be either a resist composition for alkaline development or a resist composition for organic solvent development.

The composition of the embodiment of the present invention is typically a chemically amplified resist composition.

The composition of the embodiment of the present invention includes a compound represented by General Formula (I) which will be described later (hereinafter also referred to as a specific compound) and an acid-decomposable resin.

Mechanism by which the objects of the present invention can be accomplished through such a configuration is not necessarily clear, but is presumed as follows by the present inventors.

That is, in ordinary compositions in the related art, in a case where photoacid generators and acid diffusion control agents are added to the composition only as an individual compound, the photoacid generators or the acid diffusion control agents are easily aggregated with each other, respectively. Therefore, in the ordinary compositions in the related art, a portion having a high (or low) concentration of the photoacid generators and a portion having a high (or low) concentration of the acid diffusion control agents are present in a resist film thus formed, and thus, non-uniformity in the concentration ratio of the photoacid generators and the acid diffusion control agents is likely to occur. As a result, in a case where the resist film is exposed, unevenness in the amount and the diffusion of an acid generated in the resist film also occurs, which causes non-uniformity in the width of a pattern obtained after development.

On the other hand, since the specific compound includes both of a structure having a function corresponding to a photoacid generator (a moiety corresponding to "$M_1^+ A^-$") and a structure having a function corresponding to a photodegradable type acid diffusion control agent ("—$B^- M_2^+$")

in one molecule, it is possible to keep a presence ratio of each of the structures constant in the resist film.

Therefore, the present inventors have presumed that even in a case where the resist film is exposed, the amount and the diffusion of an acid generated in the resist film are likely to be uniform and the width of a pattern obtained after development is stabilized.

In addition, in the specific compound, a nitrogen anion in the group represented by W is inside the organic group, and thus, modification of the specific compound or the acid-decomposable resin due to an interaction between the nitrogen anion and the acid-decomposable resin hardly occurs. Therefore, the present inventors have presumed that even in a case where the composition of the embodiment of the present invention is stored for a long period of time, the composition can be easily stabilized, and a pattern having excellent LWR performance can be obtained even in a case of long-term storage.

Hereinafter, the components of the composition of the embodiment of the present invention will be described.
[Specific Compound]

The composition of the embodiment of the present invention includes a specific compound.

The specific compound is a compound represented by General Formula (I).

In General Formula (I), $M_1^+$ and $M_2^+$ each independently represent an organic cation.

The organic cation will be described later.

In General Formula (I), L represents a divalent organic group.

Examples of the divalent organic group include —COO—, —CONH—, —CO—, —O—, an alkylene group (which preferably has 1 to 6 carbon atoms, and may be linear or branched), a cycloalkylene group (preferably having 3 to 15 carbon atoms), an alkenylene group (preferably having 2 to 6 carbon atoms), and a divalent linking group formed by combination of a plurality of these groups.

One or more of the methylene groups constituting a cycloalkane ring of the cycloalkylene group may be substituted with a carbonyl carbon and/or a heteroatom (an oxygen atom and the like).

It is also preferable that the divalent linking group has a group selected from the group consisting of —S—, —SO—, and —SO$_2$—.

Among those, L is preferably a group represented by General Formula (L).

In General Formula (L), *$^A$ represents a bonding position to A$^-$ in General Formula (I).

In General Formula (L), *$^B$ represents a bonding position to B$^-$ in General Formula (I).

In General Formula (L), LA represents —(C(R$_{LA1}$)(R$_{LA2}$))$_{XA}$—.

XA represents an integer of 1 or more, and is preferably 1 to 10, and more preferably 1 to 3.

R$_{LA1}$ and R$_{LA2}$ each independently represent a hydrogen atom or a substituent.

The substituents of R$_{LA1}$ and R$_{LA2}$ are each independently preferably a fluorine atom or a fluoroalkyl group, more preferably the fluorine atom or a perfluoroalkyl group, and still more preferably the fluorine atom or a perfluoromethyl group.

In a case where XA is 2 or more, XA pieces of R$_{LA1}$'s may be the same as or different from each other.

In a case where XA is 2 or more, XA pieces of R$_{LA2}$'s may be the same as or different from each other.

—(C(R$_{LA1}$)(R$_{LA2}$))— is preferably —CH$_2$—, —CHF—, —CH(CF$_3$)—, or —CF$_2$—.

Among those, —(C(R$_{LA1}$)(R$_{LA2}$))— which is directly bonded to A$^-$ in General Formula (I) is preferably —CH$_2$—, —CHF—, —CH(CF$_3$)—, or —CF$_2$—.

—(C(R$_{LA1}$)(R$_{LA2}$))—'s other than —(C(R$_{LA1}$)(R$_{LA2}$))— which is directly bonded to A$^-$ in General Formula (I) are each independently preferably —CH$_2$—, —CHF—, or —CF$_2$—.

In General Formula (L), LB represents a single bond, an ester group (—COO—), or a sulfonyl group (—SO$_2$—).

In General Formula (L), LC represents a single bond, an alkylene group, a cycloalkylene group, or a group formed by combination thereof ("-alkylene group-cycloalkylene group-" and the like).

The alkylene group may be linear or branched.

The alkylene group preferably has 1 to 5 carbon atoms, more preferably has 1 or 2 carbon atoms, and still more preferably has one carbon atom.

The cycloalkylene group preferably has 3 to 15 carbon atoms, and more preferably has 5 to 10 carbon atoms.

The cycloalkylene group may be a monocycle or a polycycle.

Examples of the cycloalkylene group include a norbornanediyl group and an adamantanediyl group.

As a substituent which may be contained in the cycloalkylene group, an alkyl group (which may be linear or branched, and preferably has 1 to 5 carbon atoms) is preferable.

One or more of the methylene groups constituting a cycloalkane ring of the cycloalkylene group may be substituted with a carbonyl carbon and/or a heteroatom (an oxygen atom and the like).

In a case where LC is "-alkylene group-cycloalkylene group-", the alkylene group moiety is preferably present on the LB side.

In a case where the LB is the single bond, LC is preferably the single bond or the cycloalkylene group.

In General Formula (L), LD represents a single bond, an ether group (—O—), a carbonyl group (—CO—), or an ester group (—COO—).

In General Formula (L), LE represents a single bond or —(C(R$_{LE1}$)(R$_{LE2}$))$_{XE}$—.

XE in —(C(R$_{LE1}$)(R$_{LE2}$))$_{XE}$— represents an integer of 1 or more, and is preferably 1 to 10, and more preferably 1 to 3.

R$_{LE1}$ and R$_{LE2}$ each independently represent a hydrogen atom or a substituent.

In a case where XE is 2 or more, XE pieces of R$_{LE1}$'s may be the same as or different from each other.

In a case where XE is 2 or more, XE pieces of R$_{LE2}$'s may be the same as or different from each other.

Among those, —(C(R$_{LE1}$)(R$_{LE2}$))— is preferably —CH$_2$—.

In a case where LB, LC, and LD are the single bonds in General Formula (L), it is preferable that LE is also the single bond.

In General Formula (I), A$^-$ represents an acid anion group.

The acid anion group is a group having an anion atom.

Specifically, A$^-$ is preferably a group represented by either of General Formulae (A-1) and (A-2).

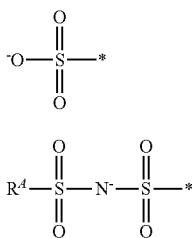

A-1

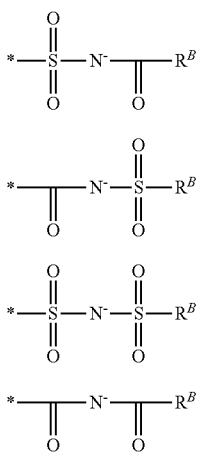

A-2

B-1

B-2

B-3

B-4

In General Formulae (A-1) and (A-2), * represents a bonding position.

In General Formula (A-2), $R^A$ represents an organic group.

$R^A$ is preferably an alkyl group.

The alkyl group may be linear or branched.

The alkyl group preferably has 1 to 10 carbon atoms, and more preferably has 1 to 5 carbon atoms.

As the substituent which may be contained in the alkyl group, a fluorine atom is preferable.

The alkyl group having a fluorine atom as a substituent may or may not be a perfluoroalkyl group.

In General Formula (I), $B^-$ represents a group represented by any of General Formulae (B-1) to (B-4).

$B^-$ is preferably the group represented by any of General Formulae (B-1) to (B-3), and more preferably the group represented by either of General Formulae (B-1) and (B-2).

In General Formulae (B-1) to (B-4), * represents a bonding position.

In General Formulae (B-1) to (B-4), $R^B$ represents an organic group.

$R^B$ is preferably a cycloalkyl group, an aromatic ring group, or an alkyl group.

In a case where $R^B$ is the cycloalkyl group, the cycloalkyl group preferably has 3 to 15 carbon atoms, and more preferably has 5 to 10 carbon atoms.

The cycloalkyl group may be a monocycle or a polycycle.

Examples of the cycloalkyl group include a norbornyl group and an adamantyl group.

As a substituent which may be contained in the cycloalkyl group, an alkyl group (which may be linear or branched, and preferably has 1 to 5 carbon atoms) is preferable.

One or more of the carbon atoms which are ring member atoms of the cycloalkyl group may be substituted with carbonyl carbon atoms.

In a case where $R^B$ is the aromatic ring group, the aromatic ring group may or may not have a heteroatom. The aromatic ring group may be either a monocycle or a polycycle. The aromatic ring group preferably has 5 to 12 carbon atoms, and more preferably has 5 or 6 carbon atoms.

As a substituent which may be contained in the aromatic ring group, an alkyl group (which may be linear or branched, and preferably has 1 to 5 carbon atoms) which may have a fluorine atom is preferable.

In a case where $R^B$ is the alkyl group, the alkyl group may be linear or branched.

The alkyl group preferably has 1 to 10 carbon atoms, and more preferably has 1 to 5 carbon atoms.

As a substituent which may be contained in the alkyl group, a cycloalkyl group, a fluorine atom, or a cyano group is preferable.

Examples of the cycloalkyl group as the substituent include those of the cycloalkyl group described in a case where $R^B$ is the cycloalkyl group.

In a case where the alkyl group has a fluorine atom as the substituent, the alkyl group may or may not be a perfluoroalkyl group. In a case where the alkyl group has a fluorine atom as the substituent, it is also preferable that a part or all of the alkyl groups are perfluoromethyl groups.

In a compound represented by HA-L-BH in which $M_1^+$ and $M_2^+$ of the compound represented by General Formula (I) are each substituted with a hydrogen atom, a pKa of a group represented by HA is lower than a pKa of a group represented by BH.

More specifically, in a case where an acid dissociation constant is determined for the compound represented by HA-L-BH, the pKa in a case where "HA-L-BH" serves as "$A^-$-L-BH" is defined as the "pKa of a group represented by HA", and the pKa in a case where "$A^-$-L-BH" serves as "$A^-$-L-$B^-$" is defined as the "pKa of the group represented by BH".

The "pKa of the group represented by HA" and the "pKa of the group represented by BH" are each determined using "Software Package 1" or "Gaussian 16".

Above all, the pKa of the group represented by HA is preferably −12.00 to 1.00, more preferably −7.00 to 0.50, and still more preferably −5.00 to 0.00.

The pKa of the group represented by HB is preferably −4.00 to 14.00, more preferably −2.00 to 12.00, and still more preferably −1.00 to 5.00.

A difference between the pKa of the group represented by HB and the pKa of the group represented by HA ("pKa of group represented by HB"-"pKa of group represented by HA") is preferably 0.10 to 20.00, more preferably 0.50 to 17.00, and still more preferably 2.00 to 15.00.

In General Formula (I), preferred forms of the organic cations represented by $M_1^+$ and $M_2^+$ will be described in detail.

The organic cations represented by $M_1^+$ and $M_2^+$ are each independently preferably a cation represented by General Formula (ZaI) (cation (ZaI)) or a cation represented by General Formula (ZaII) (cation (ZaII)).

In General Formula (ZaI), $R^{201}$, $R^{202}$, and $R^{203}$ each independently represent an organic group.

The organic group as each of $R^{201}$, $R^{202}$, and $R^{203}$ usually has 1 to 30 carbon atoms, and preferably has 1 to 20 carbon atoms. In addition, two of $R^{201}$ to $R^{203}$ may be bonded to each other to form a ring structure, and the ring may include an oxygen atom, a sulfur atom, an ester group, an amide group, or a carbonyl group. Examples of the group formed by the bonding of two of $R^{201}$ to $R^{203}$ include an alkylene group (for example, a butylene group and a pentylene group), and —$CH_2$—$CH_2$—O—$CH_2$—$CH_2$—.

Suitable aspects of the cation in General Formula (ZaI) include a cation (ZaI-1), a cation (ZaI-2), a cation represented by General Formula (ZaI-3b) (cation (ZaI-3b)), and a cation represented by General Formula (ZaI-4b) (cation (ZaI-4b)), each of which will be described later.

First, the cation (ZaI-1) will be described.

The cation (ZaI-1) is a cation, that is, an arylsulfonium cation in which at least one of $R^{201}$, $R^{202}$, or $R^{203}$ of General Formula (ZaI) is an aryl group.

In the arylsulfonium cation, all of $R^{201}$ to $R^{203}$ may be aryl groups, or some of $R^{201}$ to $R^{203}$ may be an aryl group, and the rest may be an alkyl group or a cycloalkyl group.

In addition, one of $R^{201}$ to $R^{203}$ may be an aryl group, two of $R^{201}$ to $R^{203}$ may be bonded to each other to form a ring structure, and an oxygen atom, a sulfur atom, an ester group, an amide group, or a carbonyl group may be included in the ring. Examples of the group formed by the bonding of two of $R^{201}$ to $R^{203}$ include an alkylene group (for example, a butylene group, a pentylene group, or —$CH_2$—$CH_2$—O—$CH_2$—$CH_2$—) in which one or more methylene groups may be substituted with an oxygen atom, a sulfur atom, an ester group, an amide group, and/or a carbonyl group.

Examples of the arylsulfonium cation include a triarylsulfonium cation, a diarylalkylsulfonium cation, an aryldialkylsulfonium cation, a diarylcycloalkyl sulfonium cation, and an aryldicycloalkylsulfonium cation.

As the aryl group included in the arylsulfonium cation, a phenyl group or a naphthyl group is preferable, and the phenyl group is more preferable. The aryl group may be an aryl group which has a heterocyclic structure having an oxygen atom, a nitrogen atom, a sulfur atom, or the like. Examples of the heterocyclic structure include a pyrrole residue, a furan residue, a thiophene residue, an indole residue, a benzofuran residue, and a benzothiophene residue. In a case where the arylsulfonium cation has two or more aryl groups, the two or more aryl groups may be the same as or different from each other.

The alkyl group or the cycloalkyl group contained in the arylsulfonium cation, as necessary, is preferably a linear alkyl group having 1 to 15 carbon atoms, a branched alkyl group having 3 to 15 carbon atoms, or a cycloalkyl group having 3 to 15 carbon atoms, and examples thereof include a methyl group, an ethyl group, a propyl group, an n-butyl group, a sec-butyl group, a t-butyl group, a cyclopropyl group, a cyclobutyl group, and a cyclohexyl group.

Examples of the substituent which may be contained in each of the aryl group, the alkyl group, and the cycloalkyl group of each of $R^{201}$ to $R^{203}$ each independently include an alkyl group (for example, having 1 to 15 carbon atoms), a cycloalkyl group (for example, having 3 to 15 carbon atoms), an aryl group (for example, having 6 to 14 carbon atoms), an alkoxy group (for example, having 1 to 15 carbon atoms), a cycloalkylalkoxy group (for example, having 1 to 15 carbon atoms), a halogen atom, a hydroxyl group, and a phenylthio group.

The substituent may further have a substituent as possible, and may be in the form of an alkyl halide group such as a trifluoromethyl group, for example, in which the alkyl group has a halogen atom as a substituent.

It is also preferable that the substituent is a group having an acid-decomposable group. The acid-decomposable group is the same as the acid-decomposable group described in <Repeating Unit Having Acid-Decomposable group> which will be described later.

Next, the cation (ZaI-2) will be described.

The cation (ZaI-2) is a cation in which $R^{201}$ to $R^{203}$ in Formula (ZaI) are each independently a cation representing an organic group having no aromatic ring. Here, the aromatic ring also encompasses an aromatic ring including a heteroatom.

The organic group having no aromatic ring as each of $R^{201}$ to $R^{203}$ generally has 1 to 30 carbon atoms, and preferably 1 to 20 carbon atoms.

$R^{201}$ to $R^{203}$ are each independently preferably an alkyl group, a cycloalkyl group, an allyl group, or a vinyl group, more preferably a linear or branched 2-oxoalkyl group, a 2-oxocycloalkyl group, or an alkoxycarbonylmethyl group, and still more preferably the linear or branched 2-oxoalkyl group.

Examples of the alkyl group and the cycloalkyl group of each of $R^{201}$ to $R^{203}$ include a linear alkyl group having 1 to 10 carbon atoms or branched alkyl group having 3 to 10 carbon atoms (for example, a methyl group, an ethyl group, a propyl group, a butyl group, and a pentyl group), and a cycloalkyl group having 3 to 10 carbon atoms (for example, a cyclopentyl group, a cyclohexyl group, and a norbornyl group).

$R^{201}$ to $R^{203}$ may further be substituted with a halogen atom, an alkoxy group (for example, having 1 to 5 carbon atoms), a hydroxyl group, a cyano group, or a nitro group.

Next, the cation (ZaI-3b) will be described.

The cation (ZaI-3b) is a cation represented by General Formula (ZaI-3b).

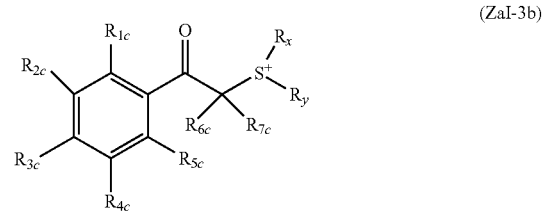

(ZaI-3b)

In General Formula (ZaI-3b), $R_{1c}$ to $R_{5c}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group, or an arylthio group.

$R_{6c}$ and $R_{7c}$ each independently represent a hydrogen atom, an alkyl group (a t-butyl group or the like), a cycloalkyl group, a halogen atom, a cyano group, or an aryl group.

$R_x$ and $R_y$ each independently represent an alkyl group, a cycloalkyl group, a 2-oxoalkyl group, a 2-oxocycloalkyl group, an alkoxycarbonylalkyl group, an allyl group, or a vinyl group.

Any two or more of $R_{1c}$ to $R_{5c}$, $R_{5c}$ and $R_{6c}$, $R_{6c}$ and $R_{7c}$, $R_{5c}$ and $R_x$, and $R_x$ and $R_y$ may each be bonded to each other to form a ring, and the ring may each independently include an oxygen atom, a sulfur atom, a ketone group, an ester bond, or an amide bond.

Examples of the ring include an aromatic or non-aromatic hydrocarbon ring, an aromatic or non-aromatic heterocycle, and a polycyclic fused ring formed by combination of two or more of these rings. Examples of the ring include a 3- to 10-membered ring, and the ring is preferably a 4- to 8-membered ring, and more preferably a 5- or 6-membered ring.

Examples of the group formed by the bonding of any two or more of $R_{1c}$ to $R_{5c}$, $R_{6c}$ and $R_{7c}$, and $R_x$ and $R_y$ include an alkylene group such as a butylene group and a pentylene group. The methylene group in this alkylene group may be substituted with a heteroatom such as an oxygen atom.

As the group formed by the bonding of $R_{5c}$ and $R_{6c}$, and $R_{5c}$ and $R_x$, a single bond or an alkylene group is preferable. Examples of the alkylene group include a methylene group and an ethylene group.

Next, the cation (ZaI-4b) will be described.

The cation (ZaI-4b) is a cation represented by General Formula (ZaI-4b).

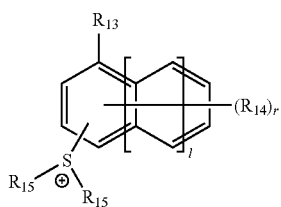

(ZaI-4b)

In General Formula (ZaI-4b), l represents an integer of 0 to 2.

r represents an integer of 0 to 8.

$R_{13}$ represents a hydrogen atom, a fluorine atom, a hydroxyl group, an alkyl group, an alkoxy group, an alkoxycarbonyl group, an alkoxyalkoxy group, or a group having a cycloalkyl group (which may be the cycloalkyl group itself or a group including the cycloalkyl group in a part thereof). These groups may have a substituent.

$R_{14}$ represents a hydroxyl group, an alkyl group, an alkoxy group, an alkoxycarbonyl group, an alkylcarbonyl group, an alkylsulfonyl group, a cycloalkylsulfonyl group, or a group having a cycloalkyl group (which may be the cycloalkyl group itself or a group including the cycloalkyl group in a part thereof). These groups may have a substituent. In a case where $R_{14}$'s are present in a plural number, $R_{14}$'s each independently represent the group such as a hydroxyl group.

$R_{15}$'s each independently represent an alkyl group, a cycloalkyl group, or a naphthyl group. These groups may have a substituent. Two $R_{15}$'s may be bonded to each other to form a ring. In a case where two $R_{15}$'s are bonded to each other to form a ring (preferably a 5- to 8-membered ring, and more preferably a 5- or 6-membered ring), a heteroatom such as an oxygen atom and a nitrogen atom, in addition to $S^+$, may be included in the ring skeleton. In one aspect, two $R_{15}$'s are alkylene groups and are preferably bonded to each other to form a ring structure.

In General Formula (ZaI-4b), the alkyl group of each of $R_{13}$, $R_{14}$, and $R_{15}$ is linear or branched. The alkyl group preferably has 1 to 10 carbon atoms. As the alkyl group, a methyl group, an ethyl group, an n-butyl group, a t-butyl group, or the like is more preferable.

Next, General Formula (ZaII) will be described.

In General Formula (ZaII), $R^{204}$ and $R^{205}$ each independently represent an aryl group, an alkyl group, or a cycloalkyl group.

As the aryl group of each of $R^{204}$ and $R^{205}$, a phenyl group or a naphthyl group is preferable, and the phenyl group is more preferable. The aryl group of each of $R^{204}$ and $R^{205}$ may be an aryl group which has a heterocycle having an oxygen atom, a nitrogen atom, a sulfur atom, or the like. Examples of the skeleton of the aryl group having a heterocycle include pyrrole, furan, thiophene, indole, benzofuran, and benzothiophene.

As the alkyl group and the cycloalkyl group of each of $R^{204}$ and $R^{205}$, a linear alkyl group having 1 to 10 carbon atoms or a branched alkyl group having 3 to 10 carbon atoms (for example, a methyl group, an ethyl group, a propyl group, a butyl group, and a pentyl group), or a cycloalkyl group having 3 to 10 carbon atoms (for example, a cyclopentyl group, a cyclohexyl group, and a norbornyl group) is preferable.

The aryl group, the alkyl group, and the cycloalkyl group of each of $R^{204}$ and $R^{205}$ may each independently have a substituent. Examples of the substituent which may be contained in each of the aryl group, the alkyl group, and the cycloalkyl group of each of $R^{204}$ and $R^{205}$ include an alkyl group (for example, having 1 to 15 carbon atoms), a cycloalkyl group (for example, having 3 to 15 carbon atoms), an aryl group (for example, having 6 to 15 carbon atoms), an alkoxy group (for example, having 1 to 15 carbon atoms), a halogen atom, a hydroxyl group, and a phenylthio group.

The molecular weight of the specific compound is preferably 300 to 3,000, more preferably 500 to 2,000, and still more preferably 700 to 1,500.

The content of the specific photoacid generator is preferably 0.1% to 35% by mass, more preferably 1% to 30% by mass, and still more preferably 5% to 25% by mass with respect to the total solid content of the composition.

Furthermore, the solid content is intended to mean a component forming a resist film, and does not include a solvent. In addition, as long as the component is one forming a resist film, it is regarded as a solid content even in a case where it has a property and a state of a liquid.

The specific compounds may be used singly or in combination of two or more kinds thereof. In a case where two or more kinds of the specific compounds are used, a total content thereof is preferably within the suitable content range.

Preferred examples of the specific compound are shown below. Combinations of an anion (a moiety corresponding to A⁻-L-B⁻) and a cation (a moiety corresponding to $M_1^+$ or $M_2^+$) in the following exemplified compounds may be exchanged as appropriate.

In addition, a numerical value described for each specific compound is the pKa of the group represented by HA (numerical value shown on the left side) and the pKa of the group represented by BH (numerical value shown on the right side) in a case where $M_1^+$ and $M_2^+$ of each specific compound are each substituted with a hydrogen atom to form a compound represented by HA-L-BH.

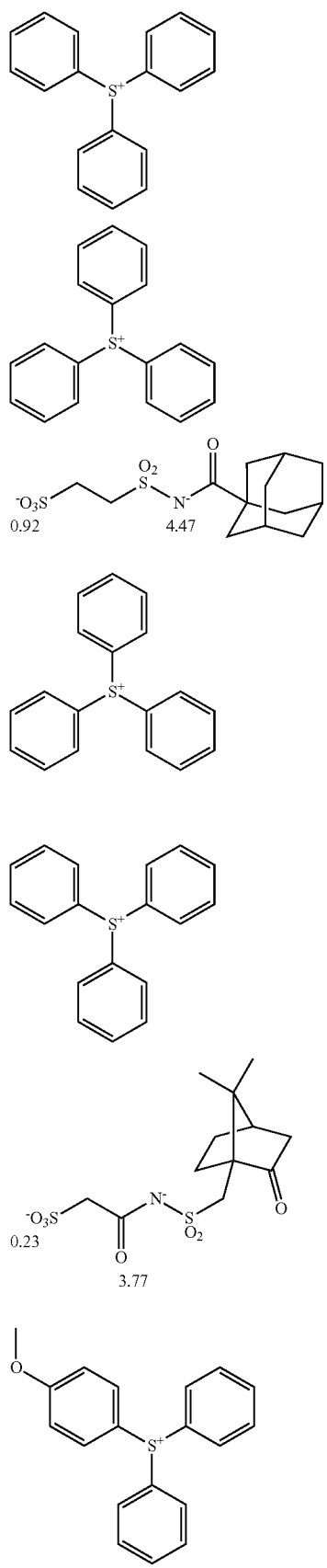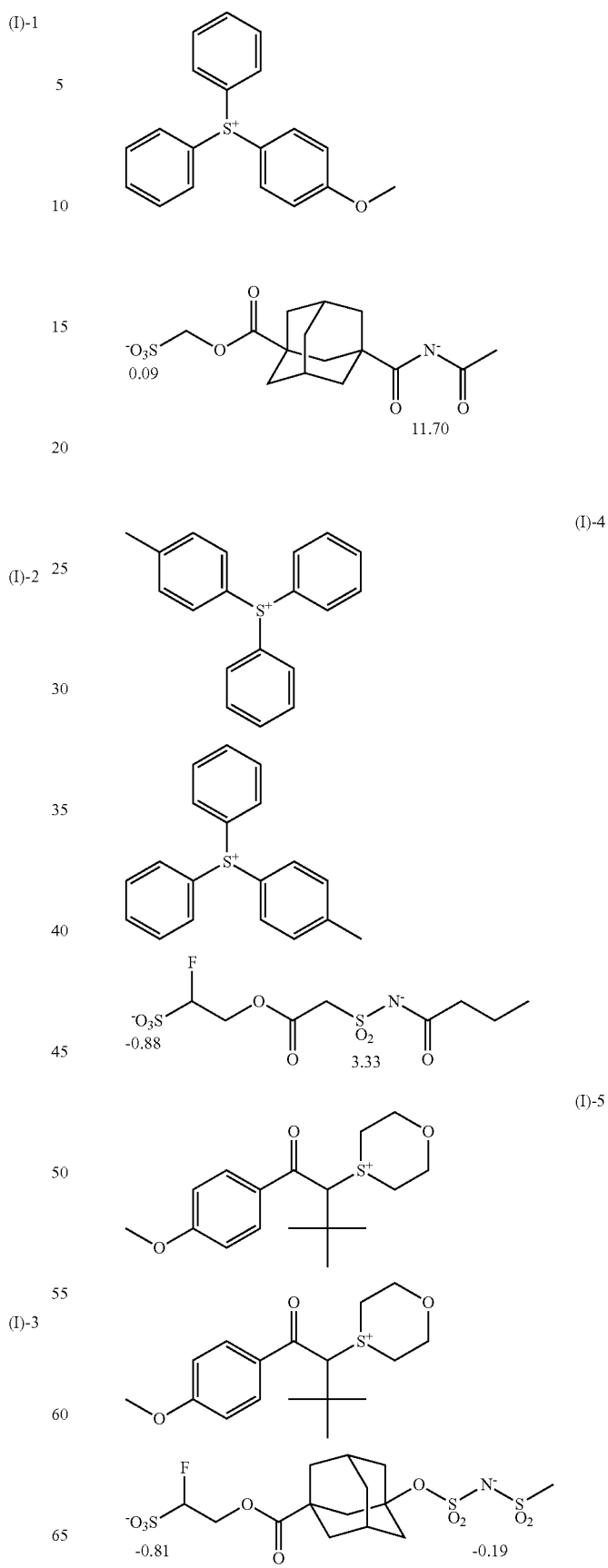

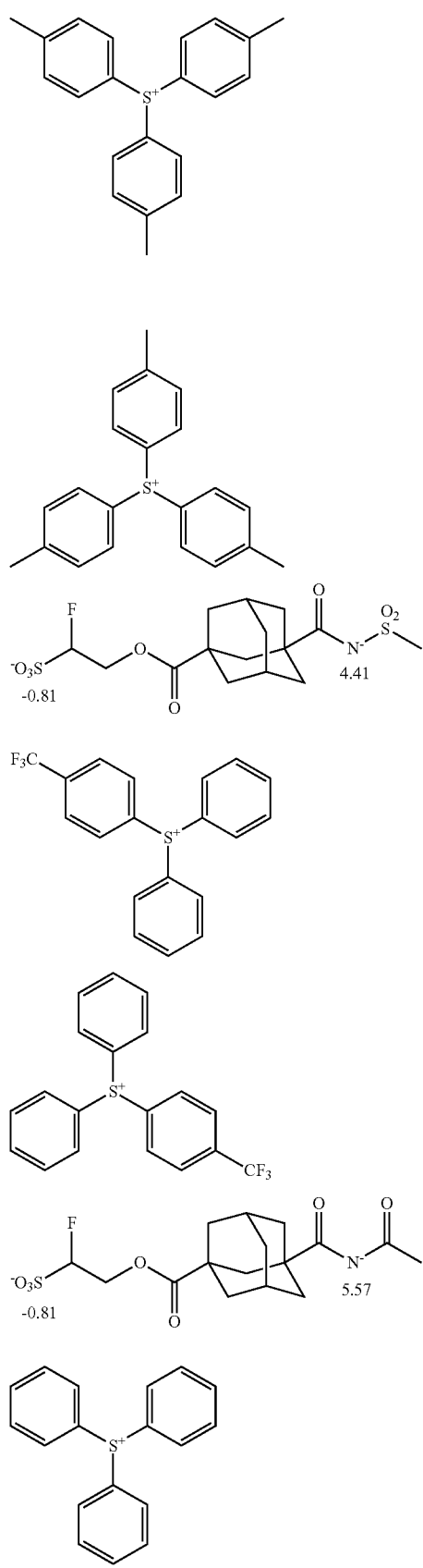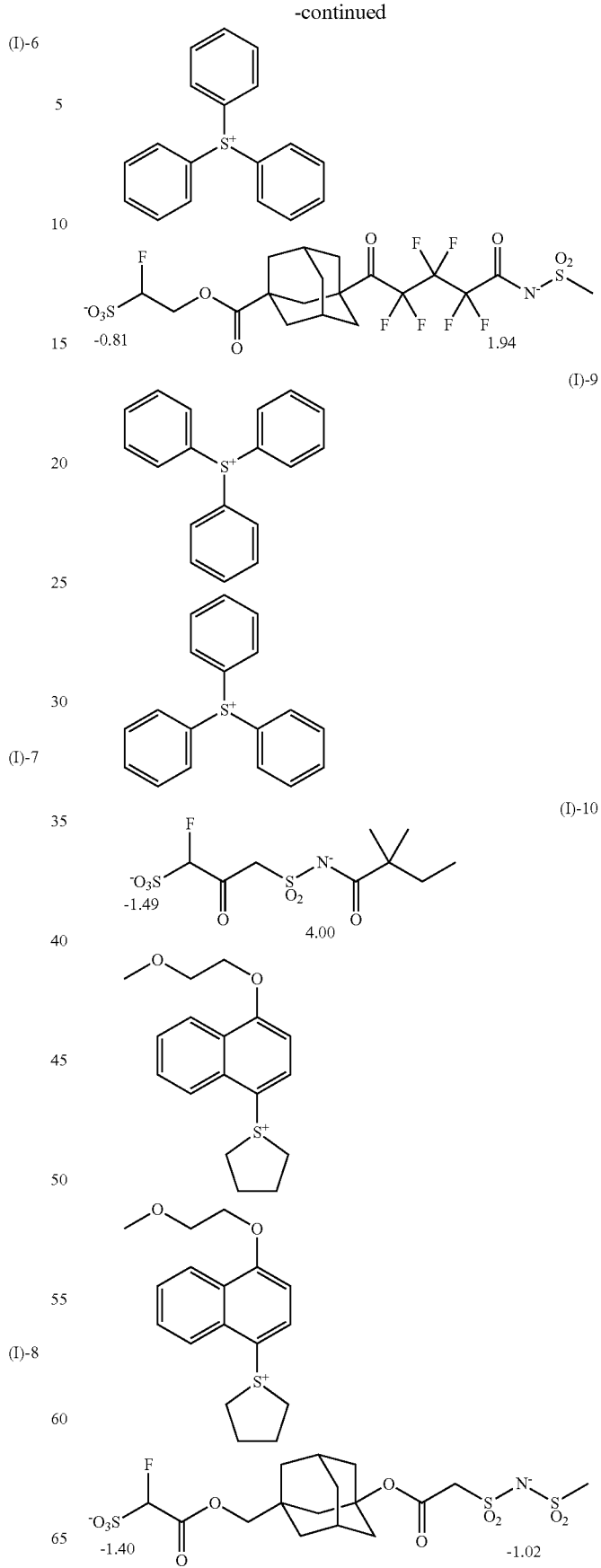

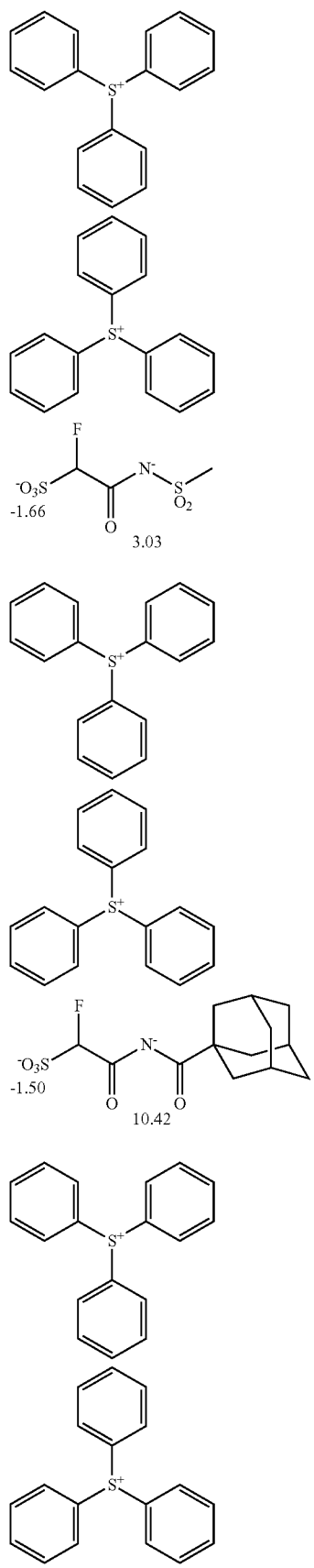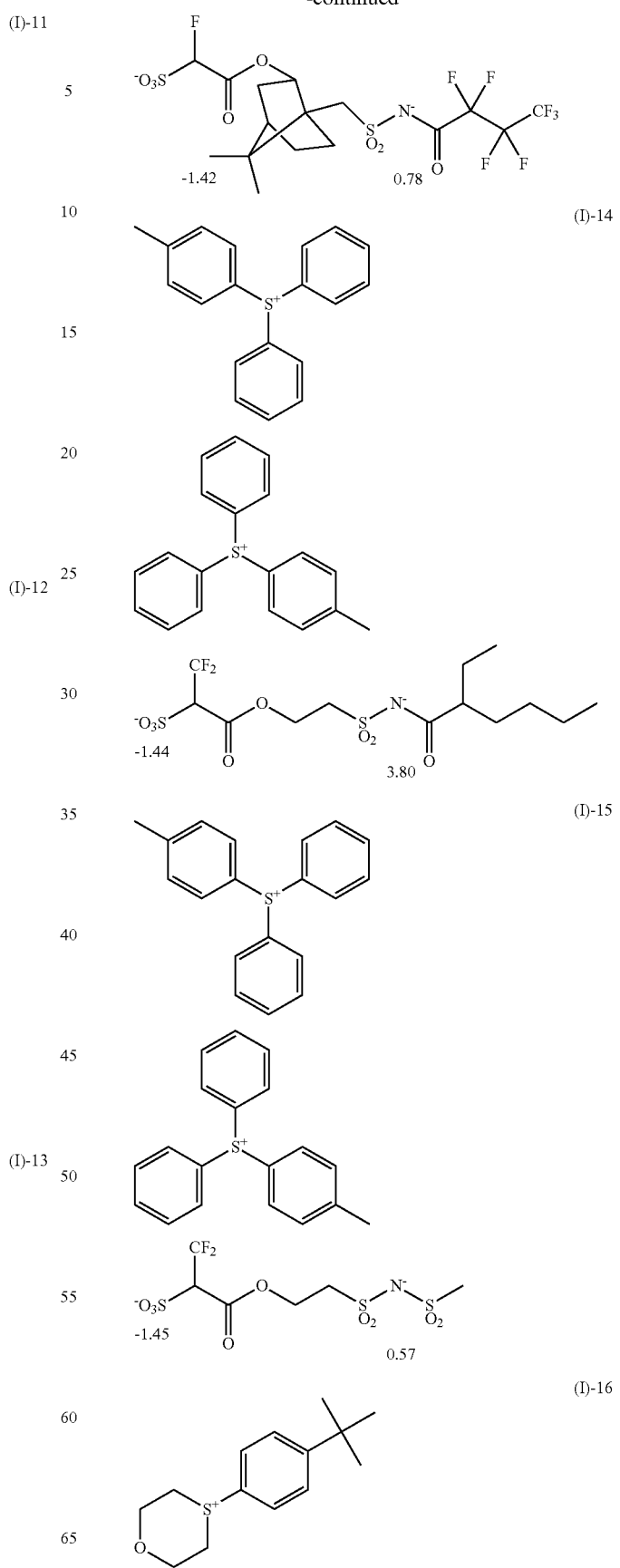

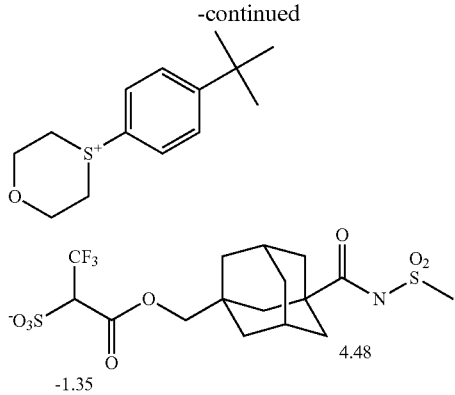
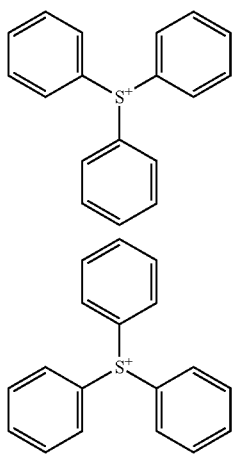
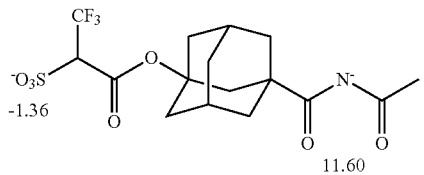
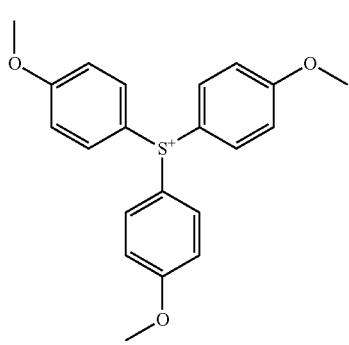
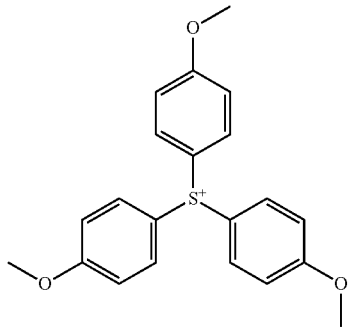
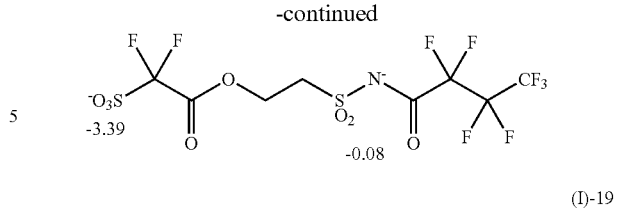
(I)-19
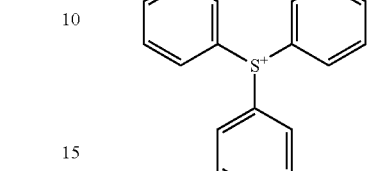
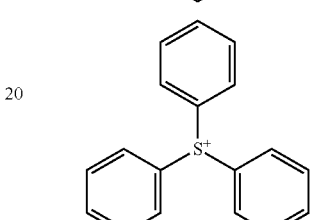
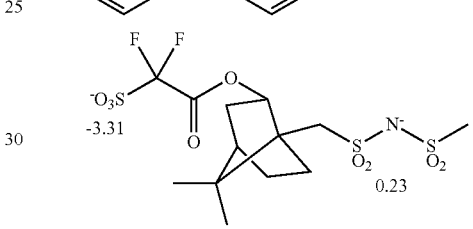
(I)-20
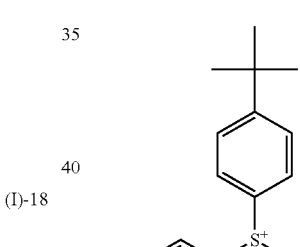
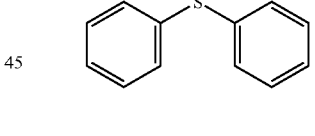
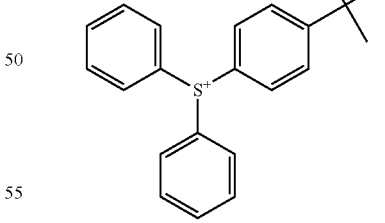
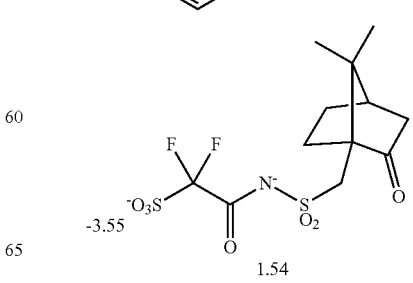

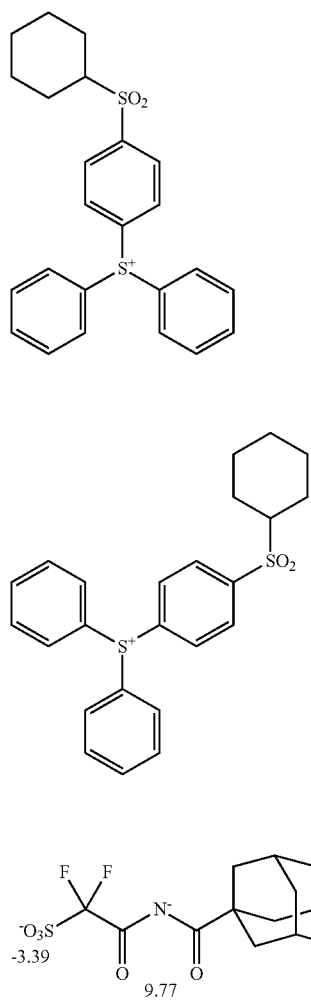
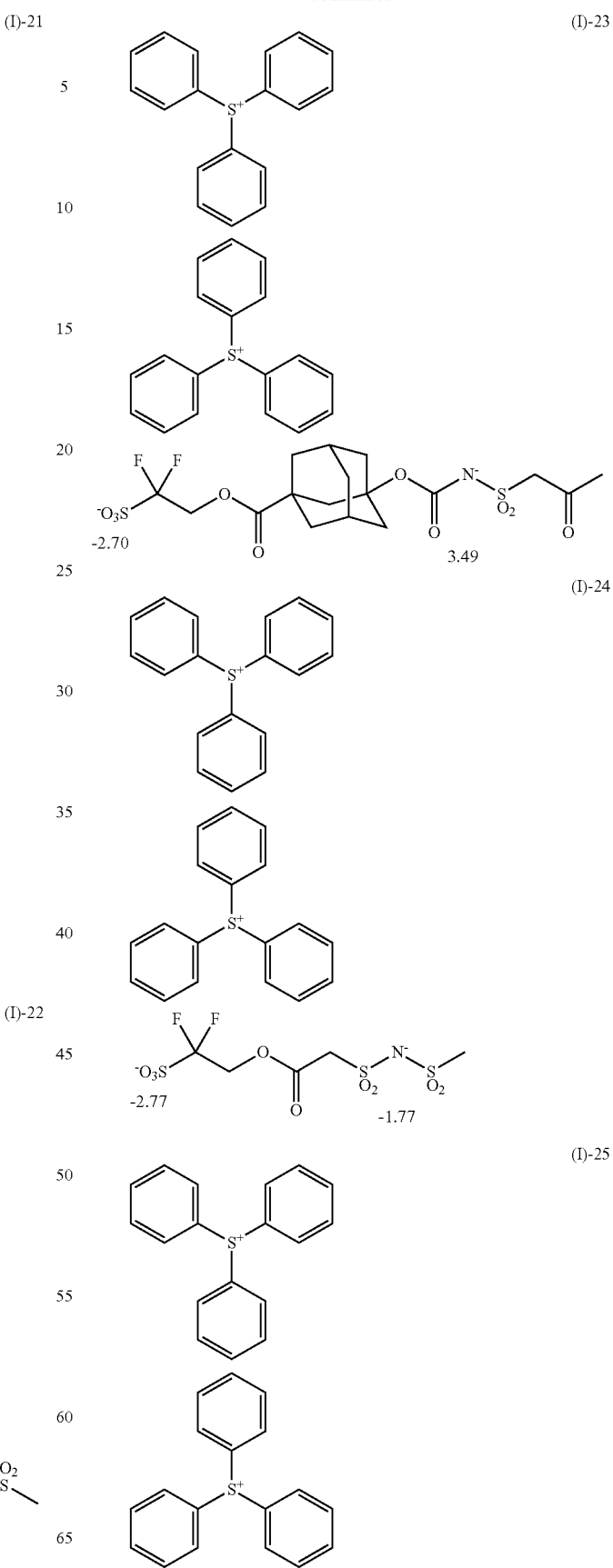

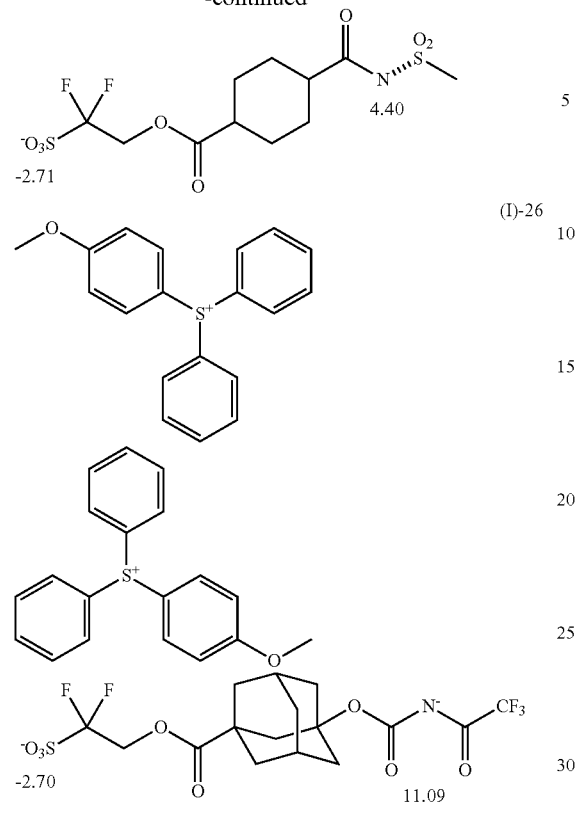

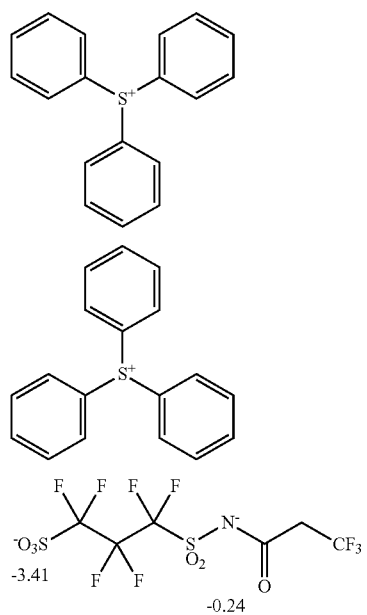
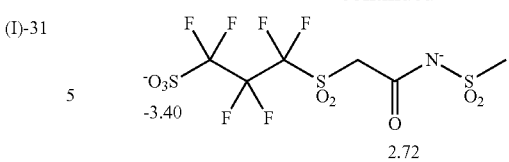
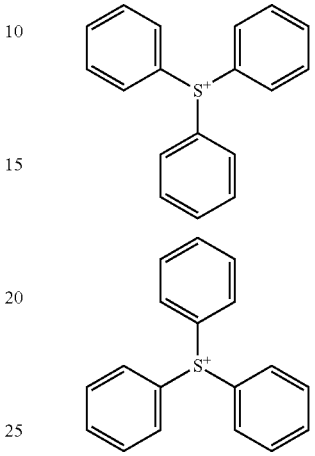
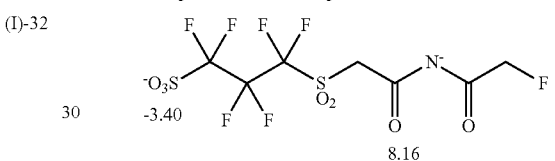
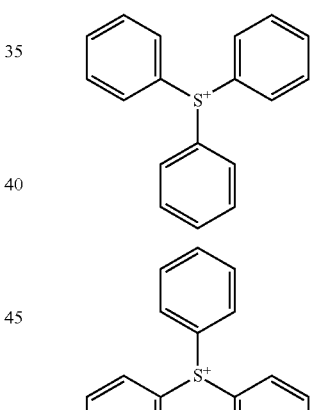
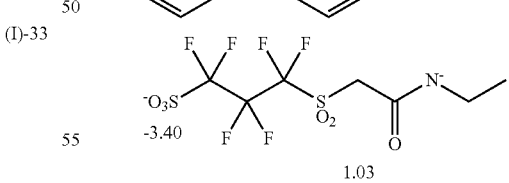
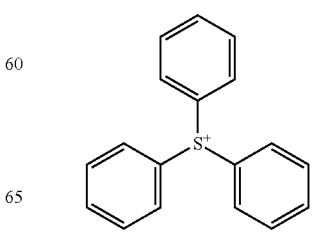

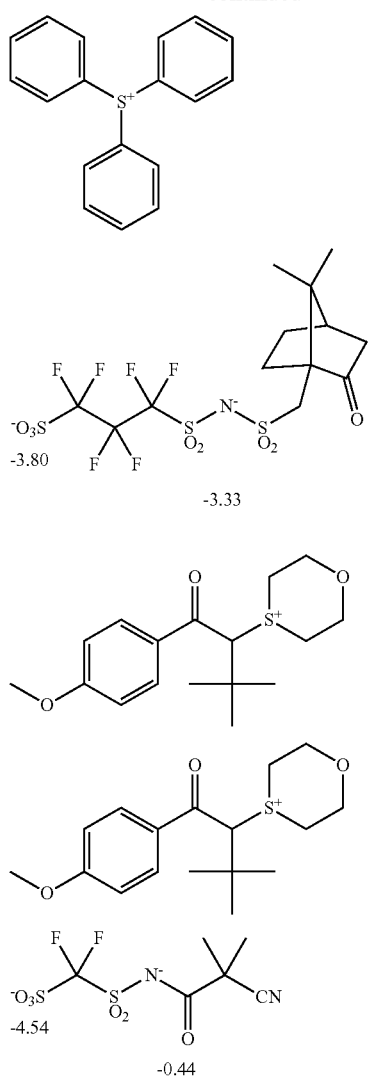
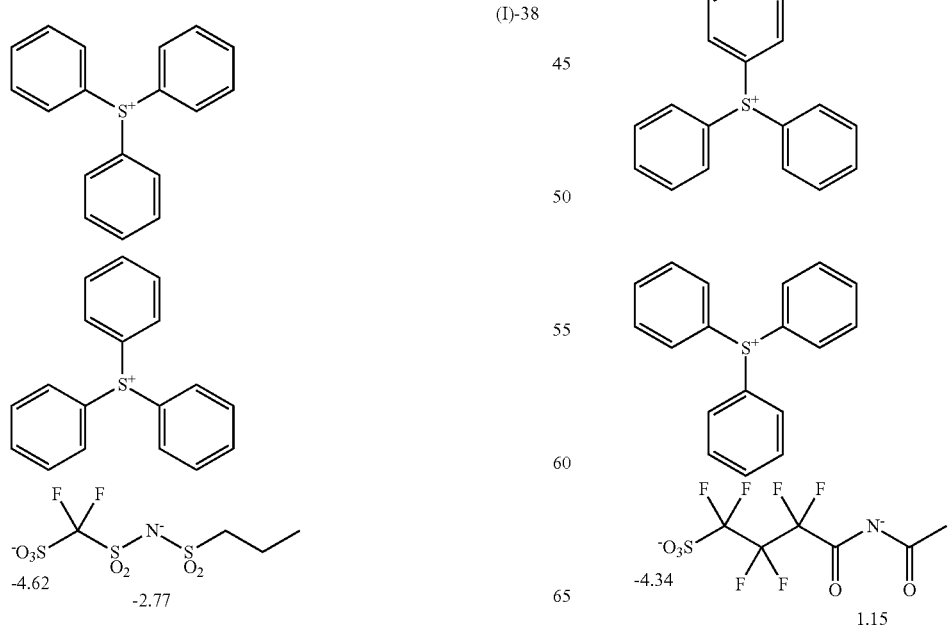

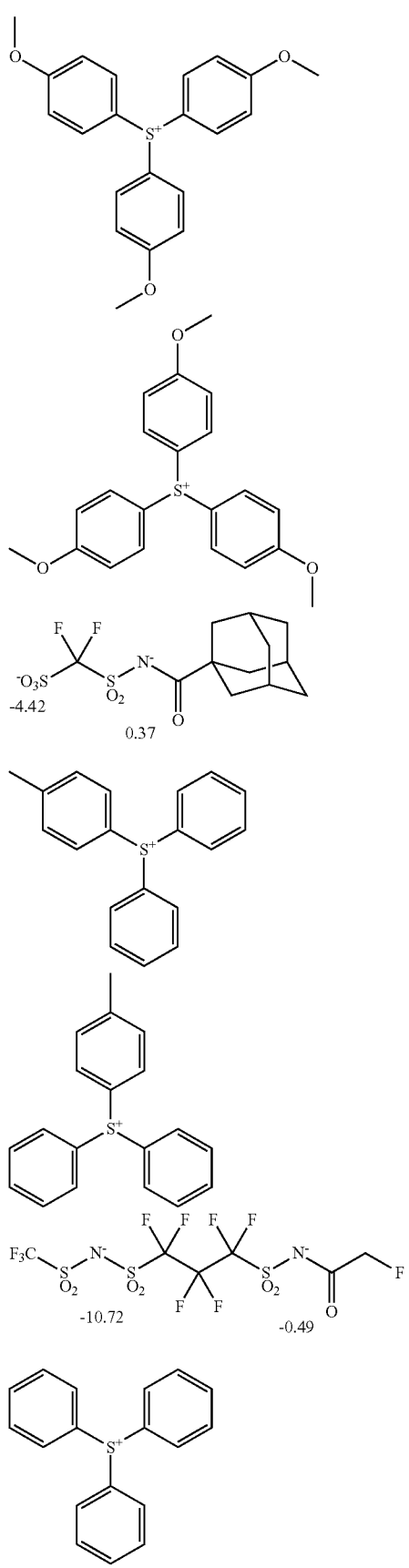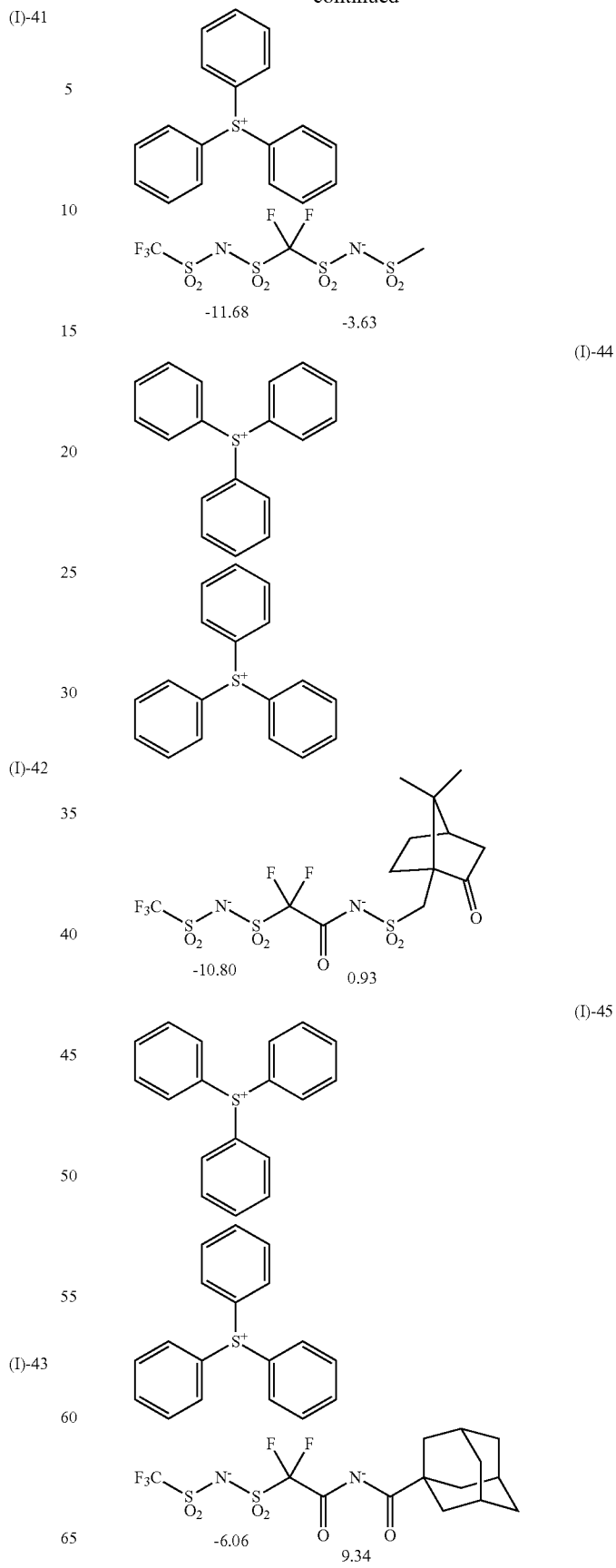

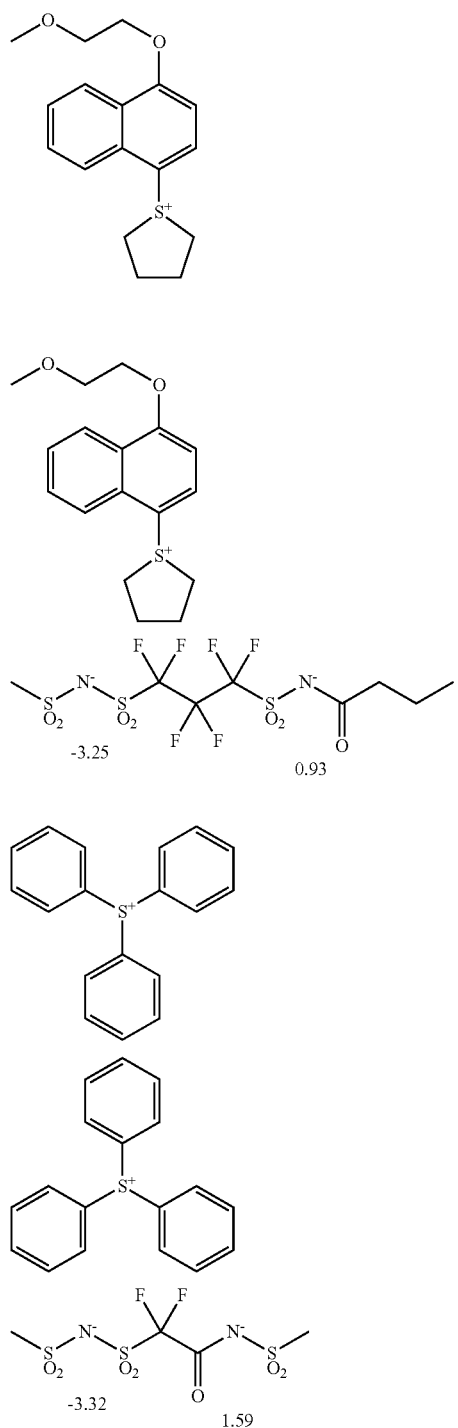
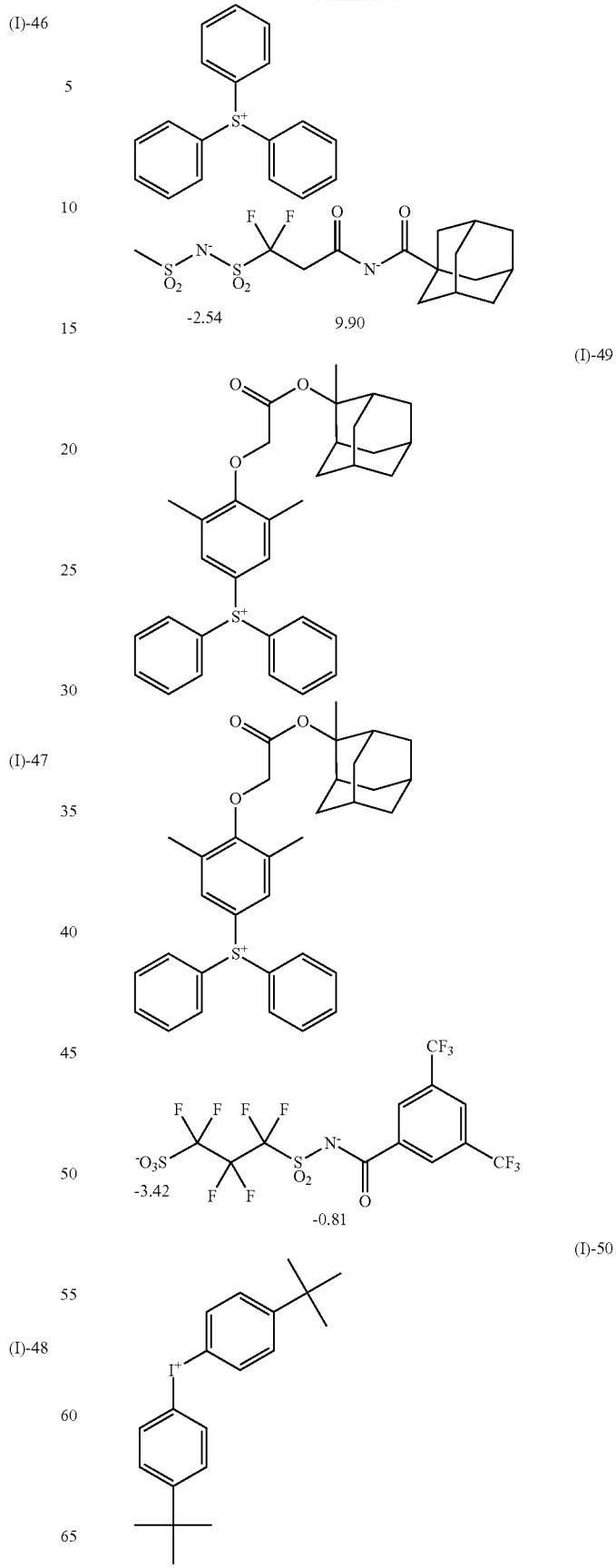

-continued

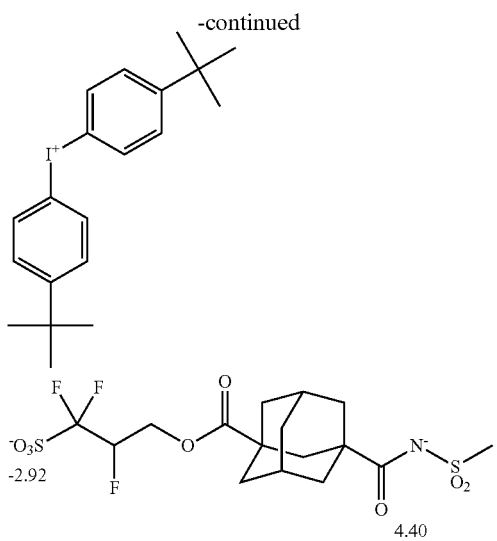

[Acid-Decomposable Resin (Resin (A))]

The composition of the embodiment of the present invention includes a resin (hereinafter also referred to as an "acid-decomposable resin" or a "resin (A)") having a polarity that increases through decomposition by the action of an acid.

That is, in the pattern forming method of an embodiment of the present invention which will be described later, typically, in a case where an alkaline developer is adopted as the developer, a positive tone pattern is suitably formed, and in a case where an organic developer is adopted as the developer, a negative tone pattern is suitably formed.

The resin (A) usually includes a repeating unit having a group having a polarity that increases through decomposition by the action of an acid (hereinafter also referred to as an "acid-decomposable group"), and preferably includes a repeating unit having an acid-decomposable group.

<Repeating Unit Having Acid-Decomposable Group>

The acid-decomposable group is a group that decomposes by the action of an acid to produce a polar group. The acid-decomposable group preferably has a structure in which the polar group is protected by an eliminable group that is eliminated by the action of an acid. That is, the resin (A) has a repeating unit having a group that decomposes by the action of an acid to produce a polar group. A resin having this repeating unit has an increased polarity by the action of an acid, and thus has an increased solubility in an alkaline developer, and a decreased solubility in an organic solvent.

As the polar group, an alkali-soluble group is preferable, and examples thereof include an acidic group such as a carboxyl group, a phenolic hydroxyl group, a fluorinated alcohol group, a sulfonic acid group, a phosphoric acid group, a sulfonamide group, a sulfonylimide group, an (alkyl sulfonyl)(alkylcarbonyl)methylene group, an (alkylsulfonyl)(alkylcarbonyl)imide group, a bis(alkylcarbonyl)methylene group, a bis(alkylcarbonyl)imide group, a bis(alkylsulfonyl)methylene group, a bis(alkylsulfonyl)imide group, a tris(alkylcarbonyl)methylene group, and a tris (alkylsulfonyl)methylene group, and an alcoholic hydroxyl group.

Among those, as the polar group, the carboxyl group, the phenolic hydroxyl group, the fluorinated alcohol group (preferably a hexafluoroisopropanol group), or the sulfonic acid group is preferable.

Examples of the eliminable group that is eliminated by the action of an acid include groups represented by Formulae (Y1) to (Y4).

—C($Rx_1$)($Rx_2$)($Rx_3$)      Formula (Y1):

—C(=O)OC($Rx_1$)($Rx_2$)($Rx_3$)      Formula (Y2):

—C($R_{36}$)($R_{37}$)(O$R_{38}$)      Formula (Y3):

—C(Rn)(H)(Ar)      Formula (Y4):

In Formula (Y1) and Formula (Y2), $Rx_1$ to $Rx_3$ each independently represent an (linear or branched) alkyl group or (monocyclic or polycyclic) cycloalkyl group, an (linear or branched) alkenyl group, or an (monocyclic or polycyclic) aryl group. Further, in a case where all of $Rx_1$ to $Rx_3$ are (linear or branched) alkyl groups, it is preferable that at least two of $Rx_1$, $Rx_2$, or $Rx_3$ are methyl groups.

Above all, it is preferable that $Rx_1$ to $Rx_3$ each independently represent a linear or branched alkyl group, and it is more preferable that $Rx_1$ to $Rx_3$ each independently represent the linear alkyl group.

Two of $Rx_1$ to $Rx_3$ may be bonded to each other to form a monocycle or a polycycle. As the alkyl group of each of $Rx_1$ to $Rx_3$, an alkyl group having 1 to 5 carbon atoms, such as a methyl group, an ethyl group, an n-propyl group, an isopropyl group, an n-butyl group, an isobutyl group, and a t-butyl group, is preferable.

As the cycloalkyl group of each of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the aryl group as each of $Rx_1$ to $Rx_3$, an aryl group having 6 to 10 carbon atoms is preferable, and examples thereof include a phenyl group, a naphthyl group, and an anthryl group.

As the alkenyl group of each of $Rx_1$ to $Rx_3$, a vinyl group is preferable.

A cycloalkyl group is preferable as the ring formed by the bonding of two of $Rx_1$ to $Rx_3$. As the cycloalkyl group formed by the bonding of two of $Rx_1$ to $Rx_3$, a monocyclic cycloalkyl group such as a cyclopentyl group or a cyclohexyl group, or a polycyclic cycloalkyl group such as a norbornyl group, a tetracyclodecanyl group, a tetracyclododecanyl group, or an adamantyl group is preferable, and a monocyclic cycloalkyl group having 5 or 6 carbon atoms is more preferable.

In the cycloalkyl group formed by the bonding of two of $Rx_1$ to $Rx_3$, for example, one of the methylene groups constituting the ring may be substituted with a heteroatom such as an oxygen atom, a group having a heteroatom, such as a carbonyl group, or a vinylidene group. In addition, in these cycloalkyl groups, one or more of the ethylene groups constituting the cycloalkane ring may be substituted with a vinylene group.

With regard to the group represented by Formula (Y1) or Formula (Y2), for example, an aspect in which $Rx_1$ is a methyl group or an ethyl group, and $Rx_2$ and $Rx_3$ are bonded to each other to form a cycloalkyl group is preferable.

In Formula (Y3), $R_{36}$ to $R_{38}$ each independently represent a hydrogen atom or a monovalent organic group. $R_{37}$ and $R_{38}$ may be bonded to each other to form a ring. Examples of the monovalent organic group include an alkyl group, a cycloalkyl group, an aryl group, an aralkyl group, and an alkenyl group. It is also preferable that $R_{36}$ is the hydrogen atom.

Further, the alkyl group, the cycloalkyl group, the aryl group, and the aralkyl group may include a heteroatom such as an oxygen atom, and/or a group having a heteroatom, such as a carbonyl group. For example, in the alkyl group, the cycloalkyl group, the aryl group, and the aralkyl group, one or more of the methylene groups may be substituted with a heteroatom such as an oxygen atom and/or a group having a heteroatom, such as a carbonyl group.

In addition, $R_{38}$ and another substituent contained in the main chain of the repeating unit may be bonded to each other to form a ring. A group formed by the mutual bonding of $R_{38}$ and another substituent on the main chain of the repeating unit is preferably an alkylene group such as a methylene group.

As Formula (Y3), a group represented by Formula (Y3-1) is preferable.

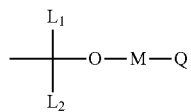

(Y3-1)

Here, $L_1$ and $L_2$ each independently represent a hydrogen atom, an alkyl group, a cycloalkyl group, an aryl group, or a group formed by combination thereof (for example, a group formed by combination of an alkyl group and an aryl group).

M represents a single bond or a divalent linking group.

Q represents an alkyl group which may include a heteroatom, a cycloalkyl group which may include a heteroatom, an aryl group which may include a heteroatom, an amino group, an ammonium group, a mercapto group, a cyano group, an aldehyde group, or a group formed by combination thereof (for example, a group formed by combination of an alkyl group and a cycloalkyl group).

In the alkyl group and the cycloalkyl group, for example, one of the methylene groups may be substituted with a heteroatom such as an oxygen atom or a group having a heteroatom, such as a carbonyl group.

In addition, it is preferable that one of $L_1$ or $L_2$ is a hydrogen atom, and the other is an alkyl group, a cycloalkyl group, an aryl group, or a group formed by combination of an alkylene group and an aryl group.

At least two of Q, M, or $L_1$ may be bonded to each other to form a ring (preferably a 5- or 6-membered ring).

From the viewpoint of pattern miniaturization, $L_2$ is preferably a secondary or tertiary alkyl group, and more preferably the tertiary alkyl group. Examples of the secondary alkyl group include an isopropyl group, a cyclohexyl group, and a norbornyl group, and examples of the tertiary alkyl group include a tert-butyl group and an adamantyl group. In these aspects, since the glass transition temperature (Tg) and the activation energy are increased, it is possible to suppress fogging in addition to ensuring film hardness.

In Formula (Y4), Ar represents an aromatic ring group. Rn represents an alkyl group, a cycloalkyl group, or an aryl group. Rn and Ar may be bonded to each other to form a non-aromatic ring. Ar is more preferably an aryl group.

From the viewpoint that the acid decomposability of the repeating unit is excellent, in a case where a non-aromatic ring is directly bonded to a polar group (or a residue thereof) in an eliminable group that protects the polar group, it is also preferable that a ring member adjacent to the ring member atom directly bonded to the polar group (or a residue thereof) in the non-aromatic ring has no halogen atom such as a fluorine atom as a substituent.

In addition, the eliminable group that is eliminated by the action of an acid may be a 2-cyclopentenyl group having a substituent (an alkyl group and the like), such as a 3-methyl-2-cyclopentenyl group, and a cyclohexyl group having a substituent (an alkyl group and the like), such as 1,1,4,4-tetramethylcyclohexyl group.

As the repeating unit having an acid-decomposable group, a repeating unit represented by Formula (A) is also preferable.

(A)

$L_1$ represents a divalent linking group which may have a fluorine atom or an iodine atom, $R_1$ represents a hydrogen atom, a fluorine atom, an iodine atom, a fluorine atom, an alkyl group which may have an iodine atom, or an aryl group which may have a fluorine atom or an iodine atom, and $R_2$ represents an eliminable group that is eliminated by the action of an acid and may have a fluorine atom or an iodine atom. It should be noted that at least one of $L_1$, $R_1$, or $R_2$ has a fluorine atom or an iodine atom.

$L_1$ represents a divalent linking group which may have a fluorine atom or an iodine atom. Examples of the divalent linking group which may have a fluorine atom or an iodine atom include —CO—, —O—, —S—, —SO—, —SO$_2$—, a hydrocarbon group which may have a fluorine atom or an iodine atom (for example, an alkylene group, a cycloalkylene group, an alkenylene group, and an arylene group), and a linking group formed by the linking of a plurality of these groups. Among those, as $L_1$, —CO—, an arylene group, an alkylene group having a fluorine atom or an iodine atom, or -arylene group-alkylene group having a fluorine atom or an iodine atom— is preferable.

As the arylene group, a phenylene group is preferable.

The alkylene group may be linear or branched. The number of carbon atoms of the alkylene group is not particularly limited, but is preferably 1 to 10, and more preferably 1 to 3.

The total number of fluorine atoms and iodine atoms included in the alkylene group having a fluorine atom or an iodine atom is not particularly limited, but is preferably 2 or more, more preferably 2 to 10, and still more preferably 3 to 6.

$R_1$ represents a hydrogen atom, a fluorine atom, an iodine atom, an alkyl group which may have a fluorine atom or an iodine atom, or an aryl group which may have a fluorine atom or an iodine atom.

The alkyl group may be linear or branched. The number of carbon atoms of the alkyl group is not particularly limited, but is preferably 1 to 10, and more preferably 1 to 3.

The total number of fluorine atoms and iodine atoms included in the alkyl group having a fluorine atom or an iodine atom is not particularly limited, but is preferably 1 or more, more preferably 1 to 5, and still more preferably 1 to 3.

The alkyl group may include a heteroatom such as an oxygen atom other than a halogen atom.

$R_2$ represents an eliminable group that is eliminated by the action of an acid and may have a fluorine atom or an iodine atom.

Among those, examples of the eliminable group include groups represented by Formulae (Z1) to (Z4).

$-C(Rx_{11})(Rx_{12})(Rx_{13})$.                 Formula (Z1):

$-C(=O)OC(Rx_{11})(Rx_{12})(Rx_{13})$.       Formula (Z2):

$-C(R_{136})(R_{137})(OR_{138})$.              Formula (Z3):

$-C(Rn_1)(H)(Ar_1)$                     Formula (Z4):

In Formulae (Z1) and (Z2), $Rx_{11}$ to $Rx_{13}$ each independently represent an (linear or branched) alkyl group which may have a fluorine atom or an iodine atom, a (monocyclic or polycyclic) cycloalkyl group which may have a fluorine atom or an iodine atom, an (linear or branched) alkenyl group which may have a fluorine atom or an iodine atom, or an (monocyclic or polycyclic) aryl group which may have a fluorine atom or an iodine atom. Further, in a case where all of $Rx_{11}$ to $Rx_{13}$ are each an (linear or branched) alkyl group, it is preferable that at least two of $Rx_{11}$, $Rx_{12}$, or $Rx_{13}$ are methyl groups.

$Rx_{11}$ to $Rx_{13}$ are the same as $Rx_1$ to $Rx_3$ in Formulae (Y1) and (Y2) described above, respectively, except that they may have a fluorine atom or an iodine atom, and have the same definitions and suitable ranges as those of the alkyl group, the cycloalkyl group, the alkenyl group, and the aryl group.

In Formula (Z3), $R_{136}$ to $R_{138}$ each independently represent a hydrogen atom, or a monovalent organic group which may have a fluorine atom or an iodine atom. $R_{137}$ and $R_{138}$ may be bonded to each other to form a ring. Examples of the monovalent organic group which may have a fluorine atom or an iodine atom include an alkyl group which may have a fluorine atom or an iodine atom, a cycloalkyl group which may have a fluorine atom or an iodine atom, an aryl group which may have a fluorine atom or an iodine atom, an aralkyl group which may have a fluorine atom or an iodine atom, and a group formed by combination thereof (for example, a group formed by combination of the alkyl group and the cycloalkyl group).

Incidentally, the alkyl group, the cycloalkyl group, the aryl group, and the aralkyl group may include a heteroatom such as an oxygen atom, in addition to the fluorine atom and the iodine atom. That is, in the alkyl group, the cycloalkyl group, the aryl group, and the aralkyl group, for example, one of the methylene groups may be substituted with a heteroatom such as an oxygen atom or a group having a heteroatom, such as a carbonyl group.

In addition, $R_{138}$ and another substituent contained in the main chain of the repeating unit may be bonded to each other to form a ring. In this case, a group formed by the mutual bonding of $R_{138}$ and another substituent on the main chain of the repeating unit is preferably an alkylene group such as a methylene group.

As Formula (Z3), a group represented by Formula (Z3-1) is preferable.

(Z3-1)

Here, $L_{11}$ and $L_{12}$ each independently represent a hydrogen atom; an alkyl group which may have a heteroatom selected from the group consisting of a fluorine atom, an iodine atom, and an oxygen atom; a cycloalkyl group which may have a heteroatom selected from the group consisting of a fluorine atom, an iodine atom, and an oxygen atom; an aryl group which may have a heteroatom selected from the group consisting of a fluorine atom, an iodine atom, and an oxygen atom; or a group formed by combination thereof (for example, a group formed by combination of an alkyl group and a cycloalkyl group, each of which may have a heteroatom selected from the group consisting of a fluorine atom, an iodine atom, and an oxygen atom).

$M_1$ represents a single bond or a divalent linking group.

$Q_1$ represents an alkyl group which may have a heteroatom selected from the group consisting of a fluorine atom, an iodine atom, and an oxygen atom; a cycloalkyl group which may have a heteroatom selected from the group consisting of a fluorine atom, an iodine atom, and an oxygen atom; an aryl group which may have a heteroatom selected from the group consisting of a fluorine atom, an iodine atom, and an oxygen atom; an amino group; an ammonium group; a mercapto group; a cyano group; an aldehyde group; a group formed by combination thereof (for example, a group formed by combination of the alkyl group and the cycloalkyl group, each of which may have a heteroatom selected from the group consisting of a fluorine atom, an iodine atom, and an oxygen atom).

In Formula (Z4), $Ar_1$ represents an aromatic ring group which may have a fluorine atom or an iodine atom. $Rn_1$ is an alkyl group which may have a fluorine atom or an iodine atom, a cycloalkyl group which may have a fluorine atom or an iodine atom, or an aryl group which may have a fluorine atom or an iodine atom. $Rn_1$ and $Ar_1$ may be bonded to each other to form a non-aromatic ring.

As the repeating unit having an acid-decomposable group, a repeating unit represented by General Formula (AI) is also preferable.

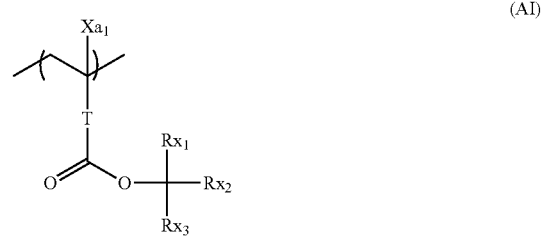

(AI)

In General Formula (AI), $Xa_1$ represents a hydrogen atom, or an alkyl group which may have a substituent.

T represents a single bond or a divalent linking group.

$Rx_1$ to $Rx_3$ each independently represent an (linear or branched) alkyl group, a (monocyclic or polycyclic) cycloalkyl group, an (linear or branched) alkenyl group, or an (monocyclic or polycyclic) aryl group. It should be noted that in a case where all of $Rx_1$ to $Rx_3$ are (linear or branched) alkyl groups, it is preferable that at least two of $Rx_1$, $Rx_2$, or $Rx_3$ are methyl groups.

Two of $Rx_1$ to $Rx_3$ may be bonded to each other to form a monocycle or polycycle (a monocyclic or polycyclic cycloalkyl group and the like).

Examples of the alkyl group which may have a substituent, represented by $Xa_1$, include a methyl group and a group represented by —CH$_2$—R$_{11}$. R$_{11}$ represents a halogen atom (a fluorine atom or the like), a hydroxyl group, or a monovalent organic group, examples thereof include an alkyl group having 5 or less carbon atoms, which may be substituted with a halogen atom, an acyl group having 5 or less carbon atoms, which may be substituted with a halogen atom, and an alkoxy group having 5 or less carbon atoms, which may be substituted with a halogen atom; and an alkyl group having 3 or less carbon atoms is preferable, and a methyl group is more preferable. Xa$_1$ is preferably a hydrogen atom, a methyl group, a trifluoromethyl group, or a hydroxymethyl group.

Examples of the divalent linking group of T include an alkylene group, an aromatic ring group, a —COO-Rt- group, and an —O-Rt- group. In the formulae, Rt represents an alkylene group or a cycloalkylene group.

T is preferably a single bond or the —COO-Rt- group. In a case where T represents the —COO-Rt- group, Rt is preferably an alkylene group having 1 to 5 carbon atoms, and more preferably a —CH$_2$— group, a —(CH$_2$)$_2$— group, or a —(CH$_2$)$_3$— group.

As the alkyl group of each of Rx$_1$ to Rx$_3$, an alkyl group having 1 to 4 carbon atoms, such as a methyl group, an ethyl group, an n-propyl group, an isopropyl group, an n-butyl group, an isobutyl group, and a t-butyl group, is preferable.

As the cycloalkyl group of each of Rx$_1$ to Rx$_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the aryl group as each of Rx$_1$ to Rx$_3$, an aryl group having 6 to 10 carbon atoms is preferable, and examples thereof include a phenyl group, a naphthyl group, and an anthryl group.

As the alkenyl group of each of Rx$_1$ to Rx$_3$, a vinyl group is preferable.

As the cycloalkyl group formed by the bonding of two of Rx$_1$ to Rx$_3$, a monocyclic cycloalkyl group such as a cyclopentyl group and a cyclohexyl group is preferable, and in addition, a polycyclic cycloalkyl group such as a norbornyl group, a tetracyclodecanyl group, a tetracyclododecanyl group, and an adamantyl group is also preferable. Among those, a monocyclic cycloalkyl group having 5 or 6 carbon atoms is preferable.

In the cycloalkyl group formed by the bonding of two of Rx$_1$ to Rx$_3$, for example, one of the methylene groups constituting the ring may be substituted with a heteroatom such as an oxygen atom, a group having a heteroatom, such as a carbonyl group, or a vinylidene group. In addition, in the cycloalkyl group, one or more of the ethylene groups constituting the cycloalkane ring may be substituted with a vinylene group.

With regard to the repeating unit represented by General Formula (AI), for example, an aspect in which Rx$_1$ is a methyl group or an ethyl group, and Rx$_2$ and Rx$_3$ are bonded to each other to form the above-mentioned cycloalkyl group is preferable.

In a case where each of the groups has a substituent, examples of the substituent include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms). The substituent preferably has 8 or less carbon atoms.

The repeating unit represented by General Formula (AI) is preferably an acid-decomposable tertiary alkyl (meth) acrylate ester-based repeating unit (the repeating unit in which Xa$_1$ represents a hydrogen atom or a methyl group, and T represents a single bond).

The content of the repeating unit having an acid-decomposable group is preferably 15% by mole or more, more preferably 20% by mole or more, and still more preferably 30% by mole or more with respect to all the repeating units in the resin (A). In addition, an upper limit value thereof is preferably 80% by mole or less, more preferably 70% by mole or less, and particularly preferably 60% by mole or less.

Specific examples of the repeating unit having an acid-decomposable group are shown below, but the present invention is not limited thereto. Further, in the formulae, Xa$_1$ represents H, CH$_3$, CF$_3$, or CH$_2$OH, and Rxa and Rxb each represent a linear or branched alkyl group having 1 to 5 carbon atoms.

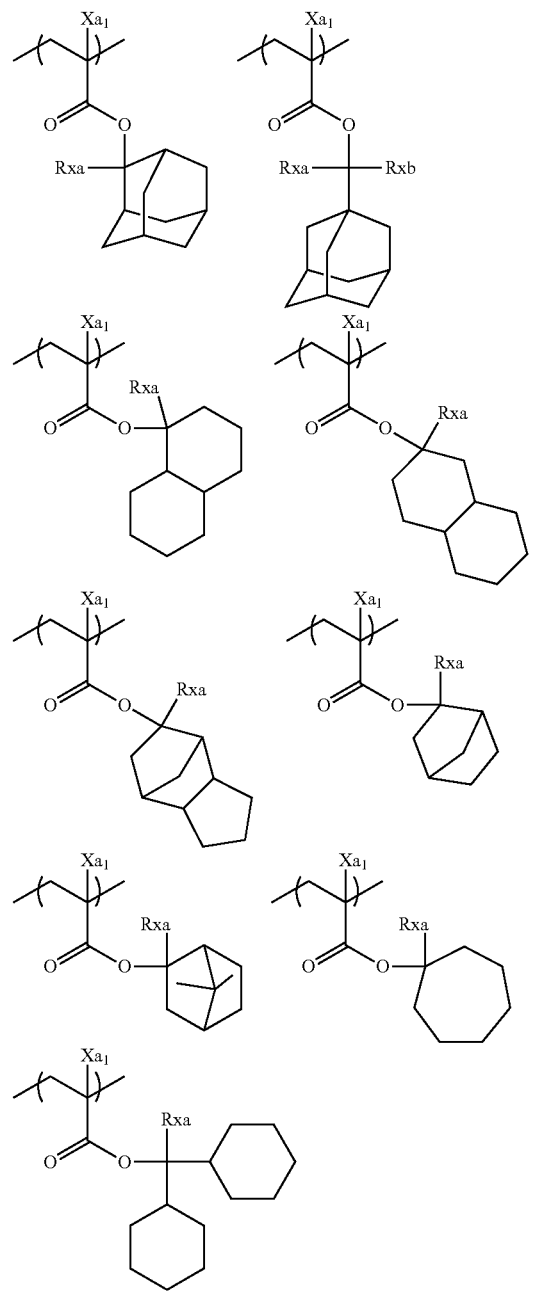

-continued
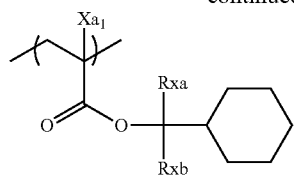
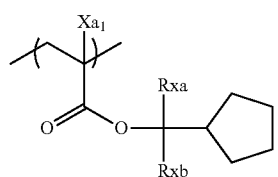
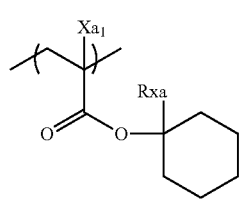
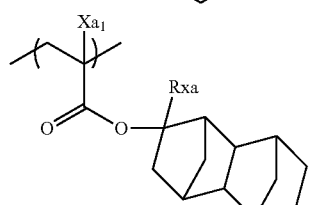
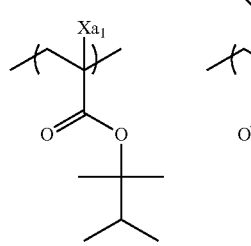
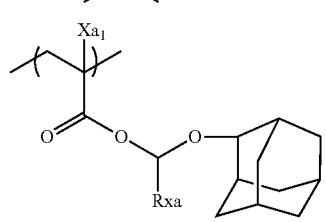
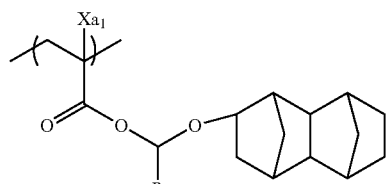
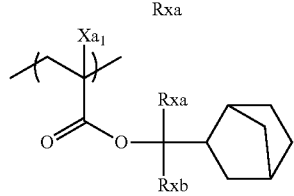
-continued
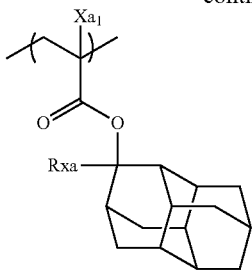
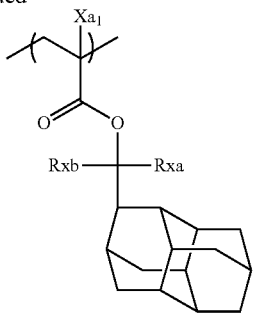
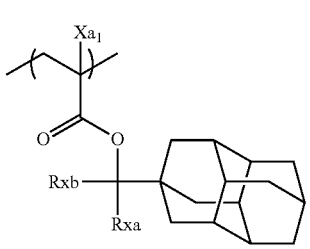
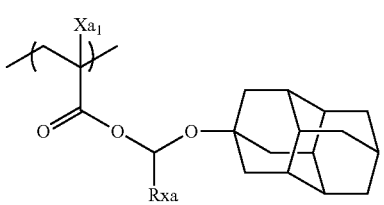
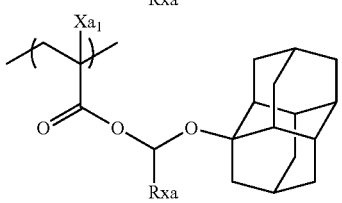
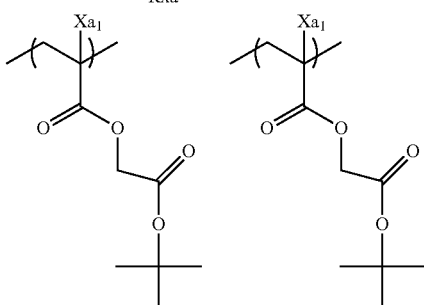
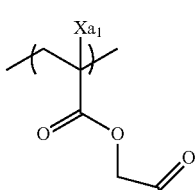
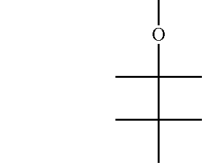

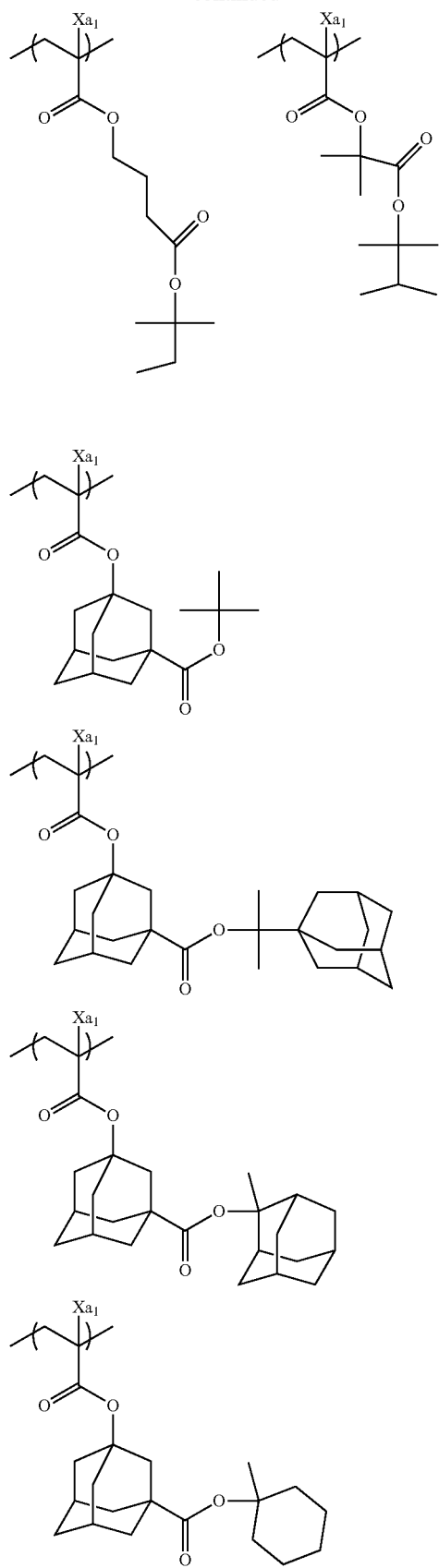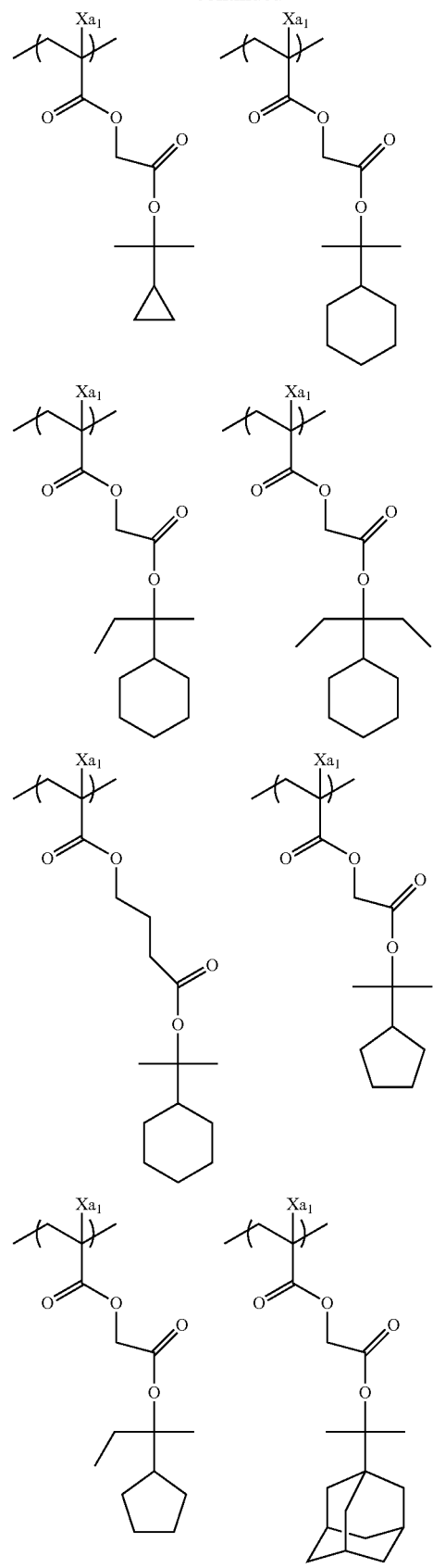

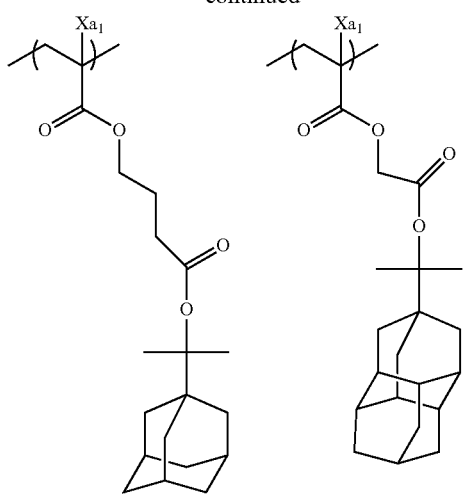
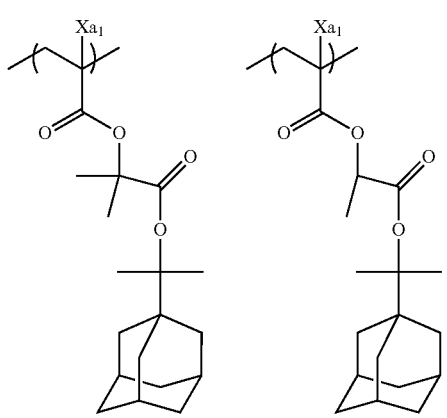
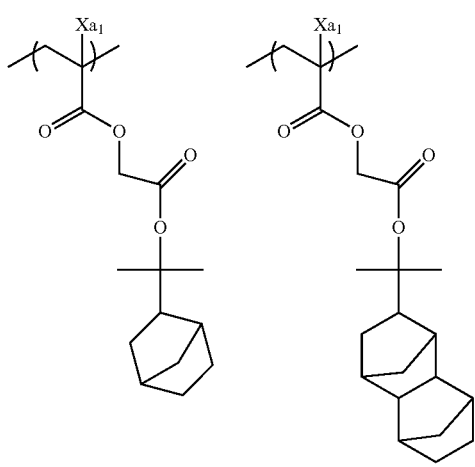
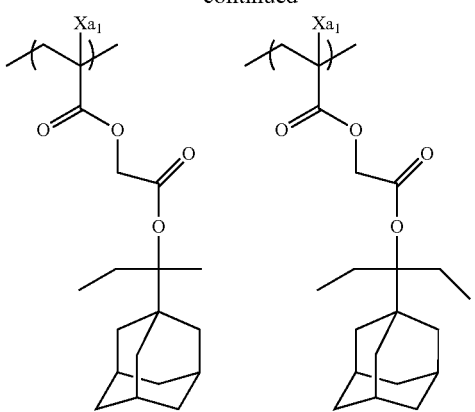
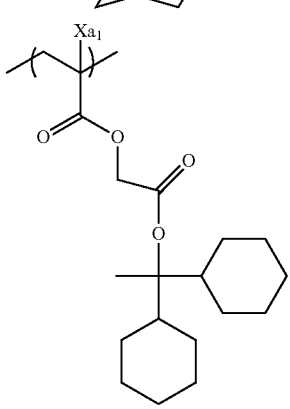
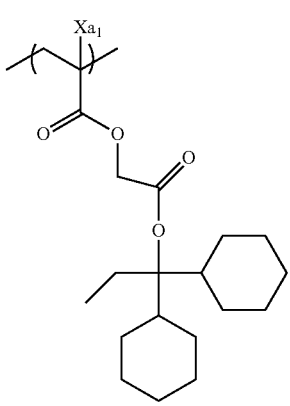
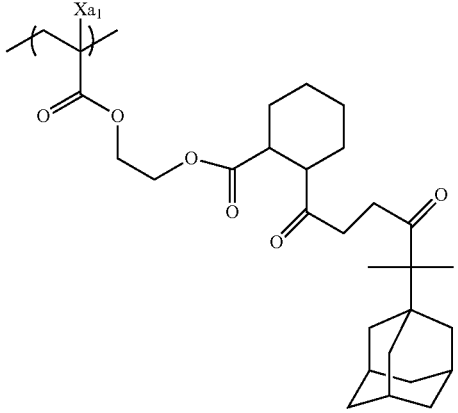

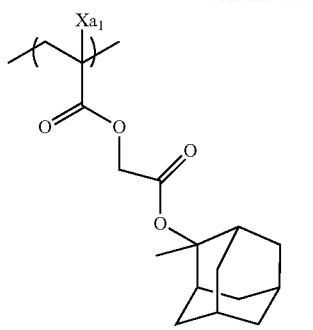
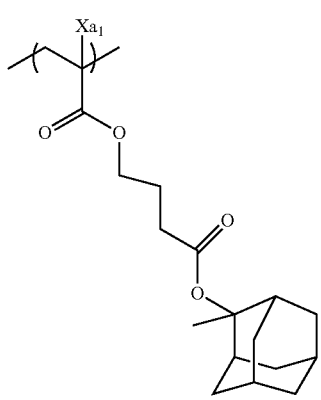
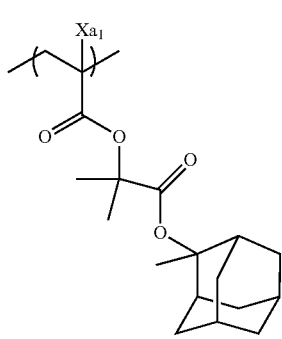
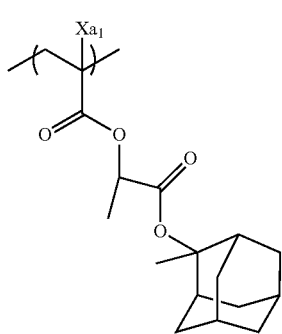
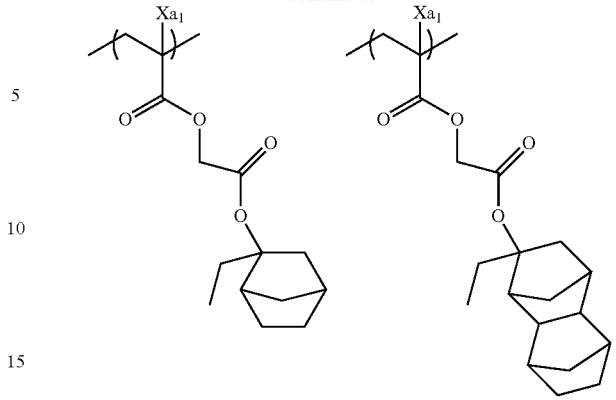
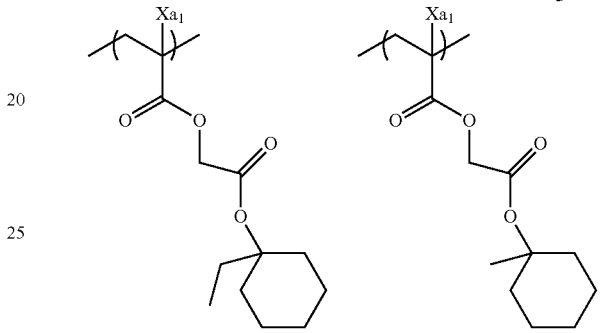
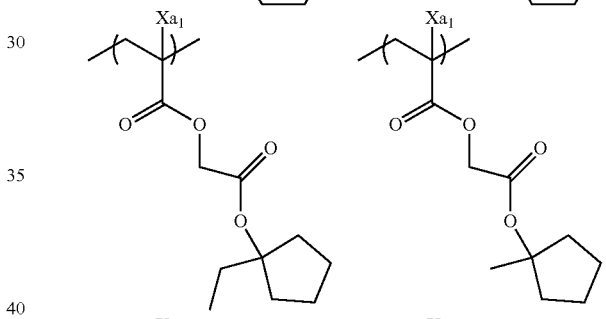
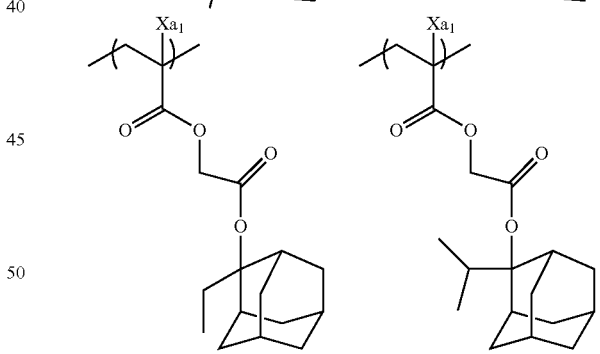
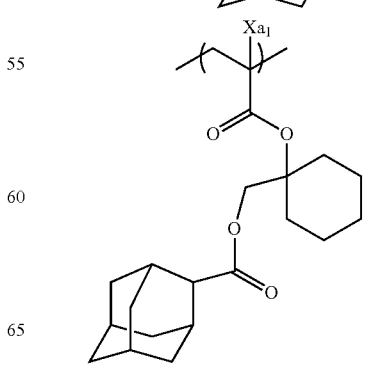

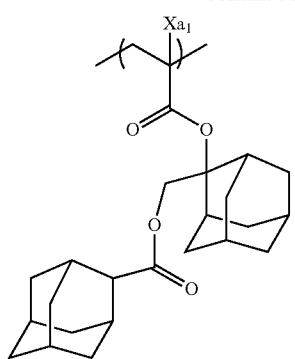
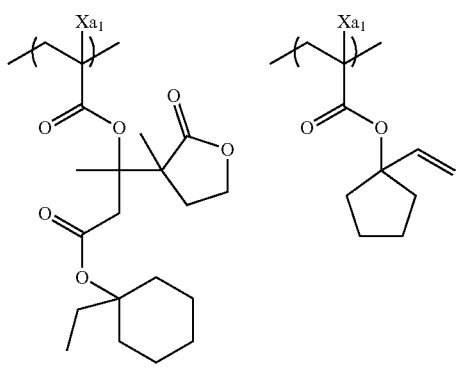
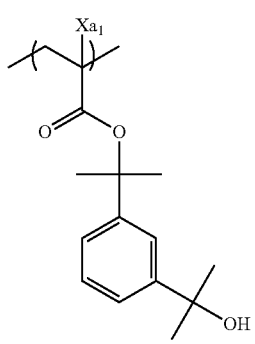
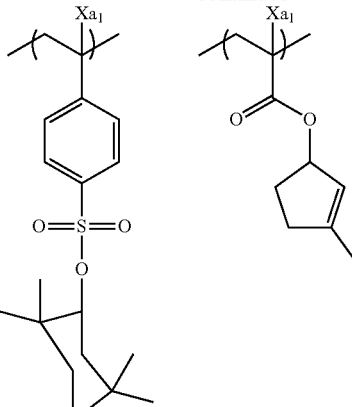
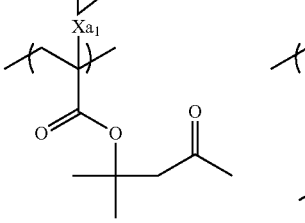
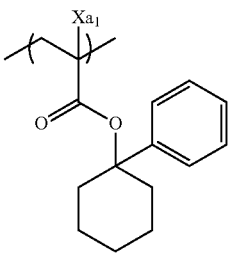
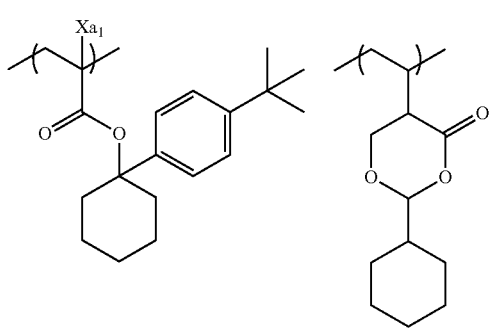

The resin (A) may include a repeating unit other than the above-mentioned repeating units.

For example, the resin (A) may include at least one repeating unit selected from the group consisting of the following group A and/or at least one repeating unit selected from the group consisting of the following group B.

Group A: A group consisting of the following repeating units (20) to (29).

(20) A repeating unit having an acid group, which will be described later.

(21) A repeating unit having a fluorine atom or an iodine atom, which will be described later.

(22) A repeating unit having a lactone group, a sultone group, or a carbonate group, which will be described later.

(23) A repeating unit having a photoacid generating group, which will be described later.

(24) A repeating Unit represented by General Formula (V-1) or General Formula (V-2), which will be described later.

(25) A repeating unit represented by Formula (A), which will be described later.

(26) A repeating unit represented by Formula (B), which will be described later.

(27) A repeating unit represented by Formula (C), which will be described later.

(28) A repeating unit represented by Formula (D), which will be described later.

(29) A repeating unit represented by Formula (E), which will be described later.

Group B: A group consisting of the following repeating units (30) to (32).

(30) A repeating unit having at least one group selected from a lactone group, a sultone group, a carbonate group, a hydroxyl group, a cyano group, or an alkali-soluble group, which will be described later.

(31) A repeating unit having an alicyclic hydrocarbon structure and not exhibiting acid decomposability described later.

(32) A repeating unit represented by General Formula (III) having neither a hydroxyl group nor a cyano group, which will be described later.

In a case where the composition of the embodiment of the present invention is used as an actinic ray-sensitive or radiation-sensitive resin composition for EUV, it is preferable that the resin (A) has at least one repeating unit selected from the group consisting of the group A.

Furthermore, in a case where the composition is used as the actinic ray-sensitive or radiation-sensitive resin composition for EUV, it is preferable that the resin (A) includes at least one of a fluorine atom or an iodine atom. In a case where the resin (A) includes both a fluorine atom and an iodine atom, the resin (A) may have one repeating unit including both a fluorine atom and an iodine atom, and the resin (A) may include two kinds of repeating units, that is, a repeating unit having a fluorine atom and a repeating unit having an iodine atom.

In addition, in a case where the composition is used as an actinic ray-sensitive or radiation-sensitive resin composition for EUV, it is also preferable that the resin (A) has a repeating unit having an aromatic group.

In a case where the composition of the embodiment of the present invention is used as an actinic ray-sensitive or radiation-sensitive resin composition for ArF, it is preferable that the resin (A) has at least one repeating unit selected from the group consisting of the group B.

Furthermore, in a case where the composition of the embodiment of the present invention is used as the actinic ray-sensitive or radiation-sensitive resin composition for ArF, it is preferable that the resin (A) includes neither a fluorine atom nor a silicon atom.

In addition, in a case where the composition is used as the actinic ray-sensitive or radiation-sensitive resin composition for ArF, it is preferable that the resin (A) does not have an aromatic group.

<Repeating Unit Having Acid Group>

The resin (A) may have a repeating unit having an acid group.

As the acid group, an acid group having a pKa of 13 or less is preferable.

As the acid group, for example, a carboxyl group, a phenolic hydroxyl group, a fluorinated alcohol group (preferably a hexafluoroisopropanol group), a sulfonic acid group, a sulfonamide group, or an isopropanol group is preferable.

In addition, in the hexafluoroisopropanol group, one or more (preferably one or two) fluorine atoms may be substituted with a group (an alkoxycarbonyl group and the like) other than a fluorine atom. —C(CF$_3$)(OH)—CF$_2$— formed as above is also preferable as the acid group. In addition, one or more fluorine atoms may be substituted with a group other than a fluorine atom to form a ring including —C(CF$_3$)(OH)—CF$_2$—.

The repeating unit having an acid group is preferably a repeating unit different from a repeating unit having the structure in which a polar group is protected by the eliminable group that is eliminated by the action of an acid as described above, and a repeating unit having a lactone group, a sultone group, or a carbonate group which will be described later.

The repeating unit having an acid group may have a fluorine atom or an iodine atom.

As the repeating unit having an acid group, a repeating unit represented by Formula (B0) is preferable.

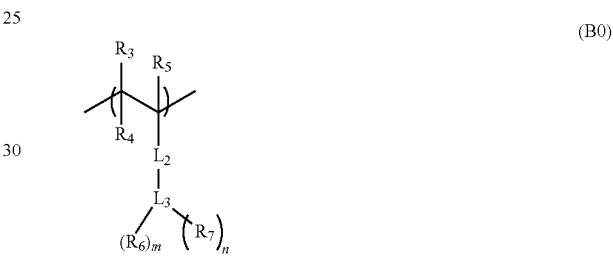

(B0)

R$_3$ represents a hydrogen atom or a monovalent organic group which may have a fluorine atom or an iodine atom.

The monovalent organic group which may have a fluorine atom or an iodine atom is preferably a group represented by -L$_4$-R$_8$. L$_4$ represents a single bond or an ester group. R$_8$ is an alkyl group which may have a fluorine atom or an iodine atom, a cycloalkyl group which may have a fluorine atom or an iodine atom, an aryl group which may have a fluorine atom or an iodine atom, or a group formed by combination thereof.

R$_4$ and R$_5$ each independently represent a hydrogen atom, a fluorine atom, an iodine atom, or an alkyl group which may have a fluorine atom or an iodine atom.

L$_2$ represents a single bond or an ester group.

L$_3$ represents an (n+m+1)-valent aromatic hydrocarbon ring group or an (n+m+1)-valent alicyclic hydrocarbon ring group. Examples of the aromatic hydrocarbon ring group include a benzene ring group and a naphthalene ring group. The alicyclic hydrocarbon ring group may be either a monocycle or a polycycle, and examples thereof include a cycloalkyl ring group.

R$_6$ represents a hydroxyl group or a fluorinated alcohol group (preferably a hexafluoroisopropanol group). Further, in a case where R$_6$ is a hydroxyl group, L$_3$ is preferably the (n+m+1)-valent aromatic hydrocarbon ring group.

R$_7$ represents a halogen atom. Examples of the halogen atom include a fluorine atom, a chlorine atom, a bromine atom, or an iodine atom.

m represents an integer of 1 or more. m is preferably an integer of 1 to 3 and more preferably an integer of 1 or 2.

n represents 0 or an integer of 1 or more. n is preferably an integer of 1 to 4.

Furthermore, (n+m+1) is preferably an integer of 1 to 5.

As the repeating unit having an acid group, a repeating unit represented by General Formula (I) is also preferable.

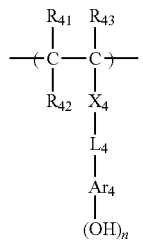
(I)

In General Formula (I), $R_{41}$, $R_{42}$, and $R_{43}$ each independently represent a hydrogen atom, an alkyl group, a cycloalkyl group, a halogen atom, a cyano group, or an alkoxycarbonyl group. It should be noted that $R_{42}$ may be bonded to $Ar_4$ to form a ring, in which case $R_{42}$ represents a single bond or an alkylene group.

$X_4$ represents a single bond, —COO—, or —CONR$_{64}$—, and $R_{64}$ represents a hydrogen atom or an alkyl group.

$L_4$ represents a single bond or an alkylene group.

$Ar_4$ represents an (n+1)-valent aromatic ring group, and in a case where $Ar_4$ is bonded to $R_{42}$ to form a ring, $Ar_4$ represents an (n+2)-valent aromatic ring group.

n represents an integer of 1 to 5.

As the alkyl group represented by each of $R_{41}$, $R_{42}$, and $R_{43}$ in General Formula (I), an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group is preferable, an alkyl group having 8 or less carbon atoms is more preferable, and an alkyl group having 3 or less carbon atoms is still more preferable.

The cycloalkyl group of each of $R_{41}$, $R_{42}$, and $R_{43}$ in General Formula (I) may be monocyclic or polycyclic. Among those, a monocyclic cycloalkyl group having 3 to 8 carbon atoms, such as a cyclopropyl group, a cyclopentyl group, and a cyclohexyl group, is preferable.

Examples of the halogen atom of each of $R_{41}$, $R_{42}$, and $R_{43}$ in General Formula (I) include a fluorine atom, a chlorine atom, a bromine atom, and an iodine atom, and the fluorine atom is preferable.

As the alkyl group included in the alkoxycarbonyl group of each of $R_{41}$, $R_{42}$, and $R_{43}$ in General Formula (I), the same ones as the alkyl group in each of $R_{41}$, $R_{42}$, and $R_{43}$ are preferable.

Preferred examples of the substituent in each of the groups include an alkyl group, a cycloalkyl group, an aryl group, an amino group, an amide group, a ureide group, a urethane group, a hydroxyl group, a carboxyl group, a halogen atom, an alkoxy group, a thioether group, an acyl group, an acyloxy group, an alkoxycarbonyl group, a cyano group, and a nitro group. The substituent preferably has 8 or less carbon atoms.

$Ar_4$ represents an (n+1)-valent aromatic ring group. The divalent aromatic ring group in a case where n is 1 is preferably, for example, an arylene group having 6 to 18 carbon atoms, such as a phenylene group, a tolylene group, a naphthylene group, and an anthracenylene group, or a divalent aromatic ring group including a heterocycle such as a thiophene ring, a furan ring, a pyrrole ring, a benzothiophene ring, a benzofuran ring, a benzopyrrole ring, a triazine ring, an imidazole ring, a benzimidazole ring, a triazole ring, a thiadiazole ring, and a thiazole ring. Furthermore, the aromatic ring group may have a substituent.

Specific examples of the (n+1)-valent aromatic ring group in a case where n is an integer of 2 or more include groups formed by removing any (n−1) hydrogen atoms from the above-described specific examples of the divalent aromatic ring group.

The (n+1)-valent aromatic ring group may further have a substituent.

Examples of the substituent which can be contained in the alkyl group, the cycloalkyl group, the alkoxycarbonyl group, the alkylene group, and the (n+1)-valent aromatic ring group, each mentioned above, include the alkyl groups; the alkoxy groups such as a methoxy group, an ethoxy group, a hydroxyethoxy group, a propoxy group, a hydroxypropoxy group, and a butoxy group; the aryl groups such as a phenyl group; and the like, as mentioned for each of $R_{41}$, $R_{42}$, and $R_{43}$ in General Formula (I).

Examples of the alkyl group of $R_{64}$ in —CONR$_{64}$— represented by $X_4$ ($R_{64}$ represents a hydrogen atom or an alkyl group) include an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group, and an alkyl group having 8 or less carbon atoms, is preferable.

As $X_4$, a single bond, —COO—, or —CONH— is preferable, and the single bond or —COO— is more preferable.

As the alkylene group in $L_4$, an alkylene group having 1 to 8 carbon atoms, such as a methylene group, an ethylene group, a propylene group, a butylene group, a hexylene group, and an octylene group, is preferable.

As $Ar_4$, an aromatic ring group having 6 to 18 carbon atoms is preferable, and a benzene ring group, a naphthalene ring group, and a biphenylene ring group are more preferable.

The repeating unit represented by General Formula (I) preferably comprises a hydroxystyrene structure. That is, $Ar_4$ is preferably the benzene ring group.

The repeating unit represented by General Formula (I) is preferably a repeating unit represented by General Formula (1).

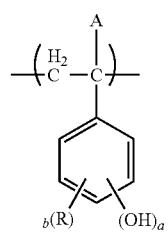
(1)

In General Formula (1),

A represents a hydrogen atom, an alkyl group, a cycloalkyl group, a halogen atom, or a cyano group.

R represents a halogen atom, an alkyl group, a cycloalkyl group, an aryl group, an alkenyl group, an aralkyl group, an alkoxy group, an alkylcarbonyloxy group, an alkylsulfonyloxy group, an alkyloxycarbonyl group, or an aryloxycarbonyl group, and in a case where a plurality of R's are present, R's may be the same as or different from each other. In a case where there are a plurality of R's, R's may be combined with each other to form a ring. As R, the hydrogen atom is preferable.
a represents an integer of 1 to 3.
b represents an integer of 0 to (5-a).
The repeating unit having an acid group is exemplified below. In the formula, a represents 1 or 2.
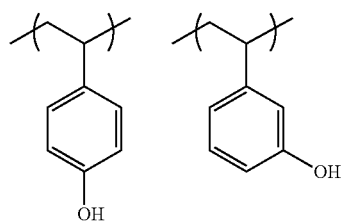
(B-1)
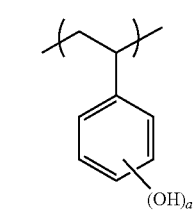
(B-2)
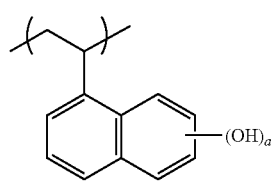
(B-3)
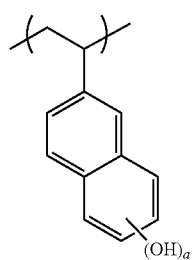
(B-4)
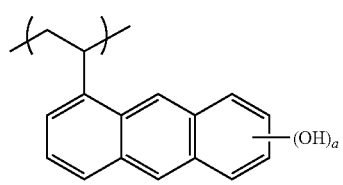
(B-5)
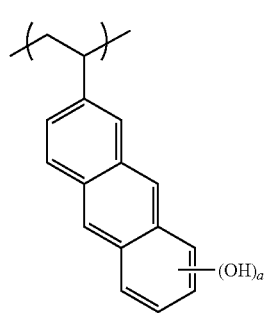
-continued
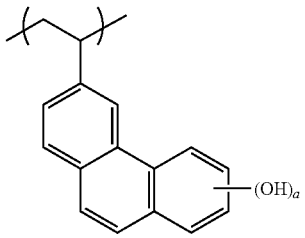
(B-6)
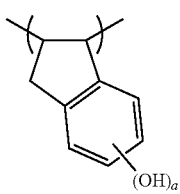
(B-7)
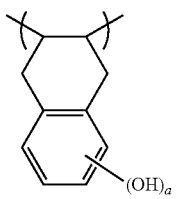
(B-8)
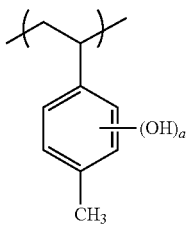
(B-9)
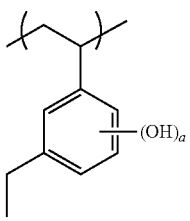
(B-10)
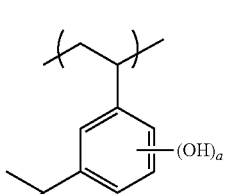
(B-11)
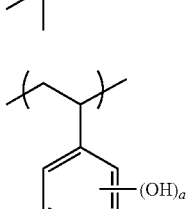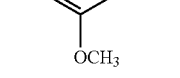
(B-12)

(B-13) 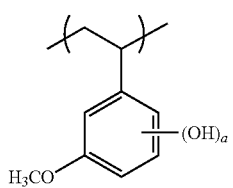
(B-14) 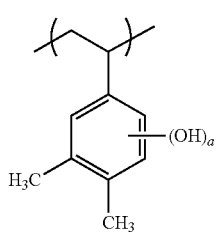
(B-15) 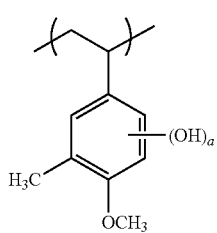
(B-16) 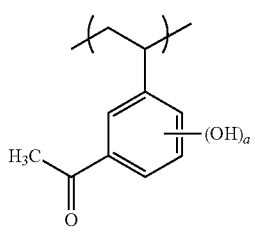
(B-17) 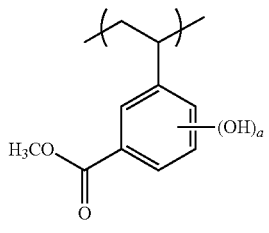
(B-18) 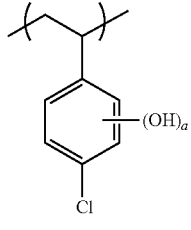
(B-19) 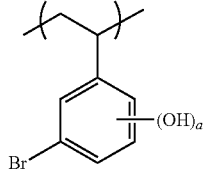
(B-20) 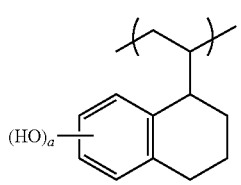
(B-21) 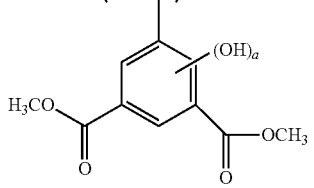
(B-22) 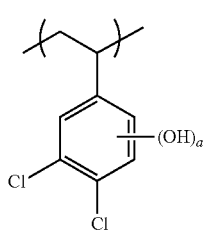
(B-23) 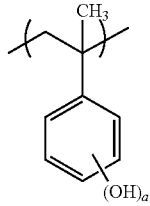
(B-24) 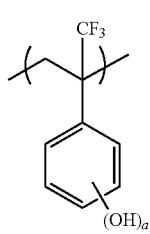
(B-25) 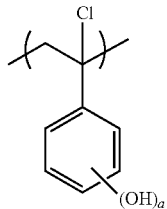
(B-26) 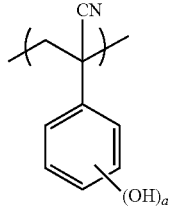

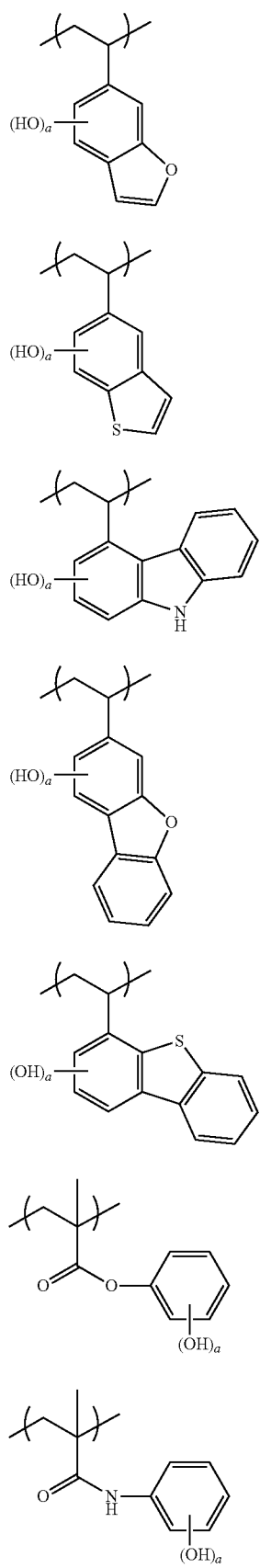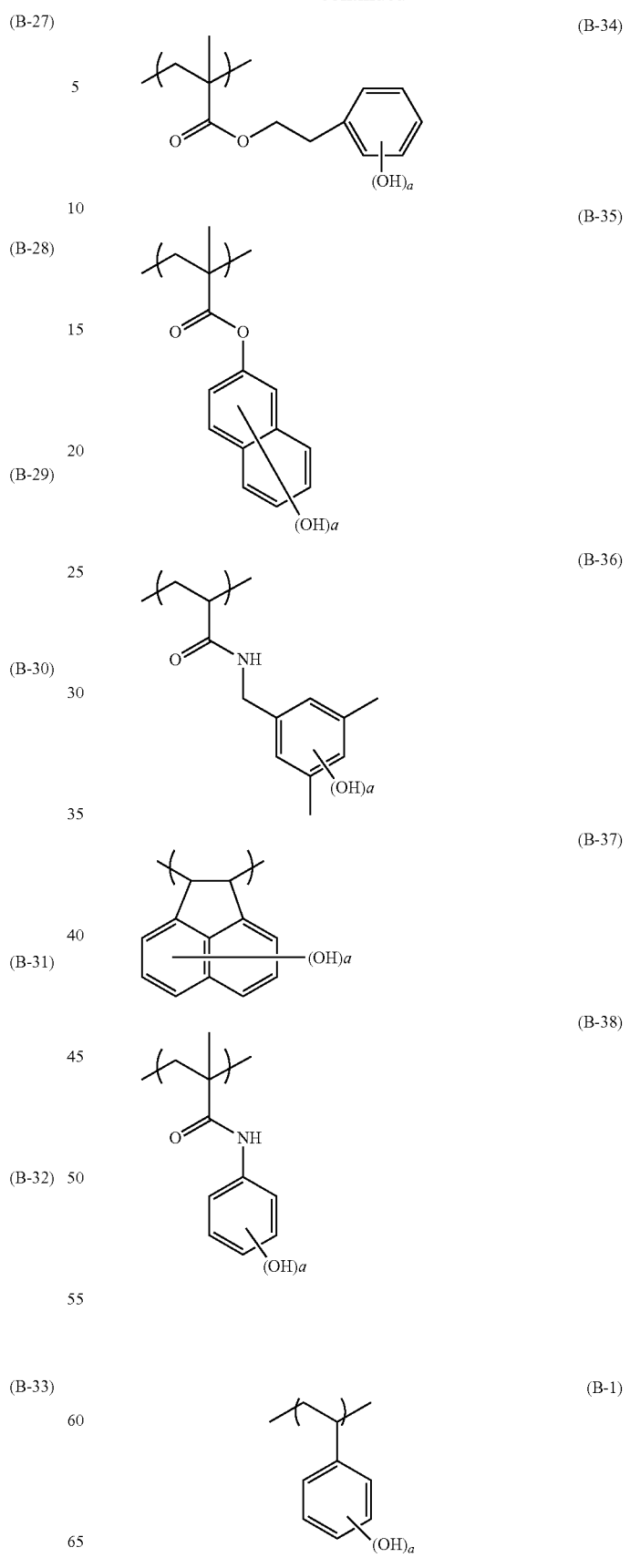

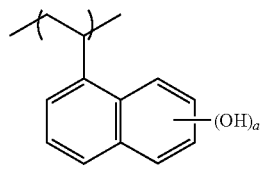 (B-2)
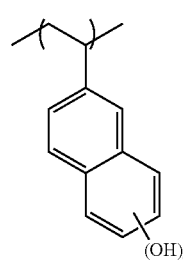 (B-3)
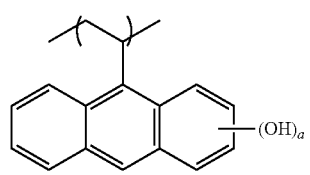 (B-4)
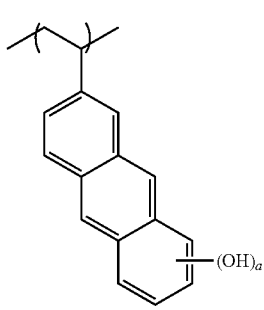 (B-5)
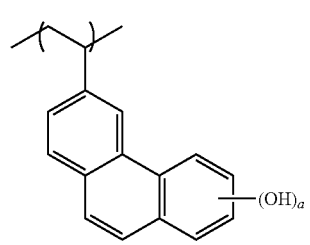 (B-6)
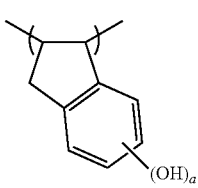 (B-7)
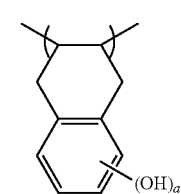 (B-8)
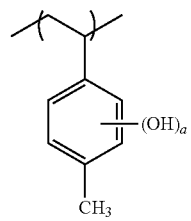 (B-9)
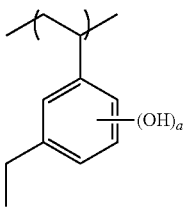 (B-10)
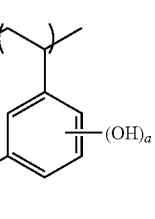 (B-11)
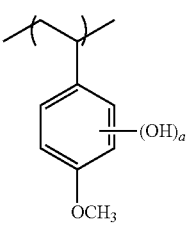 (B-12)
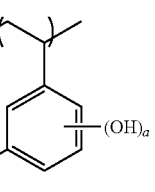 (B-13)
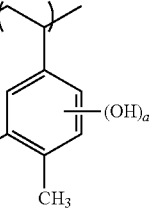 (B-14)
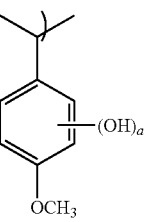 (B-15)

(B-16)
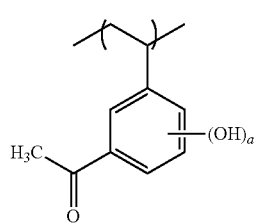
(B-17)
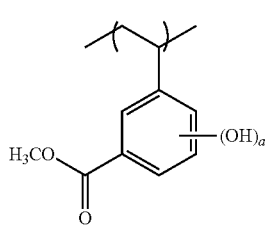
(B-18)
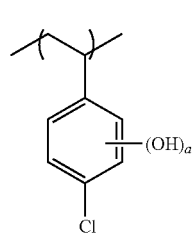
(B-19)
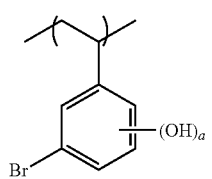
(B-20)
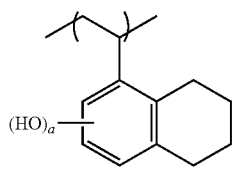
(B-21)
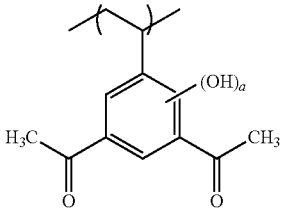
(B-22)
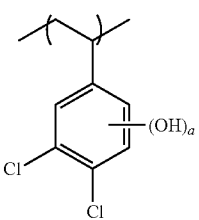
(b-23)
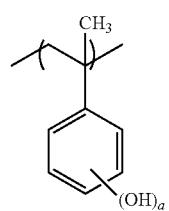
(B-24)
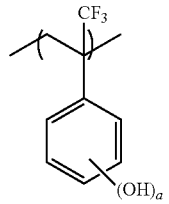
(B-25)
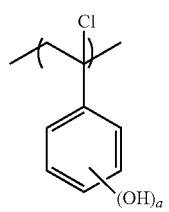
(B-26)
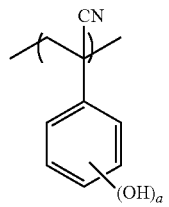
(B-27)
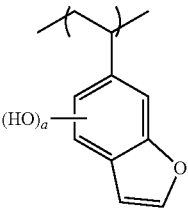
(B-28)
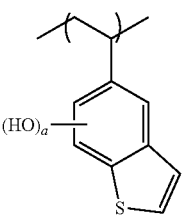
(B-29)
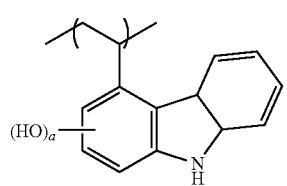

(B-30) 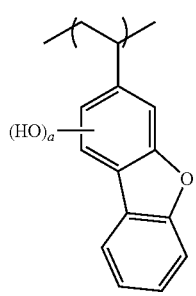
(B-31) 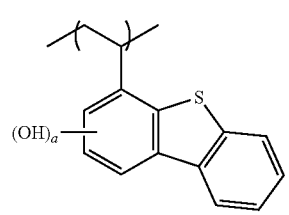
(B-32) 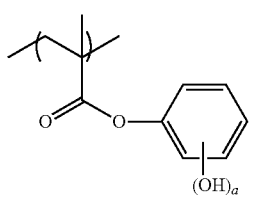
(B-33) 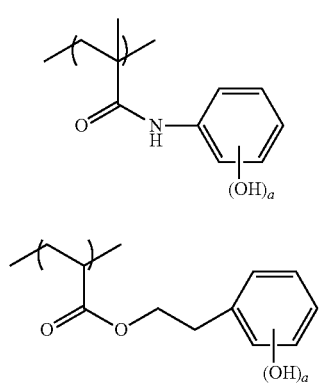
(B-34) 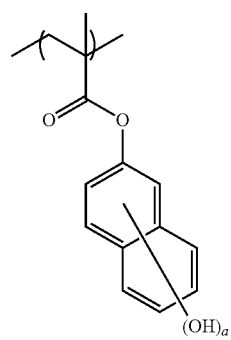
(B-35)
(B-36) 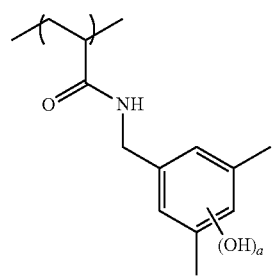
(B-37) 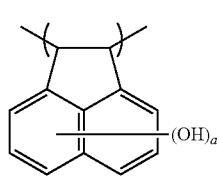
(B-38) 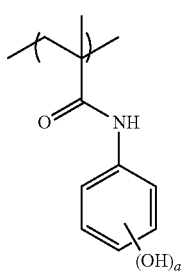
Moreover, among the repeating units, the repeating units specifically described below are preferable. In the formula, R represents a hydrogen atom or a methyl group, and a represents 2 or 3.
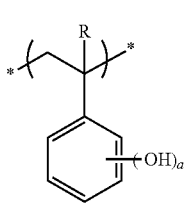 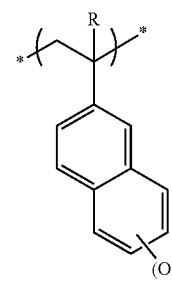
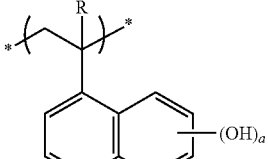 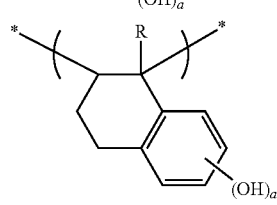
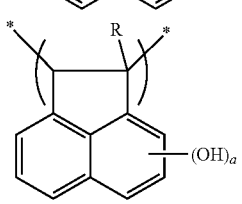 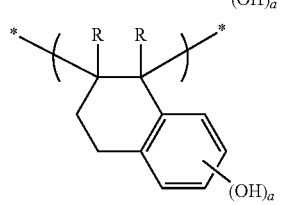

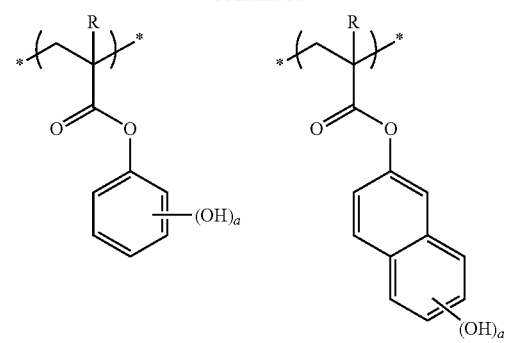
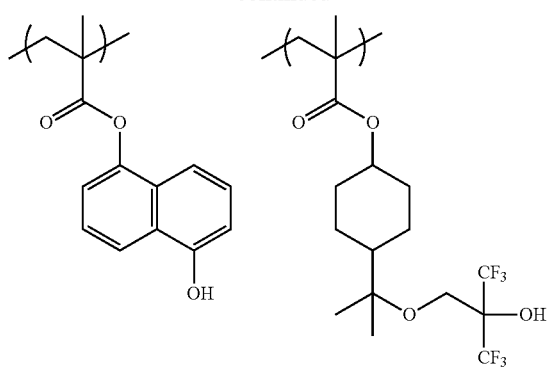
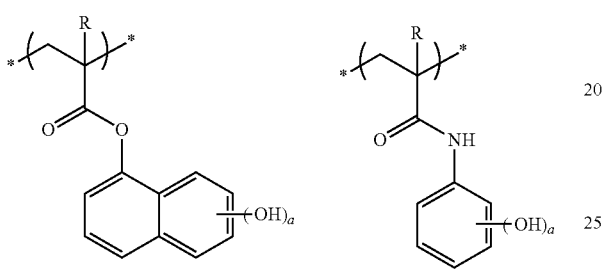
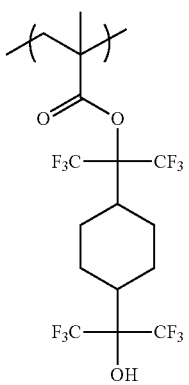
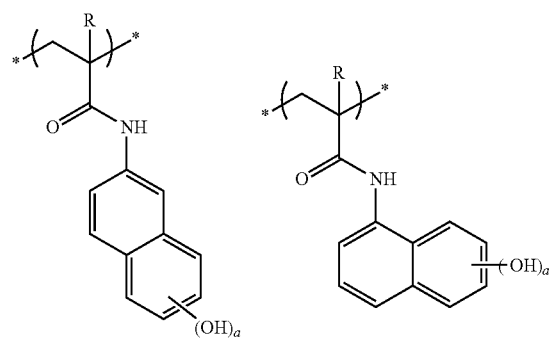
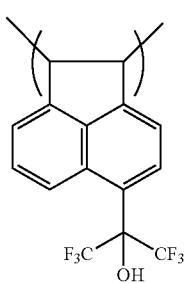
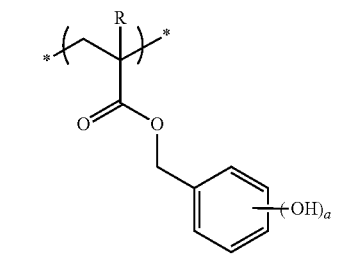
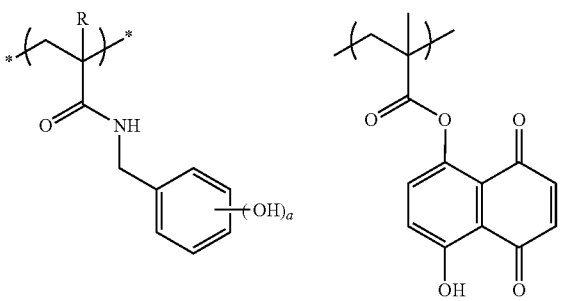
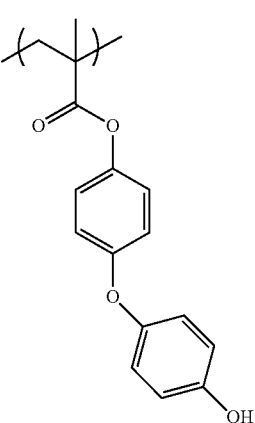

-continued

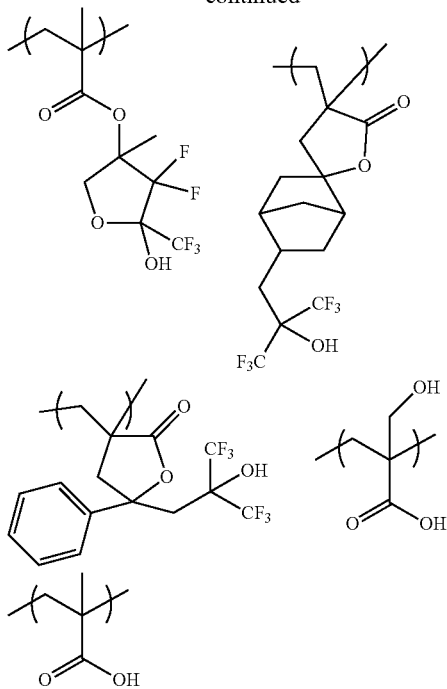

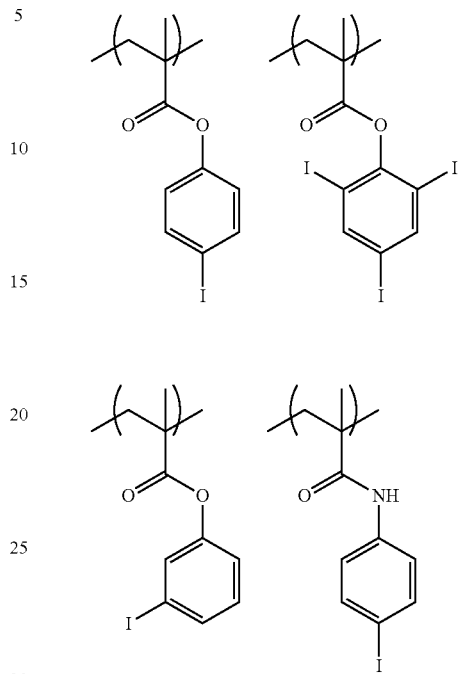

The repeating unit having a fluorine atom or an iodine atom will be exemplified below.

The content of the repeating unit having an acid group is preferably 10% by mole or more, and more preferably 15% by mole or more with respect to all the repeating units in the resin (A). In addition, an upper limit value thereof is preferably 70% by mole or less, more preferably 65% by mole or less, and still more preferably 60% by mole or less.

<Repeating Unit Having Fluorine Atom or Iodine Atom>

The resin (A) may have a repeating unit having a fluorine atom or an iodine atom in addition to the above-mentioned <Repeating Unit Having Acid-Decomposable Group> and <Repeating Unit Having Acid Group>. In addition, <Repeating Unit Having Fluorine Atom or Iodine Atom> as mentioned herein is preferably different from other kinds of repeating units belonging to the group A, such as <Repeating Unit Having Lactone Group, Sultone Group, or Carbonate Group> and <Repeating Unit Having Photoacid Generating Group>, which will be described later.

As the repeating unit having a fluorine atom or an iodine atom, a repeating unit represented by Formula (CO) is preferable.

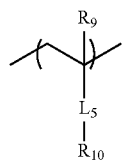

(CO)

$L_5$ represents a single bond or an ester group.

$R_9$ represents a hydrogen atom, or an alkyl group which may have a fluorine atom or an iodine atom.

$R_{10}$ represents a hydrogen atom, an alkyl group which may have a fluorine atom or an iodine atom, a cycloalkyl group which may have a fluorine atom or an iodine atom, an aryl group which may have a fluorine atom or an iodine atom, or a group formed by combination thereof.

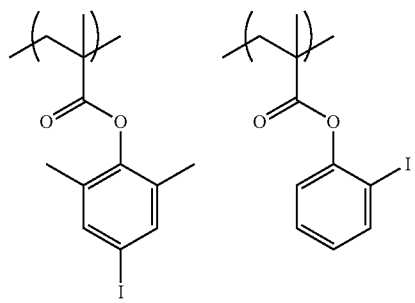

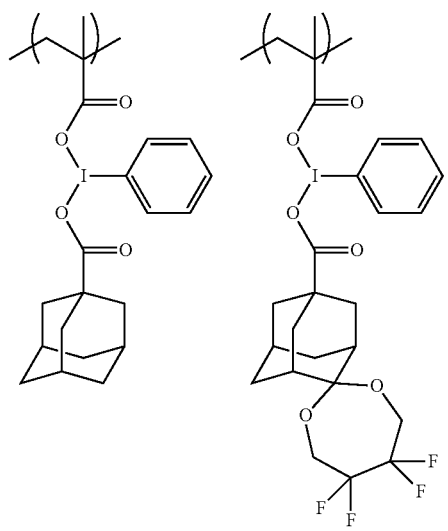

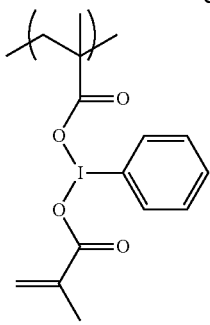

The content of the repeating unit having a fluorine atom or an iodine atom is preferably 0% by mole or more, more preferably 5% by mole or more, and still more preferably 10% by mole or more with respect to all the repeating units in the resin (A). In addition, an upper limit value thereof is preferably 50% by mole or less, more preferably 45% by mole or less, and still more preferably 40% by mole or less.

Furthermore, since the repeating unit having a fluorine atom or an iodine atom does not include <Repeating Unit Having Acid-Decomposable Group> and <Repeating Unit Having Acid Group> as described above, the content of the repeating unit having a fluorine atom or an iodine atom is also intended to mean a content of the repeating unit having a fluorine atom or an iodine atom, excluding <Repeating Unit Having Acid-Decomposable Group> and <Repeating Unit Having Acid Group>.

The total content of the repeating units including at least one of a fluorine atom or an iodine atom in the repeating units of the resin (A) is preferably 20% by mole or more, more preferably 30% by mole or more, and still more preferably 40% by mole or more with respect to all the repeating units of the resin (A). An upper limit value thereof is not particularly limited, but is, for example, 100% by mole or less.

In addition, examples of the repeating unit including at least one of a fluorine atom or an iodine atom include a repeating unit which has a fluorine atom or an iodine atom, and has an acid-decomposable group, a repeating unit which has a fluorine atom or an iodine atom, and has an acid group, and a repeating unit having a fluorine atom or an iodine atom.

<Repeating Unit Having Lactone Group, Sultone Group, or Carbonate Group>

The resin (A) may have a repeating unit having at least one selected from the group consisting of a lactone group, a sultone group, and a carbonate group (hereinafter also collectively referred to as a "repeating unit having a lactone group, a sultone group, or a carbonate group").

It is also preferable that the repeating unit having a lactone group, a sultone group, or a carbonate group has no acid group such as a hexafluoropropanol group.

The lactone group or the sultone group may have a lactone structure or a sultone structure. The lactone structure or the sultone structure is preferably a 5- to 7-membered ring lactone structure or a 5- to 7-membered ring sultone structure. Among those, the structure is more preferably a 5- to 7-membered ring lactone structure with which another ring structure is fused so as to form a bicyclo structure or a spiro structure or a 5- to 7-membered ring sultone structure with which another ring structure is fused so as to form a bicyclo structure or a spiro structure.

The resin (A) preferably has a repeating unit having a lactone group or a sultone group, formed by extracting one or more hydrogen atoms from a ring member atom of a lactone structure represented by any of General Formulae (LC1-1) to (LC1-21) or a sultone structure represented by any of General Formulae (SL1-1) to (SL1-3).

In addition, the lactone group or the sultone group may be bonded directly to the main chain. For example, a ring member atom of the lactone group or the sultone group may constitute the main chain of the resin (A).

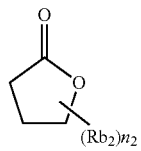

LC1-1

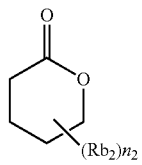

LC1-2

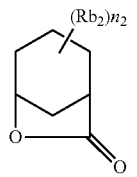

LC1-3

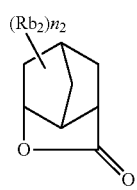

LC1-4

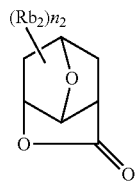

LC1-5

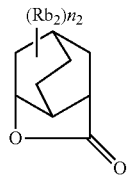

LC1-6

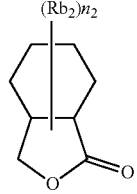

LC1-7

-continued
LC1-8 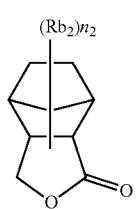
LC1-9 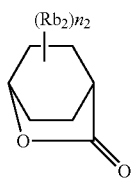
LC1-10 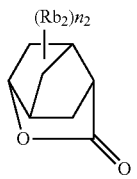
LC1-11 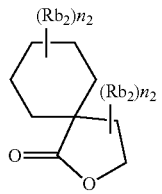
LC1-12 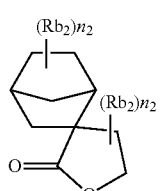
LC1-13 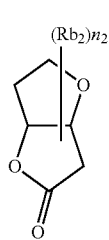
LC1-14 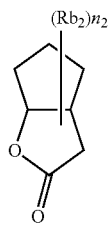
LC1-15 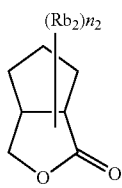
-continued
LC1-16 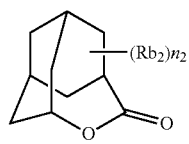
LC1-17 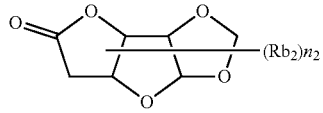
LC1-18 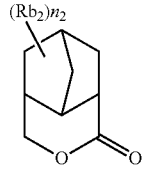
LC1-19 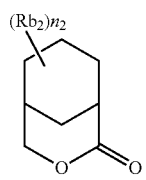
LC1-20 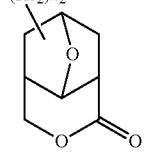
LC1-21 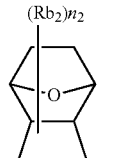
SL1-1 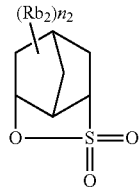
SL1-2
SL1-3
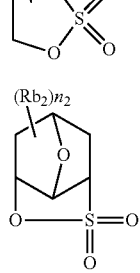
The moiety of the lactone structure or the sultone structure may have a substituent ($Rb_2$). Preferred examples of the substituent ($Rb_2$) include an alkyl group having 1 to 8 carbon atoms, a cycloalkyl group having 4 to 7 carbon atoms, an alkoxy group having 1 to 8 carbon atoms, an alkoxycarbonyl group having 1 to 8 carbon atoms, a carboxyl group, a halogen atom, a hydroxyl group, a cyano group, and an acid-decomposable group. n2 represents an integer of 0 to 4. In a case where n2 is 2 or more, $Rb_2$'s which are present in a plural number may be different from each other, and $Rb_2$'s which are present in a plural number may be bonded to each other to form a ring.

Examples of the repeating unit having a group having the lactone structure represented by any of General Formulae (LC1-1) to (LC1-21) or the sultone structure represented by any of General Formulae (SL1-1) to (SL1-3) include a repeating unit represented by General Formula (AI).

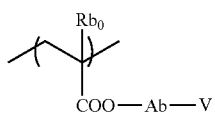

(AI)

In General Formula (AI), $Rb_0$ represents a hydrogen atom, a halogen atom, or an alkyl group having 1 to 4 carbon atoms.

Preferred examples of the substituent which may be contained in the alkyl group of $Rb_0$ include a hydroxyl group and a halogen atom.

Examples of the halogen atom of $Rb_0$ include a fluorine atom, a chlorine atom, a bromine atom, and an iodine atom. $Rb_0$ is preferably the hydrogen atom or a methyl group.

Ab represents a single bond, an alkylene group, a divalent linking group having a monocyclic or polycyclic alicyclic hydrocarbon structure, an ether group, an ester group, a carbonyl group, a carboxyl group, or a divalent group formed by combination thereof. Among those, the single bond or a linking group represented by -$Ab_1$-$CO_2$— is preferable. $Ab_1$ is a linear or branched alkylene group, or a monocyclic or polycyclic cycloalkylene group, and is preferably a methylene group, an ethylene group, a cyclohexylene group, an adamantylene group, or a norbornylene group.

V represents a group formed by extracting one hydrogen atom from a ring member atom of the lactone structure represented by any of General Formulae (LC1-1) to (LC1-21) or a group formed by extracting one hydrogen atom from a ring member atom of the sultone structure represented by any of General Formulae (SL1-1) to (SL1-3).

In a case where an optical isomer is present in the repeating unit having a lactone group or a sultone group, any of optical isomers may be used. In addition, one kind of optical isomers may be used singly or a plurality of kinds of optical isomers may be mixed and used. In a case where one kind of optical isomers is mainly used, an optical purity (ee) thereof is preferably 90 or more, and more preferably 95 or more.

As the carbonate group, a cyclic carbonic acid ester group is preferable.

As the repeating unit having a cyclic carbonic acid ester group, a repeating unit represented by General Formula (A-1) is preferable.

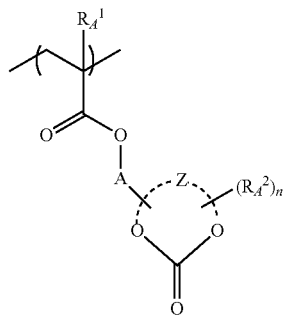

(A-1)

In General Formula (A-1), $R_A^1$ represents a hydrogen atom, a halogen atom, or a monovalent organic group (preferably a methyl group).

n represents an integer of 0 or more.

$R_A^2$ represents a substituent. In a case where n is 2 or more, $R_A^2$ which are present in a plural number may be the same as or different from each other.

A represents a single bond or a divalent linking group. As the divalent linking group, an alkylene group, a divalent linking group having a monocyclic or polycyclic alicyclic hydrocarbon structure, an ether group, an ester group, a carbonyl group, a carboxyl group, or a divalent group formed by combination thereof is preferable.

Z represents an atomic group that forms a monocycle or polycycle with a group represented by —O—CO—O— in the formula.

The repeating unit having a lactone group, a sultone group, or a carbonate group will be exemplified below.

(in the formulae, Rx represents H, $CH_3$, $CH_2OH$, or $CF_3$)

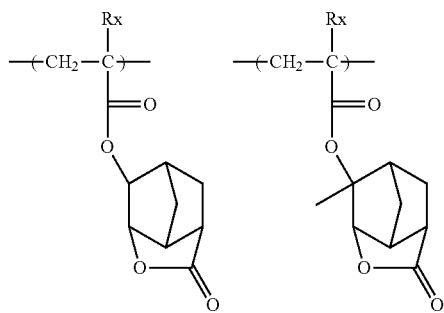

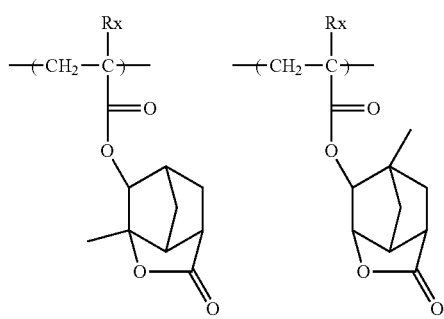

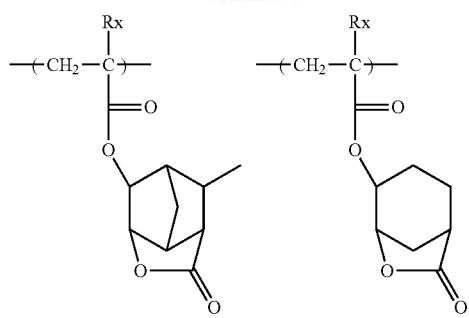
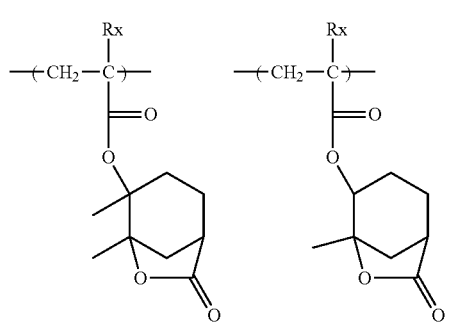
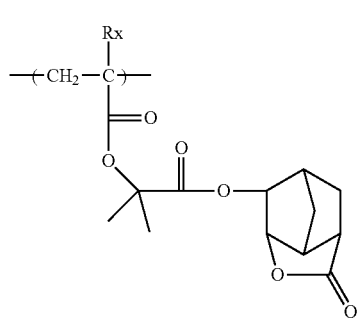
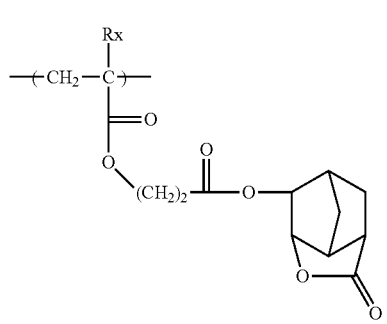
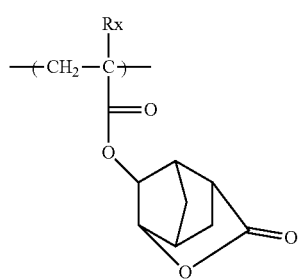
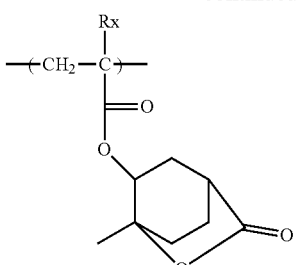
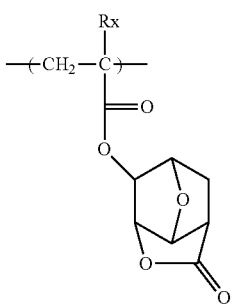
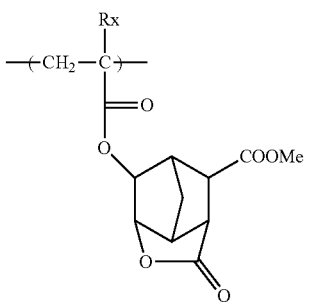
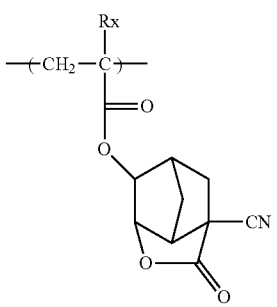
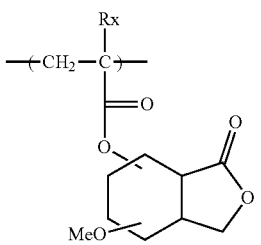
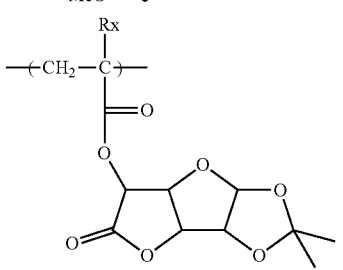

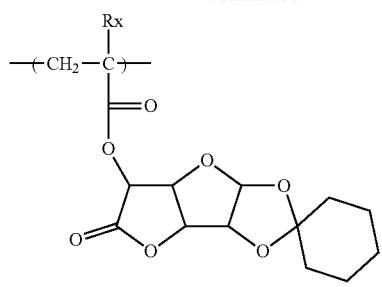
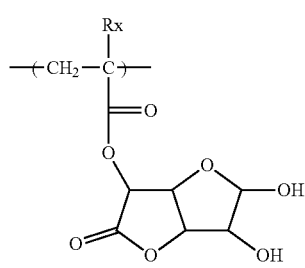
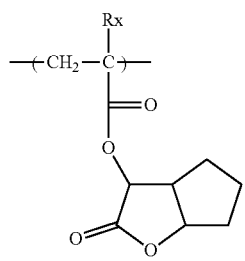
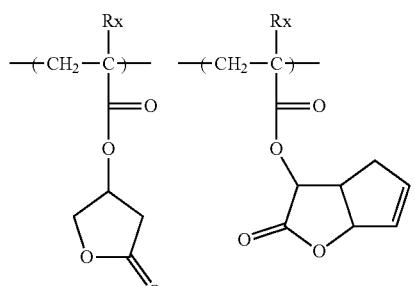
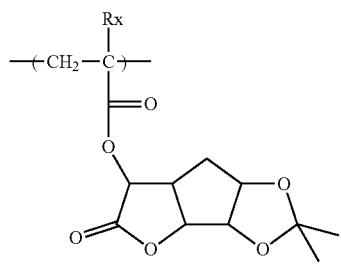
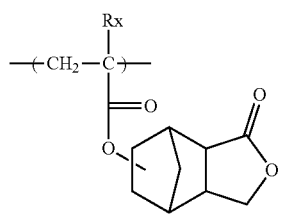
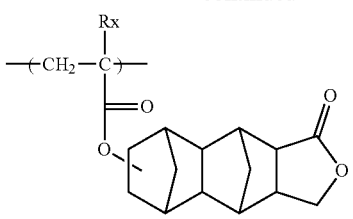
(in the formulae, Rx represents H, CH$_3$, CH$_2$OH, or CF$_3$)
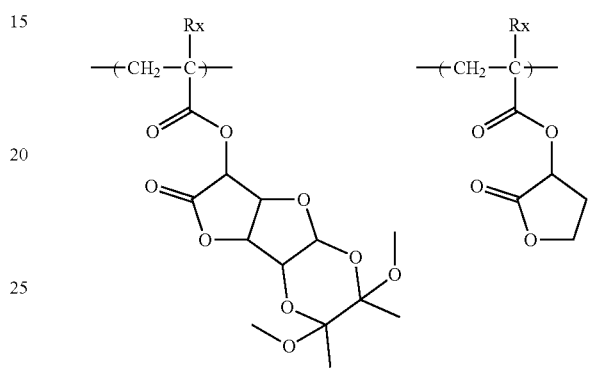
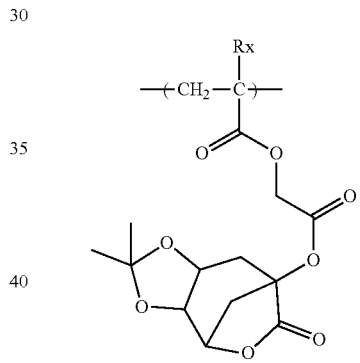
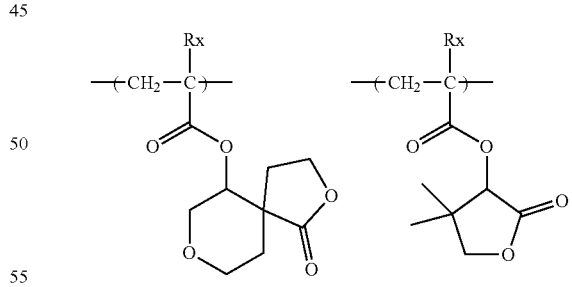
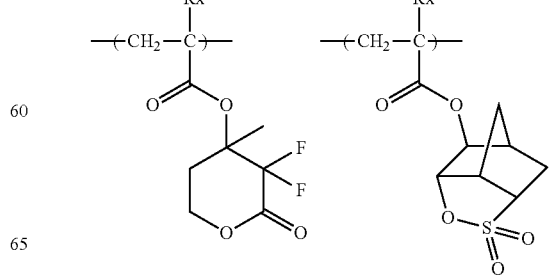

81

-continued

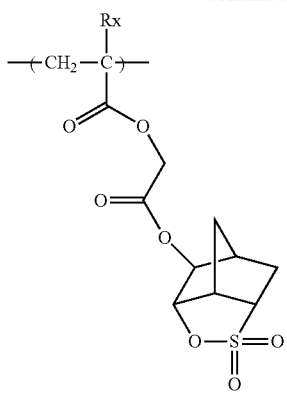

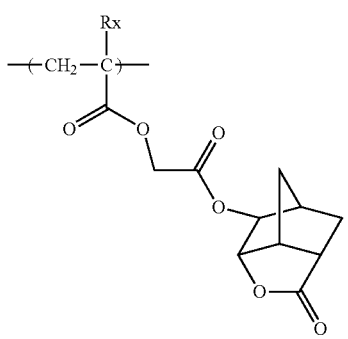

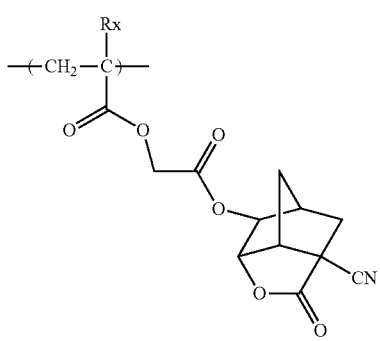

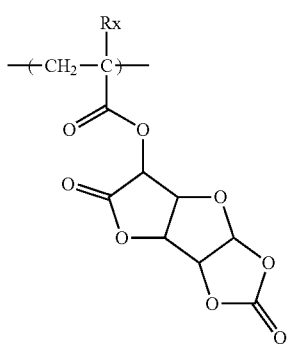

82

-continued

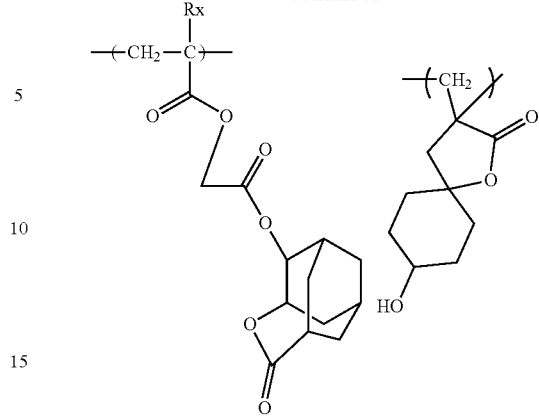

(in the formulae, Rx represents H, CH$_3$, CH$_2$OH, of CF$_3$)

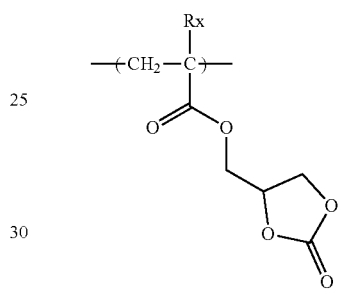

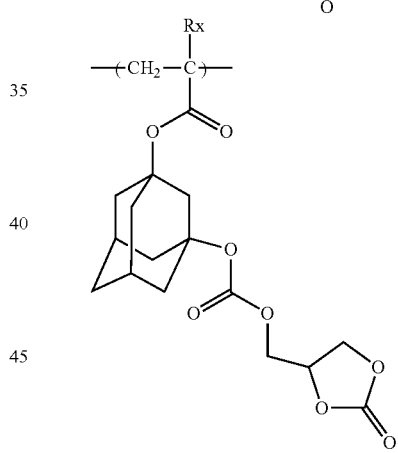

The content of the repeating unit having a lactone group, a sultone group, or a carbonate group is preferably 1% by mole or more, and more preferably 10% by mole or more with respect to all the repeating units in the resin (A). In addition, an upper limit value thereof is preferably 85% by mole or less, more preferably 80% by mole or less, still more preferably 70% by mole or less, and particularly preferably 60% by mole or less.

<Repeating Unit Having Photoacid Generating Group>

The resin (A) may have, as a repeating unit other than those above, a repeating unit having a group that generates an acid upon irradiation with actinic rays or radiation (hereinafter also referred to as a "photoacid generating group").

In this case, it can be considered that the repeating unit having a photoacid generating group corresponds to a compound that generates an acid upon irradiation with actinic rays or radiation which will be described later (also referred to as a "photoacid generator").

Examples of such the repeating unit include a repeating unit represented by General Formula (4).

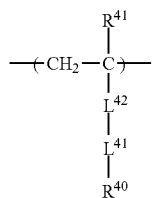
(4)

$R^{41}$ represents a hydrogen atom or a methyl group. $L^{41}$ represents a single bond or a divalent linking group. $L^{42}$ represents a divalent linking group. $R^{40}$ represents a structural moiety that decomposes upon irradiation with actinic rays or radiation to generate an acid in a side chain.

The repeating unit having a photoacid generating group is exemplified below.

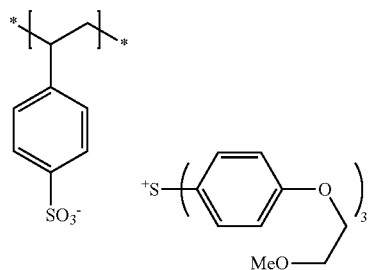

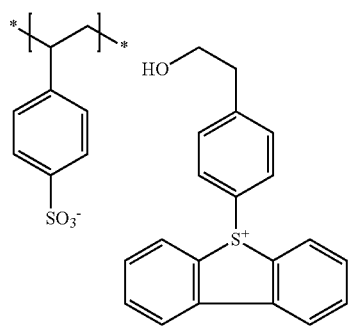

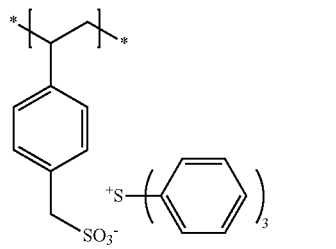

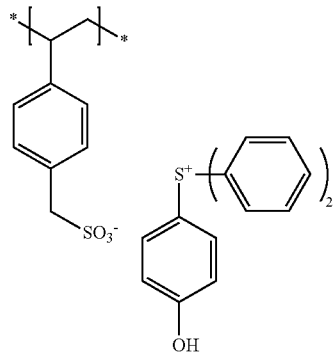

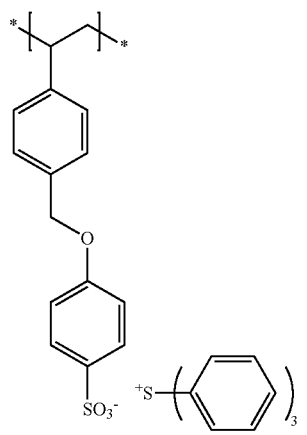

-continued

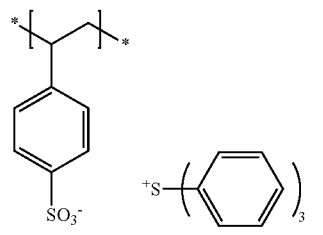

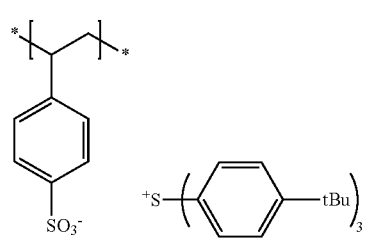

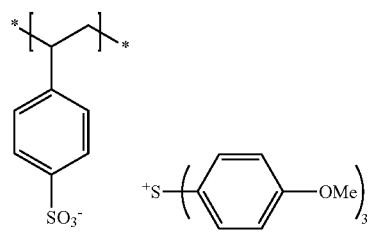

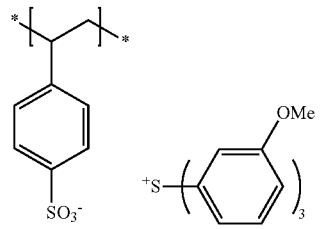

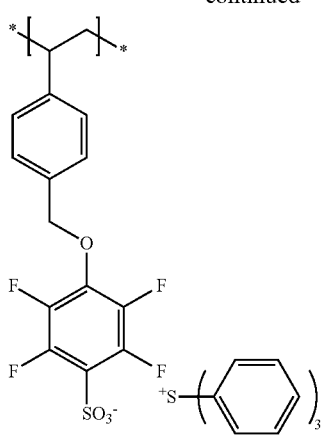
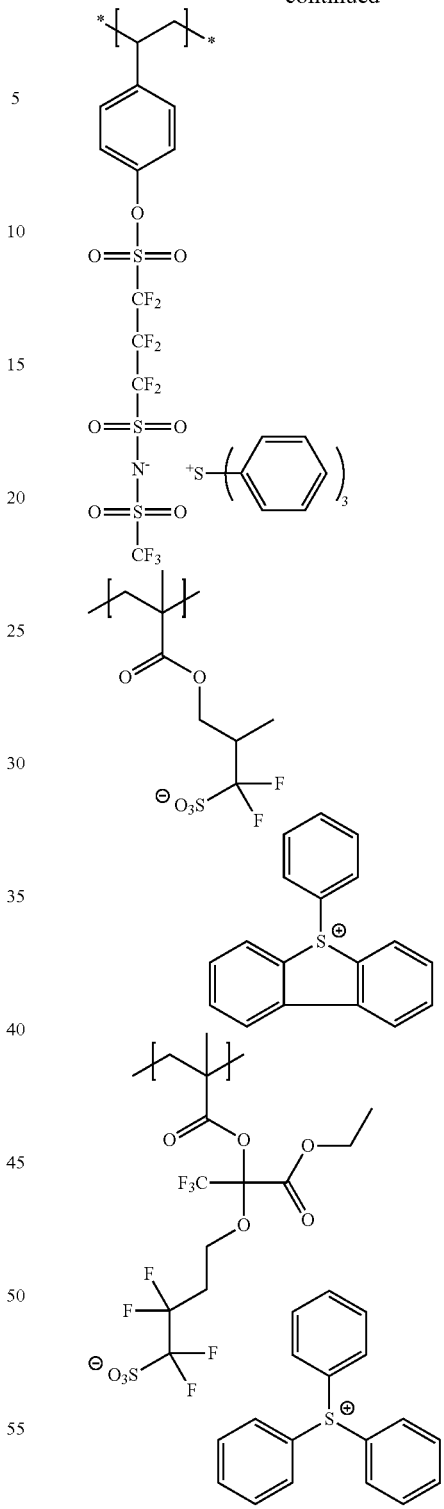
Other examples of the repeating unit represented by General Formula (4) include the repeating units described in paragraphs <0094> to <0105> of JP2014-041327A.
The content of the repeating unit having a photoacid generating group is preferably 1% by mole or more, and more preferably 5% by mole or more with respect to all the repeating units in the resin (A). In addition, an upper limit value thereof is preferably 40% by mole or less, more preferably 35% by mole or less, and still more preferably 30% by mole or less.

<Repeating Unit Represented by General Formula (V-1) or General Formula (V-2)>

The resin (A) may have a repeating unit represented by General Formula (V-1) or General Formula (V-2).

The repeating unit represented by General Formula (V-1) and General Formula (V-2) is preferably a repeating unit different from the above-mentioned repeating units.

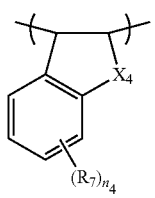
(V-1)

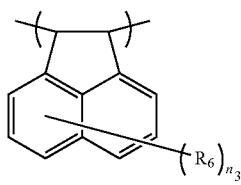
(V-2)

In the formulae, $R_6$ and $R_7$ each independently represent a hydrogen atom, a hydroxyl group, an alkyl group, an alkoxy group, an acyloxy group, a cyano group, a nitro group, an amino group, a halogen atom, an ester group (—OCOR or —COOR: R is an alkyl group or fluorinated alkyl group having 1 to 6 carbon atoms), or a carboxyl group. As the alkyl group, a linear, branched, or cyclic alkyl group having 1 to 10 carbon atoms is preferable.

$n_3$ represents an integer of 0 to 6.

$n_4$ represents an integer of 0 to 4.

$X^4$ is a methylene group, an oxygen atom, or a sulfur atom.

The repeating unit represented by General Formula (V-1) or (V-2) will be exemplified below.

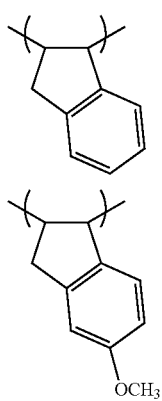 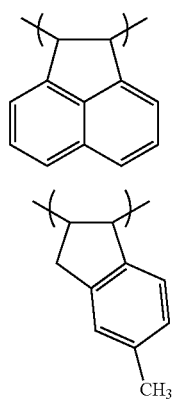

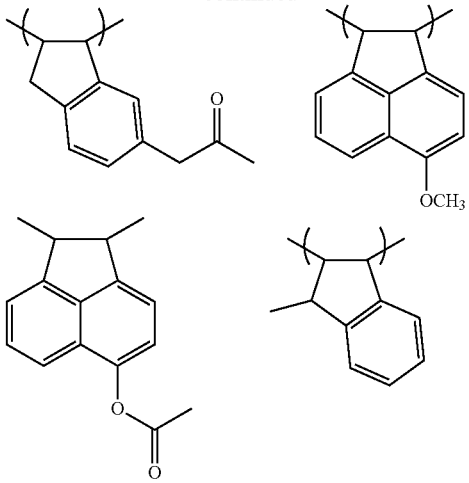

<Repeating Unit for Reducing Motility of Main Chain>

The resin (A) preferably has a high glass transition temperature (Tg) from the viewpoint that excessive diffusion of an acid generated or pattern collapse during development can be suppressed. Tg is preferably higher than 90° C., more preferably higher than 100° C., still more preferably higher than 110° C., and particularly preferably higher than 125° C. In addition, since an excessive increase in Tg causes a decrease in the dissolution rate in a developer, Tg is preferably 400° C. or lower, and more preferably 350° C. or lower.

Furthermore, in the present specification, the glass transition temperature (Tg) of a polymer such as the resin (A) is calculated by the following method. First, the Tg of a homopolymer consisting only of each repeating unit included in the polymer is calculated by a Bicerano method. Hereinafter, the calculated Tg is referred to as the "Tg of the repeating unit". Next, the mass proportion (%) of each repeating unit to all the repeating units in the polymer is calculated. Then, the Tg at each mass proportion is calculated using a Fox's equation (described in Materials Letters 62 (2008) 3152, and the like), and these are summed to obtain the Tg (° C.) of the polymer.

The Bicerano method is described in Prediction of polymer properties, Marcel Dekker Inc., New York (1993), and the like. The calculation of a Tg by the Bicerano method can be carried out using MDL Polymer (MDL Information Systems, Inc.), which is software for estimating physical properties of a polymer.

In order to raise the Tg of the resin (A) (preferably to raise the Tg to higher than 90° C.), it is preferable to reduce the motility of the main chain of the resin (A). Examples of a method for lowering the motility of the main chain of the resin (A) include the following (a) to (e) methods.

(a) Introduction of a bulky substituent into the main chain
(b) Introduction of a plurality of substituents into the main chain
(c) Introduction of a substituent that induces an interaction between the resins (A) near the main chain
(d) Formation of the main chain in a cyclic structure
(e) Linking of a cyclic structure to the main chain Furthermore, the resin (A) preferably has a repeating unit having a Tg of a homopolymer exhibiting 130° C. or higher.

In addition, the type of the repeating unit having a Tg of the homopolymer exhibiting 130° C. or higher is not particularly limited, and may be any of repeating units having a Tg of a homopolymer of 130° C. or higher calculated by the Bicerano method. Further, it corresponds to a repeating unit having a Tg of a homopolymer exhibiting 130° C. or higher, depending on the type of a functional group in the repeating units represented by Formula (A) to Formula (E) which will be described later.

(Repeating Unit Represented by Formula (A))

As an example of a specific unit for accomplishing (a) above, a method of introducing a repeating unit represented by Formula (A) into the resin (A) may be mentioned.

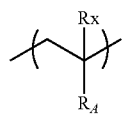
(A)

In Formula (A), $R_A$ represents a group having a polycyclic structure. $R_x$ represents a hydrogen atom, a methyl group, or an ethyl group. The group having a polycyclic structure is a group having a plurality of ring structures, and the plurality of ring structures may or may not be fused.

Specific examples of the repeating unit represented by Formula (A) include the following repeating units.

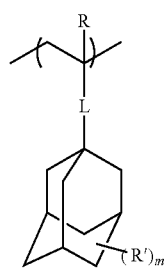
(A-1)

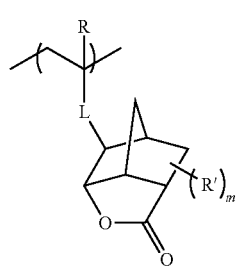
(A-2)

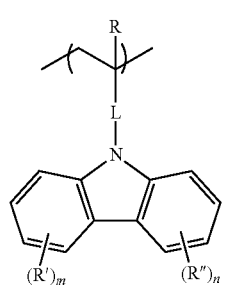
(A-3)

-continued

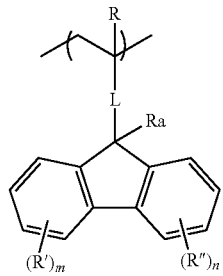
(A-4)

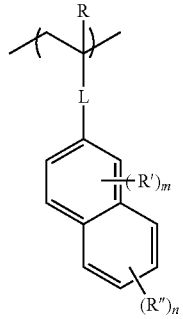
(A-5)

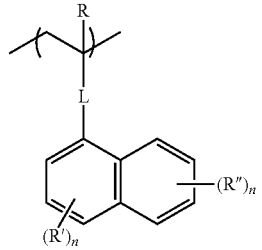
(A-6)

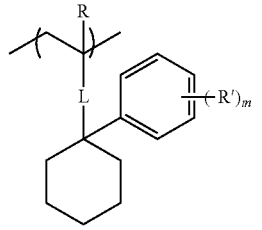
(A-7)

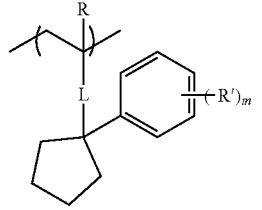
(A-8)

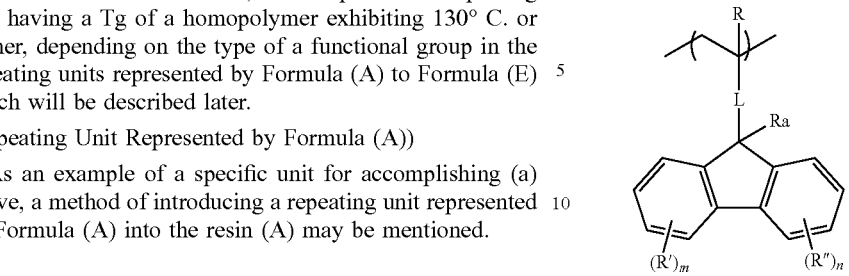
(A-9)

-continued

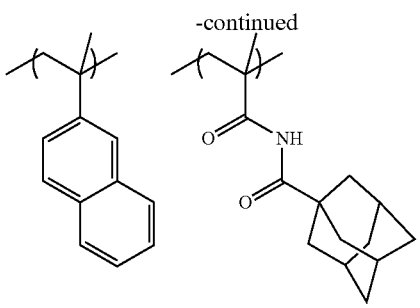

In the formulae, R represents a hydrogen atom, a methyl group, or an ethyl group.

Ra represents a hydrogen atom, an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR''' or —COOR''': R''' is an alkyl group or fluorinated alkyl group having 1 to 20 carbon atoms), or a carboxyl group. Further, the alkyl group, the cycloalkyl group, the aryl group, the aralkyl group, and the alkenyl group may each have a substituent. In addition, a hydrogen atom bonded to the carbon atom in the group represented by Ra may be substituted with a fluorine atom or an iodine atom.

Moreover, R' and R'' each independently represent an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR''' or —COOR''': R''' is an alkyl group or fluorinated alkyl group having 1 to 20 carbon atoms), or a carboxyl group. Further, the alkyl group, the cycloalkyl group, the aryl group, the aralkyl group, and the alkenyl group may each have a substituent. In addition, a hydrogen atom bonded to the carbon atom in the groups represented by each of R' and R'' may be substituted with a fluorine atom or an iodine atom.

L represents a single bond or a divalent linking group. Examples of the divalent linking group include —COO—, —CO—, —O—, —S—, —SO—, —SO$_2$—, an alkylene group, a cycloalkylene group, an alkenylene group, and a linking group in which a plurality of these groups are linked.

m and n each independently represent an integer of 0 or more. The upper limit of each of m and n is not particularly limited, but is 2 or less in many cases, and 1 or less in more cases.

(Repeating Unit Represented by Formula (B))

As an example of a specific unit for accomplishing (b) above, a method of introducing a repeating unit represented by Formula (B) into the resin (A) may be mentioned.

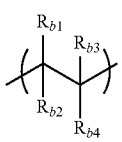

(B)

In Formula (B), $R_{b1}$ to $R_{b4}$ each independently represent a hydrogen atom or an organic group, and at least two or more of $R_{b1}$, . . . , or $R_{b4}$ represent an organic group.

Furthermore, in a case where at least one of the organic groups is a group in which a ring structure is directly linked to the main chain in the repeating unit, the types of the other organic groups are not particularly limited.

In addition, in a case where none of the organic groups is a group in which a ring structure is directly linked to the main chain in the repeating unit, at least two or more of the organic groups are substituents having three or more constituent atoms excluding hydrogen atoms.

Specific examples of the repeating unit represented by Formula (B) include the following repeating units.

(B-1)

(B-2)

(B-3)

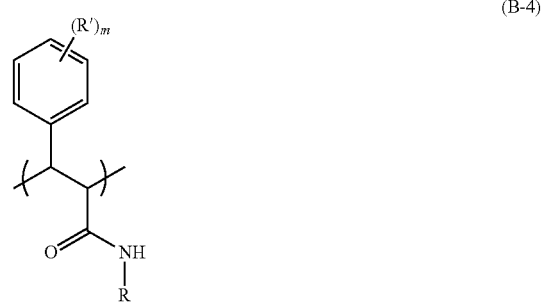

(B-4)

-continued

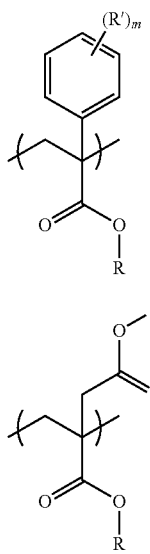

(B-5)

(B-6)

In the formula, R's each independently represent a hydrogen atom or an organic group. Examples of the organic group include an organic group such as an alkyl group, a cycloalkyl group, an aryl group, an aralkyl group, and an alkenyl group, each of which may have a substituent.

R"s each independently represent an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxyl group. Further, the alkyl group, the cycloalkyl group, the aryl group, the aralkyl group, and the alkenyl group may each have a substituent. In addition, a hydrogen atom bonded to the carbon atom in the group represented by R' may be substituted with a fluorine atom or an iodine atom.

m represents an integer of 0 or more. The upper limit of m is not particularly limited, but is 2 or less in many cases, and 1 or less in more cases.

(Repeating Unit Represented by Formula (C))

As an example of a specific unit for accomplishing (c) above, a method of introducing a repeating unit represented by Formula (C) into the resin (A) may be mentioned.

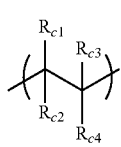

(C)

In Formula (C), $R_{c1}$ to $R_{c4}$ each independently represent a hydrogen atom or an organic group, and at least one of $R_{c1}$, . . . , or $R_{c4}$ is a group having a hydrogen-bonding hydrogen atom with a number of atoms of 3 or less from the main chain carbon. Among those, it is preferable that the group has hydrogen-bonding hydrogen atoms with a number of atoms of 2 or less (on a side closer to the vicinity of the main chain) to induce an interaction between the main chains of the resin (A).

Specific examples of the repeating unit represented by Formula (C) include the following repeating units.

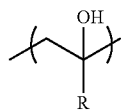

(C-1)

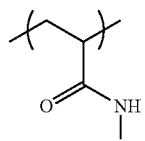

(C-2)

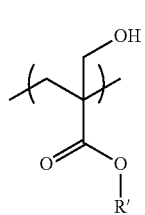

(C-3)

In the formula, R represents an organic group. Examples of the organic group include an alkyl group, a cycloalkyl group, an aryl group, an aralkyl group, an alkenyl group, and an ester group (—OCOR or —COOR: R represents an alkyl group or fluorinated alkyl group having 1 to 20 carbon atoms), each of which may have a substituent.

R' represents a hydrogen atom or an organic group. Examples of the organic group include an organic group such as an alkyl group, a cycloalkyl group, an aryl group, an aralkyl group, and an alkenyl group. In addition, a hydrogen atom in the organic group may be substituted with a fluorine atom or an iodine atom.

(Repeating Unit Represented by Formula (D))

As an example of a specific unit for accomplishing (d) above, a method of introducing a repeating unit represented by Formula (D) into the resin (A) may be mentioned.

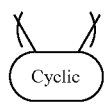

(D)

In Formula (D), "Cyclic" is a group that forms a main chain with a cyclic structure. The number of the ring-constituting atoms is not particularly limited.

Specific examples of the repeating unit represented by Formula (D) include the following repeating units.

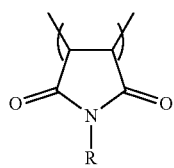

(D-1)

-continued (D-2) 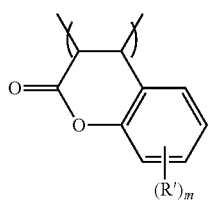

(D-3) 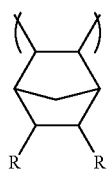

(D-4) 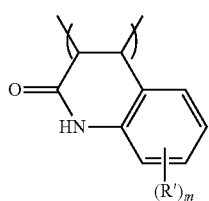

(D-5) 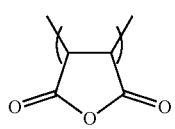

(D-6) 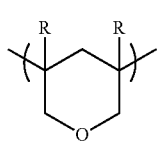

(D-7) 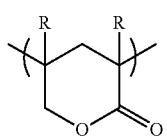

(D-8) 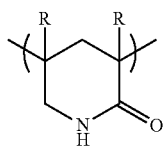

(D-9) 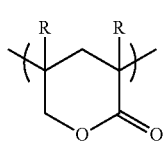

(D-10) 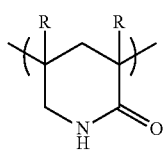

(D-11) 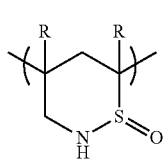

-continued (D-12) 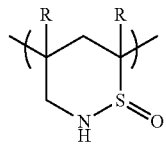

(D-13) 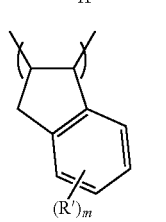

(D-14) 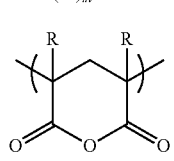

(D-15) 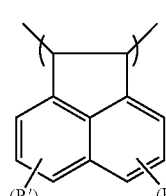

(D-16) 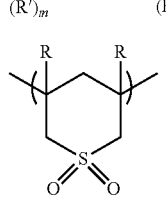

(D-17) 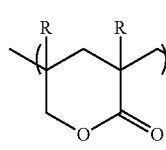

(D-18) 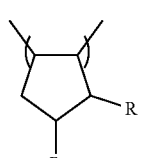

(D-19) 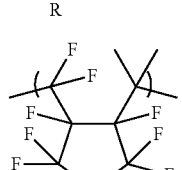

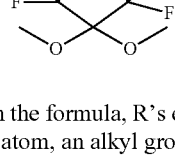

In the formula, R's each independently represent a hydrogen atom, an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxyl group. Further, the alkyl group, the cycloalkyl group, the aryl group, the aralkyl group, and the alkenyl group may each have a substituent. In addition, the hydrogen atom bonded to the carbon atom in the group represented by R may be substituted with a fluorine atom or an iodine atom.

In the formula, R"s each independently represent an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxyl group. Further, the alkyl group, the cycloalkyl group, the aryl group, the aralkyl group, and the alkenyl group may each have a substituent. In addition, a hydrogen atom bonded to the carbon atom in the group represented by R' may be substituted with a fluorine atom or an iodine atom.

m represents an integer of 0 or more. The upper limit of m is not particularly limited, but is 2 or less in many cases, and 1 or less in more cases.

(Repeating Unit Represented by Formula (E))

As an example of a specific unit for accomplishing (e) above, a method of introducing a repeating unit represented by Formula (E) into the resin (A) may be mentioned.

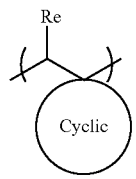
(E)

In Formula (E), Re's each independently represent a hydrogen atom or an organic group. Examples of the organic group include an alkyl group, a cycloalkyl group, an aryl group, an aralkyl group, and an alkenyl group, which may have a substituent.

The "Cyclic" is a cyclic group including a carbon atom of the main chain. The number of atoms included in the cyclic group is not particularly limited.

Specific examples of the repeating unit represented by Formula (E) include the following repeating units.

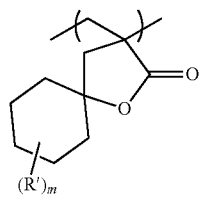
(E-1)

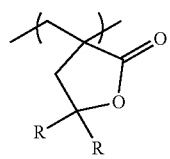
(E-2)

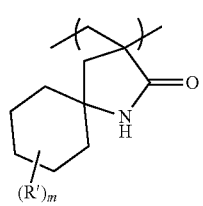
(E-3)

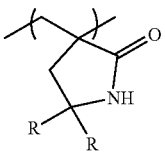
(E-4)

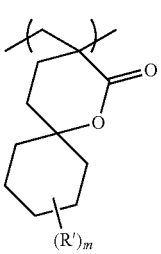
(E-5)

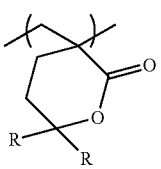
(E-6)

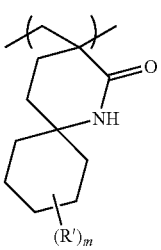
(E-7)

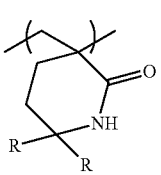
(E-8)

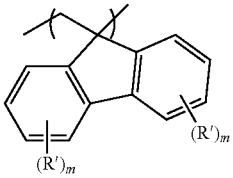
(E-9)

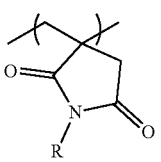
(E-10)

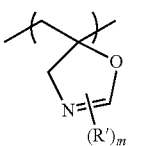
(E-11)

-continued

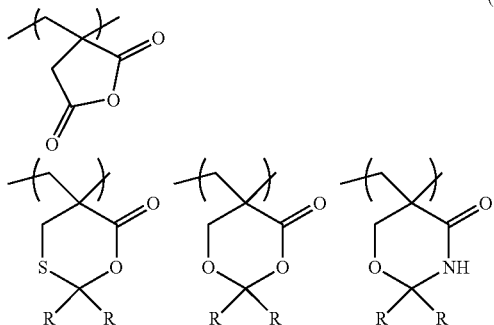
(E-12)

In the formula, R's each independently represent a hydrogen atom, an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxyl group. Further, the alkyl group, the cycloalkyl group, the aryl group, the aralkyl group, and the alkenyl group may each have a substituent. In addition, the hydrogen atom bonded to the carbon atom in the group represented by R may be substituted with a fluorine atom or an iodine atom.

R"s each independently represent a hydrogen atom, an alkyl group, a cycloalkyl group, an aryl group, an aralkyl group, an alkenyl group, a hydroxyl group, an alkoxy group, an acyloxy group, a cyano group, a nitro group, an amino group, a halogen atom, an ester group (—OCOR" or —COOR": R" is an alkyl group or fluorinated alkyl group having 1 to 20 carbon atoms), or a carboxyl group. Further, the alkyl group, the cycloalkyl group, the aryl group, the aralkyl group, and the alkenyl group may each have a substituent. In addition, a hydrogen atom bonded to the carbon atom in the group represented by R' may be substituted with a fluorine atom or an iodine atom.

m represents an integer of 0 or more. The upper limit of m is not particularly limited, but is 2 or less in many cases, and 1 or less in more cases.

In addition, in Formula (E-2), Formula (E-4), Formula (E-6), and Formula (E-8), two R's may be bonded to each other to form a ring.

The content of the repeating unit represented by Formula (E) is preferably 5% by mole or more, and more preferably 10% by mole or more with respect to all the repeating units in the resin (A). In addition, an upper limit value thereof is preferably 60% by mole or less, and more preferably 55% by mole or less.

<Repeating Unit Having at Least One Group Selected from Lactone Group, Sultone Group, Carbonate Group, Hydroxyl Group, Cyano Group, or Alkali-Soluble Group>

The resin (A) may have a repeating unit having at least one group selected from a lactone group, a sultone group, a carbonate group, a hydroxyl group, a cyano group, or an alkali-soluble group.

Examples of the repeating unit having a lactone group, a sultone group, or a carbonate group contained in the resin (A) include the repeating units described in <Repeating Unit Having Lactone Group, Sultone Group, or Carbonate Group> mentioned above. A preferred content thereof is also the same as described in <Repeating Unit Having Lactone Group, Sultone Group, or Carbonate Group> mentioned above.

The resin (A) may have a repeating unit having a hydroxyl group or a cyano group. As a result, the adhesiveness to a substrate and the affinity for a developer are improved.

The repeating unit having a hydroxyl group or a cyano group is preferably a repeating unit having an alicyclic hydrocarbon structure substituted with a hydroxyl group or a cyano group.

The repeating unit having a hydroxyl group or a cyano group preferably has no acid-decomposable group.

Examples of the repeating unit having a hydroxyl group or a cyano group include repeating units represented by General Formulae (AIIa) to (AIId).

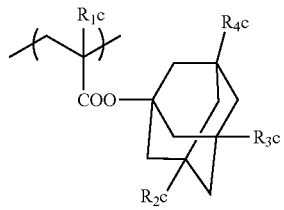
(AIIa)

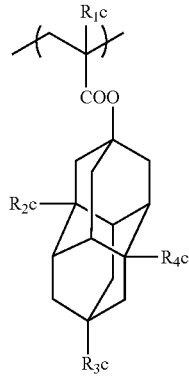
(AIIb)

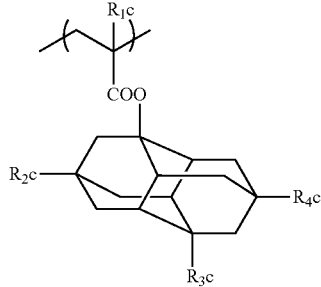
(AIIc)

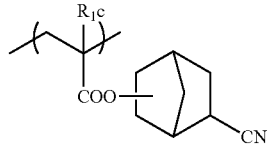
(AIId)

In General Formulae (AIIa) to (AIId), $R_{1c}$ represents a hydrogen atom, a methyl group, a trifluoromethyl group, or a hydroxymethyl group.

$R_{2c}$ to $R_{4c}$ each independently represent a hydrogen atom, a hydroxyl group, or a cyano group. It should be noted that at least one of $R_{2c}$, . . . , or $R_{4c}$ represents a hydroxyl group or a cyano group. It is preferable that one or two of $R_{2c}$ to $R_{4c}$ are hydroxyl groups, and the rest are hydrogen atoms. It is more preferable that two of $R_{2c}$ to $R_{4c}$ are hydroxyl groups and the rest are hydrogen atoms.

The content of the repeating unit having a hydroxyl group or a cyano group is preferably 5% by mole or more, and more preferably 10% by mole or more with respect to all the repeating units in the resin (A). In addition, an upper limit value thereof is preferably 40% by mole or less, more preferably 35% by mole or less, and still more preferably 30% by mole or less.

Specific examples of the repeating unit having a hydroxyl group or a cyano group are shown below, but the present invention is not limited thereto.

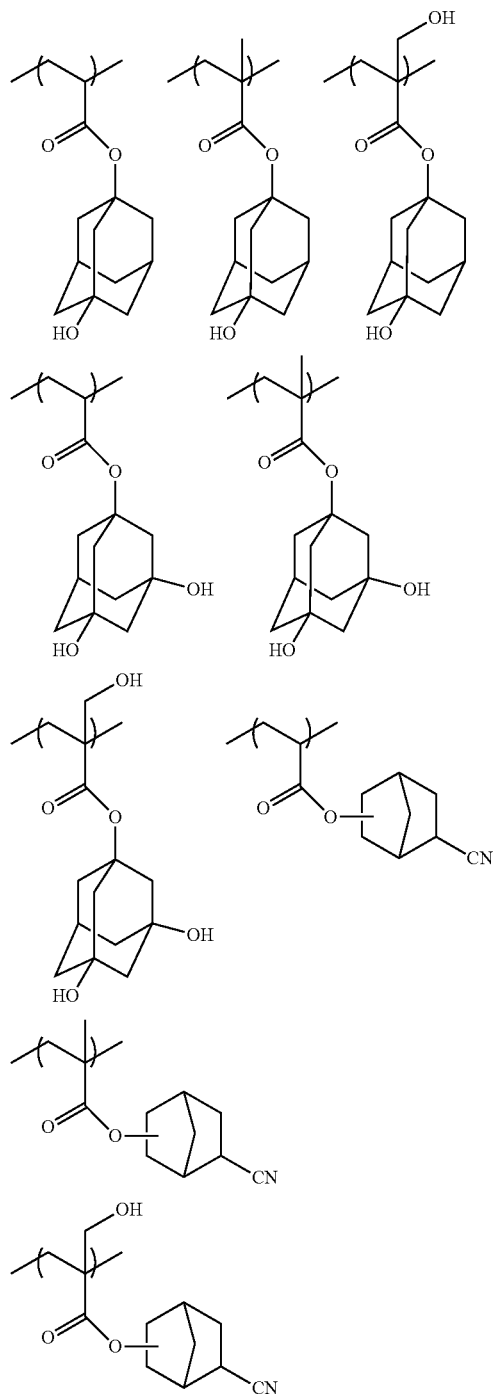

-continued

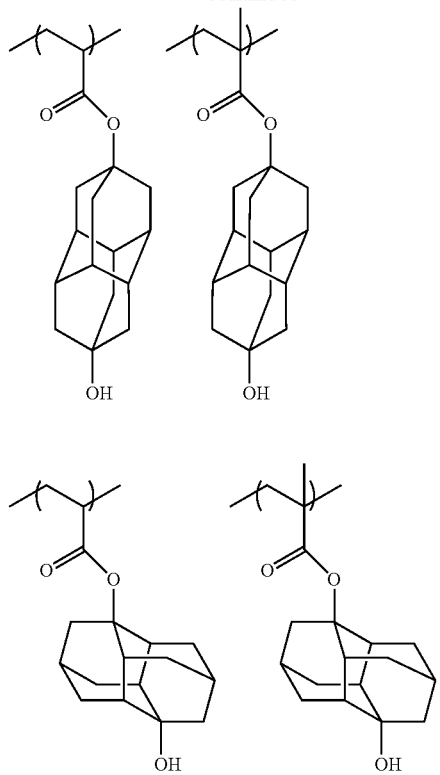

The resin (A) may have a repeating unit having an alkali-soluble group.

Examples of the alkali-soluble group include a carboxyl group, a sulfonamide group, a sulfonylimide group, a bis-sulfonylamide group, or an aliphatic alcohol group (for example, a hexafluoroisopropanol group) in which the α-position is substituted with an electron-withdrawing group, and the carboxyl group is preferable. In a case where the resin (A) includes a repeating unit having an alkali-soluble group, the resolution for use in contact holes is increased.

Examples of the repeating unit having an alkali-soluble group include a repeating unit in which an alkali-soluble group is directly bonded to the main chain of a resin such as a repeating unit with acrylic acid and methacrylic acid, or a repeating unit in which an alkali-soluble group is bonded to the main chain of the resin via a linking group. Further, the linking group may have a monocyclic or polycyclic cyclic hydrocarbon structure.

The repeating unit having an alkali-soluble group is preferably a repeating unit with acrylic acid or methacrylic acid.

The content of the repeating unit having an alkali-soluble group is preferably 0% by mole or more, more preferably 3% by mole or more, and still more preferably 5% by mole or more with respect to all the repeating units in the resin (A). An upper limit value thereof is preferably 20% by mole or less, more preferably 15% by mole or less, and still more preferably 10% by mole or less.

Specific examples of the repeating unit having an alkali-soluble group are shown below, but the present invention is not limited thereto. In the specific examples, Rx represents H, $CH_3$, $CH_2OH$, or $CF_3$.

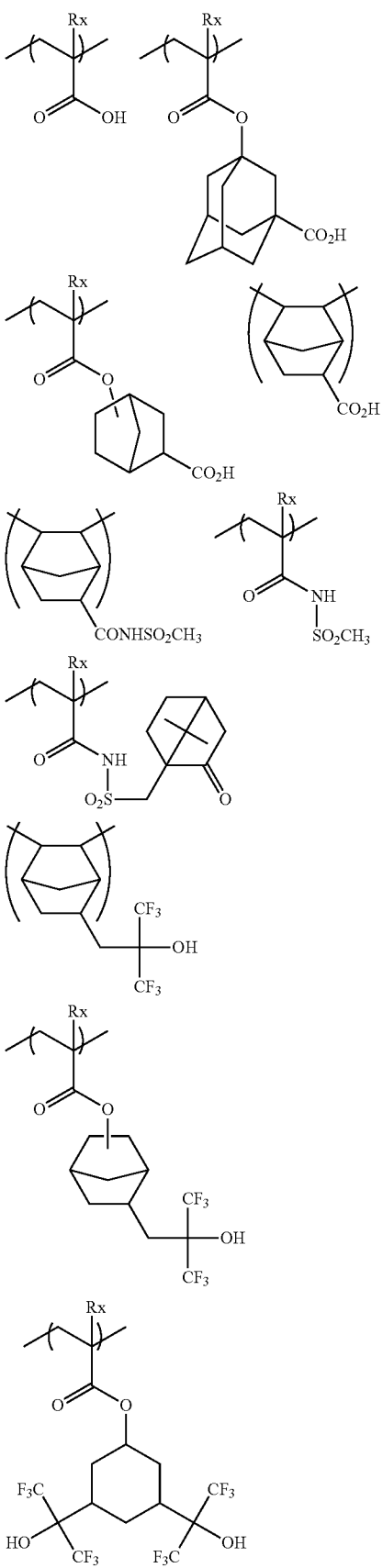

As the repeating unit having at least one group selected from a lactone group, a hydroxyl group, a cyano group, or an alkali-soluble group, a repeating unit having at least two selected from a lactone group, a hydroxyl group, a cyano group, or an alkali-soluble group is preferable, a repeating unit having a cyano group and a lactone group is more preferable, and a repeating unit having a structure in which a cyano group is substituted in the lactone structure represented by General Formula (LC1-4) is still more preferable.

<Repeating Unit Having Alicyclic Hydrocarbon Structure and not Exhibiting Acid Decomposability>

The resin (A) may have a repeating unit having an alicyclic hydrocarbon structure and not exhibiting acid decomposability. This can reduce the elution of low-molecular-weight components from the resist film into an immersion liquid during liquid immersion exposure. Examples of such the repeating unit include repeating units derived from 1-adamantyl (meth)acrylate, diadamantyl (meth)acrylate, tricyclodecanyl (meth)acrylate, and cyclohexyl (meth)acrylate.

<Repeating Unit Represented by General Formula (III) Having Neither Hydroxyl Group Nor Cyano Group>

The resin (A) may have a repeating unit represented by General Formula (III), which has neither a hydroxyl group nor a cyano group.

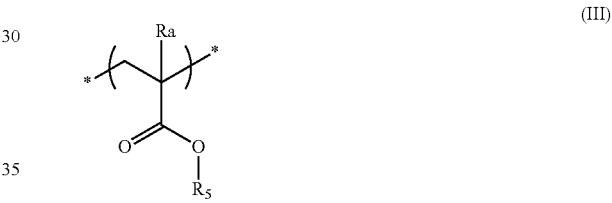

(III)

In General Formula (III), $R_5$ represents a hydrocarbon group having at least one cyclic structure and having neither a hydroxyl group nor a cyano group.

Ra represents a hydrogen atom, an alkyl group, or a —$CH_2$—O—$Ra_2$ group. In the formula, $Ra_2$ represents a hydrogen atom, an alkyl group, or an acyl group.

The cyclic structure contained in $R_5$ includes a monocyclic hydrocarbon group and a polycyclic hydrocarbon group. Examples of the monocyclic hydrocarbon group include a cycloalkyl group having 3 to 12 carbon atoms (more preferably 3 to 7 carbon atoms) or a cycloalkenyl group having 3 to 12 carbon atoms.

Examples of the polycyclic hydrocarbon group include a ring-assembled hydrocarbon group and a crosslinked cyclic hydrocarbon group.

Examples of the crosslinked cyclic hydrocarbon ring include a bicyclic hydrocarbon ring, a tricyclic hydrocarbon ring, and a tetracyclic hydrocarbon ring. Further, examples of the crosslinked cyclic hydrocarbon ring also include a fused ring formed by fusing a plurality of 5- to 8-membered cycloalkane rings.

As the crosslinked cyclic hydrocarbon group, a norbornyl group, an adamantyl group, a bicyclooctanyl group, or a tricyclo[5,2,1,0$^{2,6}$]decanyl group is preferable, and the norbornyl group or the adamantyl group is more preferable.

The alicyclic hydrocarbon group may have a substituent, and examples of the substituent include a halogen atom, an alkyl group, a hydroxyl group protected by a protective group, and an amino group protected by a protective group.

The halogen atom is preferably a bromine atom, a chlorine atom, or a fluorine atom.

As the alkyl group, a methyl group, an ethyl group, a butyl group, or a t-butyl group is preferable.

The alkyl group may further have a substituent, and examples of the substituent include a halogen atom, an alkyl group, a hydroxyl group protected by a protective group, and an amino group protected by a protective group.

Examples of the protective group include an alkyl group, a cycloalkyl group, an aralkyl group, a substituted methyl group, a substituted ethyl group, an alkoxycarbonyl group, and an aralkyloxycarbonyl group.

As the alkyl group, an alkyl group having 1 to 4 carbon atoms is preferable.

As the substituted methyl group, a methoxymethyl group, a methoxythiomethyl group, a benzyloxymethyl group, a t-butoxymethyl group, or a 2-methoxyethoxymethyl group is preferable.

The substituted ethyl group is preferably a 1-ethoxyethyl group or a 1-methyl-1-methoxyethyl group.

As the acyl group, an aliphatic acyl group having 1 to 6 carbon atoms, such as a formyl group, an acetyl group, a propionyl group, a butyryl group, an isobutyryl group, a valeryl group, and a pivaloyl group, is preferable.

As the alkoxycarbonyl group, an alkoxycarbonyl group having 1 to 4 carbon atoms is preferable.

The content of the repeating unit represented by General Formula (III), which has neither a hydroxyl group nor a cyano group, is preferably 0% to 40% by mole, and more preferably 0% to 20% by mole with respect to all the repeating units in the resin (A).

Specific examples of the repeating unit represented by General Formula (III) are shown below, but the present invention is not limited thereto. In the formulae, Ra represents H, $CH_3$, $CH_2OH$, or $CF_3$.

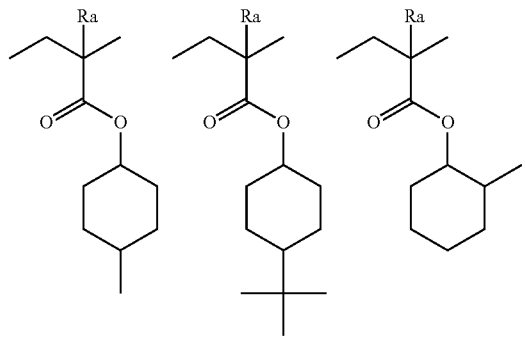

-continued

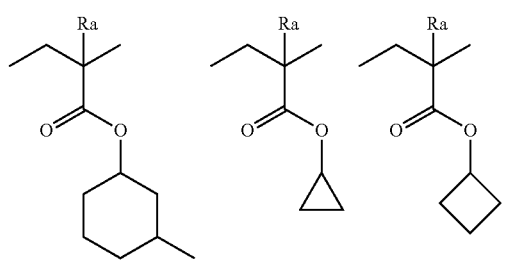

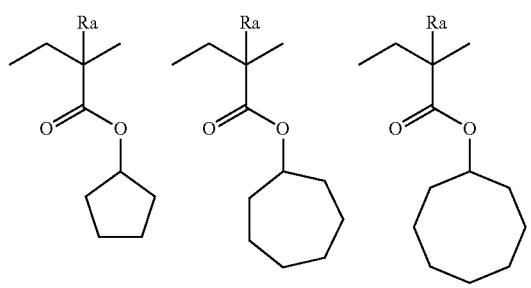

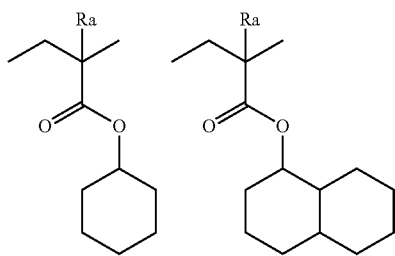

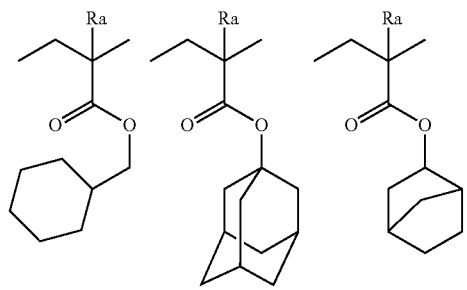

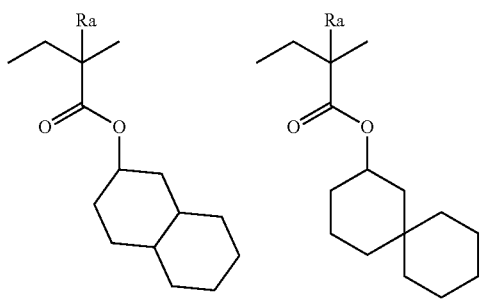

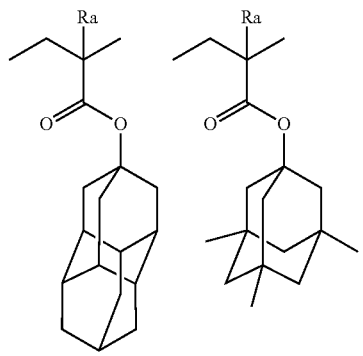

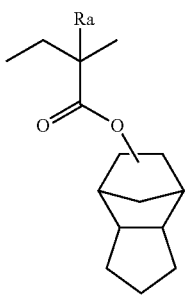

<Other Repeating Units>

The resin (A) may further have a repeating unit other than the above-mentioned repeating units.

For example, the resin (A) may have a repeating unit selected from the group consisting of a repeating unit having an oxathiane ring group, a repeating unit having an oxazolone ring group, a repeating unit having a dioxane ring group, and a repeating unit having a hydantoin ring group.

Such repeating units will be exemplified below.

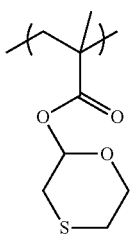 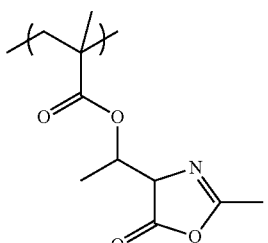

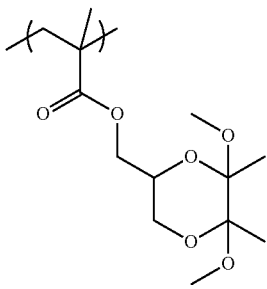

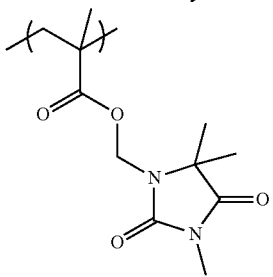

The resin (A) may have a variety of repeating structural units, in addition to the repeating structural units described above, for the purpose of adjusting dry etching resistance, suitability for a standard developer, adhesiveness to a substrate, a resist profile, resolving power, heat resistance, sensitivity, and the like.

As the resin (A), all the repeating units also preferably include (meth)acrylate-based repeating units (particularly in a case where the composition is used as an actinic ray-sensitive or radiation-sensitive resin composition for ArF).

In this case, any of a resin in which all of the repeating units are methacrylate-based repeating units, a resin in which all of the repeating units are acrylate-based repeating units, and a resin in which all of the repeating units are methacrylate-based repeating units and acrylate-based repeating units can be used, and it is preferable that the amount of the acrylate-based repeating units is 50% by mole or less with respect to all the repeating units.

The resin (A) can be synthesized in accordance with an ordinary method (for example, radical polymerization).

The weight-average molecular weight of the resin (A) as a value expressed in terms of polystyrene by a GPC method is preferably 1,000 to 200,000, more preferably 3,000 to 20,000, and still more preferably 5,000 to 15,000. By setting the weight-average molecular weight of the resin (A) to 1,000 to 200,000, deterioration of heat resistance and dry etching resistance can be further suppressed. In addition, deterioration of developability and deterioration of film forming property due to high viscosity can also be further suppressed.

The dispersity (molecular weight distribution) of the resin (A) is usually 1 to 5, preferably 1 to 3, more preferably 1.2 to 3.0, and still more preferably 1.2 to 2.0. The smaller the dispersity, the more excellent the resolution and the resist shape, and the smoother the side wall of the resist pattern, the more excellent the roughness.

In the composition of the embodiment of the present invention, the content of the resin (A) is preferably 50% to 99.9% by mass, and more preferably 60% to 99.0% by mass with respect to the total solid content of the composition.

Furthermore, the solid content is intended to mean components excluding the solvent in the composition, and any of components other than the solvent are regarded as the solid content even in a case where they are liquid components.

In addition, the resin (A) may be used singly or in combination of a plurality thereof.

[Photoacid Generator]

The composition of the embodiment of the present invention may include a compound that generates an acid upon irradiation with actinic rays or radiation (hereinafter also referred to as an "acid generator").

Furthermore, the photoacid generator as mentioned herein corresponds to an acid generator which is usually used to cause a deprotection reaction of a resin component (a deprotection reaction of an acid-decomposable resin) or to cause a crosslinking reaction of a resin component.

As the photoacid generator, a compound that generates an organic acid upon irradiation with actinic rays or radiation is preferable. Examples thereof include a sulfonium salt compound, an iodonium salt compound, a diazonium salt compound, a phosphonium salt compound, an imidosulfonate compound, an oxime sulfonate compound, a diazodisulfone compound, a disulfone compound, and an o-nitrobenzyl sulfonate compound.

As the photoacid generators, known compounds that generate an acid upon irradiation with actinic rays or radiation can be used singly or as a mixture thereof, appropriately selected and used. For example, the known compounds disclosed in paragraphs <0125> to <0319> of the specification of US2016/0070167A1, paragraphs <0086> to <0094> of the specification of US2015/0004544A1, and paragraphs <0323> to <0402> of the specification of US2016/0237190A1 can be suitably used as the photoacid generator.

As the photoacid generator, for example, a compound represented by Formula (ZI), Formula (ZII), or Formula (ZIII) is preferable.

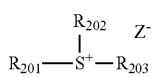

(ZI)

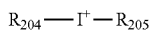

(ZII)

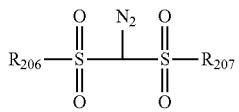

(ZIII)

$R_{201}$, $R_{202}$, $R_{203}$, $R_{204}$, and $R_{205}$ in General Formulae (ZI) and (ZII) are the same as $R^{201}$, $R^{202}$, $R^{203}$, $R^{204}$, and $R^{205}$ in General Formulae (ZaI) and (ZaII), respectively, mentioned above in the description of the specific compound.

In other words, the cationic moieties in General Formulae (ZI) and (ZII) are the same as the cation (ZaI) and the cation (ZaII) mentioned above in the description of the specific compound, respectively.

In addition, in General Formula (ZIII), $R_{206}$ and $R_{207}$ are the same as $R_{204}$ and $R_{205}$ in General Formula (ZII), respectively. That is, in General Formula (ZIII), $R_{206}$ and $R_{207}$ are the same as $R^{204}$ and $R^{205}$ in General Formula (ZaII), respectively.

In General Formulae (ZI) and (ZII), $Z^-$ represents a non-nucleophilic anion (anion having an extremely low ability to cause a nucleophilic reaction).

Examples of the anion include a sulfonate anion (an aliphatic sulfonate anion, an aromatic sulfonate anion, a camphor sulfonate anion, and the like), a carboxylate anion (an aliphatic carboxylate anion, an aromatic carboxylate anion, an aralkyl carboxylate anion, and the like), a sulfonylimide anion, a bis(alkylsulfonyl)imide anion, and a tris(alkylsulfonyl)methide anion.

As $Z^-$ in Formula (ZI) and $Z^-$ in Formula (ZII), the anion represented by Formula (3) is preferable.

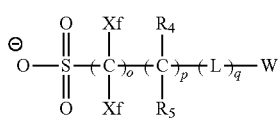

(3)

In Formula (3), o represents an integer of 1 to 3. p represents an integer of 0 to 10. q represents an integer of 0 to 10.

Xf represents a fluorine atom or an alkyl group substituted with at least one fluorine atom. The alkyl group preferably has 1 to 10 carbon atoms, and more preferably has 1 to 4 carbon atoms. In addition, a perfluoroalkyl group is preferable as the alkyl group substituted with at least one fluorine atom.

Xf is preferably a fluorine atom or a perfluoroalkyl group having 1 to 4 carbon atoms, and more preferably a fluorine atom or $CF_3$. In particular, it is preferable that both Xf's are fluorine atoms.

$R_4$ and $R_5$ each independently represent a hydrogen atom, a fluorine atom, an alkyl group, or an alkyl group substituted with at least one fluorine atom. In a case where $R_4$'s and $R_5$'s are each present in a plural number, $R_4$'s and $R_5$'s may each be the same as or different from each other.

The alkyl group represented by each of $R_4$ and $R_5$ may have a substituent, and preferably has 1 to 4 carbon atoms. $R_4$ and $R_5$ are each preferably a hydrogen atom.

Specific examples and suitable aspects of the alkyl group substituted with at least one fluorine atom are the same ones as the specific examples and the suitable aspects of Xf in Formula (3), respectively.

L represents a divalent linking group. In a case where L's are present in a plural number, they may be the same as or different from each other.

Examples of the divalent linking group include —O—CO—O—, —COO—, —OCO—, —CONH—, —NHCO—, —CO—, —O—, —S—, —SO—, —SO$_2$—, an alkylene group (preferably having 1 to 6 carbon atoms), a cycloalkylene group (preferably having 3 to 15 carbon atoms), an alkenylene group (preferably having 2 to 6 carbon atoms), and a divalent linking group formed by combination of a plurality of these groups. Among those, —O—CO—O—, —COO—, —OCO—, —CONH—, —NHCO—, —CO—, —O—, —SO$_2$—, —O—CO—O-alkylene group-, -alkylene group-O—CO—O—, —COO-alkylene group-, —OCO-alkylene group-, —CONH-alkylene group-, or —NHCO-alkylene group—is preferable; and —O—CO—O—, —O—CO—O-alkylene group-, -alkylene group-O—CO—O—, —COO—, —OCO—, —CONH—, —SO$_2$—, —COO-alkylene group-, or —OCO-alkylene group—is more preferable.

W represents an organic group including a cyclic structure. Among those, W is preferably a cyclic organic group.

Examples of the cyclic organic group include an alicyclic group, an aryl group, and a heterocyclic group.

The alicyclic group may be monocyclic or polycyclic. Examples of the monocyclic alicyclic group include monocyclic cycloalkyl groups such as a cyclopentyl group, a cyclohexyl group, and a cyclooctyl group. Examples of the polycyclic alicyclic group include polycyclic cycloalkyl groups such as a norbornyl group, a tricyclodecanyl group, a tetracyclodecanyl group, a tetracyclododecanyl group, and an adamantyl group. Among those, an alicyclic group having a bulky structure having 7 or more carbon atoms, such as a norbornyl group, a tricyclodecanyl group, a tetracyclodecanyl group, a tetracyclododecanyl group, and an adamantyl group, is preferable.

The aryl group may be monocyclic or polycyclic. Examples of the aryl group include a phenyl group, a naphthyl group, a phenanthryl group, and an anthryl group.

The heterocyclic group may be monocyclic or polycyclic. The polycyclic heterocyclic group can further suppress acid diffusion. Further, the heterocyclic group may have aromaticity or may not have aromaticity. Examples of the heterocycle having aromaticity include a furan ring, a thiophene ring, a benzofuran ring, a benzothiophene ring, a dibenzofuran ring, a dibenzothiophene ring, and a pyridine ring. Examples of the heterocycle not having aromaticity include a tetrahydropyran ring, a lactone ring, a sultone ring, and a decahydroisoquinoline ring. As the heterocycle in the heterocyclic group, the furan ring, the thiophene ring, the pyridine ring, or the decahydroisoquinoline ring is particularly preferable.

The cyclic organic group may have a substituent. Examples of the substituent include an alkyl group (which may be either linear or branched, preferably having 1 to 12 carbon atoms), a cycloalkyl group (which may be any of a monocycle, a polycycle, and a spirocycle, and preferably has 3 to 20 carbon atoms), an aryl group (preferably having 6 to 14 carbon atoms), a hydroxyl group, an alkoxy group, an ester group, an amide group, a urethane group, a ureide group, a thioether group, a sulfonamide group, and a sulfonic acid ester group. Incidentally, the carbon constituting the cyclic organic group (carbon contributing to ring formation) may be carbonyl carbon.

As the anion represented by Formula (3), $SO_3^-$—$CF_2$—$CH_2$—OCO-(L)q'-W, $SO_3^-$—$CF_2$—CHF—$CH_2$—OCO-(L)q'-W, $SO_3^-$—$CF_2$—COO-(L)q'-W, $SO_3^-$—$CF_2$—$CF_2$—$CH_2$—$CH_2$-(L)q-W, or $SO_3^-$—$CF_2$—CH($CF_3$)—OCO-(L)q'-W is preferable. Here, L, q, and W are each the same as in Formula (3). q' represents an integer of 0 to 10.

As $Z^-$ in Formula (ZI) and $Z^-$ in Formula (ZII), an anion represented by Formula (4) is also preferable.

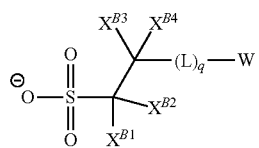

(4)

In Formula (4), $X^{B1}$ and $X^{B2}$ each independently represent a hydrogen atom or a monovalent organic group having no fluorine atom. It is preferable that $X^{B1}$ and $X^{B2}$ are each the hydrogen atom.

$X^{B3}$ and $X^{B4}$ each independently represent a hydrogen atom or a monovalent organic group. It is preferable that at least one of $X^{B3}$ or $X^{B4}$ is a fluorine atom or a monovalent organic group having a fluorine atom, and it is more preferable that both $X^{B3}$ and $X^{B4}$ are fluorine atoms or monovalent organic groups having a fluorine atom. It is still more preferable that both $X^{B3}$ and $X^{B4}$ are fluorine-substituted alkyl groups.

L, q, and W are the same as in Formula (3).

As $Z^-$ in Formula (ZI) and $Z^-$ in Formula (ZII), an anion represented by Formula (5) is preferable.

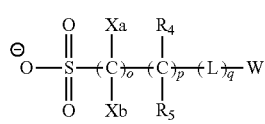

(5)

In Formula (5), Xa's each independently represent a fluorine atom or an alkyl group substituted with at least one fluorine atom. Xb's each independently represent a hydrogen atom or an organic group having no fluorine atom. The definitions and preferred aspects of o, p, q, $R_4$, $R_5$, L, and W are each the same as those in Formula (3).

As $Z^-$ in Formula (ZI) and $Z^-$ in Formula (ZII), an anion represented by Formula (6) is also preferable.

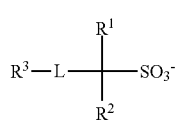

(6)

In Formula (6), $R^1$ and $R^2$ each independently represent a substituent that is not an electron-withdrawing group, or a hydrogen atom.

Examples of the substituent that is not the electron-withdrawing group include a hydrocarbon group, a hydroxyl group, an oxyhydrocarbon group, an oxycarbonyl hydrocarbon group, an amino group, a hydrocarbon-substituted amino group, and a hydrocarbon-substituted amide group.

In addition, it is preferable that the substituents which are not electron-withdrawing groups are each independently —R', —OH, —OR', —OCOR', —$NH_2$, —$NR'_2$, —NHR', or —NHCOR. R' is a monovalent hydrocarbon group.

Examples of the monovalent hydrocarbon group represented by R' include:

monovalent chain hydrocarbon groups such as alkyl groups such as a methyl group, an ethyl group, a propyl group, and a butyl group; alkenyl groups such as an ethenyl group, a propenyl group, and a butenyl group; and alkynyl groups such as an ethynyl group, a propynyl group, and a butynyl group;

monovalent alicyclic hydrocarbon groups such as cycloalkyl groups such as a cyclopropyl group, a cyclobutyl group, a cyclopentyl group, a cyclohexyl group, a norbornyl group, and an adamantyl group; and cycloalkenyl groups such as a cyclopropenyl group, a cyclobutenyl group, a cyclopentenyl group, and a norbornenyl group; and monovalent aromatic hydrocarbon groups such as aryl groups such as a phenyl group, a tolyl group, a xylyl group, a mesityl group, a naphthyl group, a methylnaphthyl group, an anthryl group, and a methylanthryl group; and aralkyl groups such as a benzyl group, a phenethyl group, a phenylpropyl group, a naphthylmethyl group, and an anthrylmethyl group.

Among those, $R^1$ and $R^2$ are each independently preferably the hydrocarbon group (preferably a cycloalkyl group) or the hydrogen atom.

In Formula (6), L represents a divalent linking group consisting of a combination of one or more linking groups S and one or more alkylene groups which may have a substituent, or a divalent linking group consisting of one or more linking groups S.

The linking group S is a group selected from the group consisting of $*^A$—O—CO—O—$*^B$, $*^A$—CO—$*^B$, $*^A$—CO—O—$*^B$, $*^A$—O—CO—$*^B$, $*^A$—O—$*^B$, $*^A$—S—$*^B$, and $*^A$—$SO_2$—$*^B$.

It should be noted that in a case where L is a "divalent linking group consisting of a combination of one or more linking groups S and one or more alkylene groups which have no substituent, which is one form of a "divalent linking group consisting of a combination of one or more linking groups S and one or more alkylene groups which may have a substituent", it is preferable that the linking group S is a group selected from the group consisting of $*^A$—O—CO—O—$*^B$, $*^A$—CO—$*^B$, $*^A$—O—CO—$*^B$, $*^A$—O—$*^B$, $*^A$—S—$*^B$, and $*^A$—$SO_2$—$*^B$. In other words, in a case where the alkylene groups in the "divalent linking group consisting of a combination of one or more linking groups S and one or more alkylene groups which may have a substituent" are all unsubstituted alkylene groups, it is preferable that the linking group S is a group selected from the group consisting of $*^A$—O—CO—O—$*^B$, $*^A$—CO—$*^B$, $*^A$—O—CO—$*^B$, $*^A$—O—$*^B$, $*^A$—S—$*^B$, and $*^A$—$SO_2$—$*^B$.

$*^A$ represents a bonding position on the $R^3$ side in Formula (6) and $*^B$ represents a bonding position on the —$SO_3^-$ side in Formula (6).

In the divalent linking group consisting of a combination of one or more linking groups S and one or more alkylene groups which may have a substituent, only one linking group S may be present, or two or more linking groups S may be present. Similarly, with regard to the alkylene group which may have a substituent, only one alkylene group which may have a substituent may be present, or two or more alkylene groups may be present. In a case where the linking groups S are present in a plural number, the linking groups S that are present in a plural number may be the same as or different from each other. In a case where the alkylene groups are present in a plural number, the alkylene groups that are present in a plural number may be the same as or different from each other.

Furthermore, the linking groups S may be successively bonded to each other. It should be noted that it is preferable that groups selected from the group consisting of $*^A$—CO—$*^B$, $*^A$—O—CO—$*^B$, and $*^A$—O—$*^B$ are successively bonded not to form "$*^A$—O—CO—O—$*^B$". In addition, it is preferable that groups selected from the group consisting of $*^A$—CO—$*^B$ and $*^A$—O—$*^B$ are successively bonded not to form any of "$*^A$—O—CO—$*^B$" and "$*^A$—CO—O—$*^B$".

Also in the divalent linking group consisting of one or more linking groups S, only one linking group S may be present, or two or more linking groups S may be present. In a case where the linking groups S are present in a plural number, the linking groups S that are present in a plural number may be the same as or different from each other.

Also in this case, it is preferable that "$*^A$—O—CO—O—$*^B$" is not formed by the successive bonding of groups selected from the group consisting of $*^A$—CO—$*^B$, $*^A$—O—CO—$*^B$, and $*^A$—O—$*^B$. In addition, it is preferable that groups selected from the group consisting of $*^A$—CO—$*^B$ and $*^A$—O—$*^B$ are successively bonded not to form any of "$*^A$—O—CO—$*^B$" and "$*^A$—CO—O—$*^B$".

It should be noted that in any case, in L, an atom at the β-position with respect to —$SO_3^-$ is not a carbon atom having a fluorine atom as a substituent.

Furthermore, in a case where the atom at the β-position is a carbon atom, the carbon atom only needs to be not directly substituted with a fluorine atom, and the carbon atom may have a substituent having a fluorine atom (for example, a fluoroalkyl group such as a trifluoromethyl group).

In addition, the atom at the β-position is, in other words, the atom in L directly bonded to —$C(R^1)(R^2)$— in Formula (6).

Above all, it is preferable that L has only one linking group S.

That is, it is preferable that L represents a divalent linking group consisting of a combination of one linking group S and one or more alkylene groups which may have a substituent, or a divalent linking group consisting of one linking group S.

L is preferably, for example, a group represented by Formula (6-2).

$*^a$—$(CR^{2a}_2)_X$-Q-$(CR^{2b}_2)_Y$—$*^b$      (6-2)

In Formula (6-2), $*^a$ represents a bonding position to $R^3$ in Formula (6).

$*^b$ represents a bonding position to —$C(R^1)(R^2)$— in Formula (6).

X and Y each independently represent an integer of 0 to 10, and is preferably an integer of 0 to 3.

$R^{2a}$ and $R^{2b}$ each independently represent a hydrogen atom or a substituent.

In a case where $R^{2a}$'s and $R^{2b}$'s are each present in a plural number, $R^{2a}$'s which are present in a plural number and $R^{2b}$'s which are present in a plural number may each be the same as or different from each other.

It should be noted that in a case where Y is 1 or more, $R^{2b}$ in $CR^{2b}_2$ which is directly bonded to —$C(R^1)(R^2)$— in Formula (6) is other than a fluorine atom.

Q represents $*^A$—O—CO—O—$*^B$, $*^A$—CO—$*^B$, $*^A$—CO—O—$*^B$, $*^A$—O—CO—$*^B$, $*^A$—O—$*^B$, $*^A$—S—$*^B$, or $*^A$—$SO_2$—$*^B$.

It should be noted that in a case where X+Y in Formula (6-2) is 1 or more and both of $R^{2a}$ and $R^{2b}$ in Formula (6-2) are all hydrogen atoms, Q represents $*^A$—O—CO—O—$*^B$, $*^A$—CO—$*^B$, $*^A$—O—CO—$*^B$, $*^A$—O—$*^B$, $*^A$—S—$*^B$, or $*^A$—$SO_2$—$*^B$.

$*^A$ represents a bonding position on the $R^3$ side in Formula (6) and $*^B$ represents a bonding position on the —$SO_3^-$ side in Formula (6).

In Formula (6), $R^3$ represents an organic group.

The organic group is not limited as long as it has one or more carbon atoms, may be a linear group (for example, a linear alkyl group) or a branched group (for example, a branched alkyl group such as a t-butyl group), and may have a cyclic structure. The organic group may or may not have a substituent. The organic group may or may not have a heteroatom (a oxygen atom, a sulfur atom, a nitrogen atom, and/or the like).

Among those, $R^3$ is preferably an organic group having a cyclic structure. The cyclic structure may be a monocycle or a polycycle, and may have a substituent. The ring in the organic group containing a cyclic structure is preferably directly bonded to L in Formula (6).

The organic group having a cyclic structure may or may not have, for example, a heteroatom (an oxygen atom, a sulfur atom, a nitrogen atom, and/or the like). The heteroatom may be substituted with one or more of carbon atoms forming the cyclic structure.

The organic group having a cyclic structure is preferably, for example, a hydrocarbon group with a cyclic structure, a lactone ring group, or a sultone ring group. Among those, the organic group having a cyclic structure is preferably a hydrocarbon group with a cyclic structure.

The hydrocarbon group with a cyclic structure is preferably a monocyclic or polycyclic cycloalkyl group. Such a group may have a substituent.

The cycloalkyl group may be a monocycle (a cyclohexyl group or the like) or a polycycle (an adamantyl group or the like), and preferably has 5 to 12 carbon atoms.

As the lactone group and the sultone group, for example, a group formed by extracting one hydrogen atom from a ring member atom constituting the lactone structure or the sultone structure in any of the structures represented by General Formulae (LC1-1) to (LC1-21) mentioned above and the structures represented by General Formulae (SL1-1) to (SL1-3) as described above is preferable.

$Z^-$ in Formula (ZI) and $Z^-$ in Formula (ZII) may be a benzenesulfonate anion, and are each preferably a benzenesulfonate anion substituted with a branched alkyl group or a cycloalkyl group.

As $Z^-$ in Formula (ZI) and $Z^-$ in Formula (ZII), an aromatic sulfonate anion represented by Formula (SA1) is also preferable.

(SA1)

In Formula (SA1),

Ar represents an aryl group, and may further have a substituent other than a sulfonate anion and a -(D-B) group. Examples of the substituent which may be further contained include a fluorine atom and a hydroxyl group.

n represents an integer of 0 or more. n is preferably 1 to 4, more preferably 2 or 3, and still more preferably 3.

D represents a single bond or a divalent linking group. Examples of the divalent linking group include an ether group, a thioether group, a carbonyl group, a sulfoxide group, a sulfone group, a sulfonic acid ester group, an ester group, and a group consisting of a combination of two or more of these.

B represents a hydrocarbon group.

It is preferable that D is the single bond and B is an aliphatic hydrocarbon structure. It is more preferable that B is an isopropyl group or a cyclohexyl group.

Preferred examples of the sulfonium cation in Formula (ZI) and the iodonium cation in Formula (ZII) are shown below.

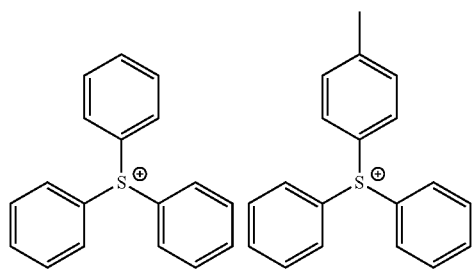

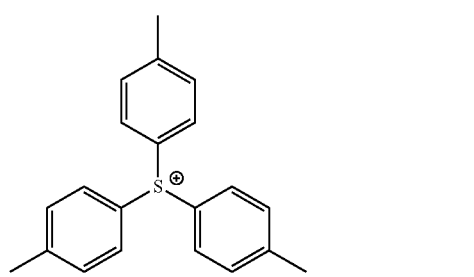

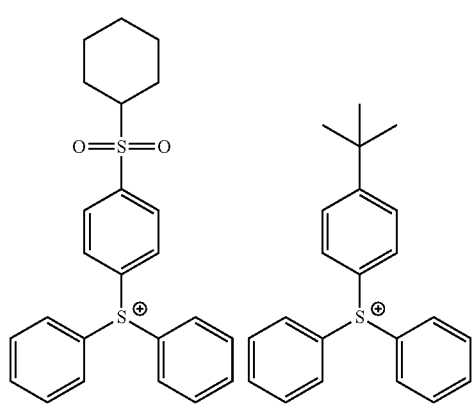

-continued

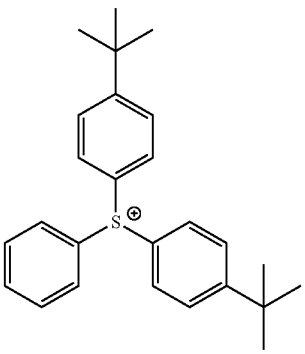

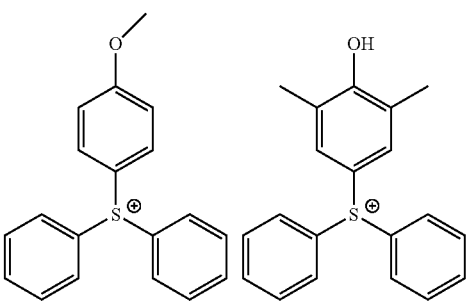

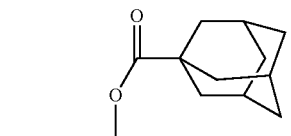

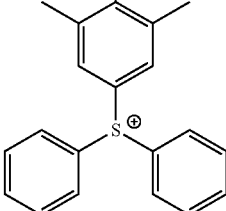

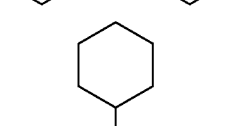

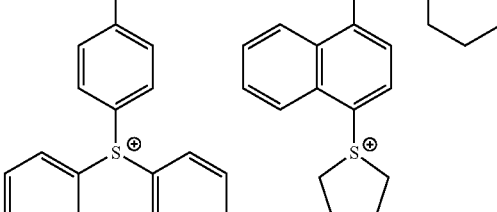

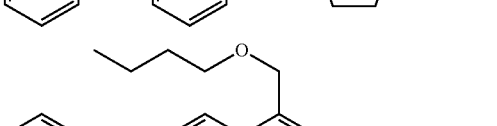

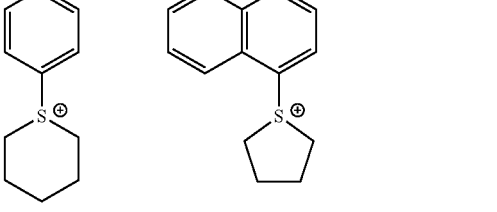

117
-continued
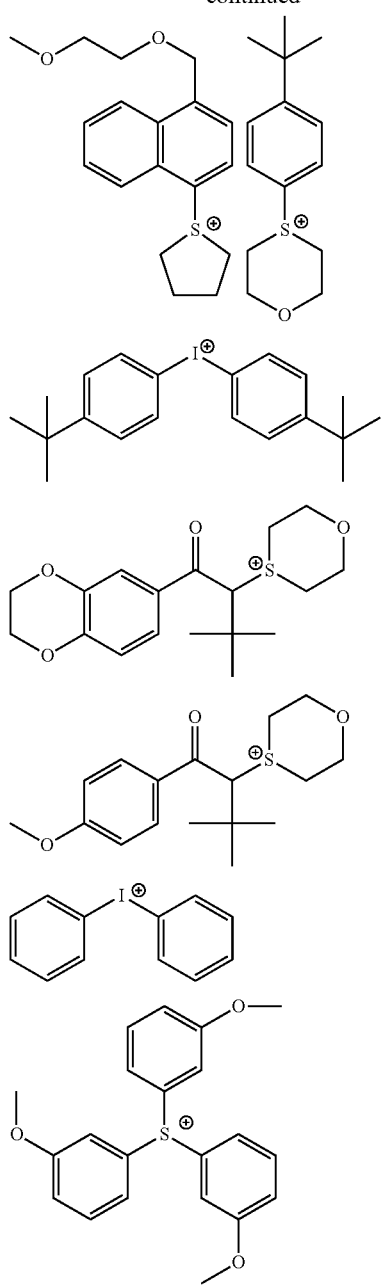
Preferred examples of the anion Z⁻ in Formula (ZI) and the anion Z⁻ in Formula (ZII) are shown below.
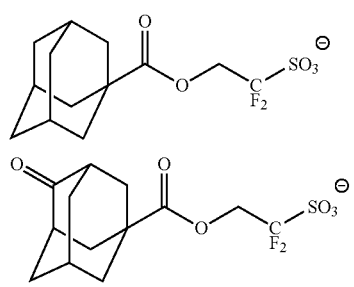
118
-continued
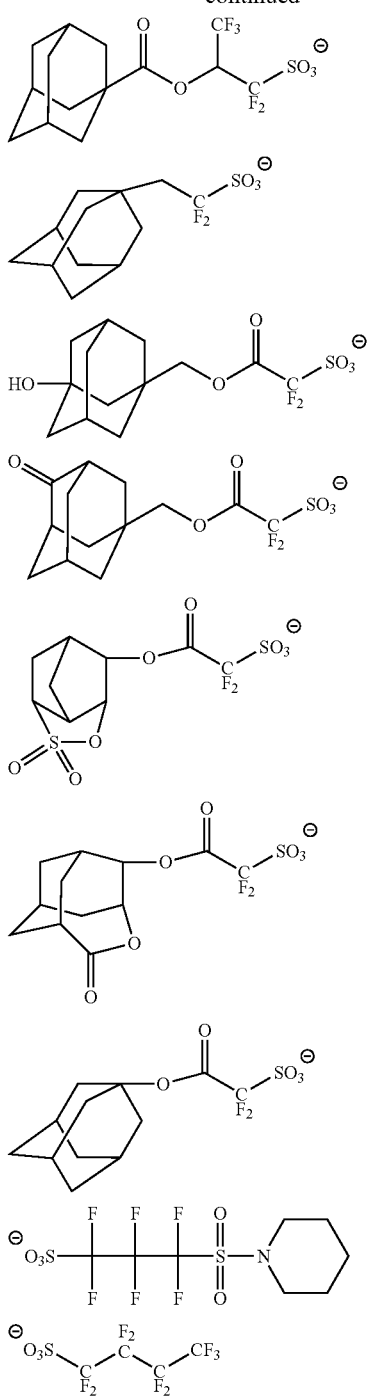

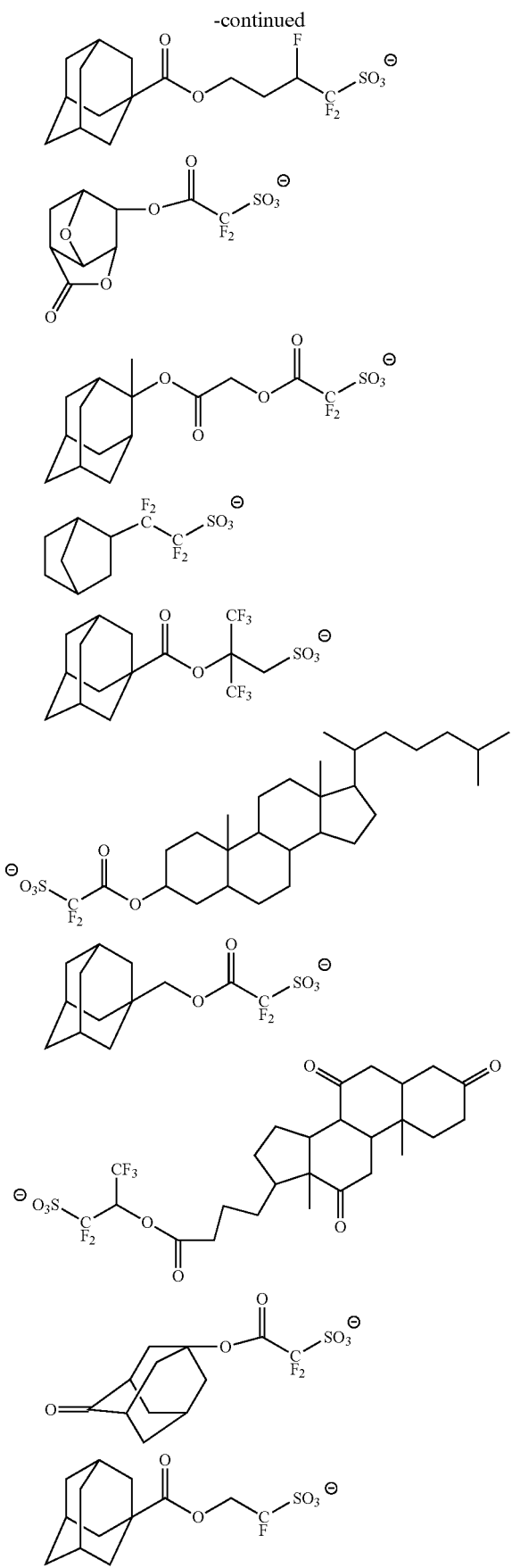
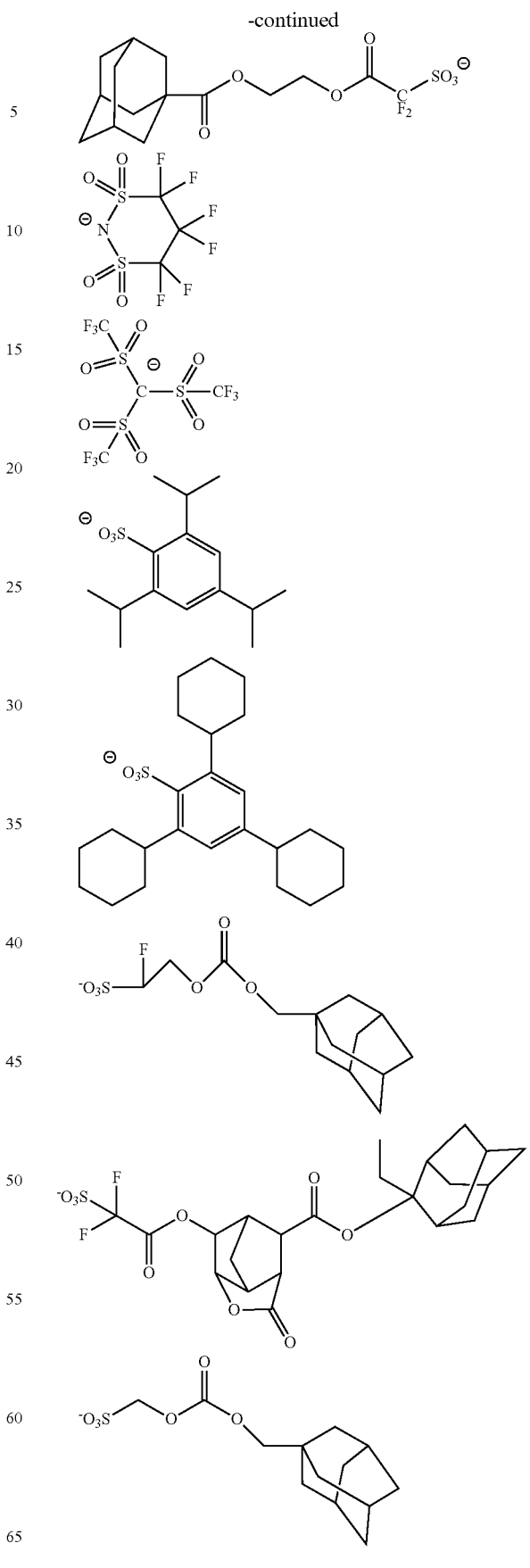

Any combination of the cations and the anions can be used as the photoacid generator.

In addition, the photoacid generator may be a so-called betaine compound having a cationic group (for example, —I$^+$— and >S$^+$—) and an anionic group (for example, —SO$_3^-$) in the same molecule, in which the cationic group and the anion group are linked via a covalent bond.

Examples of such a betaine compound include a compound (ZbI) and a compound (ZbII).

The compound (ZbI) is a compound represented by a general formula, further specified by one of $R^{201}$ to $R^{203}$ being an aryl group that has, as a substituent, any one of a group formed by extracting W from Formula (3) mentioned above, a group formed by extracting W from Formula (4) mentioned above, a group formed by extracting W from Formula (5) mentioned above, or a group formed by extracting $R^3$ from Formula (6) mentioned above in General Formula (ZaI).

The compound (ZbII) is a compound represented by a general formula, further specified by one of $R^{204}$ and $R^{205}$ being an aryl group that has, as a substituent, any one of a group formed by extracting W from Formula (3) mentioned above, a group formed by extracting W from Formula (4) mentioned above, a group formed by extracting W from Formula (5) mentioned above, or a group formed by extracting $R^3$ from Formula (6) mentioned above in General Formula (ZaII).

Examples of the photoacid generator which is a betaine compound, and the compound represented by Formula (ZIII) are shown below.

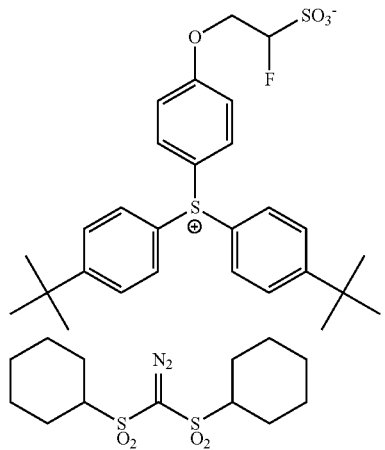

The photoacid generator may be in a form of a low-molecular-weight compound or a form incorporated into a part of a polymer. Further, a combination of the form of a low-molecular-weight compound and the form incorporated into a part of a polymer may also be used.

The photoacid generator is preferably in the form of a low-molecular-weight compound.

In a case where the photoacid generator is in the form of a low-molecular-weight compound, the molecular weight is preferably 3,000 or less, more preferably 2,000 or less, and still more preferably 1,000 or less.

In a case where the photoacid generator is included in a part of a polymer, it may be included in a part of the above-mentioned Resin X or in a resin other than Resin X.

The photoacid generators may be used singly or in combination of two or more kinds thereof.

The content of the photoacid generator (in a case where the photoacid generators are present in a plurality of kinds, a total content thereof) in the composition is preferably 0.1% to 35.0% by mass, more preferably 0.3% to 25.0% by mass, and still more preferably 0.5% to 20.0% by mass with respect to the total solid content of the composition.

In a case where a compound having the cation (ZaI-3b) or the cation (ZaI-4b) is included as the photoacid generator, the content of the photoacid generator included in the composition (in a case where the photoacid generators are present in a plurality of kinds, a total content thereof) is preferably 0.2% to 35.0% by mass, and more preferably 0.5% to 30.0% by mass with respect to the total solid content of the composition.

[Acid Diffusion Control Agent]

The composition of the embodiment of the present invention may include an acid diffusion control agent.

The acid diffusion control agent acts as a quencher that suppresses a reaction of the acid-decomposable resin in the unexposed area by excessive generated acids by trapping the acids generated from a photoacid generator and the like upon exposure. For example, a basic compound (DA), a basic compound (DB) having basicity reduced or lost upon irradiation with actinic rays or radiation, an onium salt (DC) which is a relatively weak acid with respect to an acid generator, a low-molecular-weight compound (DD) having a nitrogen atom, and a group that is eliminated by the action of an acid, an onium salt compound (DE) having a nitrogen atom in the cationic moiety, can be used as the acid diffusion control agent. In the composition of the embodiment of the present invention, a known acid diffusion control agent can be appropriately used. For example, the known compounds disclosed in paragraphs <0627> to <0664> of the specification of US2016/0070167A1, paragraphs <0095> to <0187> of the specification of US2015/0004544A1, paragraphs <0403> to <0423> of the specification of US2016/0237190A1, and paragraphs <0259> to <0328> of the specification of US2016/0274458A1 can be suitably used as the acid diffusion control agent.

<Basic Compound (DA)>

As the basic compound (DA), compounds having structures represented by Formulae (A) to (E) are preferable.

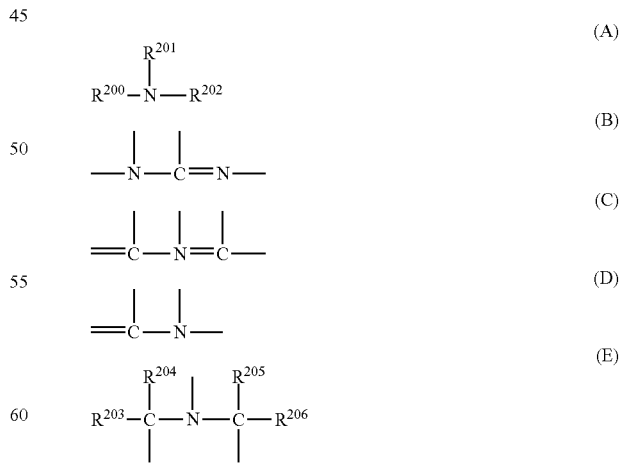

In General Formulae (A) and (E), $R^{200}$, $R^{201}$, and $R^{202}$ may be the same as or different from each other, and each independently represent a hydrogen atom, an alkyl group (preferably having 1 to 20 carbon atoms), a cycloalkyl group (preferably having 3 to 20 carbon atoms), or an aryl group (having 6 to 20 carbon atoms). $R^{201}$ and $R^{202}$ may be bonded to each other to form a ring.

$R^{203}$, $R^{204}$, $R^{205}$, and $R^{206}$ may be the same as or different from each other and each independently represent an alkyl group having 1 to 20 carbon atoms.

The alkyl group in each of General Formulae (A) and (E) may have a substituent or may be unsubstituted.

With regard to the alkyl group, the alkyl group having a substituent is preferably an aminoalkyl group having 1 to 20 carbon atoms, a hydroxyalkyl group having 1 to 20 carbon atoms, or a cyanoalkyl group having 1 to 20 carbon atoms.

The alkyl group in each of General Formulae (A) and (E) are more preferably unsubstituted.

As the basic compound (DA), guanidine, aminopyrrolidine, pyrazole, pyrazoline, piperazine, aminomorpholine, aminoalkylmorpholine, or piperidine is preferable; and a compound having an imidazole structure, a diazabicyclo structure, an onium hydroxide structure, an onium carboxylate structure, a trialkylamine structure, an aniline structure, or a pyridine structure, an alkylamine derivative having a hydroxyl group and/or an ether bond, or an aniline derivative having a hydroxyl group and/or an ether bond is more preferable.

<Basic Compound (DB) Having Basicity that is Reduced or Lost Upon Irradiation with Actinic Rays or Radiation>

The basic compound (DB) having basicity reduced or lost upon irradiation with actinic rays or radiation (hereinafter also referred to as a "compound (DB)") is a compound which has a proton-accepting functional group, and decomposes under irradiation with actinic rays or radiation to exhibit deterioration in proton-accepting properties, no proton-accepting properties, or a change from the proton-accepting properties to acidic properties.

The proton-accepting functional group refers to a functional group having a group or electron which is capable of electrostatically interacting with a proton, and for example, means a functional group with a macrocyclic structure, such as a cyclic polyether, or a functional group having a nitrogen atom having an unshared electron pair not contributing to π-conjugation. The nitrogen atom having an unshared electron pair not contributing to π-conjugation is, for example, a nitrogen atom having a partial structure represented by the following formula.

Preferred examples of the partial structure of the proton-accepting functional group include a crown ether structure, an azacrown ether structure, primary to tertiary amine structures, a pyridine structure, an imidazole structure, and a pyrazine structure.

The compound (DB) decomposes upon irradiation with actinic rays or radiation to generate a compound exhibiting deterioration in proton-accepting properties, no proton-accepting properties, or a change from the proton-accepting properties to acidic properties. Here, exhibiting deterioration in proton-accepting properties, no proton-accepting properties, or a change from the proton-accepting properties to acidic properties means a change of proton-accepting properties due to the proton being added to the proton-accepting functional group, and specifically a decrease of the equilibrium constant in chemical equilibrium in a case where a proton adduct is generated from the compound (DB) having the proton-accepting functional group and the proton.

The proton-accepting properties can be confirmed by performing pH measurement.

The acid dissociation constant pKa of the compound generated by decomposition of the compound (DB) upon irradiation with actinic rays or radiation preferably satisfies pKa<-1, and more preferably satisfies -13<pKa<-1, and still more preferably satisfies -13<pKa<-3.

Furthermore, the acid dissociation constant pKa can be determined by the above-mentioned method.

<Onium Salt (DC) which Serves as Relatively Weak Acid with Respect to Photoacid Generator>

In the composition of the embodiment of the present invention, the onium salt (DC) which is a relatively weak acid with respect to a photoacid generator can be used as the acid diffusion control agent.

In a case where the photoacid generator and the onium salt that generates an acid which is a relatively weak acid with respect to an acid generated from the photoacid generator are mixed and used, an acid generated from the photoacid generator upon irradiation with actinic rays or radiation produces an onium salt having a strong acid anion by discharging the weak acid through salt exchange in a case where the acid collides with an onium salt having an unreacted weak acid anion. In this process, the strong acid is exchanged with a weak acid having a lower catalytic ability, and thus, the acid is apparently deactivated and the acid diffusion can be controlled.

As the onium salt which serves as a relatively weak acid with respect to the photoacid generator, compounds represented by General Formulae (d1-1) to (d1-3) are preferable.

(d1-1)

(d1-2)

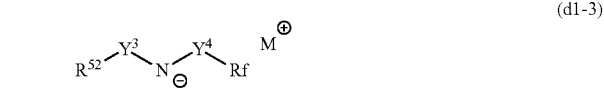

(d1-3)

In General Formulae (d1-1) to (d1-3), $R^{51}$ is a hydrocarbon group which may have a substituent. $Z^{2c}$ is a hydrocarbon group having 1 to 30 carbon atoms, may have a substituent (provided that carbon adjacent to S does not have a fluorine atom and/or a fluoroalkyl group as a substituent). In addition, it is preferable that "$Z^{2c}$—$SO_3^-$" is different from the anions represented by Formulae (3) to (6) and Formula (SA1) mentioned in the description of the photoacid generator. $R^{52}$ is an organic group (an alkyl group and the like), $Y^3$ is —$SO_2$—, a linear, branched, or cyclic alkylene group, or an arylene group, $Y^4$ is —CO— or —$SO_2$—, and Rf is a hydrocarbon group having a fluorine atom (a fluoroalkyl group and the like). $M^+$'s are each independently an ammonium cation, a sulfonium cation, or an iodonium cation.

Preferred examples of the sulfonium cation or the iodonium cation represented by $M^+$ include the sulfonium cation exemplified for General Formula (ZaI) and the iodonium cation exemplified for General Formula (ZaII).

The onium salt (DC) which is a relatively weak acid with respect to a photoacid generator may be a compound having a cationic moiety and an anionic moiety in the same molecule, in which the cationic moiety and the anionic moiety are linked by a covalent bond (hereinafter also referred to as a "compound (DCA)").

As the compound (DCA), a compound represented by any of General Formulae (C-1) to (C-3) is preferable.

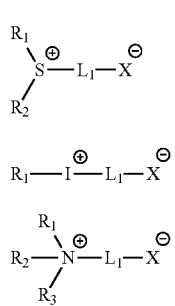

In General Formulae (C-1) to (C-3), $R_1$, $R_2$, and $R_3$ each independently represent a substituent having 1 or more carbon atoms.

$L_1$ represents a divalent linking group that links a cationic moiety with an anionic moiety, or a single bond.

—$X^-$ represents an anionic moiety selected from —$COO^-$, —$SO_3^-$, —$SO_2^-$, and —$N^-$—$R_4$. $R_4$ represents at least one of a monovalent substituent having a carbonyl group: —C(=O)—, a sulfonyl group: —S(=O)$_2$—, or a sulfinyl group: —S(=O)— at a site for linking to an adjacent N atom.

$R_1$, $R_2$, $R_3$, $R_4$, and $L_1$ may be bonded to each other to form a ring structure. In addition, in General Formula (C-3), two of $R_1$ to $R_3$ are combined with each other to represent one divalent substituent, and may be bonded to an N atom via a double bond.

Examples of the substituent having 1 or more carbon atoms in each of $R_1$ to $R_3$ include an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, and an arylaminocarbonyl group. Among those, the alkyl group, a cycloalkyl group, or the aryl group is preferable.

Examples of $L_1$ as the divalent linking group include a linear or branched alkylene group, a cycloalkylene group, an arylene group, a carbonyl group, an ether bond, an ester bond, an amide bond, an urethane bond, an urea bond, and a group formed by combination of two or more of these groups. $L_1$ is preferably the alkylene group, the arylene group, the ether bond, the ester bond, and the group formed by combination of two or more of these groups.

<Low-Molecular-Weight Compound (DD) Having Nitrogen Atom and Group that is Eliminated by Action of Acid>

The low-molecular-weight compound (DD) having a nitrogen atom and having a group that is eliminated by the action of an acid (hereinafter also referred to as a "compound (DD)") is preferably an amine derivative having a group that is eliminated by the action of an acid on the nitrogen atom.

As the group that is eliminated by the action of an acid, an acetal ester group, a carbonate group, a carbamate group, a tertiary ester group, a tertiary hydroxyl group, or a hemiaminal ether group is preferable, and the carbamate group or the hemiaminal ether group is more preferable.

The molecular weight of the compound (DD) is preferably 100 to 1,000, more preferably 100 to 700, and still more preferably 100 to 500.

The compound (DD) may have a carbamate group having a protective group on the nitrogen atom. The protective group constituting the carbamate group is represented by General Formula (d-1).

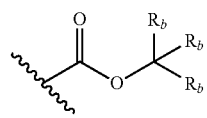

In General Formula (d-1), $R_b$'s each independently represent a hydrogen atom, an alkyl group (preferably having 1 to 10 carbon atoms), a cycloalkyl group (preferably having 3 to 30 carbon atoms), an aryl group (preferably having 3 to 30 carbon atoms), an aralkyl group (preferably having 1 to 10 carbon atoms), or an alkoxyalkyl group (preferably having 1 to 10 carbon atoms). $R_b$'s may be linked to each other to form a ring.

The alkyl group, the cycloalkyl group, the aryl group, or the aralkyl group represented by $R_b$ may be each independently substituted with a functional group such as a hydroxyl group, a cyano group, an amino group, a pyrrolidino group, a piperidino group, a morpholino group, and an oxo group, an alkoxy group, or a halogen atom. The same applies to the alkoxyalkyl group represented by $R_b$.

As $R_b$, a linear or branched alkyl group, a cycloalkyl group, or an aryl group is preferable, and the linear or branched alkyl group, or the cycloalkyl group is more preferable.

Examples of the ring formed by the mutual linking of two $R_b$'s include an alicyclic hydrocarbon, an aromatic hydrocarbon, a heterocyclic hydrocarbon, and derivatives thereof.

Examples of the specific structure of the group represented by General Formula (d-1) include, but are not limited to, the structures disclosed in paragraph <0466> of the specification of US2012/0135348A1.

The compound (DD) is preferably a compound represented by General Formula (6).

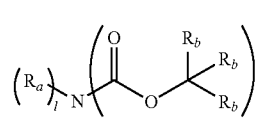

In General Formula (6), l represents an integer of 0 to 2, m represents an integer of 1 to 3, and these satisfy l+m=3.

$R_a$ represents a hydrogen atom, an alkyl group, a cycloalkyl group, an aryl group, or an aralkyl group. In a case where l is 2, two $R_a$'s may be the same as or different from each other, and the two $R_a$'s may be linked to each other to form a heterocycle with the nitrogen atom in the formula. This heterocycle may include a heteroatom other than the nitrogen atom in the formula.

$R_b$ has the same definition as $R_b$ in General Formula (d-1), and preferred examples are also the same.

In General Formula (6), the alkyl group, the cycloalkyl group, the aryl group, and the aralkyl group as $R_a$ may be each independently substituted with the same groups as the group mentioned above as a group which may be substituted in the alkyl group, the cycloalkyl group, the aryl group, and the aralkyl group as $R_b$.

Specific examples of the alkyl group, the cycloalkyl group, the aryl group, and the aralkyl group (these groups may be substituted with the groups as described above) of $R_a$ include the same groups as the specific examples as described above with respect to $R_b$.

Specific examples of the particularly preferred compound (DD) in the present invention include, but are not limited to, the compounds disclosed in paragraph <0475> of the specification of US2012/0135348A1.

<Onium Salt Compound (DE) Having Nitrogen Atom in Cationic Moiety>

The onium salt compound (DE) having a nitrogen atom in the cationic moiety (hereinafter also referred to as a "compound (DE)") is preferably a compound having a basic moiety including a nitrogen atom in the cationic moiety. The basic moiety is preferably an amino group, and more preferably an aliphatic amino group. All of the atoms adjacent to the nitrogen atom in the basic moiety are still more preferably hydrogen atoms or carbon atoms. In addition, from the viewpoint of improving basicity, it is preferable that an electron-withdrawing functional group (such as a carbonyl group, a sulfonyl group, a cyano group, and a halogen atom) is not directly linked to the nitrogen atom.

Specific preferred examples of the compound (DE) include, but are not limited to, the compounds disclosed in paragraph <0203> of the specification of US2015/0309408A1.

Preferred examples of the acid diffusion control agent are shown below.

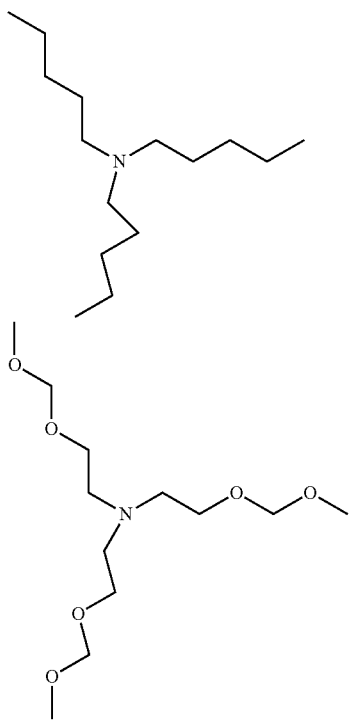

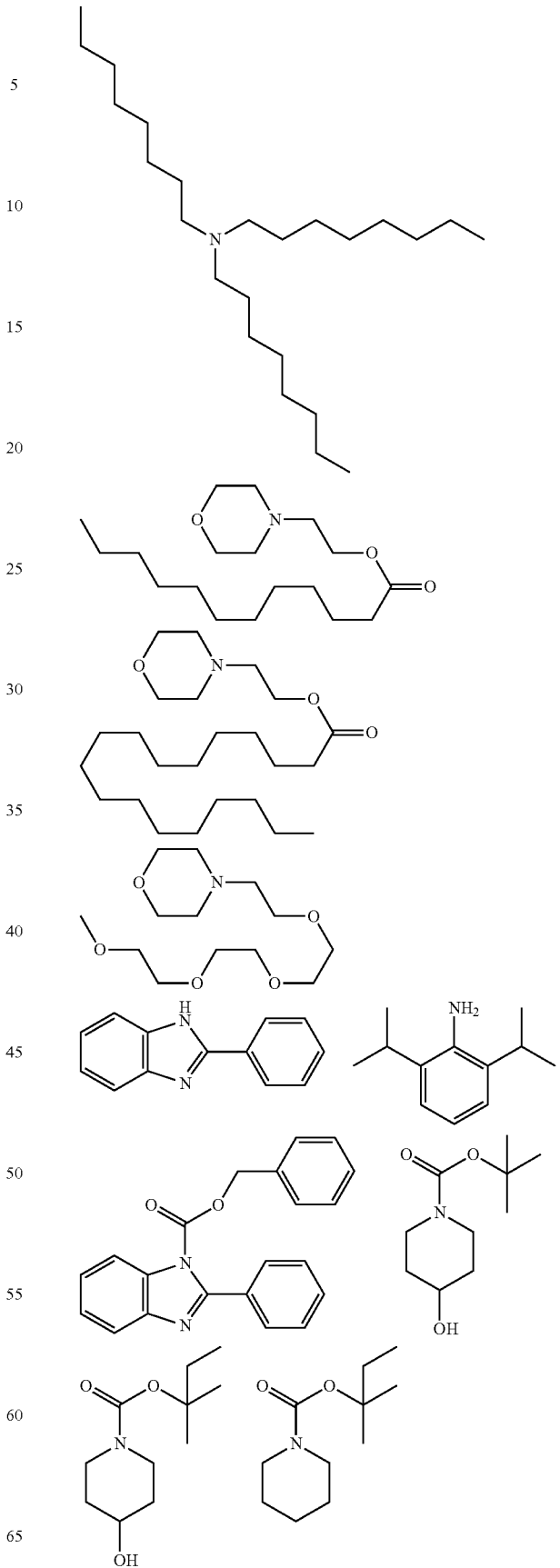

-continued

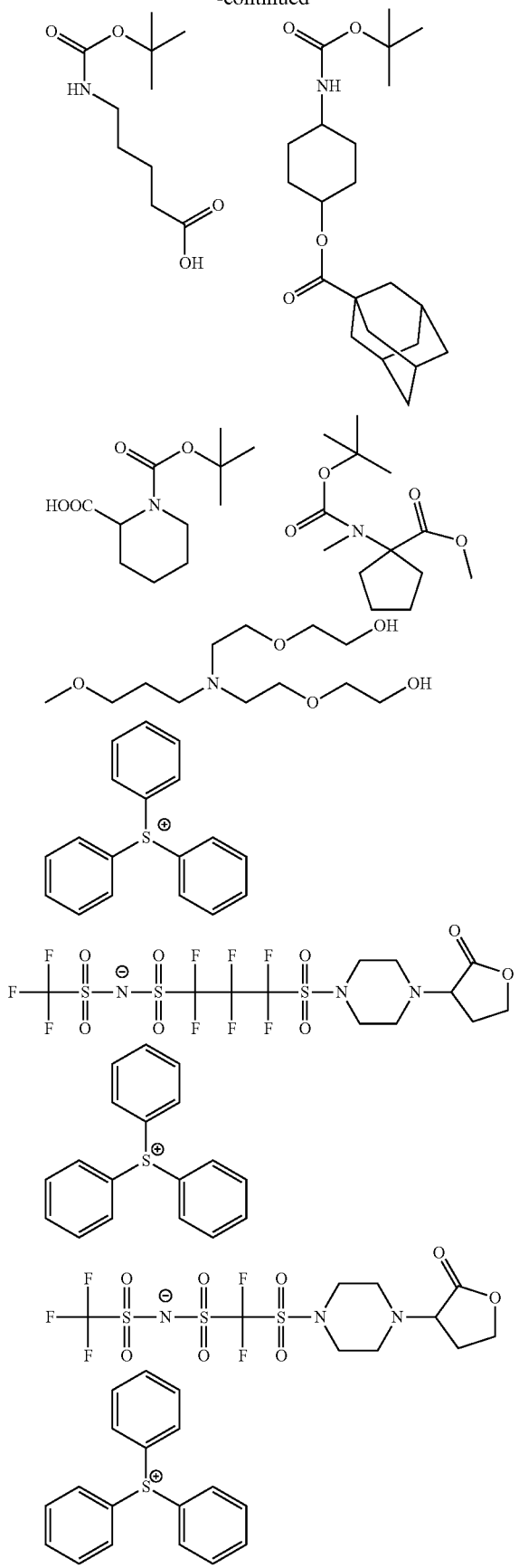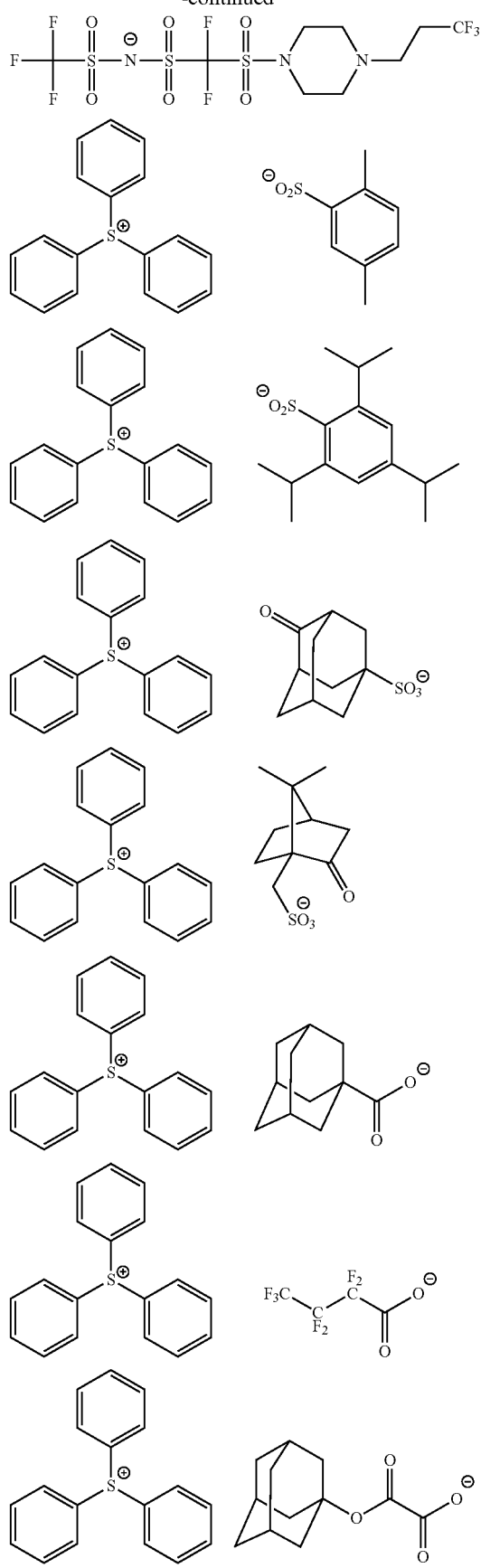

-continued
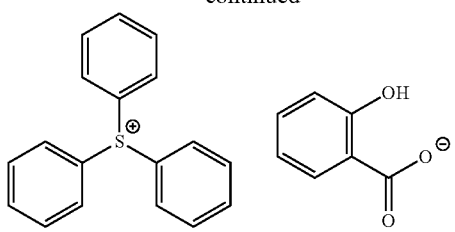
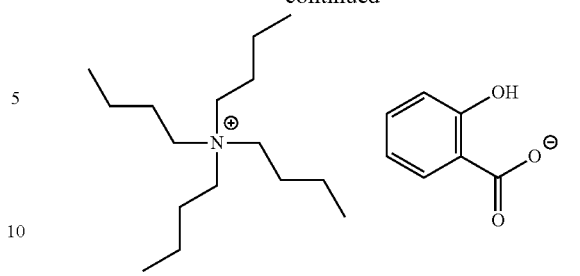
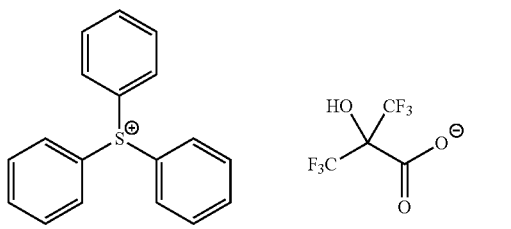
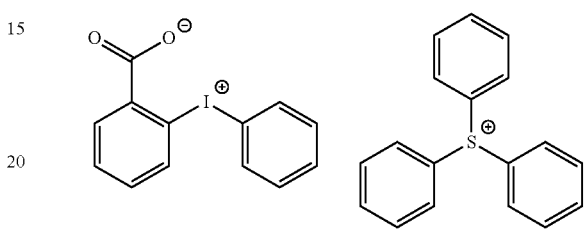
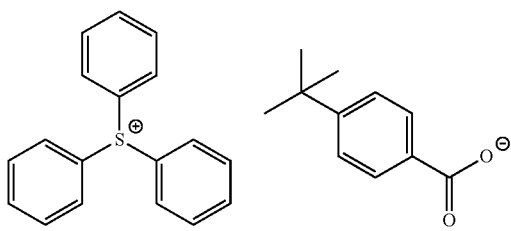
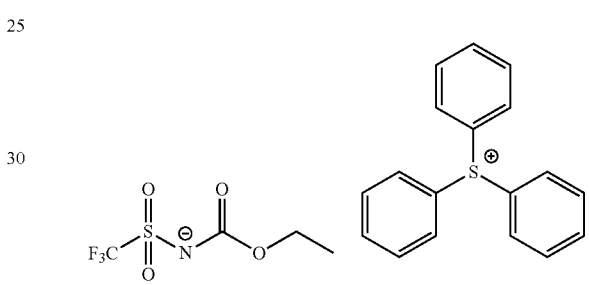
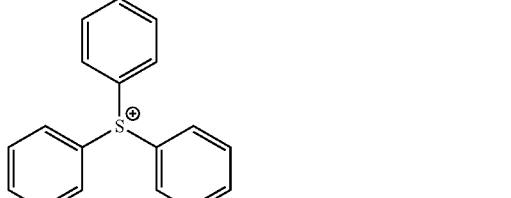
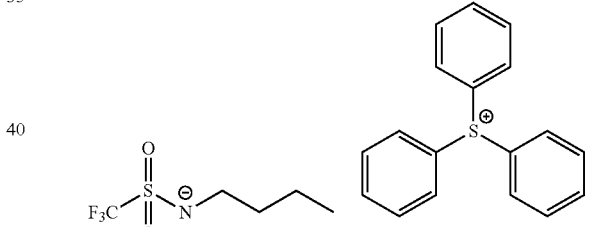
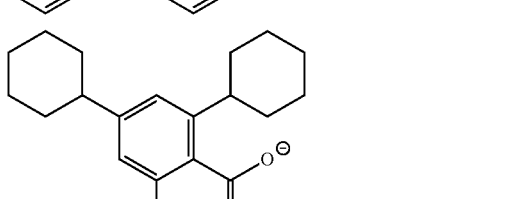
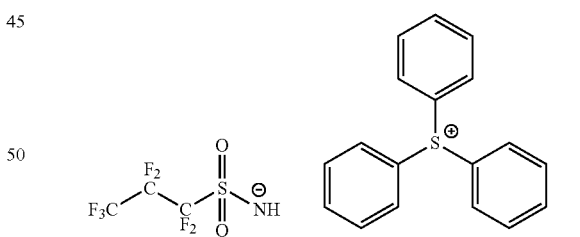
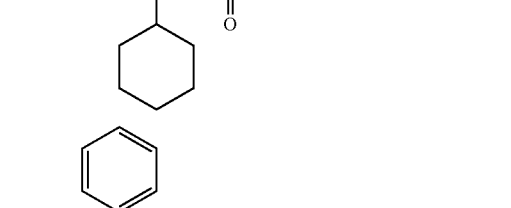
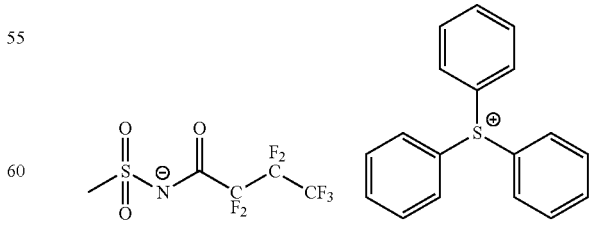
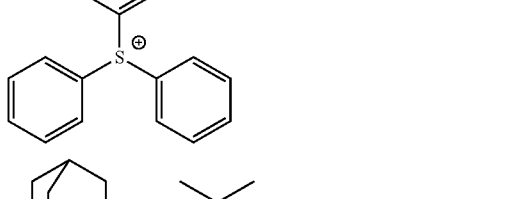
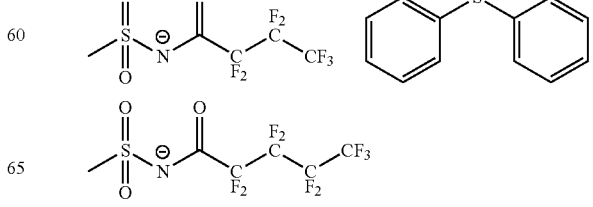

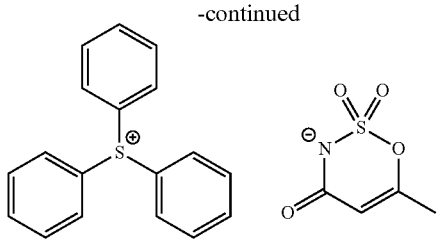

In a case where the composition of the embodiment of the present invention includes an acid diffusion control agent, the content of the acid diffusion control agent (in a case where a plurality of kinds of the acid diffusion control agents are present, a total content thereof) is preferably 0.1% to 11.0% by mass, more preferably 0.1% to 10.0% by mass, still more preferably 0.1% to 8.0% by mass, and particularly preferably 0.1% to 5.0% by mass with respect to the total solid content of the composition.

In the composition of the embodiment of the present invention, the acid diffusion control agents may be used singly or in combination of two or more kinds thereof

[Hydrophobic Resin]

The composition of the embodiment of the present invention may include a hydrophobic resin different from the resin (A), in addition to the resin (A).

Although it is preferable that the hydrophobic resin is designed to be unevenly distributed on a surface of the resist film, it does not necessarily need to have a hydrophilic group in the molecule as different from the surfactant, and does not need to contribute to uniform mixing of polar materials and non-polar materials.

Examples of the effect of addition of the hydrophobic resin include a control of static and dynamic contact angles of a surface of the resist film with respect to water and suppression of out gas.

The hydrophobic resin preferably has any one or more of a "fluorine atom", a "silicon atom", and a "$CH_3$ partial structure which is contained in a side chain moiety of a resin" from the viewpoint of uneven distribution on the film surface layer, and more preferably has two or more kinds thereof. Incidentally, the hydrophobic resin preferably has a hydrocarbon group having 5 or more carbon atoms. These groups may be contained in the main chain of the resin or may be substituted in a side chain.

In a case where hydrophobic resin includes a fluorine atom and/or a silicon atom, the fluorine atom and/or the silicon atom in the hydrophobic resin may be included in the main chain or a side chain of the resin.

In a case where the hydrophobic resin includes a fluorine atom, as a partial structure having a fluorine atom, an alkyl group having a fluorine atom, a cycloalkyl group having a fluorine atom, or an aryl group having a fluorine atom is preferable.

The alkyl group having a fluorine atom (preferably having 1 to 10 carbon atoms, and more preferably having 1 to 4 carbon atoms) is a linear or branched alkyl group in which at least one hydrogen atom is substituted with a fluorine atom, and the alkyl group may further have a substituent other than a fluorine atom.

The cycloalkyl group having a fluorine atom is a monocyclic or polycyclic cycloalkyl group in which at least one hydrogen atom is substituted with a fluorine atom, and may further have a substituent other than a fluorine atom.

Examples of the aryl group having a fluorine atom include an aryl group such as a phenyl group and a naphthyl group, in which at least one hydrogen atom is substituted with a fluorine atom, and the aryl group may further have a substituent other than a fluorine atom.

Examples of the repeating unit having a fluorine atom or a silicon atom include those exemplified in paragraph <0519> of US2012/0251948A1.

Furthermore, as described above, it is also preferable that the hydrophobic resin includes a $CH_3$ partial structure in a side chain moiety.

Here, the $CH_3$ partial structure contained in the side chain moiety in the hydrophobic resin includes a $CH_3$ partial structure contained in an ethyl group, a propyl group, and the like.

On the other hand, a methyl group bonded directly to the main chain of the hydrophobic resin (for example, an α-methyl group in the repeating unit having a methacrylic acid structure) makes only a small contribution of uneven distribution on the surface of the hydrophobic resin due to the effect of the main chain, and it is therefore not included in the $CH_3$ partial structure in the present invention.

With regard to the hydrophobic resin, reference can be made to the description in paragraphs <0348> to <0415> of JP2014-010245A, the contents of which are incorporated herein by reference.

Furthermore, the resins described in JP2011-248019A, JP2010-175859A, and JP2012-032544A, in addition to those above, can also be preferably used as the hydrophobic resin.

Preferred examples of a monomer corresponding to the repeating unit constituting the hydrophobic resin are shown below.

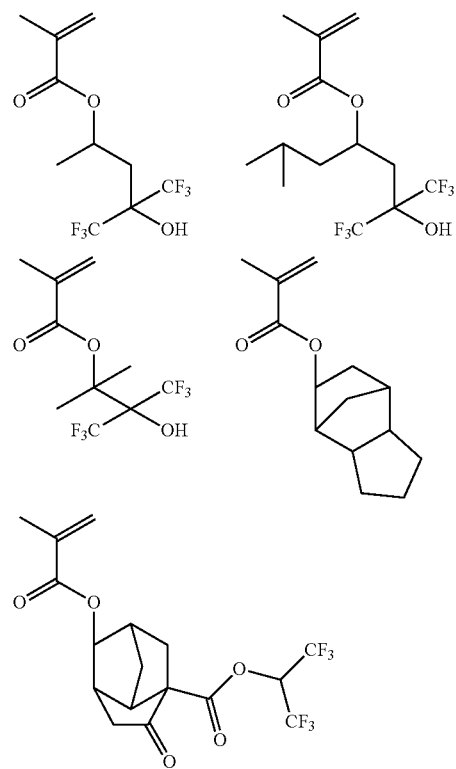

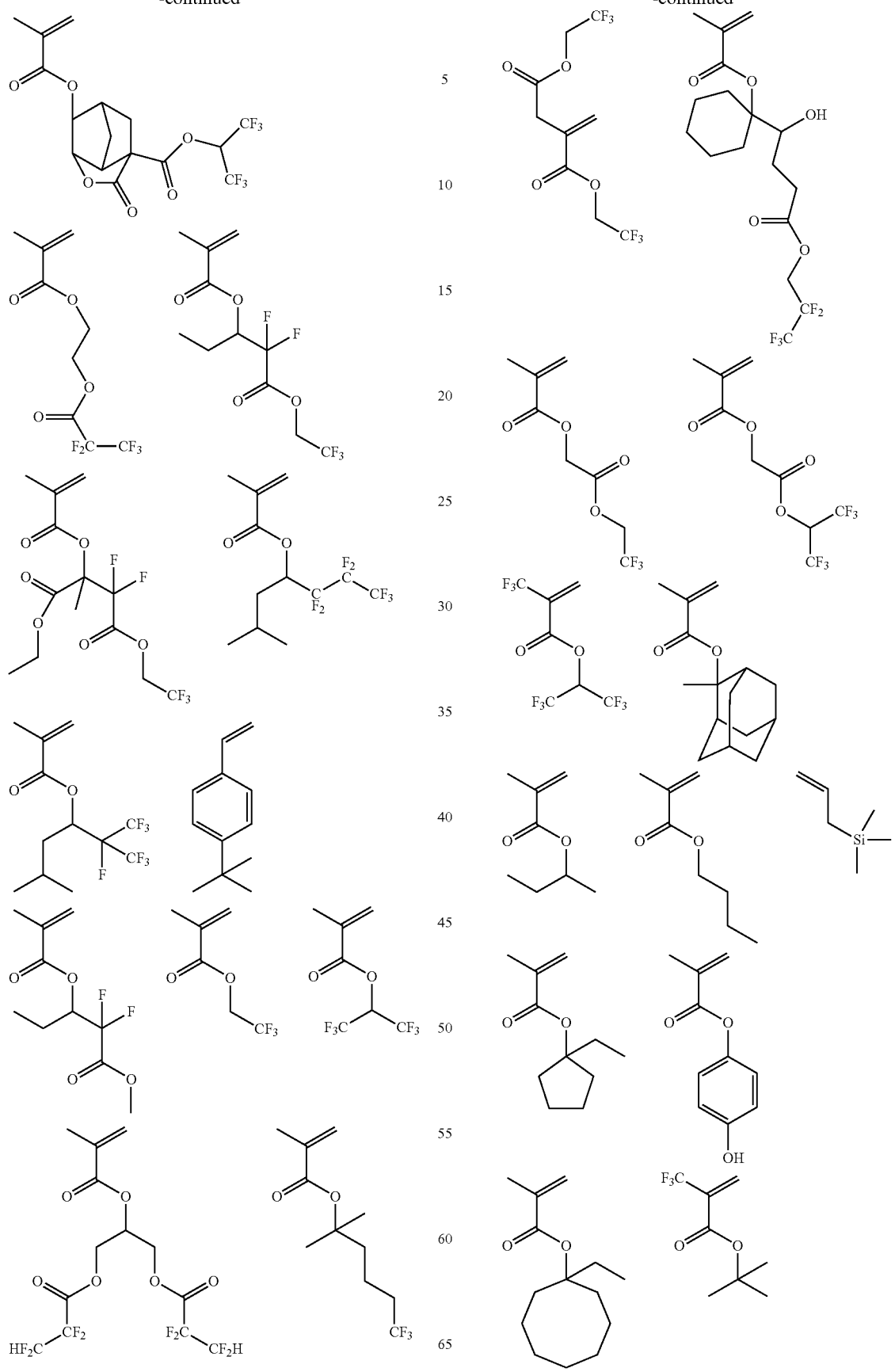

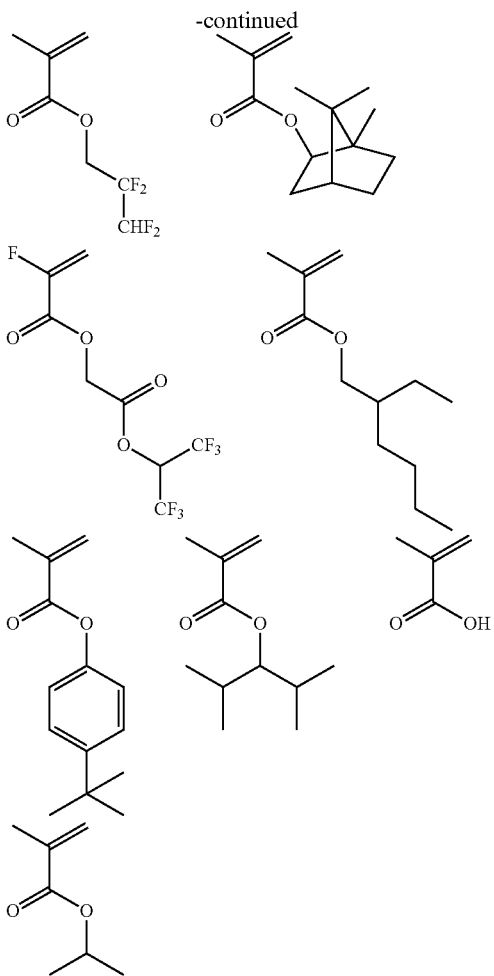

-continued

In a case where the composition of the embodiment of the present invention includes a hydrophobic resin, the content of the hydrophobic resin is preferably 0.01% to 20% by mass, more preferably 0.1% to 15% by mass, still more preferably 0.1% to 10% by mass, and particularly preferably 0.1% to 6% by mass with respect to the total solid content of the composition.

[Surfactant]

The composition of the embodiment of the present invention may include a surfactant. By incorporation of the surfactant, it is possible to form a pattern having more excellent adhesiveness and fewer development defects.

As the surfactant, fluorine-based and/or silicon-based surfactants are preferable.

Examples of the fluorine- and/or silicon-based surfactants include the surfactants described in paragraph <0276> of US2008/0248425A. In addition, EFTOP EF301 or EF303 (manufactured by Shin-Akita Chemical Co., Ltd.); FLUO-RAD FC430, 431, or 4430 (manufactured by Sumitomo 3M Japan Limited); MEGAFACE F-171, F-173, F-176, F-189, F-113, F-110, F-177, F-120, or R08 (manufactured by DIC Corporation); SURFLON S-382, SC101, 102, 103, 104, 105, or 106 (manufactured by Asahi Glass Co., Ltd.); TROYSOL S-366 (manufactured by Troy Corporation); GF-300 or GF-150 (manufactured by Toagosei Co., Ltd.); SURFLON S-393 (manufactured by AGC Seimi Chemical Co., Ltd.); EFTOP EF121, EF122A, EF122B, RF122C, EF125M, EF135M, EF351, EF352, EF801, EF802, or EF601 (manufactured by JEMCO Inc.); PF636, PF656, PF6320, or PF6520 (manufactured by OMNOVA Solutions Inc.); KH-20 (manufactured by Asahi Kasei Corporation); or FTX-204G, 208G, 218G, 230G, 204D, 208D, 212D, 218D, or 222D (manufactured by NEOS COMPANY LIMITED) may be used. In addition, a polysiloxane polymer, KP-341 (manufactured by Shin-Etsu Chemical Co., Ltd.), can also be used as the silicon-based surfactant.

Moreover, in addition to the known surfactants as shown above, a surfactant may be synthesized using a fluoroaliphatic compound manufactured using a telomerization method (also referred to as a telomer method) or an oligomerization method (also referred to as an oligomer method). Specifically, a polymer including a fluoroaliphatic group derived from fluoroaliphatic compound may be used as the surfactant. This fluoroaliphatic compound can be synthesized, for example, by the method described in JP2002-90991A.

As the polymer having a fluoroaliphatic group, a copolymer of a monomer having a fluoroaliphatic group and (poly(oxyalkylene))acrylate and/or (poly(oxyalkylene)) methacrylate is preferable, and the polymer may be unevenly distributed or block-copolymerized. Furthermore, examples of the poly(oxyalkylene) group include a poly (oxyethylene) group, a poly(oxypropylene) group, and a poly(oxybutylene) group, and the group may also be a unit such as those having alkylenes having different chain lengths within the same chain length such as poly(block-linked oxyethylene, oxypropylene, and oxyethylene) and poly(block-linked oxyethylene and oxypropylene). In addition, the copolymer of a monomer having a fluoroaliphatic group and (poly(oxyalkylene))acrylate (or methacrylate) is not limited only to a binary copolymer but may also be a ternary or higher copolymer obtained by simultaneously copolymerizing monomers having two or more different fluoroaliphatic groups or two or more different (poly(oxyalkylene)) acrylates (or methacrylates).

Examples of a commercially available surfactant thereof include MEGAFACE F-178, F-470, F-473, F-475, F-476, and F-472 (manufactured by DIC Corporation), a copolymer of acrylate (or methacrylate) having a $C_6F_{13}$ group and (poly(oxyalkylene))acrylate (or methacrylate), and a copolymer of acrylate (or methacrylate) having a $C_3F_7$ group, (poly(oxyethylene))acrylate (or methacrylate), and (poly (oxypropylene))acrylate (or methacrylate).

In addition, another surfactant other than the fluorine-based and/or silicon-based surfactants, described in paragraph <0280> of US2008/0248425A, may also be used.

These surfactants may be used singly or in combination of two or more kinds thereof.

The content of the surfactant is preferably 0.0001% to 2% by mass and more preferably 0.0005% to 1% by mass with respect to the total solid content of the composition of the embodiment of the present invention.

[Solvent]

The composition of the embodiment of the present invention may include a solvent.

The solvent preferably includes at least one solvent of (M1) propylene glycol monoalkyl ether carboxylate, or (M2) at least one selected from the group consisting of a propylene glycol monoalkyl ether, a lactic acid ester, an acetic acid ester, an alkoxypropionic acid ester, a chain ketone, a cyclic ketone, a lactone, and an alkylene carbonate as a solvent. Further, this solvent may further include components other than the components (M1) and (M2).

The present inventors have found that by using such a solvent and the above-mentioned resin (A) in combination, a pattern having a small number of development defects can be formed while improving the coating property of the composition. A reason therefor is not necessarily clear, but the present inventors have considered that since these solvents have a good balance among the solubility, the boiling point, and the viscosity of the resin (A), the unevenness of the film thickness of a composition film, the generation of precipitates during spin coating, and the like can be suppressed.

As the component (M1), at least one selected from the group consisting of propylene glycol monomethyl ether acetate (PGMEA), propylene glycol monomethyl ether propionate, and propylene glycol monoethyl ether acetate is preferable, and propylene glycol monomethyl ether acetate (PGMEA) is more preferable.

As the component (M2), the following ones are preferable.

As the propylene glycol monoalkyl ether, propylene glycol monomethyl ether (PGME), or propylene glycol monoethyl ether (PGEE) is preferable.

As the lactic acid ester, ethyl lactate, butyl lactate, or propyl lactate is preferable.

As the acetic acid ester, methyl acetate, ethyl acetate, butyl acetate, isobutyl acetate, propyl acetate, isoamyl acetate, methyl formate, ethyl formate, butyl formate, propyl formate, or 3-methoxybutyl acetate is preferable.

In addition, butyl butyrate is also preferable.

As the alkoxypropionic acid ester, methyl 3-methoxypropionate (MMP) or ethyl 3-methoxypropionate (EEP) is preferable.

As the chain ketone, 1-octanone, 2-octanone, 1-nonanone, 2-nonanone, acetone, 2-heptanone, 4-heptanone, 1-hexanone, 2-hexanone, diisobutyl ketone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, or methyl amyl ketone is preferable.

As the cyclic ketone, methyl cyclohexanone, isophorone, or cyclohexanone is preferable.

As the lactone, γ-butyrolactone is preferable.

As the alkylene carbonate, propylene carbonate is preferable.

As the component (M2), propylene glycol monomethyl ether (PGME), ethyl lactate, ethyl 3-ethoxypropionate, methyl amyl ketone, cyclohexanone, butyl acetate, pentyl acetate, γ-butyrolactone, or propylene carbonate is more preferable.

In addition to the components, it is preferable to use an ester-based solvent having 7 or more carbon atoms (preferably 7 to 14 carbon atoms, more preferably 7 to 12 carbon atoms, and still more preferably 7 to 10 carbon atoms) and 2 or less heteroatoms.

As the ester-based solvent having 7 or more carbon atoms and 2 or less heteroatoms, amyl acetate, 2-methylbutyl acetate, 1-methylbutyl acetate, hexyl acetate, pentyl propionate, hexyl propionate, butyl propionate, isobutyl isobutyrate, heptyl propionate, or butyl butanoate is preferable, and isoamyl acetate is more preferable.

As the component (M2), a component having a flash point (hereinafter also referred to as fp) of 37° C. or higher is preferably used. As such a component (M2), propylene glycol monomethyl ether (fp: 47° C.), ethyl lactate (fp: 53° C.), ethyl 3-ethoxypropionate (fp: 49° C.), methyl amyl ketone (fp: 42° C.), cyclohexanone (fp: 44° C.), pentyl acetate (fp: 45° C.), methyl 2-hydroxyisobutyrate (fp: 45° C.), γ-butyrolactone (fp: 101° C.), or propylene carbonate (fp: 132° C.) is preferable. Among those, propylene glycol monoethyl ether, ethyl lactate, pentyl acetate, or cyclohexanone is more preferable, and propylene glycol monoethyl ether or ethyl lactate is still more preferable.

In addition, the "flash point" herein means the value described in a reagent catalog of Tokyo Chemical Industry Co., Ltd. or Sigma-Aldrich Co. LLC.

The mixing mass ratio (M1/M2) of the content of the component (M1) to the component (M2) in the mixed solvent is preferably in the range of "100/0" to "15/85", and more preferably in the range of "100/0" to "40/60". In a case where such a configuration is adopted and used, it is possible to further reduce the number of development defects.

As described above, the solvent may further include components other than the components (M1) and (M2). In this case, the content of the components other than the components (M1) and (M2) is preferably in the range of 30% by mass or less, and more preferably 5% to 30% by mass with respect to the total mass of the solvent.

The content of the solvent in the composition of the embodiment of the present invention is preferably set so that the concentration of solid contents is 0.5% to 30% by mass, and more preferably set so that the concentration of solid contents is 1% to 20% by mass. With this content, the coating property of the composition of the embodiment of the present invention is more excellent.

<Other Additives>

The composition of the embodiment of the present invention may further include a resin other than those described above, a crosslinking agent, an acid proliferation agent, a dye, a plasticizer, a photosensitizer, a light absorber, an alkali-soluble resin, a dissolution inhibitor, a dissolution accelerator, or the like.

[Resist Film and Pattern Forming Method]

A resist film can be formed using the composition, and a pattern can further be formed.

The procedure of the pattern forming method using the composition is not particularly limited, but preferably has the following steps.

Step 1: a step of forming a resist film on a support (substrate), using the composition, Step 2: a step of exposing the resist film, and Step 3: a step of developing the exposed resist film using a developer to form a pattern.

Hereinafter, the procedure of each of the steps will be described in detail.

[Step 1: Resist Film Forming Step]

The step 1 is a step of forming a resist film on a support (on a substrate), using a composition.

The definition of the composition is as described above.

Hereinafter, a specific example of the method for preparing the composition will be shown.

In the composition used in the pattern forming method of the embodiment of the present invention, it is preferable that the content of metal atoms is reduced.

Hereinafter, first, a specific example of a method for reducing the content of the metal atoms in the composition will be described, and then a specific example of a method for preparing the composition will be described.

Examples of the method for reducing the content of the metal atoms in the composition include a method for adjusting the content by filtration using a filter. As for the filter pore diameter, the pore size is preferably less than 100 nm, more preferably 10 nm or less, and still more preferably 5 nm or less. As the filter, a polytetrafluoroethylene-made, polyethylene-made, or nylon-made filter is preferable. The filter may include a composite material in which the filter material is combined with an ion exchange medium. As the filter, a filter which has been washed with an organic solvent in advance may be used. In the step of filtration using a filter, plural kinds of filters connected in series or in parallel may be used. In a case of using the plural kinds of filters, a combination of filters having different pore diameters and/or materials may be used. In addition, various materials may be filtered plural times, and the step of filtering plural times may be a circulatory filtration step.

In addition, examples of a method for reducing the content of the metal atoms in the composition include a method of selecting raw materials having a low content of metals as raw materials constituting various materials in the composition, a method of subjecting raw materials constituting various materials in the composition to filtration using a filter, and a method of performing distillation under the condition for suppressing the contamination as much as possible by, for example, lining the inside of a device with TEFLON (registered trademark).

In addition, as the method for reducing the content of the metal atoms in the composition, removal with an adsorbing material may be performed, in addition to the above-mentioned filter filtration, and the filter filtration and the adsorbing material may be used in combination. As the adsorbing material, known adsorbing materials can be used, and for example, inorganic adsorbing materials such as silica gel and zeolite, and organic adsorbing materials such as activated carbon can be used.

In addition, in order to reduce the content of the metal atoms in the composition, it is necessary to prevent the incorporation of metal impurities in the production process. Sufficient removal of metal impurities from a production device can be confirmed by measuring the content of metal components included in a washing liquid used to wash the production device.

Next, a specific example of the method for preparing the composition will be described.

In the production of the composition, for example, it is preferable to dissolve various components such as the resin and the photoacid generator as described above in a solvent, and then perform filtration (which may be circulatory filtration) using a plurality of filters having different materials. For example, it is preferable to connect a polyethylene-made filter with a pore diameter of 50 nm, a nylon-made filter with a pore diameter of 10 nm, and a polyethylene-made filter with a pore diameter of 3 to 5 nm in permuted connection, and then perform filtration. As for the filtration, a method of performing circulatory filtration twice or more is also preferable. Further, the filtration step also has an effect of reducing the content of the metal atoms in the composition. A smaller pressure difference among the filters is more preferable, and the pressure difference is generally 0.1 MPa or less, preferably 0.05 MPa or less, and more preferably 0.01 MPa or less. A smaller pressure difference between the filter and the charging nozzle is also preferable, and the pressure difference is generally 0.5 MPa or less, preferably 0.2 MPa or less, and more preferably 0.1 MPa or less.

In addition, as a method for performing circulatory filtration using a filter in the production of the composition, for example, a method of performing circulatory filtration twice or more using a polytetrafluoroethylene-made filter having a pore diameter of 50 nm is also preferable.

It is preferable to subject the inside of a device for producing the composition to gas replacement with an inert gas such as nitrogen. With this, it is possible to suppress dissolution of an active gas such as oxygen in the composition.

The composition is filtered by a filter and then charged into a clean container. It is preferable that the composition charged in the container is subjected to cold storage. This enables performance deterioration caused by the lapse of time to be suppressed. A shorter time from completion of the charge of the composition into the container to initiation of cold storage is more preferable, and the time is generally 24 hours or shorter, preferably 16 hours or shorter, more preferably 12 hours or shorter, and still more preferably 10 hours or shorter. The storage temperature is preferably 0° C. to 15° C., more preferably 0° C. to 10° C., and still more preferably 0° C. to 5° C.

Next, a method of forming a resist film on a substrate using the composition will be described.

Examples of the method of forming a resist film on a substrate using the composition include a method of applying the composition onto a substrate.

The composition can be applied onto a substrate (for example, silicon and silicon dioxide coating) as used in the manufacture of integrated circuit elements by a suitable application method such as ones using a spinner or a coater. As the application method, spin application using a spinner is preferable. The rotation speed upon spin application using a spinner is preferably 1,000 to 3,000 rpm.

After applying the composition, the substrate may be dried to form a resist film. In addition, various underlying films (an inorganic film, an organic film, or an antireflection film) may be formed on the underlayer of the resist film.

Examples of the drying method include a method of heating and drying. The heating may be performed using a unit included in an ordinary exposure machine and/or an ordinary development machine, and may also be performed using a hot plate or the like. The heating temperature is preferably 80° C. to 150° C., more preferably 80° C. to 140° C., and still more preferably 80° C. to 130° C. The heating time is preferably 30 to 1,000 seconds, more preferably 60 to 800 seconds, and still more preferably 60 to 600 seconds.

The film thickness of the resist film is not particularly limited, but is preferably 10 to 150 nm, and more preferably 15 to 100 nm, from the viewpoint that a fine pattern having higher accuracy can be formed.

Moreover, a topcoat may be formed on the upper layer of the resist film, using the topcoat composition.

It is preferable that the topcoat composition is not mixed with the resist film and can be uniformly applied onto the upper layer of the resist film.

Furthermore, it is preferable to dry the resist film before forming the topcoat. Then, the topcoat composition can be applied onto the obtained resist film by the same unit as the method for forming a resist film, and further dried to form a topcoat.

The film thickness of the topcoat is preferably 10 to 200 nm, and more preferably 20 to 100 nm.

The topcoat composition includes, for example, a resin, an additive, and a solvent.

As the resin, the same resin as the above-mentioned hydrophobic resin can be used. The content of the resin is preferably 50% to 99.9% by mass, and more preferably 60% to 99.7% by mass with respect to the total solid content of the topcoat composition.

As the additive, the above-mentioned acid diffusion control agent can be used. In addition, a compound having a radical trapping group such as a compound having an N-oxy free radical group can also be used. Examples of such a compound include a [4-(benzoyloxy)-2,2,6,6-tetramethylpiperidinooxy] radical. The content of the additive is preferably 0.01% to 20% by mass, and more preferably 0.1% to 15% by mass with respect to the total solid content of the topcoat composition.

It is preferable that the solvent does not dissolve a resist film, and examples of the solvent include an alcohol-based solvent (4-methyl-2-pentanol and the like), an ether-based solvent (diisoamyl ether and the like), an ester-based solvent, a fluorine-based solvent, and a hydrocarbon-based solvent (n-decane and the like).

The content of the solvent in the topcoat composition is preferably set so that the concentration of solid contents is 0.5% to 30% by mass, and more preferably set so that the concentration of solid contents is 1% to 20% by mass.

In addition, the topcoat composition may include a surfactant in addition to the above-mentioned additive, and as the surfactant, a surfactant which may be included in the composition of the embodiment of the present invention can be used. The content of the surfactant is preferably 0.0001% to 2% by mass, and more preferably 0.0005% to 1% by mass with respect to the total solid content of the topcoat composition.

In addition, the topcoat is not particularly limited, a topcoat known in the related art can be formed by the methods known in the related art, and a topcoat can be formed in accordance with, for example, the description in paragraphs <0072> to <0082> of JP2014-059543A.

It is preferable that a topcoat including a basic compound as described in JP2013-061648A, for example, is formed on a resist film. Specific examples of the basic compound which can be included in the topcoat include a basic compound which may be included in the composition of the embodiment of the present invention.

In addition, the topcoat preferably includes a compound which includes at least one group or bond selected from the group consisting of an ether bond, a thioether bond, a hydroxyl group, a thiol group, a carbonyl bond, and an ester bond.

[Step 2: Exposing Step]

The step 2 is a step of exposing the resist film.

Examples of the exposing method include a method of irradiating a resist film thus formed with actinic rays or radiation through a predetermined mask.

Examples of the actinic rays or radiation include infrared light, visible light, ultraviolet light, far ultraviolet light, extreme ultraviolet light, X-rays, and electron beams, preferably a far ultraviolet light having a wavelength of 250 nm or less, more preferably a far ultraviolet light having a wavelength of 220 nm or less, and particularly preferably a far ultraviolet light having a wavelength of 1 to 200 nm, specifically, KrF excimer laser (248 nm), ArF excimer laser (193 nm), $F_2$ excimer laser (157 nm), EUV (13 nm), X-rays, and electron beams.

It is preferable to perform baking (heating) before performing development after the exposure. The baking accelerates a reaction in the exposed area, and the sensitivity and the pattern shape are improved.

The heating temperature is preferably 80° C. to 150° C., more preferably 80° C. to 140° C., and still more preferably 80° C. to 130° C.

The heating time is preferably 10 to 1,000 seconds, more preferably 10 to 180 seconds, and still more preferably 30 to 120 seconds.

The heating may be performed using a unit included in an ordinary exposure machine and/or an ordinary development machine, and may also be performed using a hot plate or the like.

This step is also referred to as a post-exposure baking.

[Step 3: Developing Step]

The step 3 is a step of developing the exposed resist film using a developer to form a pattern.

Examples of the developing method include a method in which a substrate is immersed in a tank filled with a developer for a certain period of time (a dip method), a method in which development is performed by heaping a developer up onto the surface of a substrate by surface tension, and then leaving it to stand for a certain period of time (a puddle method), a method in which a developer is sprayed on the surface of a substrate (a spray method), and a method in which a developer is continuously jetted onto a substrate rotating at a constant rate while scanning a developer jetting nozzle at a constant rate (a dynamic dispense method).

Furthermore, after the step of performing development, a step of stopping the development may be carried out while substituting the solvent with another solvent.

The developing time is not particularly limited as long as it is a period of time where the unexposed area of a resin is sufficiently dissolved and is preferably 10 to 300 seconds, and more preferably 20 to 120 seconds.

The temperature of the developer is preferably 0° C. to 50° C., and more preferably 15° C. to 35° C.

Examples of the developer include an alkaline developer and an organic solvent developer.

As the alkaline developer, it is preferable to use an aqueous alkaline solution including an alkali. The type of the aqueous alkaline solution is not particularly limited, but examples thereof include an aqueous alkaline solution including a quaternary ammonium salt typified by tetramethylammonium hydroxide, an inorganic alkali, a primary amine, a secondary amine, a tertiary amine, an alcoholamine, a cyclic amine, or the like. Among those, the aqueous solutions of the quaternary ammonium salts typified by tetramethylammonium hydroxide (TMAH) are preferable as the alkaline developer. An appropriate amount of an alcohol, a surfactant, or the like may be added to the alkaline developer. The alkali concentration of the alkaline developer is usually 0.1% to 20% by mass. Further, the pH of the alkaline developer is usually 10.0 to 15.0.

The organic solvent developer is a developer including an organic solvent.

The vapor pressure of the organic solvent included in the organic solvent developer (in a case of a mixed solvent, a vapor pressure as a whole) is preferably 5 kPa or less, more preferably 3 kPa or less, and still more preferably 2 kPa or less at 20° C. By setting the vapor pressure of the organic solvent to 5 kPa or less, evaporation of the developer on a substrate or in a development cup is suppressed, the temperature uniformity in a wafer plane is improved, and as a result, the dimensional uniformity in the wafer plane is enhanced.

Examples of the organic solvent used in the organic solvent developer include known organic solvents, and include an ester-based solvent, a ketone-based solvent, an alcohol-based solvent, an amide-based solvent, an ether-based solvent, and a hydrocarbon-based solvent.

It is preferable to use an ester-based solvent having 7 or more carbon atoms (preferably 7 to 14 carbon atoms, more preferably 7 to 12 carbon atoms, and still more preferably 7 to 10 carbon atoms), and 2 or less heteroatoms as the organic solvent included in the organic solvent developer, from the viewpoint that swelling of the resist film can be suppressed in a case where EUV and electron beams are used in the exposing step.

The heteroatom of the ester-based solvent is an atom other than a carbon atom and a hydrogen atom, and examples thereof include an oxygen atom, a nitrogen atom, and a sulfur atom. The number of the heteroatoms is preferably 2 or less.

As the ester-based solvent having 7 or more carbon atoms and 2 or less heteroatoms, amyl acetate, isoamyl acetate, 2-methylbutyl acetate, 1-methylbutyl acetate, hexyl acetate, pentyl propionate, hexyl propionate, butyl propionate, isobutyl isobutyrate, heptyl propionate, butyl butanoate, or the like is preferable, and isoamyl acetate is more preferable.

In a case where EUV and electron beams are used in the exposing step, a mixed solvent of the ester-based solvent and the hydrocarbon-based solvent or a mixed solvent of the ketone-based solvent and the hydrocarbon-based solvent may be used instead of the ester-based solvent having 7 or more carbon atoms and having 2 or less heteroatoms as the organic solvent included in the organic solvent developer. Also in this case, it is effective in suppressing the swelling of the resist film.

In a case where the ester-based solvent and the hydrocarbon-based solvent are used in combination, it is preferable to use isoamyl acetate as the ester-based solvent. In addition, from the viewpoint of adjusting the solubility of the resist film, a saturated hydrocarbon-based solvent (for example, octane, nonane, decane, dodecane, undecane, and hexadecane) is preferable as the hydrocarbon-based solvent.

In a case where the ketone-based solvent and the hydrocarbon-based solvent are used in combination, it is preferable to use 2-heptanone as the ketone-based solvent. In addition, from the viewpoint of adjusting the solubility of the resist film, a saturated hydrocarbon-based solvent (for example, octane, nonane, decane, dodecane, undecane, and hexadecane) is preferable as the hydrocarbon-based solvent.

In a case of using the mixed solvent, the content of the hydrocarbon-based solvent depends on the solvent solubility of the resist film, it is not particularly limited, and therefore, the content may be appropriately adjusted to determine a necessary amount of the hydrocarbon-based solvent.

A plurality of the organic solvents may be mixed or the organic solvent may be used in admixture with a solvent other than those described above or water. It should be noted that in order to fully exert the effects of the present invention, the moisture content of the developer as a whole is preferably less than 10% by mass, and the developer is more preferably substantially free of the moisture. The concentration of the organic solvent (in a case of mixing a plurality of the organic solvents, a total thereof) in the developer is preferably 50% by mass or more, more preferably 50% to 100% by mass, still more preferably 85% to 100% by mass, particularly preferably 90% to 100% by mass, and most preferably 95% to 100% by mass.

[Other Steps]

It is preferable that the pattern forming method includes a step of performing washing using a rinsing liquid after Step 3.

Examples of the rinsing liquid used in the rinsing step after the step of performing development using the developer include pure water. Further, an appropriate amount of a surfactant may be added to pure water.

An appropriate amount of a surfactant may be added to the rinsing liquid.

A method for the rinsing step is not particularly limited, but examples thereof include a method in which a rinsing liquid is continuously jetted on a substrate rotated at a constant rate (a rotation application method), a method in which a substrate is immersed in a tank filled with a rinsing liquid for a certain period of time (a dip method), and a method in which a rinsing liquid is sprayed on a substrate surface (a spray method).

Furthermore, the pattern forming method of the embodiment of the present invention may include a heating step (postbaking) after the rinsing step. By the present step, the developer and the rinsing liquid remaining between and inside the patterns are removed by baking. In addition, the present step also has an effect that a resist pattern is annealed and the surface roughness of the pattern is improved. The heating step after the rinsing step is usually performed at 40° C. to 250° C. (preferably 90° C. to 200° C.) for usually 10 seconds to 3 minutes (preferably 30 to 120 seconds).

In addition, an etching treatment on the substrate may be carried out using a pattern thus formed as a mask.

That is, the substrate (or the underlayer film and the substrate) may be processed using the pattern thus formed in Step 3 as a mask to form a pattern on the substrate.

A method for processing the substrate (or the underlayer film and the substrate) is not particularly limited, but a method in which a pattern is formed on a substrate by subjecting the substrate (or the underlayer film and the substrate) to dry etching using the pattern thus formed in Step 3 as a mask is preferable.

The dry etching may be one-stage etching or multi-stage etching. In a case where the etching is etching including a plurality of stages, the etchings at the respective stages maybe the same treatment or different treatments.

For etching, any of known methods can be used, and various conditions and the like are appropriately determined according to the type of a substrate, usage, and the like. Etching can be carried out, for example, in accordance with Journal of The International Society for Optical Engineering (Proc. of SPIE), Vol. 6924, 692420 (2008), JP2009-267112A, and the like. In addition, the etching can also be carried out in accordance with "Chapter 4 Etching" in "Semiconductor Process Text Book, $4^{th}$ Ed., published in 2007, publisher: SEMI Japan".

Among those, oxygen plasma etching is preferable as the dry etching.

Various materials (for example, a developer, a rinsing liquid, a composition for forming an antireflection film, and a composition for forming a topcoat) other than the composition used in the pattern forming method of the embodiment of the present invention preferably have smaller amounts of impurities such as a metal (for example, Na, K, Ca, Fe, Cu, Mg, Al, Li, Cr, Ni, Sn, Ag, As, Au, Ba, Cd, Co, Pb, Ti, V, W, and Zn). The content of the impurities included in these materials is preferably, for example, 1 ppm by mass or less.

Examples of a method for reducing impurities such as a metal in various materials other than the composition include filtration using a filter. As for the filter pore diameter, the pore size is preferably less than 100 nm, more preferably 10 nm or less, and still more preferably 5 nm or less. As the filter, a polytetrafluoroethylene-made, polyethylene-made, or nylon-made filter is preferable. The filter may include a composite material in which the filter material is combined with an ion exchange medium. As the filter, a filter which has been washed with an organic solvent in advance may be used. In the step of filtration using a filter, plural kinds of filters connected in series or in parallel may be used. In a case of using the plural kinds of filters, a combination of filters having different pore diameters and/or materials may be used. In addition, various materials may be filtered plural times, and the step of filtering plural times may be a circulatory filtration step.

In addition, examples of a method for reducing impurities such as a metal in various materials other than the composition include a method of selecting raw materials having a low content of metals as raw materials constituting various materials, a method of subjecting raw materials constituting various materials to filtration using a filter, and a method of performing distillation under the condition for suppressing the contamination as much as possible by, for example, lining the inside of a device with TEFLON (registered trademark).

In addition, as the method for reducing impurities such as a metal in various materials other than the composition, removal of impurities with an adsorbing material may be performed, in addition to the above-mentioned filter filtration, and the filter filtration and the adsorbing material may be used in combination. As the adsorbing material, known adsorbing materials can be used, and for example, inorganic adsorbing materials such as silica gel and zeolite, and organic adsorbing materials such as activated carbon can be used. It is necessary to prevent the incorporation of metal impurities in the production process in order to reduce the impurities such as a metal included in the various materials other than the composition. Sufficient removal of metal impurities from a production device can be confirmed by measuring the content of metal components included in a washing liquid used to wash the production device.

A conductive compound may be added to an organic treatment liquid such as a rinsing liquid in order to prevent breakdown of chemical liquid pipes and various parts (a filter, an O-ring, a tube, or the like) due to electrostatic charging, and subsequently generated electrostatic discharging. The conductive compound is not particularly limited, but examples thereof include methanol. The addition amount is not particularly limited, but from the viewpoint that preferred development characteristics or rinsing characteristics are maintained, the addition amount is preferably 10% by mass or less, and more preferably 5% by mass or less.

For members of the chemical liquid pipe, various pipes coated with stainless steel (SUS), or a polyethylene, polypropylene, or fluorine resin (a polytetrafluoroethylene or perfluoroalkoxy resin, or the like) that has been subjected to an antistatic treatment can be used. In the same manner, for the filter or the O-ring, polyethylene, polypropylene, or a fluorine resin (a polytetrafluoroethylene or perfluoroalkoxy resin, or the like) that has been subjected to an antistatic treatment can be used.

A method for improving the surface roughness of a pattern may be applied to a pattern thus formed by the method of the embodiment of the present invention. Examples of the method for improving the surface roughness of the pattern include the method of treating a pattern by a plasma of a hydrogen-containing gas disclosed in WO2014/002808A. Additional examples of the method include known methods as described in JP2004-235468A, US2010/0020297A, JP2008-083384A, and Proc. of SPIE Vol. 8328 83280N-1 "EUV Resist Curing Technique for LWR Reduction and Etch Selectivity Enhancement".

In a case where a pattern thus formed is in the form of a line, an aspect ratio determined by dividing the height of the pattern with the line width is preferably 2.5 or less, more preferably 2.1 or less, and still more preferably 1.7 or less.

In a case where a pattern thus formed is in the form of a trench (groove) pattern or a contact hole pattern, an aspect ratio determined by dividing the height of the pattern with the trench width or the hole diameter is preferably 4.0 or less, more preferably 3.5 or less, and still more preferably 3.0 or less.

The pattern forming method of the embodiment of the present invention can also be used for forming a guide pattern in a directed self-assembly (DSA) (see, for example, ACS Nano Vol. 4, No. 8, Pages 4815-4823).

In addition, a pattern thus formed by the method can be used as a core material (core) of the spacer process disclosed in, for example, JP1991-270227A (JP-H03-270227A) and JP2013-164509A.

[Method for Manufacturing Electronic Device]

Moreover, the present invention further relates to a method for manufacturing an electronic device, including the above-described pattern forming method, and an electronic device manufactured by the manufacturing method.

The electronic device of an embodiment of the present invention is suitably mounted on electric and electronic equipment (for example, home appliances, office automation (OA)-related equipment, media-related equipment, optical equipment, telecommunication equipment, and the like).

EXAMPLES

Hereinbelow, the present invention will be described in more detail with reference to Examples. The materials, the amounts of materials used, the proportions, the treatment details, the treatment procedure, and the like shown in the Examples below may be modified as appropriate as long as the modifications do not depart from the spirit of the present invention. Therefore, the scope of the present invention should not be construed as being limited to the Examples shown below.

[Production of Composition]

Components included in actinic ray-sensitive or radiation-sensitive resin composition (hereinafter also referred to as a "composition") used in Examples or Comparative Examples, and production procedure therefor are shown below.

<Specific Compound and Comparative Compound>

(Synthesis of Specific Compound (I)-35)

A specific compound (I)-35 was synthesized based on the following scheme.

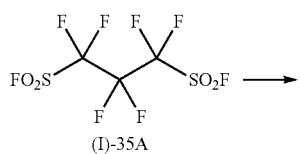

(I)-35A

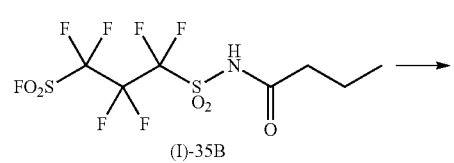

(I)-35B

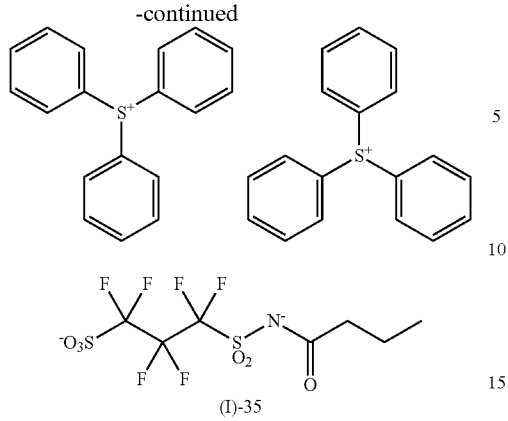

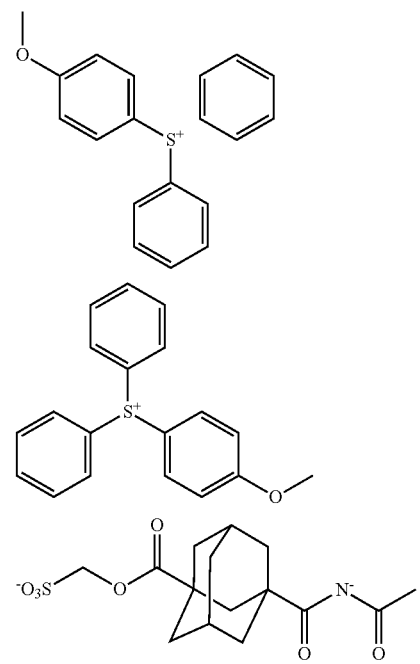

(I)-35

A solution obtained by adding butylamide (15.0 g, 172.2 mmol) and tetrahydrofuran (300 mL) into a 500-mL three-neck flask was cooled to 0° C., and then butyllithium (1.6 M hexane solution, 107.5 mL, 172.2 mmol) was added dropwise to the solution. The solution was further stirred at 0° C. for 30 minutes, and then the solution was slowly added dropwise to a THF solution (300 mL) of (I)-35A (54.45 g, 172.2 mmol) that had been cooled to 0°, thereby obtaining a mixed liquid. The obtained mixed liquid was stirred at room temperature (23° C.) for 2 hours, then 1 N hydrochloric acid was added thereto until the mixed liquid reached pH=3, and 300 mL of ethyl acetate was further added to the mixed liquid. The organic phase of the mixed liquid was washed with water (100 mL) three times, and then the solvent was evaporated from the organic phase under reduced pressure. Hexane (300 mL) was added to the obtained residue to obtain (I)-35B (33.0 g, yield: 50%) as a white solid.

(I)-35B (22.0 g, 57.40 mmol), tetrahydrofuran (300 mL), and a 5%-by-mass aqueous sodium bicarbonate solution (300 mL) were added into a 1-L eggplant flask, and the obtained solution was stirred at 60° C. for 6 hours. Tetrahydrofuran was evaporated from the solution under reduced pressure, dichloromethane (300 mL) and triphenylsulfonium bromide (39.41 g, 114.80 mmol) were added to the solution, and the mixture was stirred at room temperature for 30 minutes. The solution was transferred to a separating funnel and the organic phase was washed with water (150 mL) three times. The solvent was evaporated from the organic phase under reduced pressure, and t-butyl methyl ether was added to the obtained residue to obtain (I)-35 (41.6 g) as a white solid (yield: 80%).

The results obtained by analyzing the obtained white solid ((I)-35) by a nuclear magnetic resonance (NMR) method were as follows. $^1$H NMR (400 MHz, MeOD) δ 0.91 (t, J=7.44 Hz, 3H), 1.55-1.64 (m, 2H), 2.19 (t, J=10.08 Hz, 3H), 7.77-7.92 (m, 30H).

The following specific compounds were synthesized with reference to the synthesis method.

It should be noted that (Z)-1 is a comparative compound that does not correspond to the specific compound.

Furthermore, in the compound in which the cation in (Z)-1 is substituted with a hydrogen atom, the pKa of a group represented by —SO$_3$H and the pKa of a group represented by —COOH in the compound are −3.29 and 0.37, respectively.

(I)-3

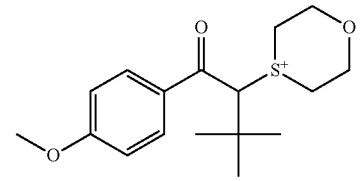

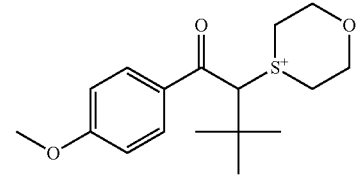

(I)-5

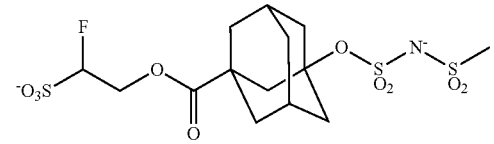

(I)-13

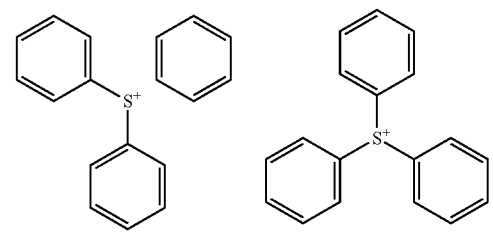

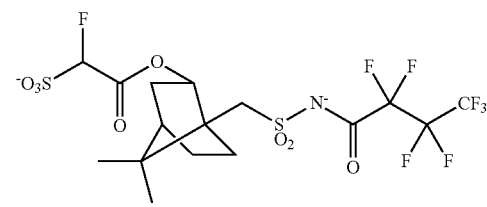

(I)-15
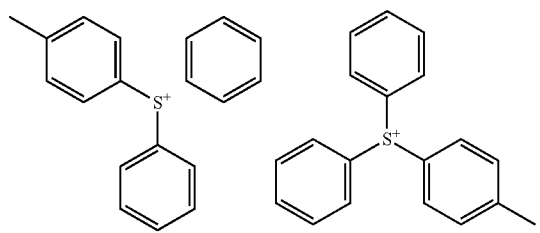
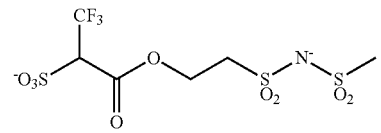
(I)-20
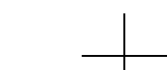
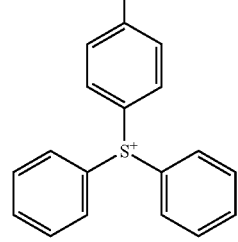
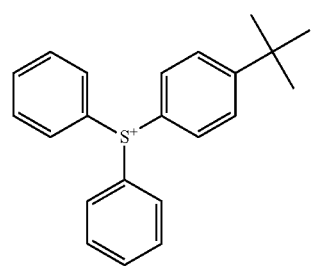
(I)-22
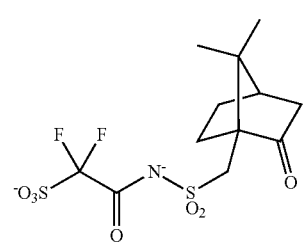
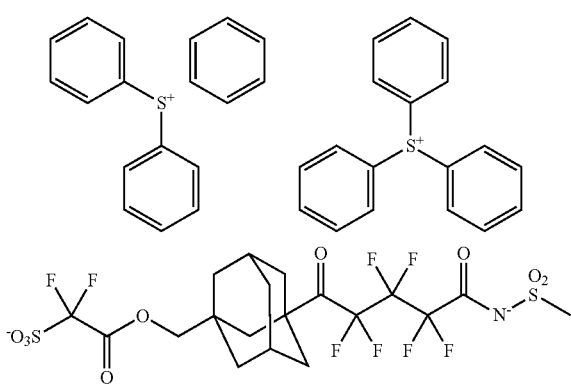
(I)-24
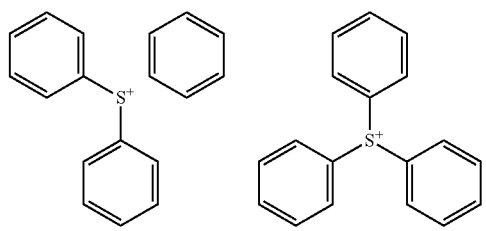
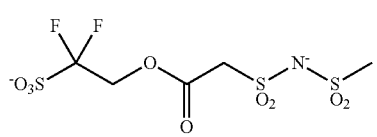
(I)-30
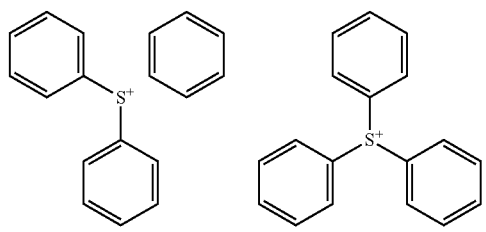
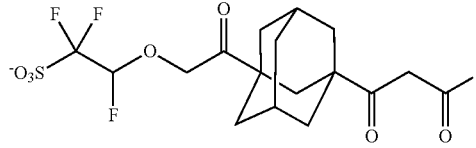
(I)-31
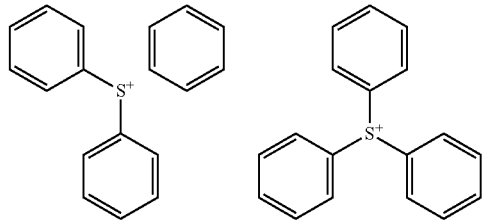
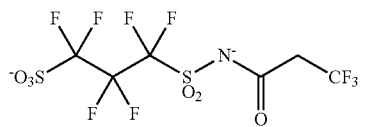
(I)-35
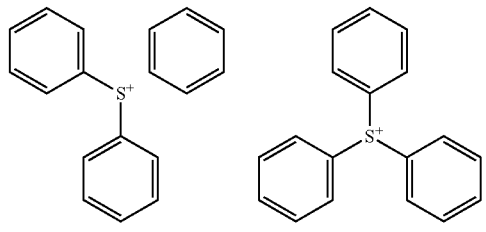
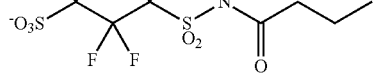

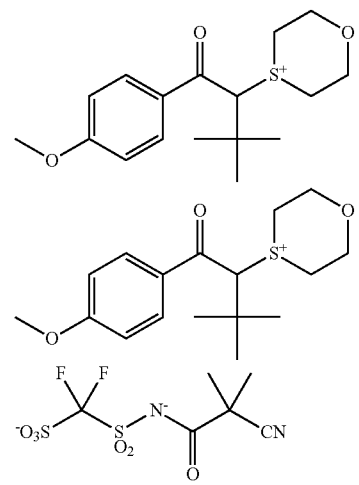
(I)-37
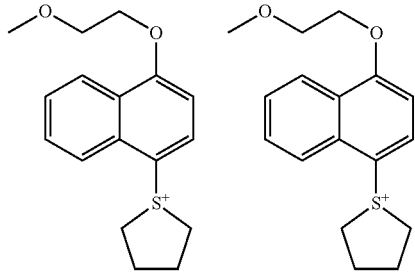
(I)-10
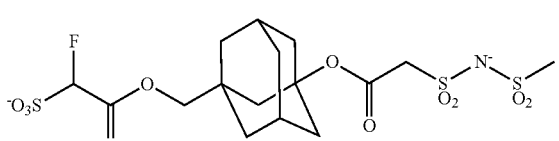
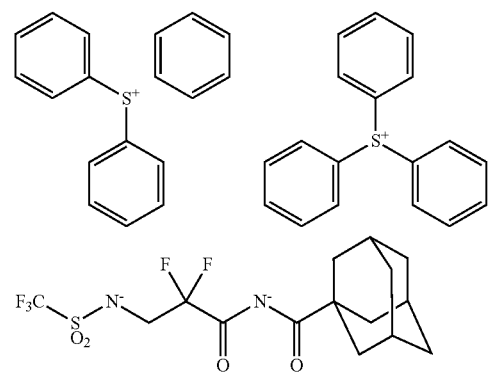
(I)-45
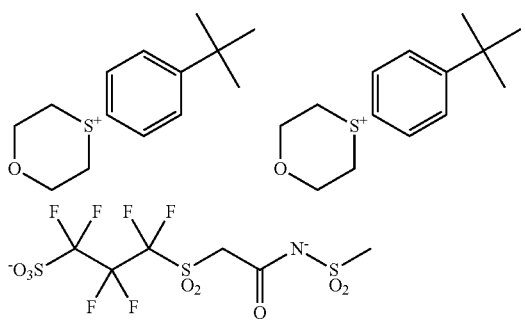
(I)-33
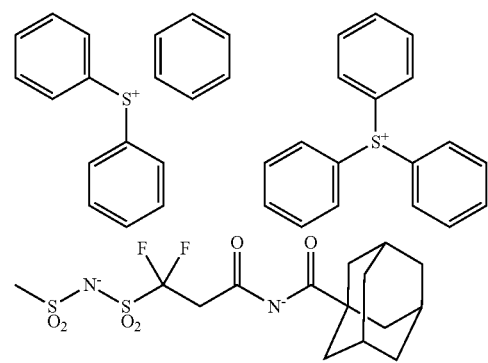
(I)-48
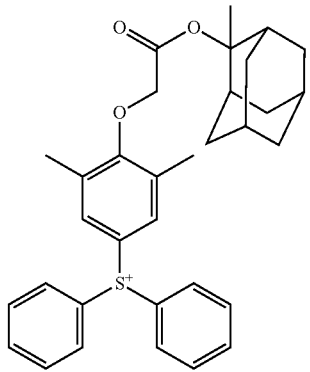
(I)-49
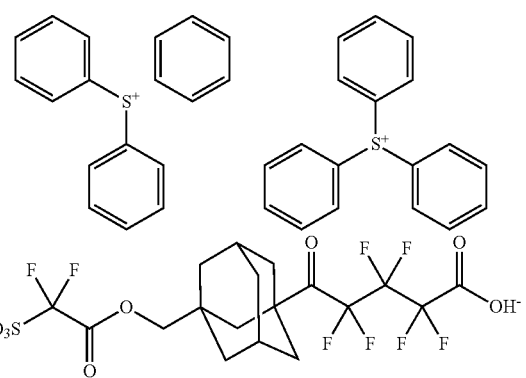
(Z)-1
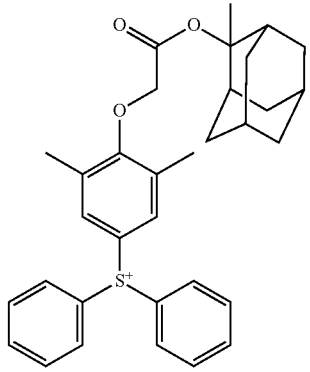

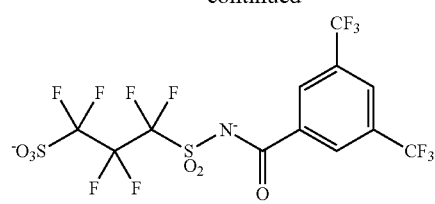
(I)-50
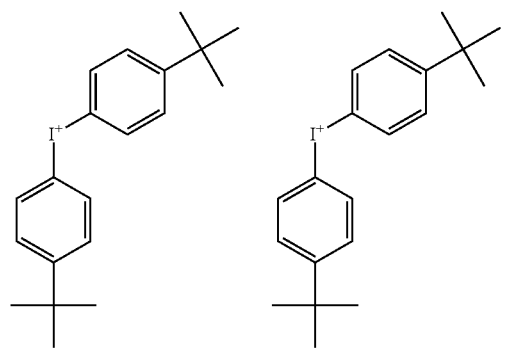
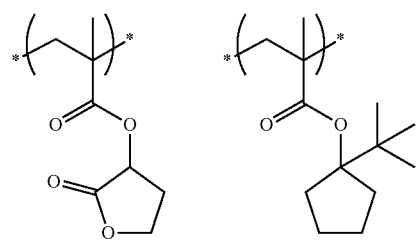
<Acid-Decomposable Resin (Resin (A))>
Acid-decomposable resins (resins (A)) used for producing the composition are shown below.
A-1
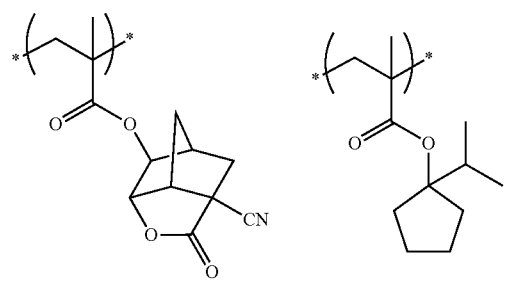
A-2
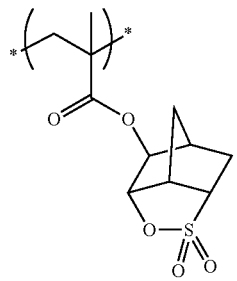
A-3
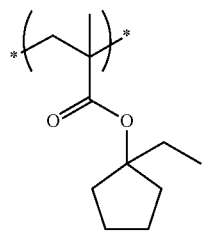
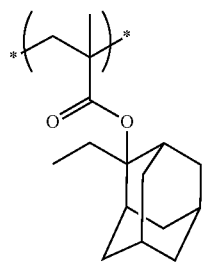
A-4
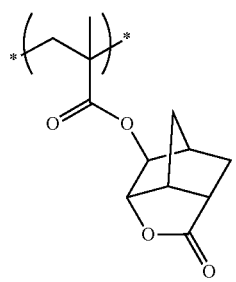
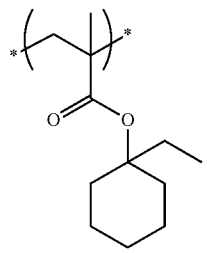
A-5
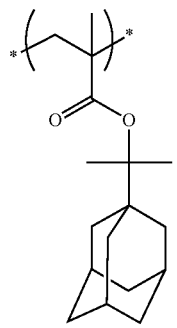

-continued
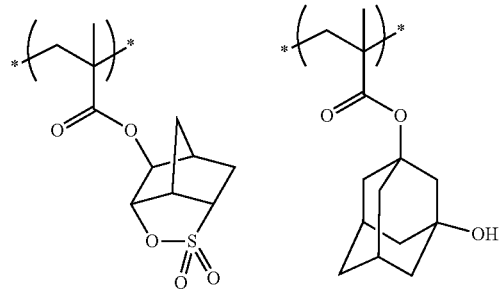
A-6
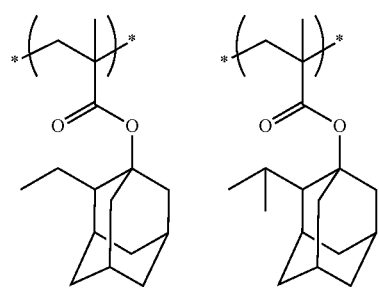
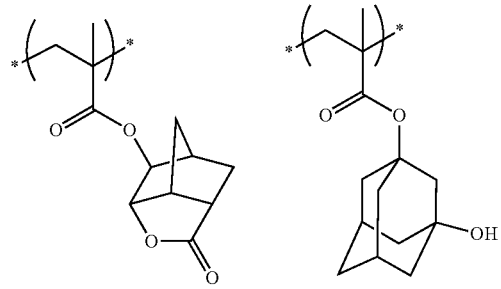
A-7
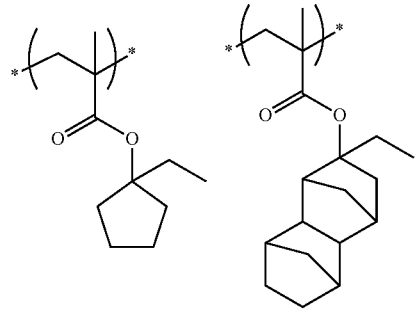
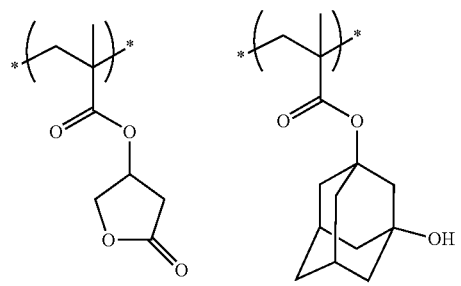
A-8
-continued
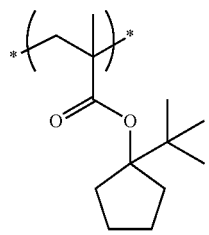
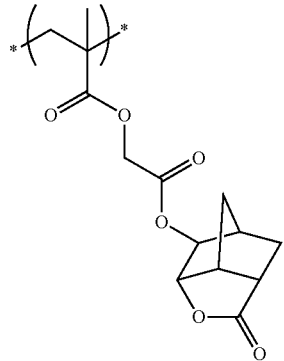
A-9
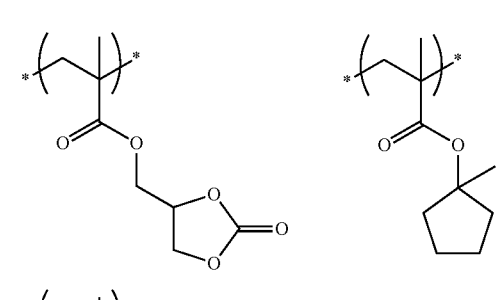
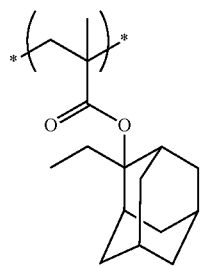
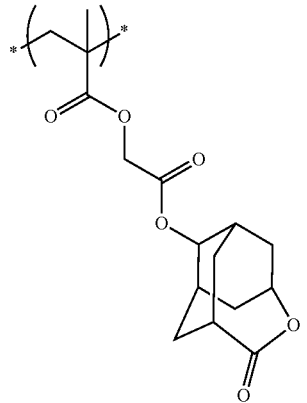
A-10

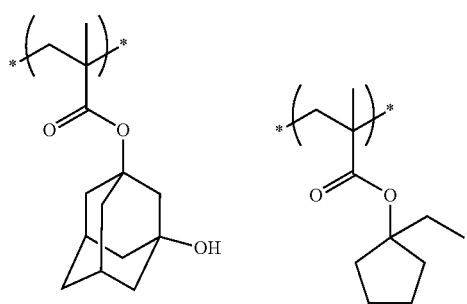
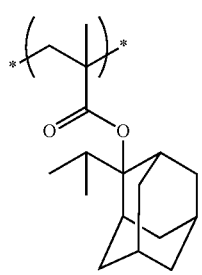
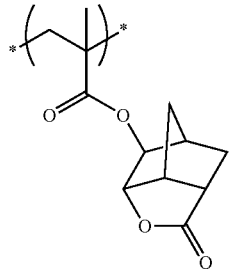
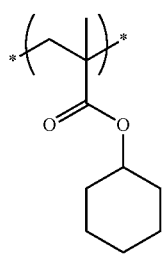
A-11
A-12
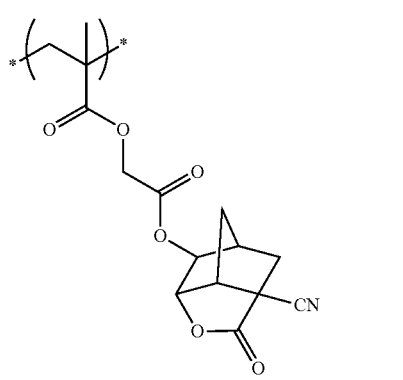
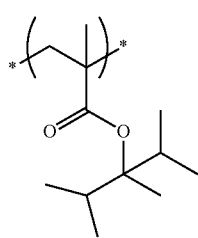
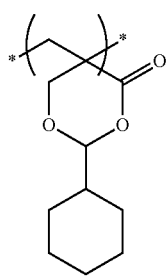
A-13
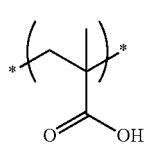
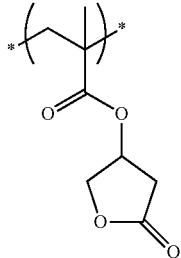
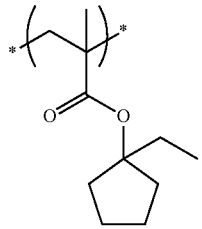
A-14
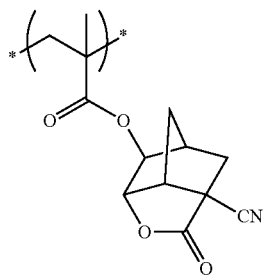
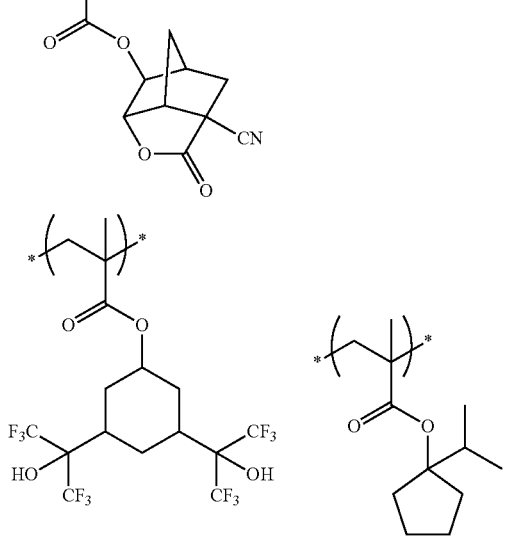
A-15
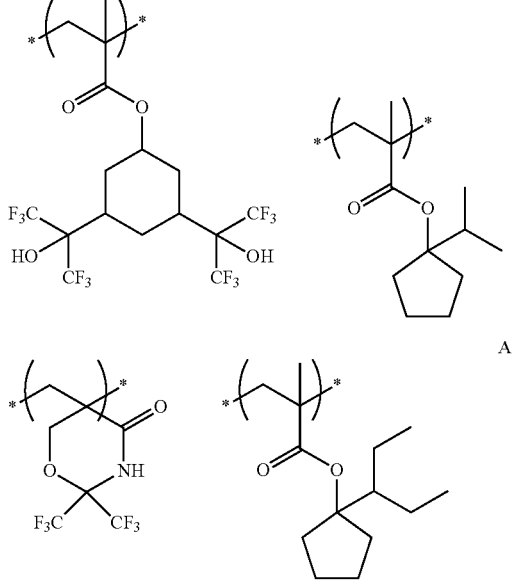

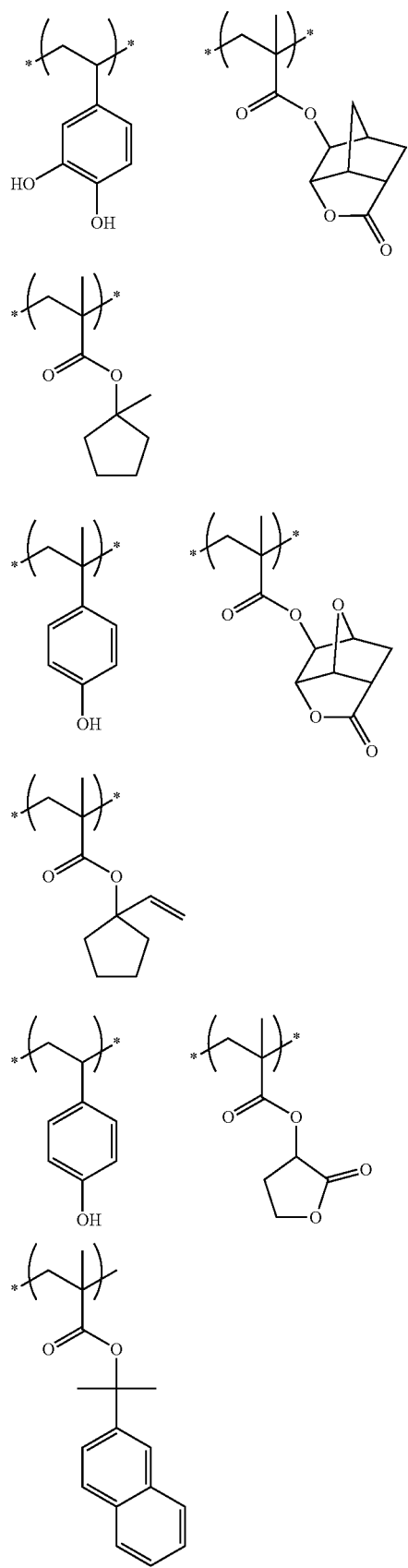
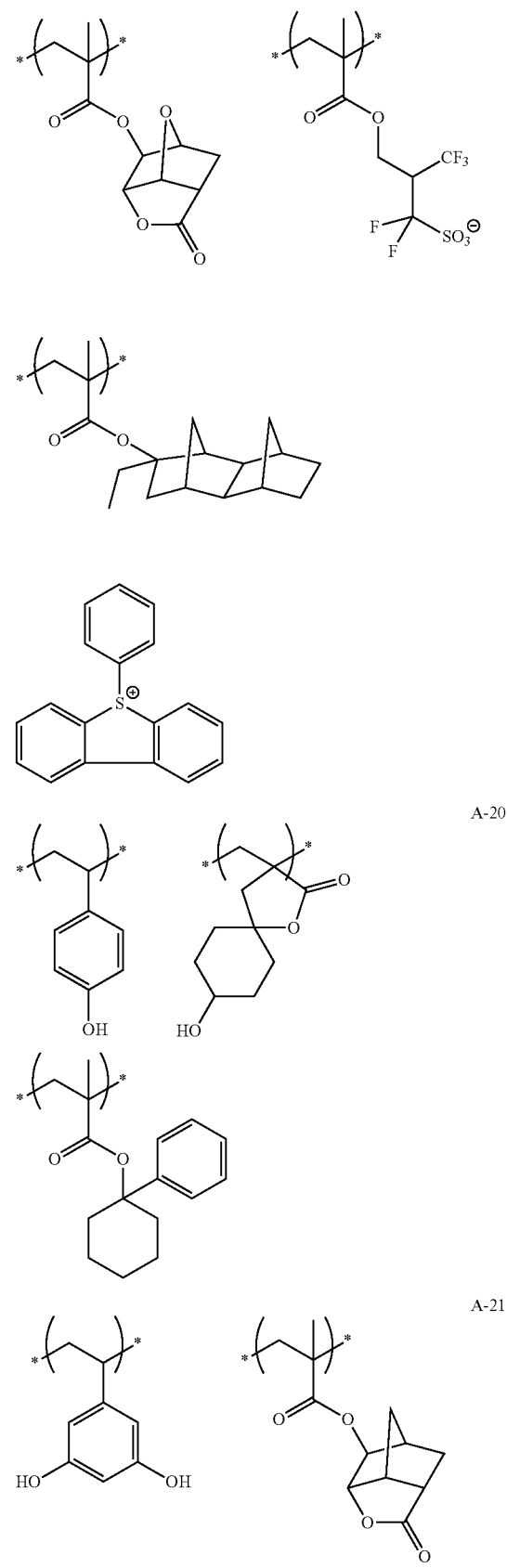

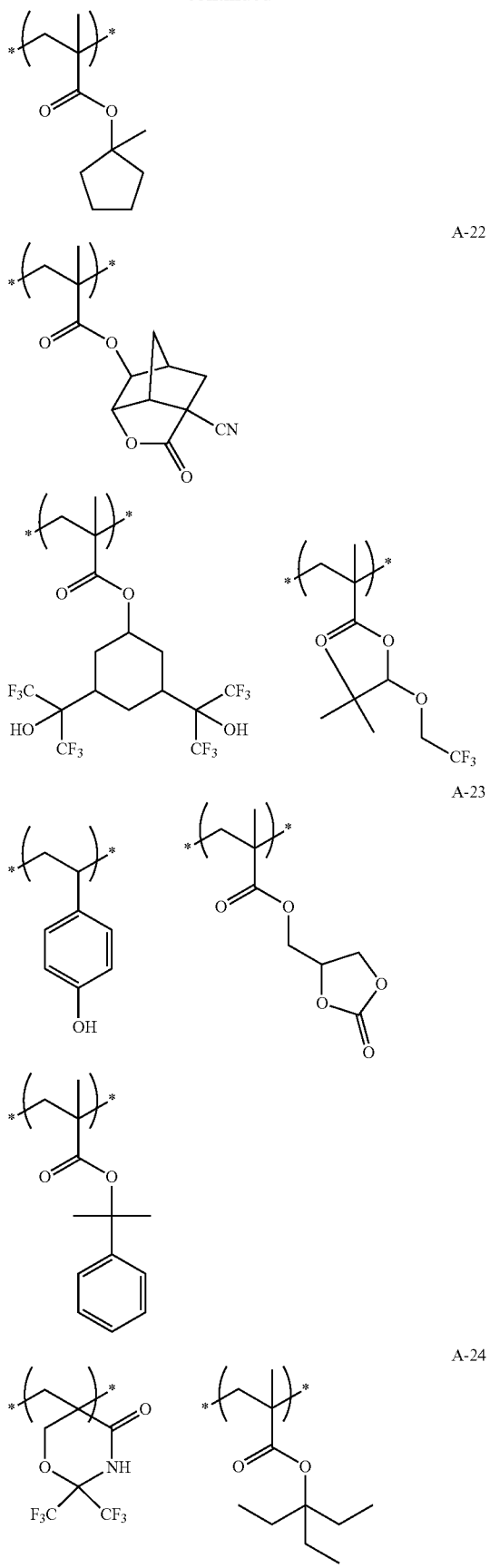

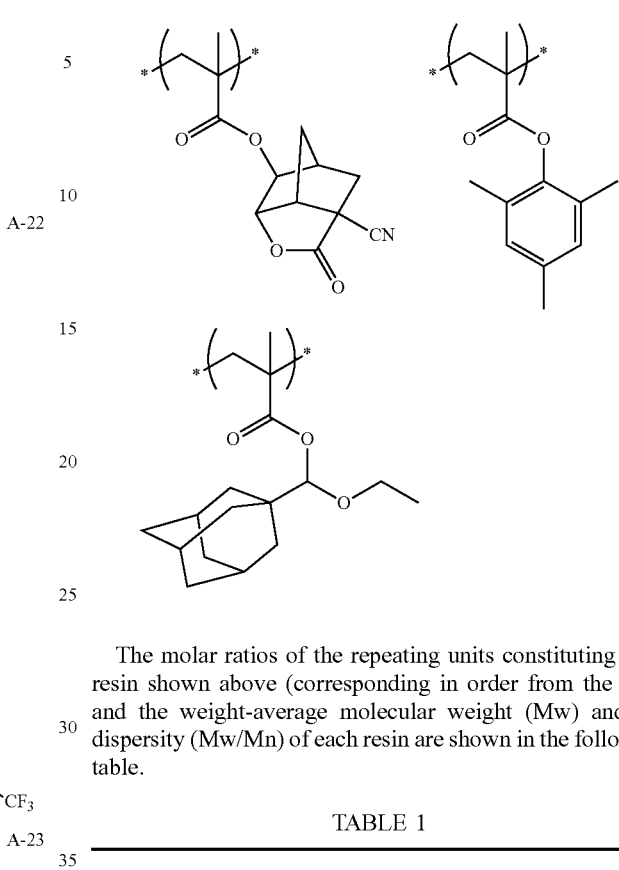

The molar ratios of the repeating units constituting each resin shown above (corresponding in order from the left), and the weight-average molecular weight (Mw) and the dispersity (Mw/Mn) of each resin are shown in the following table.

TABLE 1

| | Molar ratio of repeating unit | | | | Mw | Mw/Mn |
|---|---|---|---|---|---|---|
| Resin A-1 | 50 | 50 | — | — | 6,500 | 1.52 |
| Resin A-2 | 45 | 55 | — | — | 8,300 | 1.65 |
| Resin A-3 | 40 | 30 | 30 | — | 7,800 | 1.55 |
| Resin A-4 | 40 | 50 | 10 | — | 12,000 | 1.68 |
| Resin A-5 | 50 | 50 | — | — | 5,500 | 1.49 |
| Resin A-6 | 25 | 30 | 30 | 15 | 8,600 | 1.63 |
| Resin A-7 | 40 | 10 | 30 | 20 | 9,600 | 1.72 |
| Resin A-8 | 40 | 5 | 55 | — | 10,200 | 1.64 |
| Resin A-9 | 30 | 20 | 40 | 10 | 7,500 | 1.54 |
| Resin A-10 | 40 | 10 | 40 | 10 | 7,000 | 1.61 |
| Resin A-11 | 40 | 10 | 10 | 40 | 6,500 | 1.63 |
| Resin A-12 | 40 | 30 | 30 | — | 5,900 | 1.59 |
| Resin A-13 | 10 | 30 | 60 | — | 5,200 | 1.53 |
| Resin A-14 | 25 | 15 | 60 | — | 6,200 | 1.48 |
| Resin A-15 | 50 | 50 | — | — | 7,000 | 1.73 |
| Resin A-16 | 30 | 10 | 60 | — | 11,500 | 1.56 |
| Resin A-17 | 35 | 10 | 55 | — | 8,400 | 1.58 |
| Resin A-18 | 40 | 10 | 50 | — | 9,200 | 1.66 |
| Resin A-19 | 25 | 25 | 50 | — | 5,700 | 1.75 |
| Resin A-20 | 30 | 20 | 50 | — | 7,600 | 1.56 |
| Resin A-21 | 30 | 10 | 60 | — | 6,500 | 1.65 |
| Resin A-22 | 15 | 40 | 45 | — | 6,900 | 1.69 |
| Resin A-23 | 25 | 25 | 50 | — | 8,200 | 1.58 |
| Resin A-24 | 50 | 50 | — | — | 7,600 | 1.71 |
| Resin A-25 | 40 | 10 | 50 | — | 9,000 | 1.68 |

<Photoacid Generator>

In a case where the composition included a photoacid generator, the following photoacid generator was used.

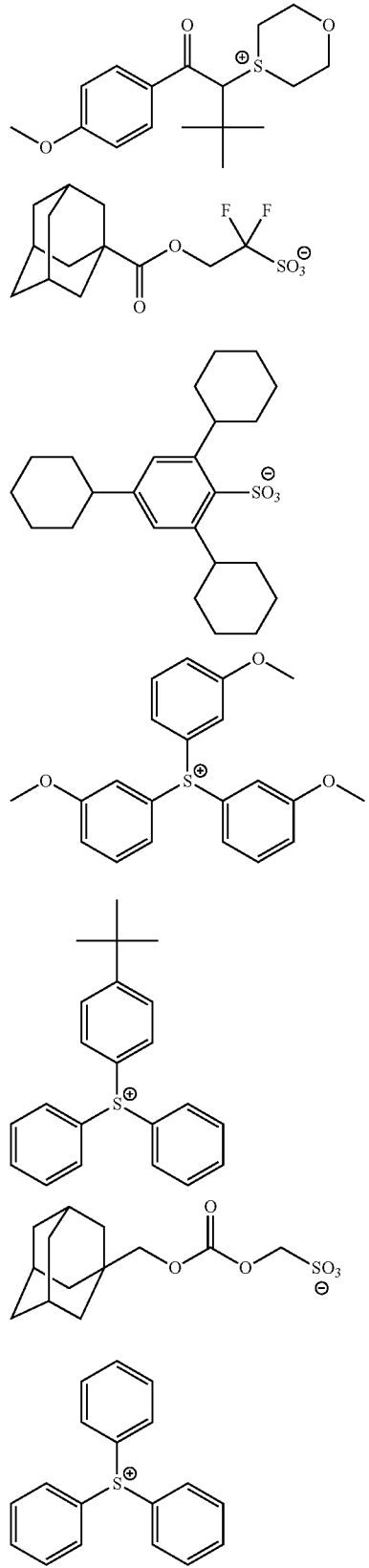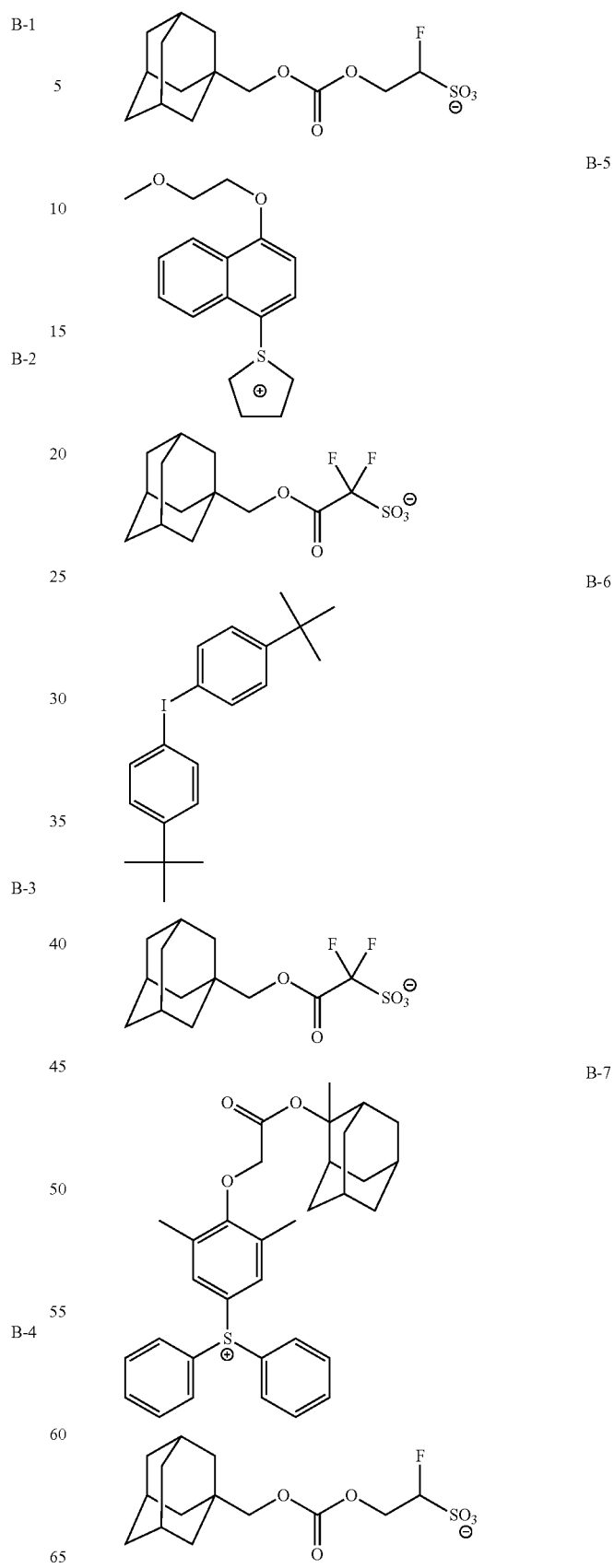

B-8
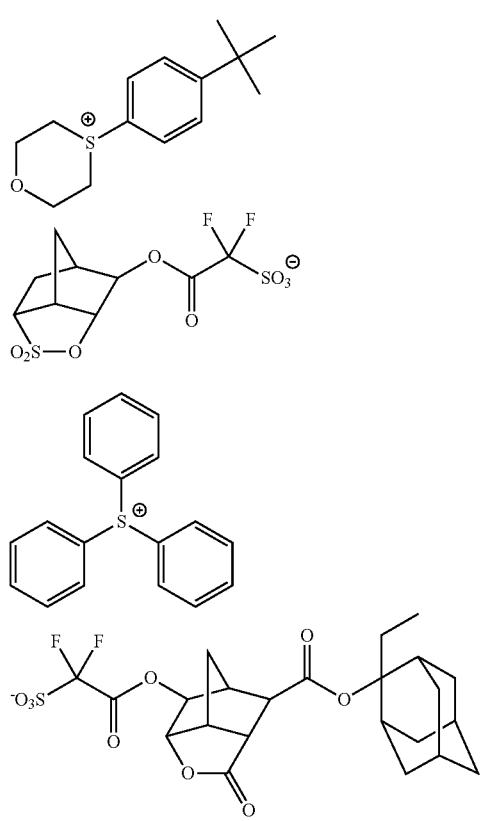
B-9
B-10
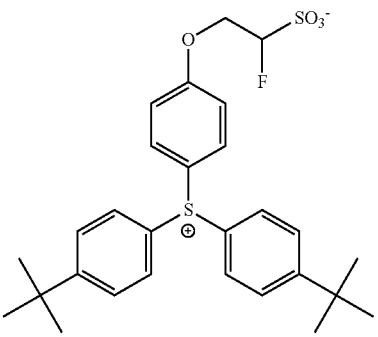
B-11
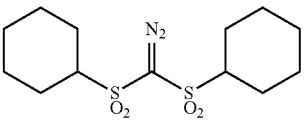
<Acid Diffusion Control Agent>
In a case where the composition included an acid diffusion control agent, the following acid diffusion control agent was used.
C-1
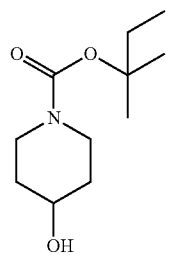
C-2
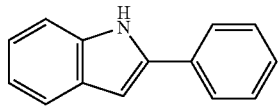
C-3
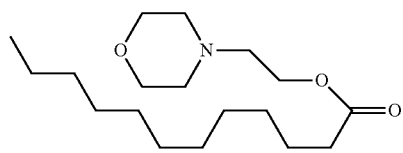
C-4
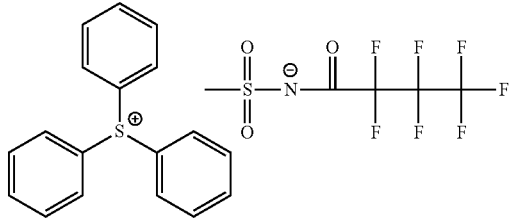
C-5
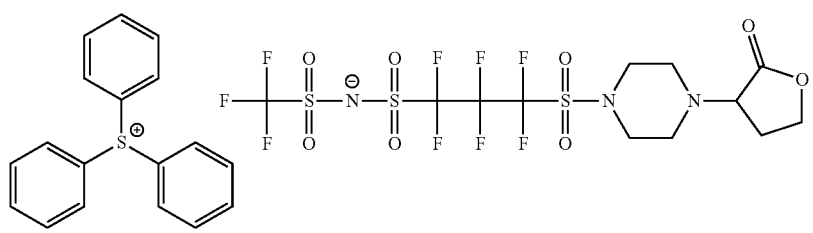

<Hydrophobic Resin>
In a case where the composition included a hydrophobic resin, a hydrophobic resin having a repeating unit based on the following monomer was used.
ME-1
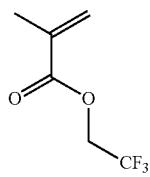
ME-2
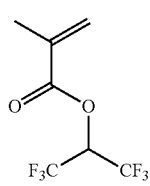
ME-3
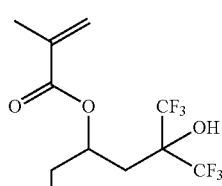
ME-4
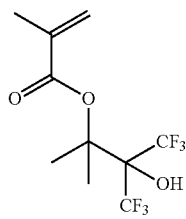
ME-5
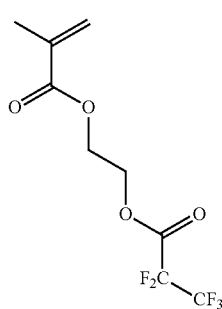
ME-6
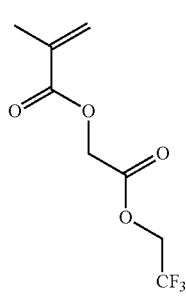
ME-7
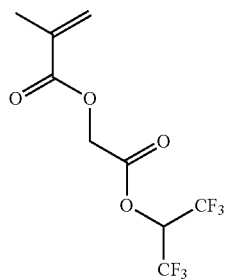
ME-8
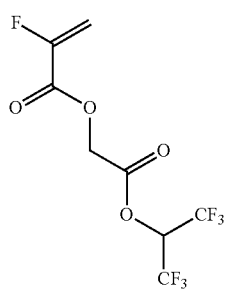
ME-9
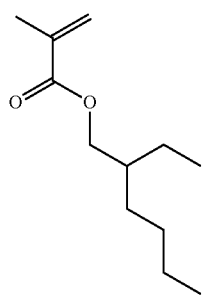
ME-10
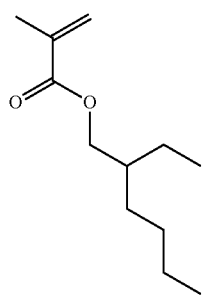
ME-11
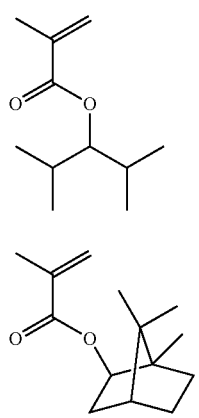
ME-12
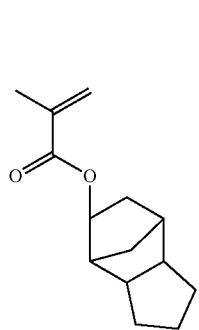

-continued

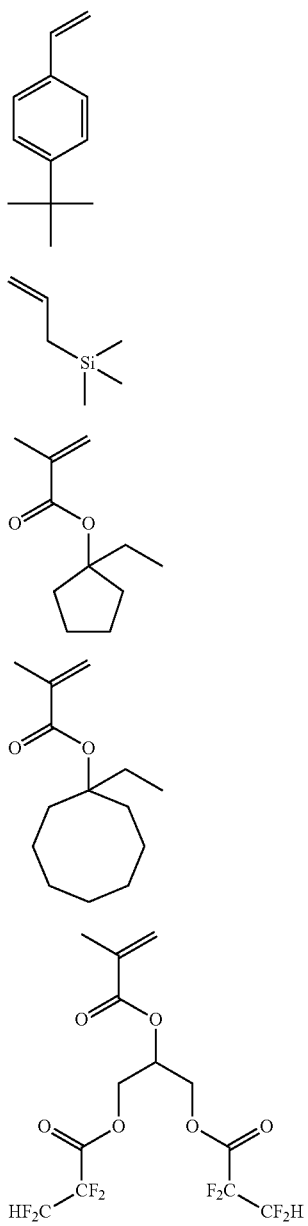

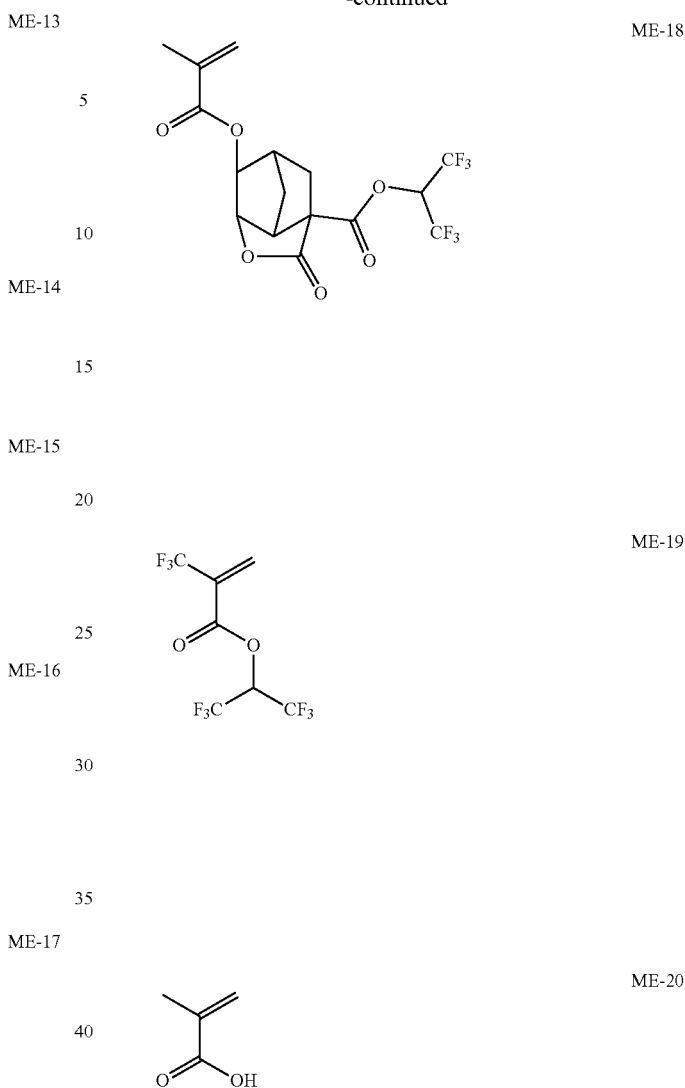

The molar ratios of the repeating units based on the respective monomers, and the weight-average molecular weight (Mw) and the dispersity (Mw/Mn) of each resin in the hydrophobic resin used in the composition are shown in the following table.

TABLE 2

|  | Molar ratio of repeating unit 1 | | Molar ratio of repeating unit 2 | | Molar ratio of repeating unit 3 | | Molar ratio of repeating unit 4 | | Mw | Mw/Mn |
|---|---|---|---|---|---|---|---|---|---|---|
| D-1 | ME-3 | 60 | ME-4 | 40 | — | — | — | — | 10,000 | 1.4 |
| D-2 | ME-15 | 50 | ME-1 | 50 | — | — | — | — | 12,000 | 1.5 |
| D-3 | ME-2 | 40 | ME-13 | 50 | ME-9 | 5 | ME-20 | 5 | 6,000 | 1.3 |
| D-4 | ME-19 | 50 | ME-14 | 50 | — | — | — | — | 9,000 | 1.5 |
| D-5 | ME-10 | 50 | ME-2 | 50 | — | — | — | — | 15,000 | 1.5 |
| D-6 | ME-17 | 50 | ME-15 | 50 | — | — | — | — | 10,000 | 1.5 |
| D-7 | ME-7 | 100 | — | | — | | — | | 23,000 | 1.7 |
| D-8 | ME-5 | 100 | — | | — | | — | | 13,000 | 1.5 |
| D-9 | ME-6 | 50 | ME-16 | 50 | — | — | — | — | 10,000 | 1.7 |
| D-10 | ME-13 | 10 | ME-18 | 85 | ME-9 | 5 | — | — | 11,000 | 1.4 |
| D-11 | ME-8 | 80 | ME-11 | 20 | — | — | — | — | 13,000 | 1.4 |

<Surfactant>

In a case where the composition included a surfactant, the following surfactants were used.

E-1: MEGAFACE F176 (manufactured by DIC Corporation, fluorine-based surfactant)
E-2: MEGAFACE R08 (manufactured by DIC Corporation, fluorine- and silicon-based surfactant)
E-3: PF656 (manufactured by OMNOVA Solutions Inc., fluorine-based surfactant)

<Solvent>

The solvents included in the composition are shown below.

F-1: Propylene glycol monomethyl ether acetate (PGMEA)
F-2: Propylene glycol monomethyl ether (PGME)
F-3: Propylene glycol monoethyl ether (PGEE)
F-4: Cyclohexanone
F-5: Cyclopentanone
F-6: 2-Heptanone
F-7: Ethyl lactate
F-8: γ-Butyrolactone
F-9: Propylene carbonate <Preparation of Composition>

(Preparation of Compositions for ArF Exposure Test (Re-1 to Re-24, Re-35, Re-36, Re-39 to Re-51, and Re-68))

The respective components shown in the following table were mixed so that the concentration of solid contents was 4% by mass. Next, the obtained mixed liquid was filtered initially through a polyethylene-made filter having a pore diameter of 50 nm, then through a nylon-made filter having a pore diameter of 10 nm, and lastly through a polyethylene-made filter having a pore diameter of 5 nm in this order to prepare a composition used for a test by ArF exposure (actinic ray-sensitive or radiation-sensitive resin composition).

Furthermore, in the composition, the solid content means all the components excluding the solvent. The obtained composition was used in Examples and Comparative Examples.

In addition, in the following table, the content (% by mass) of each component means a content with respect to the total solid content.

(Preparation of Composition for EUV Exposure Test (Re-25 to Re-34, Re-37, Re-38, Re-52 to Re-67, and Re-69))

The respective components shown in the following table were mixed so that the concentration of solid contents was 2% by mass. Next, the obtained mixed liquid was filtered initially through a polyethylene-made filter having a pore diameter of 50 nm, then through a nylon-made filter having a pore diameter of 10 nm, and lastly through a polyethylene-made filter having a pore diameter of 5 nm in this order to prepare a composition used for a test by EUV exposure (actinic ray-sensitive or radiation-sensitive resin composition).

The formulation of each composition is shown below.

Re-35 to Re-38 are the compositions used for Comparative Examples, and the others are the compositions used for Examples.

Furthermore, the column of "B Group" in the table indicates whether the group represented by W corresponds to a group represented by any of General Formulae (B-1) to (B-4) in a case where the specific compound used is applied to General Formula (I).

TABLE 3-1

| | Solid contents | | | | | | | | | | | | Solvent | |
|---|---|---|---|---|---|---|---|---|---|---|---|---|---|---|
| | Resin A | | Specific compound | | | Photoacid generator | | Acid diffusion control agent | | Hydrophobic resin | | Surfactant | | | Mixing ratio |
| | Type | % by mass | Type | B | % by mass | Type | % by mass | Type | % by mass | Type | % by mass | Type | % by mass | Type | (mass ratio) |
| Re-1 | A-3 | 88.1 | (I)-3 | B-4 | 8.6 | — | — | — | — | D-1 | 3.3 | — | — | F-1/F-8 | 85/15 |
| Re-2 | A-2 | 89.5 | (I)-5 | B-3 | 10.0 | — | — | — | — | D-5 | 0.5 | — | — | F-1/F-2 | 70/30 |
| Re-3 | A-4 | 87.6 | (I)-13 | B-1 | 9.9 | — | — | — | — | D-4 | 2.5 | — | — | F-1/F-7 | 80/20 |
| Re-4 | A-1/ A-5 | 44.4/ 44.3 | (I)-15 | B-3 | 8.6 | — | — | — | — | D-4 | 2.5 | E-1/ E-2 | 0.1/ 0.1 | F-4 | 100 |
| Re-5 | A-1 | 86.3 | (I)-20 | B-2 | 9.4 | — | — | — | — | D-8 | 4.2 | E-3 | 0.1 | F-1/F-9 | 90/10 |
| Re-6 | A-9 | 88.0 | (I)-22 | B-2 | 10.5 | — | — | — | — | D-9 | 1.5 | — | — | F-1/F-6 | 40/60 |
| Re-7 | A-7 | 90.4 | (I)-24 | B-3 | 8.1 | — | — | — | — | D-6 | 1.5 | — | — | F-1/F-5 | 50/50 |
| Re-8 | A-8 | 90.4 | (I)-30 | B-4 | 8.8 | — | — | — | — | D-11 | 0.8 | — | — | F-1 | 100 |
| Re-9 | A-11 | 88.1 | (I)-31 | B-1 | 8.6 | — | — | — | — | D-1 | 3.3 | — | — | F-1/F-2/ F-8 | 70/25/ 5 |
| Re-10 | A-6 | 90.5 | (I)-35 | B-1 | 8.3 | — | — | — | — | D-3 | 1.2 | — | — | F-1 | 100 |
| Re-11 | A-12 | 89.0 | (I)-37 | B-1 | 8.4 | — | — | — | — | D-10 | 2.5 | E-1 | 0.1 | F-7 | 100 |
| Re-12 | A-13 | 89.5 | (I)-45 | B-4 | 9.1 | — | — | — | — | D-7 | 1.4 | — | — | F-1/F-2 | 70/30 |
| Re-13 | A-10 | 89.8 | (I)-48 | B-4 | 8.7 | — | — | — | — | D-2 | 1.5 | — | — | F-1/F-3 | 90/10 |
| Re-14 | A-4 | 88.3 | (I)-13 | B-1 | 8.2 | B-1 | 1.0 | — | — | D-4 | 2.5 | — | — | F-1/F-7 | 80/20 |
| Re-15 | A-3 | 87.3 | (I)-3 | B-4 | 7.5 | B-3 | 1.9 | — | — | D-1 | 3.3 | — | — | F-1/F-8 | 85/15 |
| Re-16 | A-1/ A-5 | 43.4/ 43.4 | (I)-15 | B-3 | 8.5 | B-4 | 2.0 | — | — | D-4 | 2.5 | E-1/ E-2 | 0.1/ 0.1 | F-4 | 100 |
| Re-17 | A-7 | 89.9 | (I)-24 | B-3 | 8.4 | — | — | C-1 | 0.2 | D-6 | 1.5 | — | — | F-1/F-5 | 50/50 |
| Re-18 | A-6 | 90.2 | (I)-35 | B-1 | 8.5 | — | — | C-2 | 0.1 | D-3 | 1.2 | — | — | F-1 | 100 |
| Re-19 | A-11 | 87.5 | (I)-31 | B-1 | 9.0 | — | — | C-3 | 0.2 | D-1 | 3.3 | — | — | F-1/F-2/ F-8 | 70/25/ 5 |
| Re-20 | A-9 | 86.5 | (I)-22 | B-2 | 11.5 | — | — | C-4 | 0.5 | D-9 | 1.5 | — | — | F-1/F-6 | 40/60 |
| Re-21 | A-9 | 87.3 | (I)-22 | B-2 | 10.0 | B-1 | 0.8 | C-5 | 0.4 | D-9 | 1.5 | — | — | F-1/F-6 | 40/60 |
| Re-22 | A-3 | 91.4 | (I)-3 | B-4 | 8.6 | — | — | — | — | — | — | — | — | F-1/F-8 | 85/15 |
| Re-23 | A-2 | 90.0 | (I)-5 | B-3 | 10.0 | — | — | — | — | — | — | — | — | F-1/F-2 | 70/30 |
| Re-24 | A-4 | 90.1 | (I)-13 | B-1 | 9.9 | — | — | — | — | — | — | — | — | F-1/F-7 | 80/20 |
| Re-25 | A-17 | 91.2 | (I)-35 | B-1 | 8.8 | — | — | — | — | — | — | — | — | F-1/F-2 | 70/30 |
| Re-26 | A-15/ A-20 | 45.4/ 45.4 | (I)-45 | B-4 | 9.1 | — | — | — | — | — | — | E-1 | 0.1 | F-1/F-3 | 90/10 |

TABLE 3-1-continued

| | Solid contents | | | | | | | | | | | Solvent | |
|---|---|---|---|---|---|---|---|---|---|---|---|---|---|
| | Resin A | | Specific compound | | Photoacid generator | | Acid diffusion control agent | | Hydrophobic resin | | Surfactant | | Mixing ratio |
| | Type | % by mass | Type | B | Type | % by mass | Type | % by mass | Type | % by mass | Type | % by mass | Type | (mass ratio) |
| Re-27 | A-19 | 90.1 | (I)-24 | B-3 | 7.9 | — | — | — | D-1 | 2.0 | — | — | F-1 | 100 |
| Re-28 | A-14 | 91.2 | (I)-37 | B-1 | 8.8 | — | — | — | — | — | — | — | F-1/F-6 | 40/60 |
| Re-29 | A-20 | 90.2 | (I)-20 | B-2 | 9.8 | — | — | — | — | — | — | — | F-1/F-2 | 70/30 |
| Re-30 | A-16 | 91.4 | (I)-3 | B-4 | 8.6 | — | — | — | — | — | — | — | F-4 | 100 |
| Re-31 | A-18 | 89.5 | (I)-5 | B-3 | 10.5 | — | — | — | — | — | — | — | F-1/F-5 | 50/50 |
| Re-32 | A-17 | 89.8 | (I)-35 | B-1 | 8.1 | B-2 | 2.1 | — | — | — | — | — | F-1/F-2 | 70/30 |
| Re-33 | A-14 | 90.8 | (I)-37 | B-1 | 9.0 | — | — | C-1 | 0.2 | — | — | — | F-1/F-6 | 40/60 |
| Re-34 | A20 | 89.1 | (I)-20 | B-2 | 9.9 | B1 | 0.7 | C-4 | 0.3 | — | — | — | F-1/F-2 | 70/30 |
| Re-35 | A-9 | 87.8 | (Z)-1 | — | 10.7 | — | — | — | — | D-9 | 1.5 | — | — | F-1/F-6 | 40/60 |
| Re-36 | A-9 | 91.4 | — | — | — | B1 | 5.0 | C-4 | 2.1 | D-9 | 1.5 | — | — | F-1/F-6 | 40/60 |
| Re-37 | A-16 | 89.3 | (Z)-1 | — | 10.7 | — | — | — | — | — | — | — | — | F-1/F-6 | 40/60 |
| Re-38 | A-16 | 89.4 | — | — | — | B1 | 7.6 | C-4 | 3.0 | — | — | — | — | F-1/F-6 | 40/60 |
| Re-39 | A-2 | 83.0 | (I)-10 | B-3 | 14.5 | — | — | — | — | D-10 | 2.5 | — | — | F-1/F-8 | 85/15 |
| Re-40 | A-5 | 90.7 | (I)-33 | B-2 | 8.5 | — | — | — | — | D-11 | 0.8 | — | — | F-1 | 100 |
| Re-41 | A-9 | 79.0 | (I)-49 | B-1 | 19.5 | — | — | — | — | D-2 | 1.5 | — | — | F-1/F-3 | 90/10 |
| Re-42 | A-4 | 86.2 | (I)-50 | B-2 | 9.6 | — | — | — | — | D-8 | 4.2 | — | — | F-1/F-2 | 70/30 |
| Re-43 | A-5 | 88.1 | (I)-33 | B-2 | 8.5 | B-5 | 2.6 | — | — | D-11 | 0.8 | — | — | F-1 | 100 |
| Re-44 | A-10 | 87.8 | (1)-48 | B-4 | 8.7 | B-6 | 2.0 | — | — | D-2 | 1.5 | — | — | F-1/F-3 | 90/10 |
| Re-45 | A-4 | 83.1 | (I)-50 | B-2 | 9.6 | B-7 | 3.1 | — | — | D-8 | 4.2 | — | — | F-1/F-2 | 70/30 |
| Re-46 | A-1 | 84.5 | (I)-20 | B-2 | 9.4 | B-8 | 1.8 | — | — | D-8 | 4.2 | E-3 | 0.1 | F-1/F-9 | 90/10 |
| Re-47 | A-9 | 76.1 | (I)-49 | B-1 | 19.5 | B-9 | 2.9 | — | — | D-2 | 1.5 | — | — | F-1/F-3 | 90/10 |
| Re-48 | A-1 | 83.8 | (I)-20 | B-2 | 9.4 | B-10 | 2.5 | — | — | D-8 | 4.2 | E-3 | 0.1 | F-1/F-9 | 90/10 |
| Re-49 | A-10 | 88.9 | (I)-48 | B-4 | 8.7 | B-11 | 0.9 | — | — | D-2 | 1.5 | — | — | F-1/F-3 | 90/10 |
| Re-50 | A-2 | 83.0 | (I)-10 | B-3 | 14.5 | — | — | — | — | D-10 | 2.5 | — | — | F-1/F-8 | 85/15 |
| Re-51 | A-19 | 90.5 | (I)-10 | B-3 | 7.0 | — | — | — | — | D-10 | 2.5 | — | — | F-1/F-8 | 85/15 |
| Re-52 | A-21 | 87.9 | (I)-10 | B-3 | 12.1 | — | — | — | — | — | — | — | — | F-1/F-6 | 40/60 |
| Re-53 | A-22 | 89.9 | (I)-33 | B-2 | 10.1 | — | — | — | — | — | — | — | — | F-1/F-5 | 50/50 |
| Re-54 | A-23 | 90.2 | (I)-49 | B-1 | 9.8 | — | — | — | — | — | — | — | — | F-1/F-2 | 70/30 |
| Re-55 | A-24 | 86.7 | (I)-50 | B-2 | 13.3 | — | — | — | — | — | — | — | — | F-1 | 100 |
| Re-56 | A-25 | 78.0 | (I)-31 | B-1 | 22.0 | — | — | — | — | — | — | — | — | F-1/F-8 | 85/15 |
| Re-57 | A-19 | 79.4 | (I)-24 | B-3 | 14.6 | B-5 | 4.0 | — | — | D-1 | 2.0 | — | — | F-1 | 100 |
| Re-58 | A-20 | 88.0 | (I)-20 | B-2 | 9.8 | B-6 | 2.2 | — | — | — | — | — | — | F-1/F-2 | 70/30 |
| Re-59 | A-23 | 88.3 | (I)-49 | B-1 | 9.8 | B-7 | 1.9 | — | — | — | — | — | — | F-1/F-2 | 70/30 |
| Re-60 | A-18 | 86.4 | (I)-5 | B-3 | 10.5 | B-8 | 3.1 | — | — | — | — | — | — | F-1/F-5 | 50/50 |
| Re-61 | A-21 | 88.0 | (I)-10 | B-3 | 7.0 | B-9 | 5.0 | — | — | — | — | — | — | F-1/F-6 | 40/60 |
| Re-62 | A-14 | 88.8 | (I)-37 | B-1 | 5.1 | B-10 | 6.1 | — | — | — | — | — | — | F-1/F-6 | 40/60 |
| Re-63 | A-25 | 79.9 | (I)-31 | B-1 | 18.6 | B-11 | 1.5 | — | — | — | — | — | — | F-1/F-8 | 85/15 |
| Re-64 | A-19 | 78.8 | (I)-24 | B-3 | 14.6 | B-5 | 4.0 | C-5 | 0.6 | D-1 | 2.0 | — | — | F-1 | 100 |
| Re-65 | A-17 | 90.9 | (I)-35 | B-1 | 8.8 | — | — | C-3 | 0.3 | — | — | — | — | F-1/F-2 | 70/30 |
| Re-66 | A-23 | 87.7 | (I)-49 | B-1 | 9.8 | — | — | — | — | D-10 | 2.5 | — | — | F-1/F-2 | 70/30 |
| Re-67 | A-17 | 88.3 | (I)-35 | B-1 | 8.1 | B-2 | 2.1 | — | — | D-2 | 1.5 | — | — | F-1/F-2 | 70/30 |
| Re-68 | A-9 | 88.0 | (I)-22 | B-2 | 10.5 | — | — | — | — | D-1/ D-9 | 0.8/ 0.7 | — | — | F-1/F-6 | 40/60 |
| Re-69 | A-23 | 87.7 | (I)-49 | B-1 | 9.8 | — | — | — | — | D-10/ D-10 | 1.5/ 1.0 | — | — | F-1/F-2 | 70/30 |

[Production of Topcoat Composition]

In the present Example, in a case where a resist film was manufactured using the composition, a topcoat prepared on the resist film was further manufactured as desired.

The components used in the topcoat composition used to form the topcoat and a production procedure therefor are shown below.

weight (Mw) and the dispersity (Mw/Mn) of each resin of the resin used in the topcoat composition are shown in the following table.

Furthermore, with regard to the structures of the monomers corresponding to the repeating units shown in the table, reference can be made to the above-mentioned monomers shown in the description of <Hydrophobic Resin>.

TABLE 4

| | Molar ratio of repeating unit 1 | | Molar ratio of repeating unit 2 | | Molar ratio of repeating unit 3 | | Molar ratio of repeating unit 4 | | Mw | Mw/Mn |
|---|---|---|---|---|---|---|---|---|---|---|
| PT-1 | ME-2 | 40 | ME-11 | 30 | ME-9 | 30 | — | — | 8,000 | 1.6 |
| PT-2 | ME-2 | 50 | ME-8 | 40 | ME-3 | 10 | — | — | 5,000 | 1.5 |
| PT-3 | ME-3 | 30 | ME-4 | 65 | ME-12 | 5 | — | — | 8,500 | 1.7 |

<Resin>

The molar fractions of the repeating units based on the respective monomers, and the weight-average molecular <Additive>

The additives included in the topcoat composition are shown below.

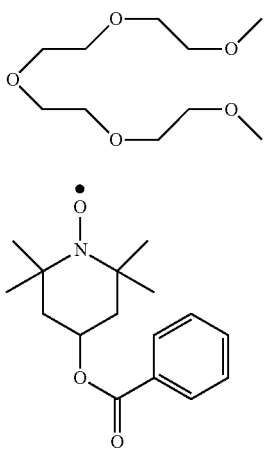

<Surfactant>

In a case where the topcoat composition included a surfactant, the following surfactant was used. E-3: PF656 (manufactured by OMNOVA Solutions Inc., fluorine-based surfactant)

<Solvent>

The solvents included in the topcoat composition are shown below. FT-1: 4-Methyl-2-pentanol (MIBC) FT-2: n-Decane FT-3: Diisoamyl ether.

<Preparation of Topcoat Composition>

A solution was prepared by dissolving the respective components in a solvent such that a formulation shown in the following table was satisfied and a concentration of solid contents of 3.8% by mass was obtained.

Then, the obtained liquid was filtered through a polyethylene filter having a pore size of 0.1 μm to prepare a topcoat composition.

TABLE 5

| | Solid contents | | | | | Solvent | |
|---|---|---|---|---|---|---|---|
| | Resin | | Additive | | Surfactant | | Mixing ratio |
| | Type | Mass (g) | Type | Mass (g) | Type | Mass (g) | Type | (mass ratio) |
| TC-1 | PT-1 | 10.0 | DT-1/DT-2 | 1.3/0.06 | — | — | FT-1/FT-2 | 70/30 |
| TC-2 | PT-2 | 10.0 | DT-3/DT-4 | 0.04/0.06 | E-3 | 0.005 | FT-1/FT-3 | 75/25 |
| TC-3 | PT-3 | 10.0 | DT-5 | 0.05 | — | — | FT-1/FT-3 | 10/90 |

-continued

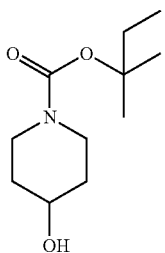

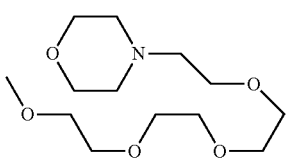

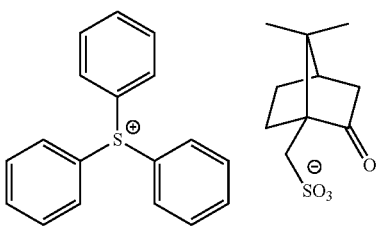

[Test]

Using the composition prepared as mentioned above, the LWR of a pattern developed under each of the following conditions was evaluated.

Furthermore, in any of the tests, a composition which had been left in an environment of 4° C. for 3 months after production thereof was used as the composition used for pattern formation (actinic ray-sensitive or radiation-sensitive resin composition).

<ArF Liquid Immersion Exposure and Organic Solvent Development>

(Pattern Formation)

A composition for forming an organic antireflection film, ARC29SR (manufactured by Brewer Science, Inc.), was applied onto a silicon wafer and baked at 205° C. for 60 seconds to form an antireflection film having a film thickness of 98 nm. The composition shown in Table 6 was applied thereon and baked at 100° C. for 60 seconds to form a resist film (actinic ray-sensitive or radiation-sensitive film) having a film thickness of 90 nm.

Furthermore, in Example 1-22, Example 1-23, and Example 1-24, a topcoat film was formed on the upper layer of the resist film (the types of topcoat compositions used are shown in Table 6). The film thickness of the topcoat film was 100 nm in any case.

The resist film was exposed via a 6% halftone mask having a 1:1 line-and-space pattern with a line width of 45 nm, using an ArF excimer laser liquid immersion scanner (XT1700i, manufactured by ASML, NA 1.20, Dipole, outer sigma: 0.950, inner sigma: 0.850, Y deflection). Ultrapure water was used as the immersion liquid.

The resist film after the exposure was baked at 90° C. for 60 seconds, developed with n-butyl acetate for 30 seconds, and then rinsed with 4-methyl-2-pentanol for 30 seconds. Then, the film was spin-dried to obtain a negative tone pattern.

(Evaluation)

In a case where a 45 nm (1:1) line-and-space pattern resolved with an optimum exposure dose upon resolving a line pattern having an average line width of 45 nm was observed from the upper part of the pattern using a critical dimension scanning electron microscope (SEM (S-9380II manufactured by Hitachi, Ltd.)). The line width of the pattern was observed at any points (100 points), and a measurement deviation thereof was evaluated with 3σ and taken as an LWR. A smaller value of LWR indicates better LWR performance. LWR (nm) is preferably 3.1 nm or less, more preferably 2.9 nm or less, and still more preferably 2.6 nm or less.

The results are shown in the following table.

Furthermore, the column of "B Group" in the table indicates whether the group represented by W corresponds to a group represented by any of General Formulae (B-1) to (B-4) in a case where the specific compound included in the composition is applied to General Formula (I).

TABLE 6

| Composition | B Group | Topcoat composition | LWR (nm) after lapse of 3 months at 4° C. |
|---|---|---|---|
| Example 1-1 Re-1 | B-4 | — | 3.0 |
| Example 1-2 Re-2 | B-3 | — | 2.7 |
| Example 1-3 Re-3 | B-1 | — | 2.4 |
| Example 1-4 Re-4 | B-3 | — | 2.7 |
| Example 1-5 Re-5 | B-2 | — | 2.5 |
| Example 1-6 Re-6 | B-2 | — | 2.5 |
| Example 1-7 Re-7 | B-3 | — | 2.8 |
| Example 1-8 Re-8 | B-4 | — | 3.1 |
| Example 1-9 Re-9 | B-1 | — | 2.4 |
| Example 1-10 Re-10 | B-1 | — | 2.4 |
| Example 1-11 Re-11 | B-1 | — | 2.5 |
| Example 1-12 Re-12 | B-4 | — | 3.0 |
| Example 1-13 Re-13 | B-4 | — | 3.1 |
| Example 1-14 Re-14 | B-1 | — | 2.4 |
| Example 1-15 Re-15 | B-4 | — | 3.1 |
| Example 1-16 Re-16 | B-3 | — | 2.8 |
| Example 1-17 Re-17 | B-3 | — | 2.9 |
| Example 1-18 Re-18 | B-1 | — | 2.5 |
| Example 1-19 Re-19 | B-1 | — | 2.4 |
| Example 1-20 Re-20 | B-2 | — | 2.4 |
| Example 1-21 Re-21 | B-2 | — | 2.4 |
| Example 1-22 Re-22 | B-4 | TC-1 | 3.0 |
| Example 1-23 Re-23 | B-3 | TC-2 | 2.8 |
| Example 1-24 Re-24 | B-1 | TC-3 | 2.5 |
| Comparative Example 1-1 Re-35 | — | — | 5.1 |
| Comparative Example 1-2 Re-36 | — | — | 4.2 |
| Example 1-25 Re-39 | B-3 | — | 2.7 |
| Example 1-26 Re-40 | B-2 | — | 2.5 |
| Example 1-27 Re-41 | B-1 | — | 2.4 |
| Example 1-28 Re-42 | B-2 | — | 2.4 |
| Example 1-29 Re-43 | B-2 | — | 2.5 |
| Example 1-30 Re-44 | B-4 | — | 3.0 |
| Example 1-31 Re-45 | B-2 | — | 2.5 |
| Example 1-32 Re-46 | B-2 | — | 2.5 |
| Example 1-33 Re-47 | B-1 | — | 2.4 |
| Example 1-34 Re-48 | B-2 | — | 2.4 |
| Example 1-35 Re-49 | B-4 | — | 3.1 |
| Example 1-36 Re-50 | B-3 | — | 2.8 |
| Example 1-37 Re-51 | B-3 | — | 2.7 |
| Example 1-38 Re-68 | B-2 | — | 2.4 |

From the results shown in the table, it was confirmed that from the viewpoint in that the LWR performance of a pattern in a case where the composition stored for a long period of time is used is more excellent, the group represented by B⁻ in the specific compound is preferably a group represented by any of General Formulae (B-1) to (B-3), and more preferably a group represented by General Formula (B-1) or General Formula (B-2).

<ArF Liquid Immersion Exposure and Alkaline Development>

(Pattern Formation)

A composition for forming an organic antireflection film, ARC29SR (manufactured by Brewer Science, Inc.), was applied onto a silicon wafer and baked at 205° C. for 60 seconds to form an antireflection film having a film thickness of 98 nm. The composition shown in Table 7 was applied thereon and baked at 100° C. for 60 seconds to form a resist film having a film thickness of 90 nm. In Example 2-22, Example 2-23, and Example 2-24, a topcoat film was formed on the upper layer of the resist film (the types of topcoat compositions used are shown in Table 7). The film thickness of the topcoat film was 100 nm in any case.

The resist film was exposed via a 6% halftone mask having a 1:1 line-and-space pattern with a line width of 45 nm, using an ArF excimer laser liquid immersion scanner (XT1700i, manufactured by ASML, NA 1.20, Dipole, outer sigma: 0.950, inner sigma: 0.890, Y deflection). Ultrapure water was used as the immersion liquid.

The resist film after the exposure was baked at 90° C. for 60 seconds, developed with an aqueous tetramethylammonium hydroxide solution (2.38%-by-mass) for 30 seconds, and then rinsed with pure water for 30 seconds. Thereafter, the resist film was spin-dried to obtain a positive tone pattern.

(Evaluation)

The obtained pattern was evaluated in the same manner as in the evaluation of the LWR of a pattern in <ArF Liquid Immersion Exposure and Organic Solvent Development>.

The results are shown in the following table.

TABLE 7

| Composition | B Group | Topcoat composition | LWR (nm) after lapse of 3 months at 4° C. |
|---|---|---|---|
| Example 2-1 Re-1 | B-4 | — | 3.1 |
| Example 2-2 Re-2 | B-3 | — | 2.7 |
| Example 2-3 Re-3 | B-1 | — | 2.5 |
| Example 2-4 Re-4 | B-3 | — | 2.8 |
| Example 2-5 Re-5 | B-2 | — | 2.4 |
| Example 2-6 Re-6 | B-2 | — | 2.4 |
| Example 2-7 Re-7 | B-3 | — | 2.9 |
| Example 2-8 Re-8 | B-4 | — | 3.0 |
| Example 2-9 Re-9 | B-1 | — | 2.4 |
| Example 2-10 Re-10 | B-1 | — | 2.4 |
| Example 2-11 Re-11 | B-1 | — | 2.6 |
| Example 2-12 Re-12 | B-4 | — | 3.1 |
| Example 2-13 Re-13 | B-4 | — | 3.1 |
| Example 2-14 Re-14 | B-1 | — | 2.4 |
| Example 2-15 Re-15 | B-4 | — | 3.0 |
| Example 2-16 Re-16 | B-3 | — | 2.7 |
| Example 2-17 Re-17 | B-3 | — | 2.9 |
| Example 2-18 Re-18 | B-1 | — | 2.4 |
| Example 2-19 Re-19 | B-1 | — | 2.5 |
| Example 2-20 Re-20 | B-2 | — | 2.5 |
| Example 2-21 Re-21 | B-2 | — | 2.4 |
| Example 2-22 Re-22 | B-4 | TC-1 | 3.0 |
| Example 2-23 Re-23 | B-3 | TC-2 | 2.9 |
| Example 2-24 Re-24 | B-1 | TC-3 | 2.5 |
| Comparative Example 2-1 Re-35 | — | — | 4.9 |
| Comparative Example 2-2 Re-36 | — | — | 4.3 |
| Example 2-25 Re-39 | B-3 | — | 2.8 |
| Example 2-26 Re-40 | B-2 | — | 2.5 |
| Example 2-27 Re-41 | B-1 | — | 2.5 |
| Example 2-28 Re-42 | B-2 | — | 2.4 |

TABLE 7-continued

|  | Composition | B Group | Topcoat composition | LWR (nm) after lapse of 3 months at 4° C. |
|---|---|---|---|---|
| Example 2-29 | Re-43 | B-2 | — | 2.4 |
| Example 2-30 | Re-44 | B-4 | — | 3.2 |
| Example 2-31 | Re-45 | B-2 | — | 2.4 |
| Example 2-32 | Re-46 | B-2 | — | 2.5 |
| Example 2-33 | Re-47 | B-1 | — | 2.4 |
| Example 2-34 | Re-48 | B-2 | — | 2.5 |
| Example 2-35 | Re-49 | B-4 | — | 3.0 |
| Example 2-36 | Re-50 | B-3 | — | 2.7 |
| Example 2-37 | Re-51 | B-3 | — | 2.7 |
| Example 2-38 | Re-68 | B-2 | — | 2.5 |

From the results shown in the table, the same tendency as the test results according to <ArF Liquid Immersion Exposure and Organic Solvent Development> was confirmed.

<EUV Exposure and Organic Solvent Development>

(Pattern Formation) A composition for forming an underlayer film, AL412 (manufactured by Brewer Science, Inc.), was applied onto a silicon wafer and baked at 205° C. for 60 seconds to form an underlying film having a film thickness of 20 nm. The composition shown in Table 8 was applied thereon and baked at 100° C. for 60 seconds to form a resist film having a film thickness of 30 nm.

The silicon wafer having the obtained resist film was subjected to patternwise irradiation using an EUV exposure device (manufactured by Exitech Ltd., Micro Exposure Tool, NA 0.3, Quadrupol, outer sigma 0.68, inner sigma 0.36). Further, as the reticle, a mask having a line size=20 nm and a line:space=1:1 was used.

The resist film after the exposure was baked at 90° C. for 60 seconds, developed with n-butyl acetate for 30 seconds, and spin-dried to obtain a negative tone pattern.

(Evaluation)

In a case where a 20 nm (1:1) line-and-space pattern resolved with an optimum exposure dose upon resolving a line pattern having an average line width of 20 nm was observed from the upper part of the pattern using a critical dimension scanning electron microscope (SEM (S-9380II manufactured by Hitachi, Ltd.)). The line width of the pattern was observed at any points (100 points), and a measurement deviation thereof was evaluated with 3σ and taken as an LWR. A smaller value of LWR indicates better LWR performance. LWR (nm) is preferably 4.3 nm or less, more preferably 3.9 nm or less, and still more preferably 3.5 nm or less.

The results are shown in the following table.

Furthermore, the column of "B Group" in the table indicates whether the group represented by B⁻ corresponds to a group represented by any of General Formulae (B-1) to (B-4) in a case where the specific compound included in the composition is applied to General Formula (I).

TABLE 8

|  | Composition | B Group | LWR (nm) after lapse of 3 months at 4° C. |
|---|---|---|---|
| Example 3-1 | Re-25 | B-1 | 3.5 |
| Example 3-2 | Re-26 | B-4 | 4.3 |
| Example 3-3 | Re-27 | B-3 | 3.7 |
| Example 3-4 | Re-28 | B-1 | 3.4 |
| Example 3-5 | Re-29 | B-2 | 3.5 |
| Example 3-6 | Re-30 | B-4 | 4.2 |
| Example 3-7 | Re-31 | B-3 | 3.9 |
| Example 3-8 | Re-32 | B-1 | 3.5 |
| Example 3-9 | Re-33 | B-1 | 3.5 |
| Example 3-10 | Re-34 | B-2 | 3.5 |

TABLE 8-continued

|  | Composition | B Group | LWR (nm) after lapse of 3 months at 4° C. |
|---|---|---|---|
| Comparative Example 3-1 | Re-37 | — | 5.9 |
| Comparative Example 3-2 | Re-38 | — | 5.0 |
| Example 3-11 | Re-52 | B-3 | 3.8 |
| Example 3-12 | Re-53 | B-2 | 3.4 |
| Example 3-13 | Re-54 | B-1 | 3.5 |
| Example 3-14 | Re-55 | B-2 | 3.5 |
| Example 3-15 | Re-56 | B-1 | 3.4 |
| Example 3-16 | Re-57 | B-3 | 4.0 |
| Example 3-17 | Re-58 | B-2 | 3.4 |
| Example 3-18 | Re-59 | B-1 | 3.4 |
| Example 3-19 | Re-60 | B-3 | 3.7 |
| Example 3-20 | Re-61 | B-3 | 3.7 |
| Example 3-21 | Re-62 | B-1 | 3.5 |
| Example 3-22 | Re-63 | B-1 | 3.4 |
| Example 3-23 | Re-64 | B-3 | 3.9 |
| Example 3-24 | Re-65 | B-1 | 3.5 |
| Example 3-25 | Re-66 | B-1 | 3.4 |
| Example 3-26 | Re-67 | B-1 | 3.4 |
| Example 3-27 | Re-69 | B-1 | 3.5 |

From the results shown in the table, the same tendency as the test results according to <ArF Liquid Immersion Exposure and Organic Solvent Development> was confirmed.

<EUV Exposure and Alkaline Development>

(Pattern Formation)

A composition for forming an underlayer film, AL412 (manufactured by Brewer Science, Inc.), was applied onto a silicon wafer and baked at 205° C. for 60 seconds to form an underlying film having a film thickness of 20 nm. A resin composition shown in Table 9 was applied thereon and baked at 100° C. for 60 seconds to form a resist film having a film thickness of 30 nm.

The silicon wafer having the obtained resist film was subjected to patternwise irradiation using an EUV exposure device (manufactured by Exitech Ltd., Micro Exposure Tool, NA 0.3, Quadrupol, outer sigma 0.68, inner sigma 0.36). Further, as a reticle, a mask having a line size=20 nm and a line:space=1:1 was used.

The resist film after the exposure was baked at 90° C. for 60 seconds, developed with an aqueous tetramethylammonium hydroxide solution (2.38%-by-mass) for 30 seconds, and then rinsed with pure water for 30 seconds. Thereafter, the resist film was spin-dried to obtain a positive tone pattern.

(Evaluation)

The obtained pattern was evaluated in the same manner as in the evaluation of the LWR of a pattern in <EUV Exposure and Organic Solvent Development>.

The results are shown in the following table.

TABLE 9

|  | Composition | B Group | LWR (nm) after lapse of 3 months at 4° C. |
|---|---|---|---|
| Example 4-1 | Re-25 | B-1 | 3.4 |
| Example 4-2 | Re-26 | B-4 | 4.2 |
| Example 4-3 | Re-27 | B-3 | 3.7 |
| Example 4-4 | Re-28 | B-1 | 3.5 |
| Example 4-5 | Re-29 | B-2 | 3.5 |
| Example 4-6 | Re-30 | B-4 | 4.3 |
| Example 4-7 | Re-31 | B-3 | 3.8 |
| Example 4-8 | Re-32 | B-1 | 3.4 |
| Example 4-9 | Re-33 | B-1 | 3.4 |
| Example 4-10 | Re-34 | B-2 | 3.4 |

TABLE 9-continued

| | Composition | B Group | LWR (nm) after lapse of 3 months at 4° C. |
|---|---|---|---|
| Comparative Example 4-1 | Re-37 | — | 5.6 |
| Comparative Example 4-2 | Re-38 | — | 5.0 |
| Example 4-11 | Re-52 | B-3 | 3.7 |
| Example 4-12 | Re-53 | B-2 | 3.4 |
| Example 4-13 | Re-54 | B-1 | 3.4 |
| Example 4-14 | Re-55 | B-2 | 3.5 |
| Example 4-15 | Re-56 | B-1 | 3.5 |
| Example 4-16 | Re-57 | B-3 | 3.9 |
| Example 4-17 | Re-58 | B-2 | 3.5 |
| Example 4-18 | Re-59 | B-1 | 3.5 |
| Example 4-19 | Re-60 | B-3 | 3.9 |
| Example 4-20 | Re-61 | B-3 | 3.7 |
| Example 4-21 | Re-62 | B-1 | 3.4 |
| Example 4-22 | Re-63 | B-1 | 3.5 |
| Example 4-23 | Re-64 | B-3 | 4.0 |
| Example 4-24 | Re-65 | B-1 | 3.6 |
| Example 4-25 | Re-66 | B-1 | 3.6 |
| Example 4-26 | Re-67 | B-1 | 3.4 |
| Example 4-27 | Re-69 | B-1 | 3.5 |

From the results shown in the table, the same tendency as the test results according to <ArF Liquid Immersion Exposure and Organic Solvent Development> was confirmed.

What is claimed is:

1. An actinic ray-sensitive or radiation-sensitive resin composition, comprising:
   a compound represented by General Formula (I); and
   an acid-decomposable resin,

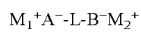

in General Formula (I), $M_1^+$ and $M_2^+$ each independently represent an organic cation,
L represents a divalent organic group,
$A^-$ represents an acid anion group,
provided that in a compound represented by HA-L-BH in which $M_1^+$ and $M_2^+$ of the compound represented by General Formula (I) are each substituted with a hydrogen atom, a pKa of a group represented by HA is lower than a pKa of a group represented by BH, and
$B^-$ represents a group represented by any of General Formulae (B-1), (B-2) and (B-4),

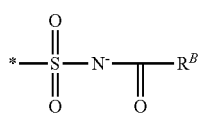

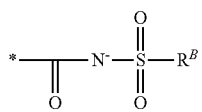

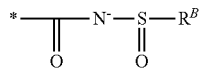

in General Formulae (B-1), (B-2) and (B-4), * represents a bonding position, and
$R^B$ represents a cycloalkyl group which may have a substituent, an aromatic ring group which may have a substituent, or an alkyl group which may have a substituent, the alkyl group not being a perfluoroalkyl group.

2. The actinic ray-sensitive or radiation-sensitive resin composition according to claim 1,
wherein $B^-$ represents a group represented by either of General Formulae (B-1) and (B-2).

3. The actinic ray-sensitive or radiation-sensitive resin composition according to claim 1,
wherein $A^-$ represents a group represented by either of General Formulae (A-1) and (A-2),

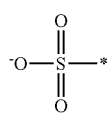

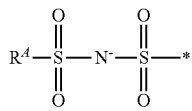

in General Formulae (A-1) and (A-2), * represents a bonding position, and
$R^A$ represents an organic group,
provided that in a compound represented by HA-L-BH in which $M_1^+$ and $M_2^+$ of the compound represented by General Formula (I) are each substituted with a hydrogen atom, a pKa of a group represented by HA is lower than a pKa of a group represented by BH.

4. The actinic ray-sensitive or radiation-sensitive resin composition according to claim 1,
wherein $R^B$ represents a cycloalkyl group which may have a substituent, an aromatic ring group which may have a substituent, or an alkyl group which may have a cycloalkyl group as a substituent.

5. A resist film formed of the actinic ray-sensitive or radiation-sensitive resin composition according to claim 1.

6. A pattern forming method comprising:
   forming a resist film on a support, using the actinic ray-sensitive or radiation-sensitive resin composition according to claim 1;
   exposing the resist film; and
   developing the exposed resist film using a developer.

7. A method for manufacturing an electronic device, comprising the pattern forming method according to claim 6.

* * * * *